(12) United States Patent
Ward et al.

(10) Patent No.: US 12,336,728 B2
(45) Date of Patent: Jun. 24, 2025

(54) FORCEPS HAVING ACTUATOR SPLAY CONTROL

(71) Applicant: GYRUS ACMI, INC., Westborough, MA (US)

(72) Inventors: Zane R. Ward, Minneapolis, MN (US); Eric J. Boone, Saint Michael, MN (US); Christian J. Fiksen, Maple Grove, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 18/467,949

(22) Filed: Sep. 15, 2023

(65) Prior Publication Data

US 2024/0074776 A1   Mar. 7, 2024

Related U.S. Application Data

(63) Continuation of application No. 16/830,181, filed on Mar. 25, 2020, now Pat. No. 11,793,534.
(Continued)

(51) Int. Cl.
*A61B 17/29* (2006.01)
*A61B 18/14* (2006.01)
(Continued)

(52) U.S. Cl.
CPC .......... *A61B 17/29* (2013.01); *A61B 18/1445* (2013.01); *A61B 2018/0091* (2013.01); *B23K 26/21* (2015.10)

(58) Field of Classification Search
CPC ............ A61B 17/2804; A61B 17/2833; A61B 17/2909; A61B 2017/2901;
(Continued)

(56) References Cited

U.S. PATENT DOCUMENTS 4,887,612 A   12/1989  Esser et al.
5,009,661 A   4/1991   Michelson
(Continued)

FOREIGN PATENT DOCUMENTS

CN      1843301      10/2006
CN      101327134 A  12/2008
(Continued)

OTHER PUBLICATIONS

US 11,497,515 B2, 11/2022, Fiksen et al. (withdrawn)
(Continued)

*Primary Examiner* — Martin T Ton
(74) *Attorney, Agent, or Firm* — Schwegman Lundberg & Woessner, P.A.

(57) ABSTRACT

Forceps with improved actuation include a housing and a body that is longitudinally slidable relative to the housing. The body having a peripheral flange extending outward towards the housing. A trigger includes an actuation surface configured to receive a force input from a user. The trigger further including at least one arm configured to transfer the received force input to the body. To inhibit lateral splaying of the at least one arm when the trigger is actuated, the housing includes a first control surface, such as a rib proximate the arm.

24 Claims, 75 Drawing Sheets

Related U.S. Application Data

(60) Provisional application No. 62/994,220, filed on Mar. 24, 2020, provisional application No. 62/841,476, filed on May 1, 2019, provisional application No. 62/826,522, filed on Mar. 29, 2019, provisional application No. 62/826,532, filed on Mar. 29, 2019.

(51) Int. Cl.
*A61B 18/00* (2006.01)
*B23K 26/21* (2014.01)

(58) Field of Classification Search
CPC .... A61B 2017/2902; A61B 2017/2903; A61B 2017/2911; A61B 2017/2912; A61B 2017/2913; A61B 2017/2915; A61B 2017/2916; A61B 2017/2917; A61B 2017/2919; A61B 17/292; A61B 17/2922; A61B 17/2924; A61B 17/2925; A61B 17/2946; A61B 17/2947; A61B 2018/1452; A61B 2018/2455
See application file for complete search history.

(56) References Cited

U.S. PATENT DOCUMENTS

| | | | |
|---|---|---|---|
| 5,286,255 A | 2/1994 | Weber | |
| 5,354,313 A | 10/1994 | Boebel | |
| 5,413,583 A | 5/1995 | Wohlers | |
| 5,496,310 A | 3/1996 | Exconde et al. | |
| 5,556,416 A | 9/1996 | Clark et al. | |
| 5,562,699 A | 10/1996 | Heimberger et al. | |
| 5,653,721 A | 8/1997 | Knodel et al. | |
| 5,683,412 A | 11/1997 | Scarfone | |
| 5,706,998 A | 1/1998 | Plyley et al. | |
| 5,776,130 A | 7/1998 | Buysse et al. | |
| 5,782,749 A | 7/1998 | Riza | |
| 5,947,984 A | 9/1999 | Whipple | |
| 6,039,733 A | 3/2000 | Buysse et al. | |
| 6,458,130 B1 | 10/2002 | Frazier et al. | |
| 6,585,735 B1 | 7/2003 | Frazier et al. | |
| 6,682,544 B2 | 1/2004 | Mastri et al. | |
| 6,752,823 B2 | 6/2004 | Prestel | |
| 7,083,618 B2 | 8/2006 | Couture et al. | |
| 7,118,587 B2 | 10/2006 | Dycus et al. | |
| 7,131,971 B2 | 11/2006 | Dycus et al. | |
| 7,481,810 B2 | 1/2009 | Dumbauld et al. | |
| 7,597,693 B2 | 10/2009 | Garrison | |
| 7,604,634 B2 | 10/2009 | Hooven | |
| 7,628,791 B2 | 12/2009 | Garrison et al. | |
| 8,475,453 B2 | 7/2013 | Marczyk et al. | |
| 8,523,893 B2 | 9/2013 | Kessler | |
| 8,523,898 B2 | 9/2013 | Bucciaglia et al. | |
| 8,540,711 B2 | 9/2013 | Dycus et al. | |
| 8,632,539 B2 | 1/2014 | Twomey et al. | |
| 8,663,270 B2 | 3/2014 | Donnigan et al. | |
| 8,672,935 B2 | 3/2014 | Okada et al. | |
| 8,702,749 B2 | 4/2014 | Twomey | |
| 8,715,277 B2 | 5/2014 | Weizman | |
| 8,734,443 B2 | 5/2014 | Hixson et al. | |
| 8,968,311 B2 | 3/2015 | Allen, IV et al. | |
| 8,968,313 B2 | 3/2015 | Larson | |
| 9,113,940 B2 | 8/2015 | Twomey | |
| 9,399,508 B2 | 7/2016 | Lakic et al. | |
| 9,592,089 B2 | 3/2017 | Lyons et al. | |
| 9,636,169 B2 | 5/2017 | Allen, IV et al. | |
| 9,668,807 B2 | 6/2017 | Sims et al. | |
| 9,681,883 B2 | 6/2017 | Windgassen et al. | |
| 9,707,031 B2 | 7/2017 | Hempstead et al. | |
| 9,820,765 B2 | 11/2017 | Allen, IV et al. | |
| 9,839,471 B2 | 12/2017 | O'Neill et al. | |
| 9,861,378 B2 | 1/2018 | Allen, IV et al. | |
| 9,867,649 B2 | 1/2018 | Hörlle | |
| 9,867,658 B2 | 1/2018 | Larson et al. | |
| 10,231,776 B2 | 3/2019 | Artale et al. | |
| 10,271,897 B2 | 4/2019 | Allen, IV et al. | |
| 10,349,963 B2 | 7/2019 | Fiksen et al. | |
| 10,413,351 B2 | 9/2019 | Worrell | |
| 10,561,433 B2 | 2/2020 | Batchelor et al. | |
| 10,849,641 B2 | 12/2020 | Boone et al. | |
| 10,869,682 B2 | 12/2020 | Drochner et al. | |
| 11,147,576 B2 | 10/2021 | Ward et al. | |
| 11,452,535 B2 | 9/2022 | Fiksen et al. | |
| 11,457,939 B2 | 10/2022 | Ward | |
| 11,464,530 B2 | 10/2022 | Blus et al. | |
| 11,529,159 B2 | 12/2022 | Fiksen et al. | |
| 11,678,899 B2 | 6/2023 | Ward et al. | |
| 11,730,502 B2 | 8/2023 | Ward et al. | |
| 11,793,534 B2 | 10/2023 | Ward et al. | |
| 11,883,049 B2 | 1/2024 | Mensch et al. | |
| 11,911,058 B2 | 2/2024 | Pham et al. | |
| 11,969,181 B2 | 4/2024 | Ward et al. | |
| 12,082,832 B2 | 9/2024 | Mensch et al. | |
| 12,193,694 B2 | 1/2025 | Butler et al. | |
| 2003/0014060 A1 | 1/2003 | Wilson et al. | |
| 2003/0018331 A1 | 1/2003 | Dycus et al. | |
| 2003/0208296 A1 | 11/2003 | Brisson et al. | |
| 2004/0087943 A1 | 5/2004 | Dycus et al. | |
| 2004/0243125 A1 | 12/2004 | Dycus et al. | |
| 2004/0260337 A1 | 12/2004 | Freed | |
| 2005/0006432 A1 | 1/2005 | Racenet et al. | |
| 2005/0119655 A1 | 6/2005 | Moses et al. | |
| 2006/0097026 A1* | 5/2006 | Shelton | A61B 17/0682 227/19 |
| 2006/0189981 A1 | 8/2006 | Dycus et al. | |
| 2006/0235438 A1 | 10/2006 | Huitema et al. | |
| 2007/0021777 A1 | 1/2007 | Fowler | |
| 2007/0078456 A1 | 4/2007 | Dumbauld et al. | |
| 2007/0106297 A1 | 5/2007 | Dumbauld et al. | |
| 2008/0314957 A1 | 12/2008 | Boudreaux | |
| 2009/0030437 A1* | 1/2009 | Houser | A61B 18/1442 422/1 |
| 2009/0112206 A1 | 4/2009 | Dumbauld et al. | |
| 2009/0198098 A1 | 8/2009 | Okada et al. | |
| 2009/0206124 A1 | 8/2009 | Hall et al. | |
| 2009/0270896 A1 | 10/2009 | Sullivan et al. | |
| 2010/0010512 A1 | 1/2010 | Taylor et al. | |
| 2010/0057085 A1 | 3/2010 | Holcomb et al. | |
| 2010/0179545 A1 | 7/2010 | Twomey et al. | |
| 2010/0274244 A1 | 10/2010 | Heard | |
| 2010/0324551 A1 | 12/2010 | Gerhardt | |
| 2011/0009864 A1 | 1/2011 | Bucciaglia et al. | |
| 2011/0184405 A1 | 7/2011 | Mueller | |
| 2012/0022583 A1 | 1/2012 | Sugalski et al. | |
| 2012/0059375 A1 | 3/2012 | Couture et al. | |
| 2012/0109186 A1 | 5/2012 | Parrott et al. | |
| 2012/0116389 A1* | 5/2012 | Houser | A61B 17/320092 606/1 |
| 2012/0184990 A1 | 7/2012 | Twomey | |
| 2012/0296371 A1 | 11/2012 | Kappus et al. | |
| 2012/0303023 A1 | 11/2012 | Bucciaglia et al. | |
| 2012/0310240 A1 | 12/2012 | Olson et al. | |
| 2013/0014375 A1 | 1/2013 | Hempstead et al. | |
| 2013/0085491 A1 | 4/2013 | Twomey et al. | |
| 2013/0131666 A1 | 5/2013 | Atwell et al. | |
| 2013/0138102 A1 | 5/2013 | Twomey et al. | |
| 2013/0218198 A1 | 8/2013 | Larson et al. | |
| 2013/0256383 A1 | 10/2013 | Aronhalt et al. | |
| 2013/0296848 A1 | 11/2013 | Allen, IV et al. | |
| 2013/0296922 A1 | 11/2013 | Allen, IV et al. | |
| 2013/0304058 A1 | 11/2013 | Kendrick | |
| 2013/0304059 A1 | 11/2013 | Allen, IV et al. | |
| 2014/0025071 A1* | 1/2014 | Sims | A61B 18/1482 606/46 |
| 2014/0107685 A1 | 4/2014 | O'neill et al. | |
| 2014/0135758 A1 | 5/2014 | Mueller | |
| 2014/0135805 A1 | 5/2014 | Windgassen et al. | |
| 2014/0228842 A1 | 8/2014 | Dycus et al. | |
| 2014/0257274 A1 | 9/2014 | Mccullough et al. | |
| 2014/0257284 A1 | 9/2014 | Artale | |
| 2014/0276666 A1 | 9/2014 | Malkowski | |
| 2014/0276803 A1 | 9/2014 | Hart | |
| 2014/0326249 A1 | 11/2014 | Cappiello et al. | |
| 2015/0082929 A1 | 3/2015 | Isomura | |

(56) References Cited

U.S. PATENT DOCUMENTS

| | | | |
|---|---|---|---|
| 2015/0088126 A1 | 3/2015 | Duffin et al. | |
| 2015/0105821 A1 | 4/2015 | Ward et al. | |
| 2015/0133915 A1 | 5/2015 | Strobl | |
| 2015/0133931 A1 | 5/2015 | Twomey et al. | |
| 2015/0150573 A1 | 6/2015 | Van Tol et al. | |
| 2015/0201953 A1 | 7/2015 | Strobl et al. | |
| 2015/0209059 A1 | 7/2015 | Trees et al. | |
| 2015/0209103 A1 | 7/2015 | Artale et al. | |
| 2015/0305803 A1 | 10/2015 | Larson et al. | |
| 2015/0331443 A1 | 11/2015 | Lamser et al. | |
| 2016/0008054 A1 | 1/2016 | Sims et al. | |
| 2016/0008056 A1 | 1/2016 | Lyons et al. | |
| 2016/0015419 A1* | 1/2016 | Hibner | A61B 17/320092 606/171 |
| 2016/0045254 A1 | 2/2016 | O'neill et al. | |
| 2016/0074101 A1 | 3/2016 | Anglese et al. | |
| 2016/0338764 A1 | 11/2016 | Krastins et al. | |
| 2016/0361107 A1 | 12/2016 | Zergiebel et al. | |
| 2017/0119459 A1 | 5/2017 | Schechter et al. | |
| 2017/0128071 A1 | 5/2017 | Holsten et al. | |
| 2017/0172700 A1 | 6/2017 | Denzinger et al. | |
| 2017/0181790 A1 | 6/2017 | Twomey et al. | |
| 2017/0196579 A1 | 7/2017 | Batchelor et al. | |
| 2017/0196625 A1 | 7/2017 | Nagtegaal | |
| 2017/0196630 A1 | 7/2017 | Nagtegaal et al. | |
| 2017/0196635 A1 | 7/2017 | Brennan et al. | |
| 2017/0196636 A1 | 7/2017 | Mccullough, Jr. et al. | |
| 2017/0238990 A1 | 8/2017 | Soni | |
| 2017/0245921 A1 | 8/2017 | Joseph et al. | |
| 2017/0273703 A1 | 9/2017 | Ding et al. | |
| 2017/0319229 A1 | 11/2017 | Brown et al. | |
| 2017/0354456 A1* | 12/2017 | Fiksen | A61B 90/03 |
| 2017/0367753 A1 | 12/2017 | Bjorn-rasmussen et al. | |
| 2018/0008338 A1 | 1/2018 | Kopp | |
| 2018/0103973 A1 | 4/2018 | Allen, IV et al. | |
| 2018/0206907 A1 | 7/2018 | Dycus et al. | |
| 2018/0243028 A1 | 8/2018 | Allen, IV et al. | |
| 2018/0333178 A1 | 11/2018 | Weisenburgh et al. | |
| 2018/0333186 A1 | 11/2018 | Leuck et al. | |
| 2018/0338792 A1 | 11/2018 | Allen, IV et al. | |
| 2018/0368850 A1 | 12/2018 | Shelton, IV et al. | |
| 2019/0015124 A1 | 1/2019 | Williams et al. | |
| 2019/0059989 A1 | 2/2019 | Heiliger | |
| 2019/0083819 A1 | 3/2019 | Mitchell et al. | |
| 2019/0175187 A1 | 6/2019 | P V R | |
| 2019/0175256 A1 | 6/2019 | Butler | |
| 2019/0216464 A1 | 7/2019 | Baril et al. | |
| 2019/0298399 A1 | 10/2019 | Boone et al. | |
| 2020/0000512 A1 | 1/2020 | Heiliger | |
| 2020/0163687 A1 | 5/2020 | Ding et al. | |
| 2020/0222070 A1 | 7/2020 | Stamm et al. | |
| 2020/0289191 A1 | 9/2020 | Soni | |
| 2020/0305901 A1 | 10/2020 | Fiksen et al. | |
| 2020/0305902 A1 | 10/2020 | Ward et al. | |
| 2020/0305904 A1 | 10/2020 | Holman et al. | |
| 2020/0305905 A1 | 10/2020 | Fiksen et al. | |
| 2020/0305907 A1 | 10/2020 | Ward | |
| 2020/0305909 A1 | 10/2020 | Mensch et al. | |
| 2020/0305910 A1 | 10/2020 | Mensch et al. | |
| 2020/0305911 A1 | 10/2020 | Pham et al. | |
| 2020/0305912 A1 | 10/2020 | Blus et al. | |
| 2020/0305916 A1 | 10/2020 | Butler et al. | |
| 2020/0305917 A1 | 10/2020 | Ward et al. | |
| 2020/0305958 A1 | 10/2020 | Ward et al. | |
| 2020/0305959 A1 | 10/2020 | Ward et al. | |
| 2020/0305960 A1 | 10/2020 | Butler et al. | |
| 2020/0305962 A1 | 10/2020 | Ward et al. | |
| 2020/0305965 A1 | 10/2020 | Pham et al. | |
| 2021/0000536 A1 | 1/2021 | Davies et al. | |
| 2021/0085418 A1 | 3/2021 | Olichney et al. | |
| 2021/0346044 A1 | 11/2021 | Fiksen et al. | |
| 2022/0409226 A1 | 12/2022 | Fiksen et al. | |
| 2023/0371967 A1 | 11/2023 | Ward et al. | |
| 2024/0260985 A1 | 8/2024 | Ward et al. | |
| 2024/0390021 A1 | 11/2024 | Mensch et al. | |

FOREIGN PATENT DOCUMENTS

| | | |
|---|---|---|
| CN | 101815461 | 8/2010 |
| CN | 103381106 A | 11/2013 |
| CN | 104095680 A | 10/2014 |
| CN | 104414742 A | 3/2015 |
| CN | 107771060 | 3/2018 |
| CN | 108463182 | 8/2018 |
| CN | 114206239 A | 3/2022 |
| CN | 114554983 A | 5/2022 |
| CN | 114206239 B | 7/2024 |
| CN | 114554983 B | 10/2024 |
| EP | 2347725 A1 | 7/2011 |
| EP | 2659848 A2 | 11/2013 |
| EP | 2735274 A1 | 5/2014 |
| EP | 2974685 A1 | 1/2016 |
| EP | 3946090 | 1/2025 |
| JP | 2010284551 A | 12/2010 |
| JP | 2013230367 A | 11/2013 |
| JP | 2013230369 A | 11/2013 |
| JP | 2015534858 A | 12/2015 |
| JP | 2017070797 A | 4/2017 |
| JP | 2022527801 A | 6/2022 |
| JP | 2022527953 A | 6/2022 |
| JP | 7475363 | 4/2024 |
| JP | 2024051111 A | 4/2024 |
| JP | 2024144691 A | 10/2024 |
| JP | 7608356 | 12/2024 |
| SG | 11202110190 U | 8/2024 |
| SG | 11202110191X | 8/2024 |
| WO | WO-2009070780 A1 | 6/2009 |
| WO | WO-2016100667 A2 | 6/2016 |
| WO | WO-2019014164 A1 | 1/2019 |
| WO | WO-2020205372 A1 | 10/2020 |
| WO | WO-2020205374 A1 | 10/2020 |
| WO | WO-2020205380 A1 | 10/2020 |
| WO | WO-2020205381 A1 | 10/2020 |

OTHER PUBLICATIONS

"U.S. Appl. No. 16/829,182, 312 Amendment filed Aug. 2, 2021", 8 pgs.

"U.S. Appl. No. 16/829,182, 312 Amendment filed Aug. 24, 2021", 8 pgs.

"U.S. Appl. No. 16/829,182, Notice of Allowance mailed Jun. 1, 2021", 12 pgs.

"U.S. Appl. No. 16/829,182, PTO Response to Rule 312 Communication mailed Aug. 13, 2021", 2 pgs.

"U.S. Appl. No. 16/829,182, PTO Response to Rule 312 Communication mailed Aug. 30, 2021", 2 pgs.

"U.S. Appl. No. 16/829,545, Non Final Office Action mailed Mar. 30, 2022", 22 pgs.

"U.S. Appl. No. 16/829,545, Notice of Allowance mailed Jun. 2, 2022", 11 pgs.

"U.S. Appl. No. 16/829,545, Response filed May 4, 2022 to Non Final Office Action mailed Mar. 30, 2022", 11 pgs.

"U.S. Appl. No. 16/830,079, Examiner Interview Summary mailed Mar. 11, 2022", 2 pgs.

"U.S. Appl. No. 16/830,079, Examiner Interview Summary mailed Jul. 25, 2022", 2 pgs.

"U.S. Appl. No. 16/830,079, Final Office Action mailed Jun. 8, 2022", 16 pgs.

"U.S. Appl. No. 16/830,079, Final Office Action mailed Jul. 18, 2023", 20 pgs.

"U.S. Appl. No. 16/830,079, Non Final Office Action mailed Jan. 26, 2022", 14 pgs.

"U.S. Appl. No. 16/830,079, Non Final Office Action mailed Mar. 9, 2023", 20 pgs.

"U.S. Appl. No. 16/830,079, Non Final Office Action mailed Sep. 15, 2022", 18 pgs.

"U.S. Appl. No. 16/830,079, Notice of Allowance mailed Sep. 20, 2023", 10 pgs.

"U.S. Appl. No. 16/830,079, Response filed Mar. 11, 2022 to Non Final Office Action mailed Jan. 26, 2022", 11 pgs.

(56) References Cited

OTHER PUBLICATIONS

"U.S. Appl. No. 16/830,079, Response filed Apr. 12, 2023 to Non Final Office Action mailed Mar. 9, 2023", 13 pgs.
"U.S. Appl. No. 16/830,079, Response filed Aug. 8, 2022 to Final Office Action mailed Jun. 8, 2022", 11 pgs.
"U.S. Appl. No. 16/830,079, Response filed Aug. 31, 2023 to Final Office Action mailed Jul. 18, 2023", 7 pgs.
"U.S. Appl. No. 16/830,079, Response filed Dec. 15, 2022 to Non Final Office Action mailed Sep. 15, 2022", 10 pgs.
"U.S. Appl. No. 16/830,122, Advisory Action mailed Apr. 25, 2023", 3 pgs.
"U.S. Appl. No. 16/830,122, Examiner Interview Summary mailed Feb. 1, 2023", 2 pgs.
"U.S. Appl. No. 16/830,122, Final Office Action mailed Feb. 13, 2023", 19 pgs.
"U.S. Appl. No. 16/830,122, Final Office Action mailed May 6, 2022", 17 pgs.
"U.S. Appl. No. 16/830,122, Non Final Office Action mailed Jun. 21, 2023", 19 pgs.
"U.S. Appl. No. 16/830,122, Non Final Office Action mailed Aug. 29, 2022", 17 pgs.
"U.S. Appl. No. 16/830,122, Non Final Office Action mailed Dec. 21, 2021", 14 pgs.
"U.S. Appl. No. 16/830,122, Response filed Mar. 21, 2022 to Non Final Office Action mailed Dec. 21, 2021", 9 pgs.
"U.S. Appl. No. 16/830,122, Response filed Apr. 13, 2023 to Final Office Action mailed Feb. 13, 2023", 9 pgs.
"U.S. Appl. No. 16/830,122, Response filed Aug. 4, 2022 to Final Office Action mailed May 6, 2022", 10 pgs.
"U.S. Appl. No. 16/830,122, Response filed Sep. 19, 2023 to Non Final Office Action mailed Jun. 21, 2023", 10 pgs.
"U.S. Appl. No. 16/830,122, Response filed Nov. 29, 2022 to Non Final Office Action mailed Aug. 29, 2022", 10 pgs.
"U.S. Appl. No. 16/830,125, Examiner Interview Summary mailed Nov. 15, 2023", 2 pgs.
"U.S. Appl. No. 16/830,125, Final Office Action mailed Sep. 12, 2023", 18 pgs.
"U.S. Appl. No. 16/830,125, Non Final Office Action mailed Feb. 28, 2023", 19 pgs.
"U.S. Appl. No. 16/830,125, Response filed May 23, 2023 to Non Final Office Action mailed Feb. 28, 2023", 12 pgs.
"U.S. Appl. No. 16/830,130, Final Office Action mailed Feb. 1, 2023", 11 pgs.
"U.S. Appl. No. 16/830,130, Non Final Office Action mailed Dec. 9, 2022", 17 pgs.
"U.S. Appl. No. 16/830,130, Notice of Allowance mailed Apr. 19, 2023", 8 pgs.
"U.S. Appl. No. 16/830,130, Response filed Jan. 4, 2023 to Non Final Office Action mailed Dec. 9, 2022", 14 pgs.
"U.S. Appl. No. 16/830,130, Response filed Apr. 3, 2023 to Final Office Action mailed Feb. 1, 2023", 10 pgs.
"U.S. Appl. No. 16/830,130, Supplemental Notice of Allowability mailed Apr. 27, 2023", 2 pgs.
"U.S. Appl. No. 16/830,140, Notice of Allowance mailed Jun. 11, 2021", 11 pgs.
"U.S. Appl. No. 16/830,140, Supplemental Notice of Allowability mailed Jun. 28, 2021", 6 pgs.
"U.S. Appl. No. 16/830,150, Advisory Action mailed May 18, 2022", 3 pgs.
"U.S. Appl. No. 16/830,150, Examiner Interview Summary mailed Oct. 17, 2022", 2 pgs.
"U.S. Appl. No. 16/830,150, Examiner Interview Summary mailed Dec. 10, 2021", 3 pgs.
"U.S. Appl. No. 16/830,150, Final Office Action mailed Mar. 30, 2022", 19 pgs.
"U.S. Appl. No. 16/830,150, Final Office Action mailed May 3, 2023", 25 pgs.
"U.S. Appl. No. 16/830,150, Non Final Office Action mailed Jan. 18, 2023", 24 pgs.
"U.S. Appl. No. 16/830,150, Non Final Office Action mailed Sep. 7, 2022", 20 pgs.
"U.S. Appl. No. 16/830,150, Non Final Office Action mailed Oct. 29, 2021", 15 pgs.
"U.S. Appl. No. 16/830,150, Notice of Allowance mailed Aug. 16, 2023", 18 pgs.
"U.S. Appl. No. 16/830,150, Notice of Allowance mailed Sep. 22, 2023", 7 pgs.
"U.S. Appl. No. 16/830,150, Response filed Feb. 10, 2023 to Non Final Office Action mailed Jan. 18, 2023", 13 pgs.
"U.S. Appl. No. 16/830,150, Response filed May 5, 2022 to Final Office Action mailed Mar. 30, 2022", 14 pgs.
"U.S. Appl. No. 16/830,150, Response filed Jun. 21, 2022 to Advisory Action mailed May 18, 2022", 16 pgs.
"U.S. Appl. No. 16/830,150, Response filed Jun. 26, 2023 to Final Office Action mailed May 3, 2023", 15 pgs.
"U.S. Appl. No. 16/830,150, Response filed Oct. 12, 2022 to Non Final Office Action mailed Sep. 7, 2022", 13 pgs.
"U.S. Appl. No. 16/830,150, Response filed Dec. 10, 2021 to Non Final Office Action mailed Oct. 29, 2021", 13 pgs.
"U.S. Appl. No. 16/830,162, Examiner Interview Summary mailed May 9, 2022", 2 pgs.
"U.S. Appl. No. 16/830,162, Examiner Interview Summary mailed Jul. 17, 2023", 3 pgs.
"U.S. Appl. No. 16/830,162, Final Office Action mailed Apr. 20, 2023", 23 pgs.
"U.S. Appl. No. 16/830,162, Non Final Office Action mailed Mar. 1, 2022", 24 pgs.
"U.S. Appl. No. 16/830,162, Non Final Office Action mailed Sep. 22, 2022", 22 pgs.
"U.S. Appl. No. 16/830,162, Response filed Jun. 1, 2022 to Non Final Office Action mailed Mar. 1, 2022", 11 pgs.
"U.S. Appl. No. 16/830,162, Response filed Jul. 12, 2023 to Final Office Action mailed Apr. 20, 2023", 8 pgs.
"U.S. Appl. No. 16/830,162, Response filed Dec. 22, 2022 to Non Final Office Action mailed Sep. 22, 2022", 8 pgs.
"U.S. Appl. No. 16/830,163, Final Office Action mailed Nov. 16, 2023", 13 pgs.
"U.S. Appl. No. 16/830,163, Non Final Office Action mailed May 2, 2023", 9 pgs.
"U.S. Appl. No. 16/830,163, Response filed Feb. 8, 2023 to Restriction Requirement mailed Dec. 12, 2022", 8 pgs.
"U.S. Appl. No. 16/830,163, Response filed Aug. 2, 2023 to Non Final Office Action mailed May 2, 2023", 8 pgs.
"U.S. Appl. No. 16/830,163, Restriction Requirement mailed Dec. 12, 2022", 11 pgs.
"U.S. Appl. No. 16/830,175, Corrected Notice of Allowability mailed Sep. 9, 2022", 2 pgs.
"U.S. Appl. No. 16/830,175, Examiner Interview Summary mailed May 4, 2022", 2 pgs.
"U.S. Appl. No. 16/830,175, Non Final Office Action mailed Mar. 7, 2022", 16 pgs.
"U.S. Appl. No. 16/830,175, Notice of Allowance mailed Jun. 1, 2022", 12 pgs.
"U.S. Appl. No. 16/830,175, Response filed May 3, 2022 to Non Final Office Action mailed Mar. 7, 2022", 10 pgs.
"U.S. Appl. No. 16/830,176, Corrected Notice of Allowability mailed Apr. 14, 2023", 2 pgs.
"U.S. Appl. No. 16/830,176, Examiner Interview Summary mailed Aug. 23, 2022", 2 pgs.
"U.S. Appl. No. 16/830,176, Final Office Action mailed Jun. 8, 2022", 18 pgs.
"U.S. Appl. No. 16/830,176, Non Final Office Action mailed Nov. 16, 2022", 14 pgs.
"U.S. Appl. No. 16/830,176, Non Final Office Action mailed Dec. 8, 2021", 16 pgs.
"U.S. Appl. No. 16/830,176, Notice of Allowance mailed Apr. 4, 2023", 10 pgs.
"U.S. Appl. No. 16/830,176, Response filed Feb. 8, 2023 to Non Final Office Action mailed Nov. 16, 2022", 8 pgs.
"U.S. Appl. No. 16/830,176, Response filed Mar. 4, 2022 to Non Final Office Action mailed Dec. 8, 2021", 9 pgs.

(56) References Cited

OTHER PUBLICATIONS

"U.S. Appl. No. 16/830,176, Response filed Sep. 8, 2022 to Final Office Action mailed Jun. 8, 2022", 9 pgs.
"U.S. Appl. No. 16/830,181, Corrected Notice of Allowability mailed Aug. 11, 2023", 3 pgs.
"U.S. Appl. No. 16/830,181, Non Final Office Action mailed Apr. 25, 2023", 9 pgs.
"U.S. Appl. No. 16/830,181, Notice of Allowance mailed Aug. 7, 2023", 9 pgs.
"U.S. Appl. No. 16/830,181, Response filed Jul. 24, 2023 to Non Final Office Action mailed Apr. 25, 2023", 11 pgs.
"U.S. Appl. No. 16/830,192, Corrected Notice of Allowability mailed Oct. 21, 2022", 2 pgs.
"U.S. Appl. No. 16/830,192, Corrected Notice of Allowability mailed Nov. 18, 2022", 2 pgs.
"U.S. Appl. No. 16/830,192, Notice of Allowance mailed Jul. 12, 2022", 8 pgs.
"U.S. Appl. No. 16/830,199, Examiner Interview Summary mailed Mar. 22, 2022", 2 pgs.
"U.S. Appl. No. 16/830,199, Final Office Action mailed Feb. 2, 2022", 43 pgs.
"U.S. Appl. No. 16/830,199, Non Final Office Action mailed Aug. 13, 2021", 35 pgs.
"U.S. Appl. No. 16/830,199, Notice of Allowance mailed May 26, 2022", 11 pgs.
"U.S. Appl. No. 16/830,199, Response filed May 2, 2022 to Final Office Action mailed Feb. 2, 2022", 15 pgs.
"U.S. Appl. No. 16/830,199, Response filed Nov. 15, 2021 to Non Final Office Action mailed Aug. 13, 2021", 15 pgs.
"U.S. Appl. No. 16/830,201, Non Final Office Action mailed Apr. 7, 2023", 17 pgs.
"U.S. Appl. No. 16/830,201, Response filed May 15, 2023 to Non Final Office Action mailed Apr. 7, 2023", 14 pgs.
"U.S. Appl. No. 17/820,953, Non Final Office Action mailed May 9, 2023", 15 pgs.
"U.S. Appl. No. 17/820,953, Response filed Aug. 9, 2023 to Non Final Office Action mailed May 9, 2023", 11 pgs.
"U.S. Appl. No. 18/307,111, Preliminary Amendment filed Aug. 21, 2023", 6 pgs.
"Bevel (Definition)", Merriam-Webster.com Dictionary, [Online] Retrieved from the internet: <https://www.merriam-webster.com/dictionary/bevel> Accessed Aug. 10, 2021, (2021), 9 pgs.
"Chamfer (Definition)", Merriam-Webster, <www.merriam-webster.com/dictionary/chamfer>. Accessed Aug. 5, 2021, (2021), 10 pgs.
"Chinese Application Serial No. 202080026544.9, Office Action mailed Oct. 31, 2023", W/English Translation, 21 pgs.
"Chinese Application Serial No. 202080026544.9, Voluntary Amendment filed Jun. 20, 2022", with English translation of claims, 11 pgs.
"Chinese Application Serial No. 202080032466.3, Office Action mailed Sep. 22, 2023", W/English Translation, 24 pgs.
"Costa Rica Application Serial No. 2021-0537, Office Action mailed Feb. 14, 2022", with machine translation, 5 pgs.
"Costa Rican Application Serial No. 2021-0536, Office Action mailed Feb. 14, 2022", with machine translation, 5 pgs.
"Costa Rican Application Serial No. 2021-0536, Office Action mailed Oct. 27, 2021", with machine translation, 3 pgs.
"Costa Rican Application Serial No. 2021-0537, Office Action mailed Oct. 29, 2021", with machine translation, 3 pgs.
"Costa Rican Application Serial No. 2021-0537, Response filed Dec. 22, 2021 to Office Action mailed Oct. 29, 2021", with machine translation, 30 pgs.
"Dominican Republic Application Serial No. P2021-0203, Office Action mailed Oct. 1, 2021", with machine translation, 3 pgs.
"Dominican Republic Application Serial No. P2021-0203, Response filed Apr. 20, 2022 to Office Action mailed Oct. 1, 2021", with machine translation, 8 pgs.
"Dominican Republic Application Serial No. P2021-0204, Office Action mailed Oct. 12, 2021", with machine translation, 3 pgs.
"Dominican Republic Application Serial No. P2021-0204, Response filed Apr. 20, 2022 to Office Action mailed Oct. 12, 2021", with machine translation, 12 pgs.
"European Application Serial No. 20720253.2, Communication Pursuant to Article 94(3) EPC mailed Apr. 5, 2023", 4 pgs.
"European Application Serial No. 20720253.2, Response filed May 17, 2022 to Communication pursuant to Rules 161(1) and 162 EPC mailed Nov. 18, 2021", 13 pgs.
"European Application Serial No. 20720253.2, Response filed Aug. 2, 2023 to Communication Pursuant to Article 94(3) EPC mailed Apr. 5, 2023", 188 pgs.
"European Application Serial No. 20720261.5, Communication Pursuant to Article 94(3) EPC mailed Sep. 28, 2023", 8 pgs.
"European Application Serial No. 20720261.5, Response filed May 13, 2022 to Communication pursuant to Rules 161(1) and 162 EPC mailed Nov. 12, 2021", 10 pgs.
"International Application Serial No. PCT/US2020/024740, International Preliminary Report on Patentability mailed Oct. 14, 2021", 8 pgs.
"International Application Serial No. PCT/US2020/024740, International Search Report mailed Jun. 16, 2020", 4 pgs.
"International Application Serial No. PCT/US2020/024740, Written Opinion mailed Jun. 16, 2020", 6 pgs.
"International Application Serial No. PCT/US2020/024744, International Search Report mailed Jul. 6, 2020", 4 pgs.
"International Application Serial No. PCT/US2020/024744, Written Opinion mailed Jul. 6, 2020", 8 pgs.
"International Application Serial No. PCT/US2020/024764, International Search Report mailed Jun. 18, 2020", 4 pgs.
"International Application Serial No. PCT/US2020/024764, Written Opinion mailed Jun. 18, 2020", 6 pgs.
"International Application Serial No. PCT/US2020/024775, International Preliminary Report on Patentability mailed Oct. 14, 2021", 9 pgs.
"International Application Serial No. PCT/US2020/024775, International Search Report mailed Jul. 21, 2020", 7 pgs.
"International Application Serial No. PCT/US2020/024775, Written Opinion mailed Jul. 21, 2020", 7 pgs.
"Japanese Application Serial No. 2021-558621, Final Notification of Reasons for Refusal mailed Oct. 24, 2023", w/ English Translation, 6 pgs.
"Japanese Application Serial No. 2021-558621, Notification of Reasons for Refusal mailed May 9, 2023", w/ English translation, 8 pgs.
"Japanese Application Serial No. 2021-558621, Response filed Aug. 3, 2023 to Notification of Reasons for Refusal mailed May 9, 2023", w/English claims, 12 pgs.
"Japanese Application Serial No. 2021-558624, Notification of Reasons for Refusal mailed May 30, 2023", w/ English translation, 11 pgs.
"Japanese Application Serial No. 2021-558624, Response filed Aug. 16, 2023 to Notification of Reasons for Refusal mailed May 30, 2023", w/ english claims, 8 pgs.
"Mexican Application Serial No. MX/a/2021/011966, Office Action mailed Oct. 22, 2021", with machine translation, 9 pgs.
"Mexican Application Serial No. MX/a/2021/011966, Response filed Nov. 30, 2021 to Office Action mailed Oct. 22, 2021", with machine translation, 9 pgs.
"Mexican Application Serial No. MX/a/2021/011967, Office Action mailed Oct. 22, 2021", with machine translation, 9 pgs.
"Mexican Application Serial No. MX/a/2021/011967, Response filed Nov. 30, 2021 to Office Action mailed Oct. 22, 2021", with machine translation, 9 pgs.
"Singapore Application Serial No. 11202110190U, Search Report and Written Opinion mailed Sep. 22, 2023", 8 pgs.
"Singapore Application Serial No. 11202110191X, Search Report and Written Opinion mailed Sep. 22, 2023", 10 pgs.
U.S. Appl. No. 18/611,965, filed Mar. 21, 2024, Forceps Including Actuation Limiting.
"U.S Appl. No. 16/830,122, Notice of Allowance mailed May 22, 2024", 11 pgs.
"U.S Appl. No. 16/830,125, Response filed May 23, 2024 to Non Final Office Action mailed Feb. 26, 2024", 9 pgs.

(56) References Cited

OTHER PUBLICATIONS

"U.S Appl. No. 16/830,122, Supplemental Notice of Allowability mailed Jun. 5, 2024", 2 pgs.
"U.S Appl. No. 18/307,111, Response filed Jun. 26, 2024 to Non Final Office Action mailed Mar. 27, 2024", 8 pgs.
"U.S Appl. No. 17/820,953, Non Final Office Action mailed Jul. 2, 2024", 21 pgs.
"Japanese Application Serial No. 2021-558624, Examiners Decision of Final Refusal mailed Nov. 28, 2023", w English Translation, 6 pgs.
"U.S Appl. No. 16/830,122, Final Office Action mailed Dec. 6, 2023", 15 pgs.
"U.S Appl. No. 16/830,125, Response filed Dec. 12, 2023 to Final Office Action mailed Sep. 12, 2023", 11 pgs.
"U.S Appl. No. 16/830,079, Corrected Notice of Allowability mailed Dec. 20, 2023", 3 pgs.
"U.S Appl. No. 16/830,162, Notice of Allowance mailed Dec. 28, 2023", 7 pgs.
"U.S Appl. No. 16/830,150, Corrected Notice of Allowability mailed Jan. 11, 2024", 2 pgs.
"U.S Appl. No. 16/830,162, Corrected Notice of Allowability mailed Jan. 12, 2024", 2 pgs.
"U.S Appl. No. 16/830,163, Response filed Jan. 16, 2024 to Final Office Action mailed Nov. 16, 2023", 7 pgs.
"Japanese Application Serial No. 2021-558621, Response filed Jan. 17, 2024 to Final Notification of Reasons for Refusal mailed Oct. 24, 2023", w English Claims, 6 pgs.
"Dominican Republic Application Serial No. P2021-0204, Office Action mailed Oct. 26, 2023", with machine translation, 15 pgs.
"Dominican Republic Application Serial No. P2021-0203, Office Action mailed Oct. 25, 2023", with machine translation, 13 pgs.
"U.S Appl. No. 16/830,163, Advisory Action mailed Jan. 31, 2024", 4 pgs.
"Chinese Application Serial No. 202080032466.3, Response filed Jan. 17, 2024 to Office Action mailed Sep. 22, 2023", w english claims, 10 pgs.
"European Application Serial No. 20720261.5, Response filed Feb. 2, 2024 to Communication Pursuant to Article 94(3) EPC mailed Sep. 28, 2023", 191 pgs.
"U.S Appl. No. 16/830,122, Response filed Feb. 6, 2024 to Final Office Action mailed Dec. 6, 2023", 6 pgs.
"U.S Appl. No. 16/830,125, Non Final Office Action mailed Feb. 26, 2024", 18 pgs.
"Singapore Application Serial No. 11202110190U, Response filed Feb. 22, 2024 to Search Report and Written Opinion mailed Sep. 22, 2023", with English claims, 11 pgs.
"Singapore Application Serial No. 11202110191X, Response filed Feb. 21, 2024 to Search Report and Written Opinion mailed Sep. 22, 2023", in English, 7 pgs.
"U.S Appl. No. 17/820,953, Final Office Action mailed Mar. 1, 2024", 15 pgs.
"Adjacent", Merriam-Webster.com Dictionary, Merriam-Webster, [Online]. Retrieved from the Internet: https: www.merriam-webster.com dictionary adjacent, (Feb. 23, 2024), 11 pgs.
"U.S Appl. No. 16/830,122, Advisory Action mailed Mar. 6, 2024", 3 pgs.
"Chamfer", Merriam-Webster.com Dictionary, Merriam-Webster, [Online]. Retrieved from the Internet: https: www.merriam-webster.com dictionary adjacent, 9 pgs.
"Bevel", Merriam-Webster.com Dictionary, Merriam-Webster, [Online]. Retrieved from the Internet: https: www.merriam-webster.com dictionary adjacent, 12 pgs.
"U.S Appl. No. 16/830,122, Examiner Interview Summary mailed Apr. 23, 2024", 2 pgs.
"U.S Appl. No. 16/830,122, Response filed May 6, 24 to Advisory Action mailed Mar. 6, 2024", 7 pgs.
"U.S Appl. No. 16/830,125, Examiner Interview Summary mailed Apr. 29, 2024", 2 pgs.
"U.S. Appl. No. 17/820,953, Advisory Action mailed Apr. 19, 2024", 3 pgs.
"U.S. Appl. No. 17/820,953, Response filed Apr. 11, 2024 to Final Office Action mailed Mar. 1, 2024", 13 pgs.
"U.S Appl. No. 18/307,111, Non Final Office Action mailed Mar. 27, 2024", 22 pgs.
"Chinese Application Serial No. 202080026544.9, Response filed Mar. 13, 2024 to Office Action mailed Oct. 31, 2023", w/ current English claims, 15 pgs.
"Chinese Application Serial No. 202080026544.9, Response to Telephone Notification filed Apr. 23, 2024", with English claims, 8 pgs.
"Chinese Application Serial No. 202080032466.3, Office Action mailed Mar. 22, 2024", w/English translation, 21 pgs.
"European Application Serial No. 20720253.2, Communication Pursuant to Article 94(3) EPC mailed Mar. 13, 2024", 5 pgs.
"Japanese Application Serial No. 2021-558621, Examiners Decision of Final Refusal mailed Apr. 9, 2024", w/English Translation, 2 pgs.
"Japanese Application Serial No. 2021-558624, Response filed Feb. 28, 2024 to Examiners Decision of Final Refusal mailed Nov. 28, 2023", w/ english claims, 8 pgs.
U.S. Appl. No. 16/830,163, filed Mar. 25, 2020, Forceps Motion Transfer Assembly.
U.S. Appl. No. 16/830,150, filed Mar. 25, 2020, Forceps Drive Shaft.
U.S. Appl. No. 18/480,971, filed Oct. 4, 2023, Forceps Drive Shaft.
U.S. Appl. No. 16/830,079, filed Mar. 25, 2020, Forceps Drive Shaft Control.
U.S. Appl. No. 16/830,175 U.S. Pat. No. 11,464,530, filed Mar. 25, 2020, Forceps Guide Plug.
U.S. Appl. No. 16/830,122, filed Mar. 25, 2020, Forceps Including Rotationally Locked Shafts.
U.S. Appl. No. 16/830,125, filed Mar. 25, 2020, Forceps Drive Systems.
U.S. Appl. No. 16/830,176 U.S. Pat. No. 11,678,899, filed Mar. 25, 2020, Forceps Actuation Systems.
U.S. Appl. No. 18/307,111, filed Apr. 26, 2023, Forceps Actuation Systems.
U.S. Appl. No. 16/830,181 U.S. Pat. No. 11,793,534, filed Mar. 25, 2020, Forceps Having Actuator Splay Control.
U.S. Appl. No. 16/830,140 U.S. Pat. No. 11,147,576, filed Mar. 25, 2020, Nested Forceps Subassemblies and Methods of Assembly.
U.S. Appl. No. 16/830,162, filed Mar. 25, 2020, Forceps Including Actuation Limiting.
U.S. Appl. No. 16/830,192 U.S. Pat. No. 11,529,159, filed Mar. 25, 2020, Forceps Jaw Flanges.
U.S. Appl. No. 16/830,199 U.S. Pat. No. 11,452,535, filed Mar. 25, 2020, Forceps Jaw Flanges.
U.S. Appl. No. 17/820,953, filed Aug. 19, 2022, Forceps Jaw Flanges.
U.S. Appl. No. 16/830,130 U.S. Pat. No. 11,730,502, filed Mar. 25, 2020, Forceps Guide Tube.
"U.S. Appl. No. 16/830,125, Notice of Allowance mailed Sep. 5, 2024", 11 pgs.
"U.S. Appl. No. 16/830,125, Supplemental Notice of Allowability mailed Oct. 3, 2024", 2 pgs.
"U.S. Appl. No. 16/830,163, Examiner Interview Summary mailed Dec. 17, 2024", 2 pgs.
"U.S. Appl. No. 16/830,163, Non Final Office Action mailed Sep. 16, 2024", 12 pgs.
"U.S. Appl. No. 16/830,163, Response filed Dec. 16, 2024 to Non Final Office Action mailed Sep. 16, 2024", 7 pgs.
"U.S. Appl. No. 17/820,953, Final Office Action mailed Dec. 13, 2024", 22 pgs.
"U.S. Appl. No. 17/820,953, Response filed Oct. 1, 2024 to Non Final Office Action mailed Jul. 2, 2024", 11 pgs.
"U.S. Appl. No. 18/307,111, Examiner Interview Summary mailed Nov. 25, 2024", 2 pgs.
"U.S. Appl. No. 18/307,111, Final Office Action mailed Oct. 4, 2024", 19 pgs.
"U.S. Appl. No. 18/307,111, Response filed Dec. 3, 2024 to Final Office Action mailed Oct. 4, 2024", 7 pgs.
"U.S. Appl. No. 18/611,965, Non Final Office Action mailed Oct. 24, 2024", 16 pgs.

(56) References Cited

OTHER PUBLICATIONS

"Australian Application Serial No. 2020253238, First Examination Report mailed Sep. 5, 2024", 4 pgs.
"Australian Application Serial No. 2020253804, First Examination Report mailed Sep. 5, 2024", 4 pgs.
"Australian Application Serial No. 2020253804, Response filed Nov. 8, 2024 to First Examination Report mailed Sep. 5, 2024", w/ claims, 12 pgs.
"Australian Application Serial No. 2020253804, Subsequent Examination Report mailed Nov. 25, 2024", 3 pgs.
"Chinese Application Serial No. 202080032466.3, Response filed Jul. 18, 2024 to Office Action mailed Mar. 22, 2024", w/ current English claims, 12 pgs.
"Costa Rica Application Serial No. 2021-0537, Office Action mailed Jul. 11, 2024", with machine translation, 2 pg.
"European Application Serial No. 20720253.2, Response filed Sep. 10, 2024 to Communication Pursuant to Article 94(3) EPC mailed Mar. 13, 2024", 5 pgs.
"Flat", Merriam-Webster.com Dictionary, [Online]. Retrieved from the Internet: <Merriam-Webster, https://www.merriam-webster.com/dictionary/flat>, (Dec. 3, 2024), 24 pgs.
"Japanese Application Serial No. 2021-558621, Response filed Aug. 2, 2024 to Examiners Decision of Final Refusal mailed Apr. 9, 2024", w/ english claims, 10 pgs.
"Korean Application Serial No. 10-2021-7035248, Notice of Preliminary Rejection mailed Oct. 10, 2024", W/English Translation, 13 pgs.
"Korean Application Serial No. 10-2021-7035249, Notice of Preliminary Rejection mailed Oct. 24, 2024", w/ English translation, 13 pgs.
"Mexican Application Serial No. MX/a/2021/011966, Office Action mailed Sep. 25, 2024", with machine translation, 5 pgs.
"Planar", Merriam-Webster.com Dictionary, [Online]. Retrieved from the Internet: <Merriam-Webster, https://www.merriam-webster.com/dictionary/planar>, (Dec. 3, 2024), 9 pgs.
U.S. Appl. No. 18/786,865, filed Jul. 29, 2024, Forceps Including Rotationally Locked Shafts.
U.S. Appl. No. 18/969,734, filed Dec. 5, 2024, Forceps Drive Systems.
"U.S. Appl. No. 18/307,111, Notice of Allowance mailed Dec. 27, 2024", 13 pgs.
"Korean Application Serial No. 10-2021-7035249, Response filed Dec. 24, 2024 to Notice of Preliminary Rejection mailed Oct. 24, 2024", w english claims, 28 pgs.
"Korean Application Serial No. 10-2021-7035248, Response filed Jan. 9, 2025 to Notice of Preliminary Rejection mailed Oct. 10, 2024", W English Claims, 24 pgs.
"U.S. Appl. No. 18/611,965, Response filed Jan. 21, 2025 to Non Final Office Action mailed Oct. 24, 2024", 8 pgs.
"Australian Application Serial No. 2020253238, Response filed Jan. 23, 2025 to First Examination Report mailed Sep. 5, 2024", 13 pgs.
"U.S. Appl. No. 17/820,953, Examiner Interview Summary mailed Feb. 11, 2025", 2 pgs.
"U.S. Appl. No. 17/820,953, Response filed Feb. 13, 2025 to Final Office Action mailed Dec. 13, 2024", 11 pgs.
"U.S. Appl. No. 17/820,953, Advisory Action mailed Feb. 25, 2025", 3 pgs.
"Australian Application Serial No. 2020253804, Response filed Feb. 6, 2025 to Subsequent Examination Report mailed Nov. 25, 2024", 4 pgs.
"U.S. Appl. No. 18/307,111, PTO Response to Rule 312 Communication mailed Mar. 6, 2025", 2 pgs.

\* cited by examiner

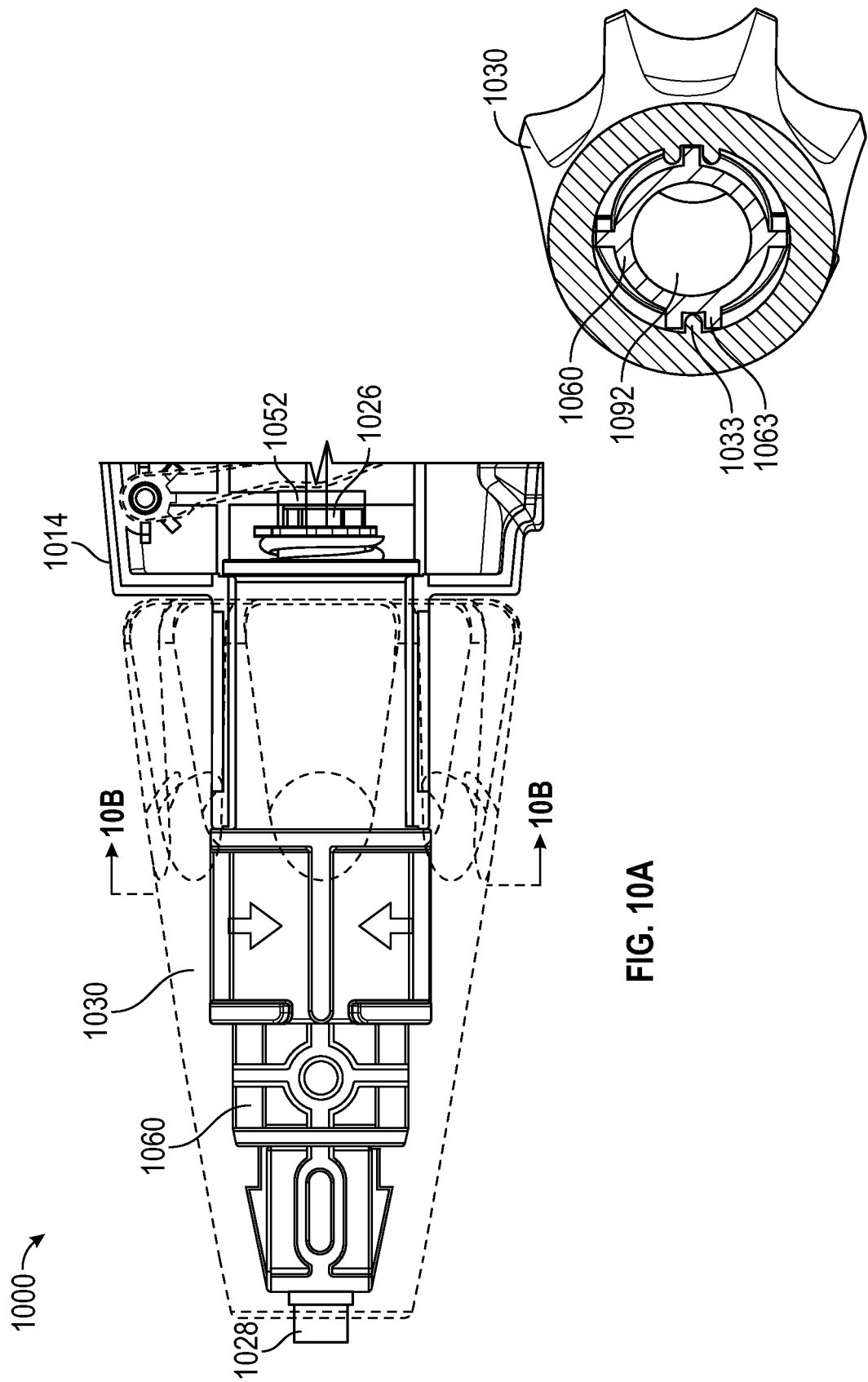

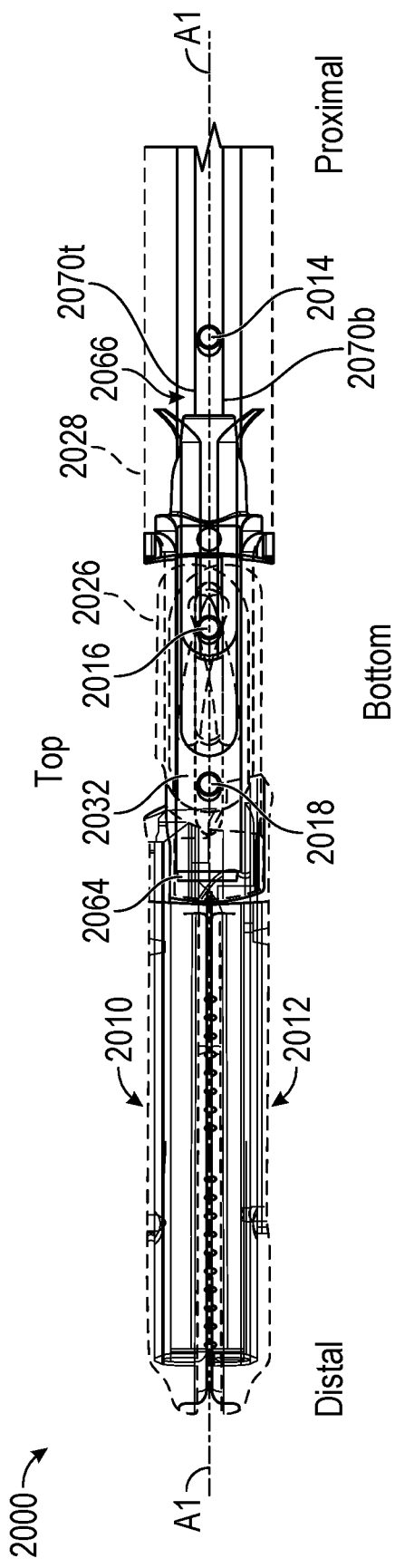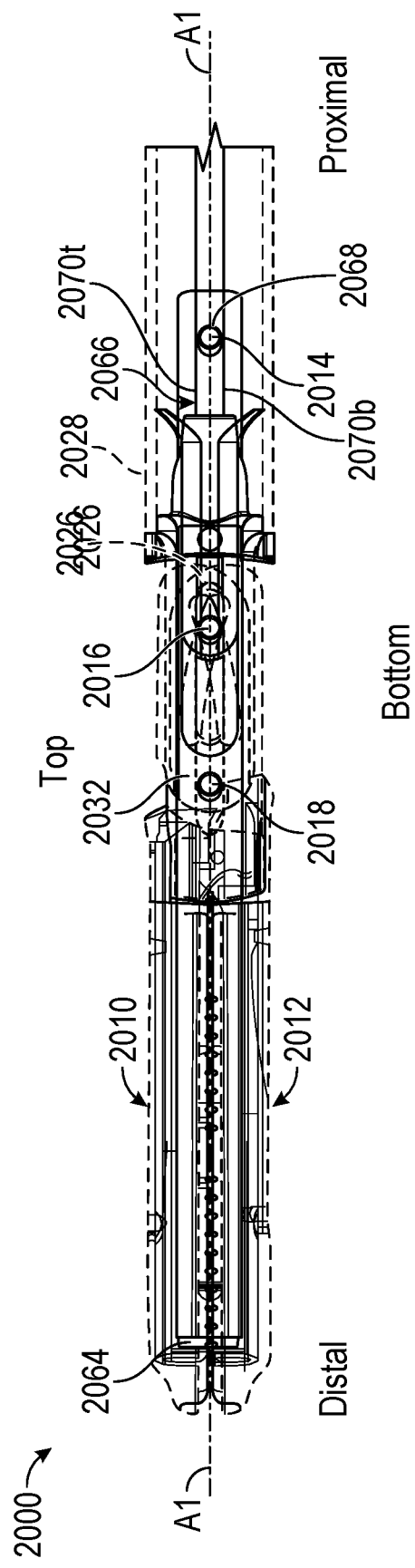
FIG. 26A
FIG. 26B

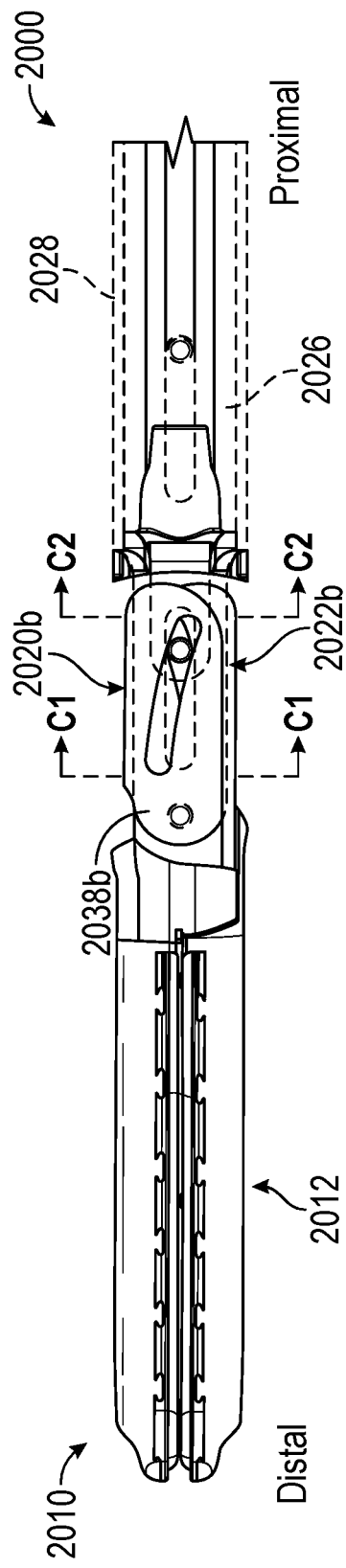
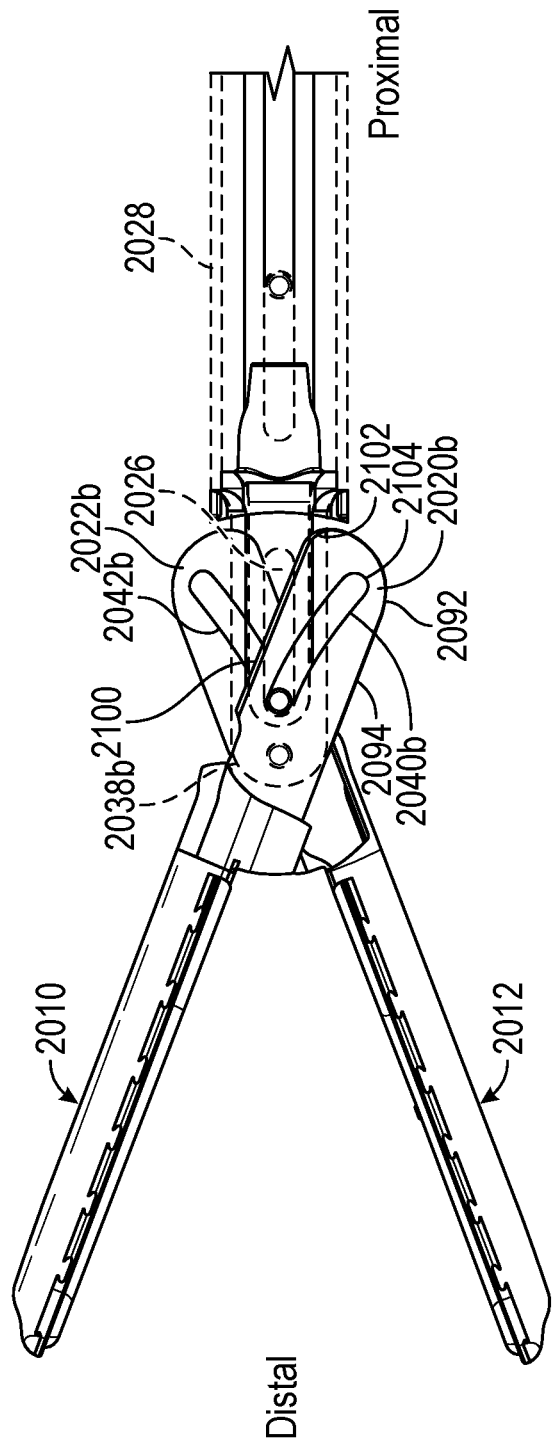
FIG. 42
FIG. 43

FORCEPS HAVING ACTUATOR SPLAY CONTROL

PRIORITY CLAIM

This application is a Continuation of U.S. patent application Ser. No. 16/830,181, filed Mar. 25, 2020, entitled "FORCEPS HAVING ACTUATOR SPLAY CONTROL," which claims priority to U.S. Ser. No. 62/826,532, filed on Mar. 29, 2019, entitled "BLADE ASSEMBLY FOR FORCEPS", U.S. Ser. No. 62/826,522 filed on Mar. 29, 2019, entitled "SLIDER ASSEMBLY FOR FORCEPS," U.S. Ser. No. 62/841,476, filed on May 1, 2019, entitled "FORCEPS WITH CAMMING JAWS", and U.S. Ser. No. 62/994,220, filed on Mar. 24, 2020, entitled "FORCEPS DEVICES AND METHODS", the disclosures of which are incorporated by reference in their entireties.

TECHNICAL FIELD

This document pertains generally, but not by way of limitation, to systems and methods for actuating end effectors of medical devices. In particular, the systems and methods can be used with a forceps having an actuatable jaw and/or a blade.

BACKGROUND

Medical devices for diagnosis and treatment, including but not limited to forceps, are used for medical procedures such as laparoscopic and open surgeries. Forceps can be used to manipulate, engage, grasp, or otherwise affect an anatomical feature, such as a vessel or other tissue. Such medical devices can include an end effector that is one or more of: rotatable, openable, closeable, extendable, retractable and capable of supplying an input such as electromagnetic energy or ultrasound.

For example, jaws located at a distal end of a forceps are typically actuated via elements at a handpiece of the forceps to cause the jaws to open and close and thereby engage the vessel or other tissue. Forceps may also include an extendable and retractable blade, such as blades that can be extended distally between a pair of jaws.

There is a need for improved medical devices, including forceps. Aspects described herein provide a variety of improvements over conventional forceps and other medical devices having a handpiece including an actuation system that controls an end effector.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIG. 10A illustrates a side view of a portion of the forceps of FIG. 1A with a rotational actuator in phantom.

FIG. 10B is cross-sectional view of the rotational actuator and an outer hub shown in FIG. 10A along line 10B-10B' with the rotational actuator shown in solid.

FIG. 26A illustrates a side view of a portion of a forceps with an inner shaft and an outer shaft shown in phantom with a blade retracted.

FIG. 26B illustrates a side view of a portion of a forceps with an inner shaft and an outer shaft shown in phantom with a blade extended.

FIG. 42 illustrates a side view of a portion of a forceps with an inner shaft and an outer shaft shown in phantom.

FIG. 43 illustrates a side view of a portion of a forceps with an inner shaft and an outer shaft shown in phantom.

DETAILED DESCRIPTION

A medical device including a handpiece that operates an end effector allows a surgeon to control the end effector of the device to actuate one or more functions of the end effector. Actuation of the end effector can be facilitated by one or more actuation systems of the handpiece that can retract, extend or rotate one or more shafts to control the actions of the end effector.

The present inventors have recognized, among other things, that conventional medical devices including a handpiece that actuates an end effector can be improved to reduce packaging space, simplify design and manufacturing, improve a user's experience, increase stability and prevent damage to the forceps.

This disclosure is generally related to medical devices, such as surgical instruments. Although the present application is described with reference to a forceps, other end effectors can be used with and operated by the handpiece described herein. In addition, other handpieces can be connected to and can control the end effectors described herein. This disclosure includes examples of handpieces including one or more actuation systems, examples of end effectors, and examples where the disclosed actuation systems and end effectors can be used together in a medical device.

The forceps can include a medical forceps, a cutting forceps, an electrosurgical forceps, or any other type of forceps. The forceps can include an end effector that is controlled by a handpiece including an actuation system to be one or more of: rotatable, openable, closeable, extendable, and capable of supplying electromagnetic energy or ultrasound. For example, jaws located at a distal end of the forceps can be actuated via one or more actuators at a handpiece of the forceps to cause the jaws to open, close and rotate to engage a vessel or other tissue. Forceps may also include an extendable and retractable blade, such as blades that can be extended distally in between a pair of jaws to separate a first tissue from a second tissue.

Figure 1A:
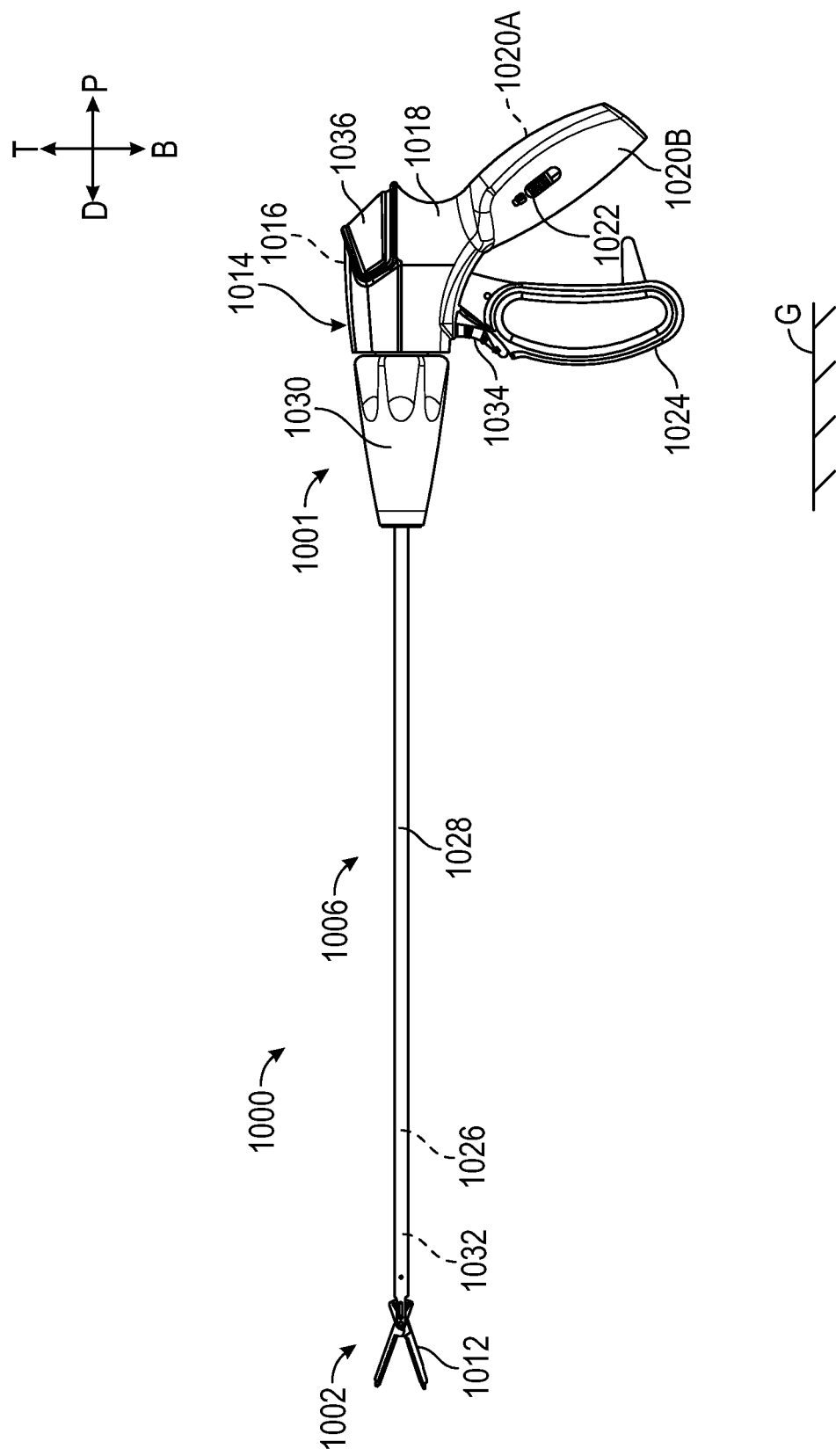
FIG. 1A illustrates a side view of a forceps showing jaws in an open position.
Figure 1B:
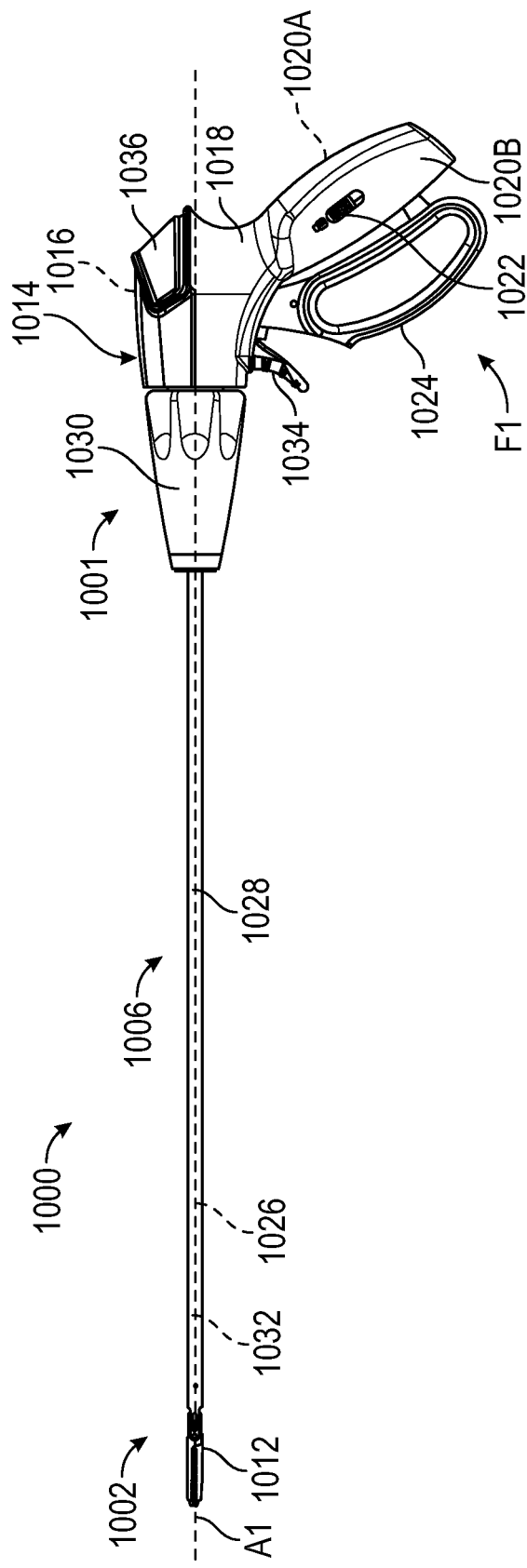
FIG. 1B illustrates a side view of the forceps of FIG. 1A showing the jaws in a closed position.
Figure 2:
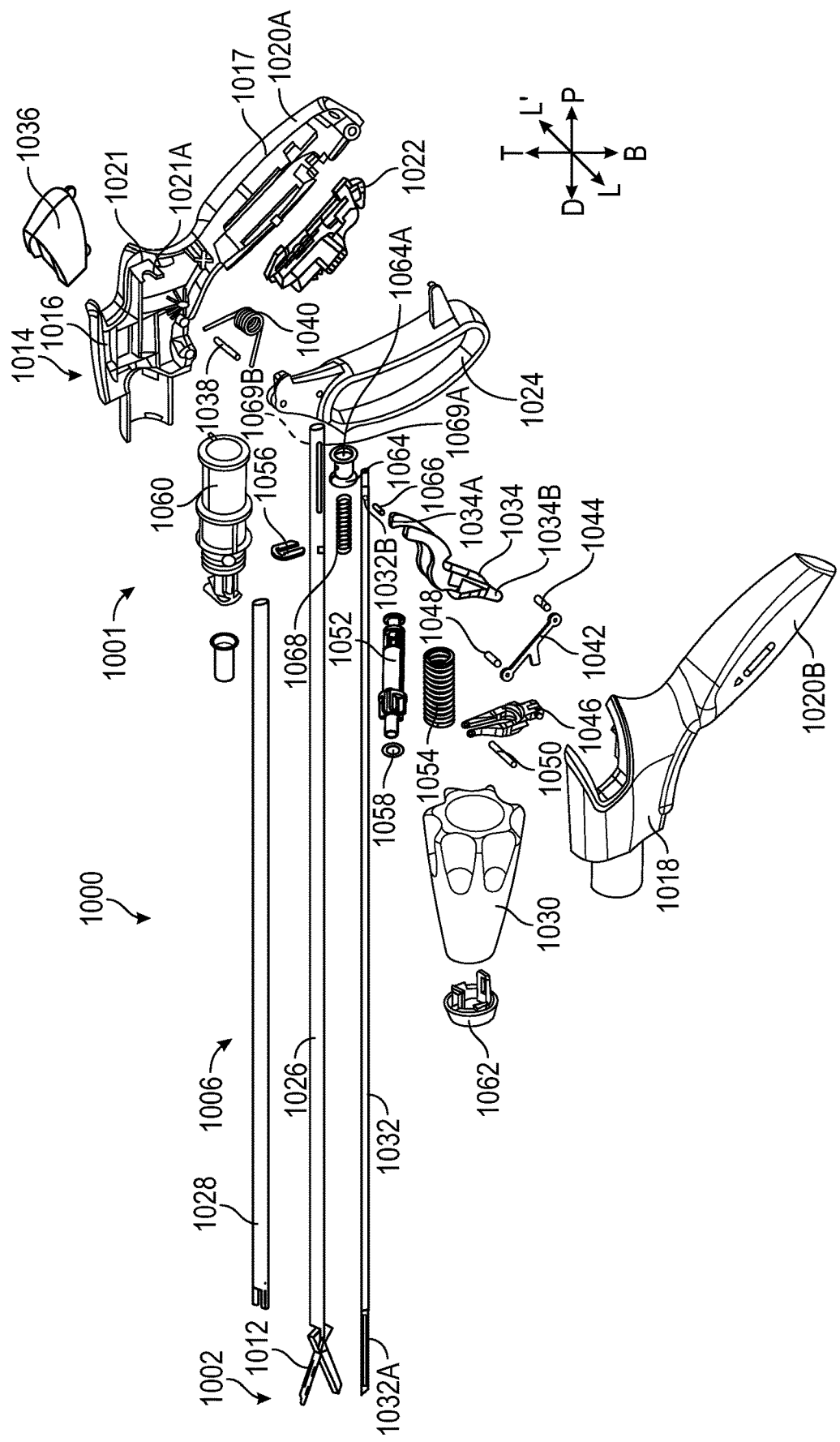
FIG. 2 illustrates an exploded view of some components of the forceps of FIG. 1A.

FIG. 1A illustrates a side view of a forceps 1000 with jaws 1012 in an open position. FIG. 1B illustrates a side view of the forceps 1000 with the jaws 1012 in a closed position. FIG. 2 illustrates an exploded view of some components of the forceps 1000 of FIG. 1A. FIGS. 1A, 1B and 2 are described together. Directional descriptors such as proximal and distal are used within their ordinary meaning in the art. The proximal direction P and distal direction D are indicated on the axes provided in FIG. 1A and FIG. 2. FIG. 2 also shows the lateral directions L and L', as well as top T and bottom B directions, which are defined when the forceps 1000 is held level with respect to a ground G in an upright orientation as shown in FIG. 1A. Opposite to the lateral directions L and L', is the medial direction, in other words, the medial direction is towards the centerline, or a longitudinal axis of the forceps 1000 (FIG. 1B).

The illustrative forceps 1000 can include a handpiece 1001 at a proximal end, and an end effector 1002 at a distal end. An intermediate portion 1006 can extend between the handpiece 1001 and the end effector 1002 to operably couple the handpiece 1001 to the end effector 1002. Various movements of the end effector 1002 can be controlled by one or more actuation systems of the handpiece 1001. In the illustrative example, the end effector 1002 can include the jaws 1012 that are capable of opening and closing. The end effector 1002 can be rotated along a longitudinal axis A1 (FIG. 1B) of the forceps 1000. The end effector 1002 can include a cutting blade 1032A (FIG. 2) and an electrode for applying electromagnetic energy. All actuation system functions and all end effector actions are not required in all examples. The functions described herein can be provided in any combination.

An overview of features of the forceps 1000 is provided in FIGS. 1A, 1B, 2, 3A-3E and 4A-4C. Further detailed illustration of example motion transfer assemblies is provided in FIGS. 5A, 5B, 6A, 6B, 7A, 7B, 8A and 8B. The illustrated motion transfer assemblies provide transmission of forces received from a user via clamping and rotational actuators (e.g., a lever 1024 and a rotational actuator 1030), to the jaws 1012 of the forceps 1000 to actuate clamping and rotation of the jaws 1012.

As shown broadly in FIGS. 1A and 1B, with support from FIG. 2, the forceps 1000 can include the jaws 1012, a housing 1014, a lever 1024, a drive shaft 1026, an outer shaft 1028, a rotational actuator 1030, a blade assembly (a blade shaft 1032 and a blade 1032A of FIG. 2), a trigger 1034 and an activation button 1036. In this example, the end effector 1002, or a portion of the end effector 1002 can be one or more of: opened, closed, rotated, extended, retracted, and electromagnetically energized (e.g., electrically energized). In some examples, the energy can be radio-frequency energy.

To operate the end effector 1002, the user can displace the lever 1024 proximally by applying Force F1 (FIG. 1B) to drive the jaws 1012 from the open position (FIG. 1A) to the closed position (FIG. 1B). In the example of forceps 1000, moving the jaws 1012 from the open position to the closed position allows a user to clamp down on and compress a tissue. The handpiece 1001 can also allow a user to rotate the end effector 1002. For example, rotating rotational actuator 1030 causes the end effector 1002 to rotate by rotating both the drive shaft 1026 and the outer shaft 1028 together.

In some examples, with the tissue compressed between the jaws 1012, a user can depress the activation button 1036 to cause an electromagnetic energy, or in some examples, ultrasound, to be delivered to the end effector 1002, such as to an electrode. Application of electromagnetic energy can be used to seal or otherwise affect the tissue being clamped. In some examples, the electromagnetic energy can cause tissue to be coagulated, cauterized, sealed, ablated, desiccated or can cause controlled necrosis. Example electrodes are described herein, but electromagnetic energy can be applied to any suitable electrode.

The handpiece 1001 can enable a user to extend and retract a blade 1032A attached to a distal end of a blade shaft 1032 (FIG. 2). The blade 1032A can be extended by displacing the trigger 1034 proximally. The blade 1032A can be retracted by allowing the trigger 1034 to return distally to a default position. The default position of the trigger 1034 is shown in FIG. 1A. In some examples, as described herein, the handpiece 1001 can include features that inhibit the blade 1032A from being extended until the jaws 1012 are at least partially closed, or fully closed.

The forceps 1000 can be used to perform a treatment on a patient, such as a surgical procedure. In an example, a distal portion of the forceps 1000, including the jaws 1012, can be inserted into a body of a patient, such as through an incision or another anatomical feature of the patient's body. While a proximal portion of the forceps 1000, including housing 1014 remains outside the incision or another anatomical feature of the body. Actuation of the lever 1024 causes the jaws 1012 to clamp onto a tissue. The rotational actuator 1030 can be rotated via a user input to rotate the jaws 1012 for maneuvering the jaws 1012 at any time during the procedure. Activation button 1036 can be actuated to provide electrical energy to jaws 1012 to coagulate, cauterize or seal the tissue within the closed jaws 1012. Trigger 1034 can be moved to translate the blade 1032A distally to cut the tissue within the jaws 1012.

In some examples, the forceps 1000, or other medical device, may not include all the features described or may include additional features and functions, and the operations may be performed in any order. The handpiece 1001 can be used with a variety of other end effectors to perform other methods.

As shown in the combination of FIG. 1A, FIG. 1B and FIG. 2, the forceps 1000 can include various components. For example, a first housing portion 1016 and a second housing portion 1018. As shown in FIG. 2, the first housing portion 1016 and the second housing portion 1018 can mate at a coupling joint 1017. The housing 1014 can include, or be coupled to, a handle portion 1020A and 1020B, such as a fixed handle that is configured to be held in the hand of a user during use.

The housing 1014 can be a frame that provides structural support between components of the forceps 1000. The housing 1014 is shown as housing at least a portion of the actuation systems associated with the handpiece 1001 for actuating the end effector 1002. However, some or all of the actuation components need not necessarily be housed within the housing 1014. Components described herein may be completely housed within the housing 1014 through all or a portion of the range of motion of the components of the actuation system; partially housed through all or a portion of the range of motion of the components of the actuation system; or completely external to the housing 1014 during all or a portion of the range of motion of the components of the actuation system associated with the handpiece 1001. In some examples, the housing 1014 provides a rigid structure for attachment of components, but the housing 1014 does not necessarily house the components completely, or only houses a portion of some of the components.

With continued reference to FIG. 1A, FIG. 1B and FIG. 2, the drive shaft 1026 can extend through the housing 1014 and out of a distal end of the housing 1014, or distally beyond housing 1014. The jaws 1012 can be connected to a distal end of the drive shaft 1026. The outer shaft 1028 can be a hollow tube positioned around the drive shaft 1026. A distal end of the outer shaft 1028 can be located adjacent the jaws 1012 and the jaws 1012 can be connected to the outer shaft 1028. The distal ends of the drive shaft 1026 and the outer shaft 1028 can be rotationally locked (e.g., rotationally constrained) to the jaws 1012. The rotational actuator 1030 can be positioned around the distal end of the housing 1014. In the illustrative example, the rotational actuator 1030 is indirectly connected to a proximal end of the outer shaft 1028 by an outer hub 1060, however, in some examples the rotational actuator 1030 can be directly connected to the proximal end of the outer shaft 1028 or can integrally include the features of the outer hub 1060. In some examples, various rotational constraints described herein can be employed independently. In other words, some examples can employ a single rotational constraint between the rotational actuator 1030 and the jaws 1012, while in other examples, the rotational constraint can include multiple rotational constraints at different locations along the longitudinal axis A1, such as a first rotational constraint proximate or within the handpiece 1001, and a second rotational constraint proximate the end effector 1002 and distal of the handpiece 1001, as described further in various examples herein.

The outer shaft 1028 can extend distally beyond the rotational actuator 1030. The blade shaft 1032 can extend through the drive shaft 1026 and the outer shaft 1028. A distal end of the blade shaft 1032 including the blade 1032A can be located adjacent to the jaws 1012. A proximal end of the blade shaft 1032 can be within the housing 1014.

A proximal portion 1034A (FIG. 2) of the trigger 1034 can be connected to the blade shaft 1032 within the housing 1014. A distal portion 1034B (FIG. 2) of the trigger 1034 can extend outside of the housing 1014 adjacent, and in some examples, nested with the lever 1024 in the default or unactuated positions shown in FIG. 1A. Activation button 1036 can be coupled to the housing 1014. Activation button 1036 can actuate electronic circuitry within housing 1014 that can send electromagnetic energy through forceps 1000 to the jaws 1012. When the user presses on the activation button 1036, the activation button 1036 can move relative to the housing 1014. For example, when the activation button 1036 is pressed, an electrical switch on a flexible printed circuit board that is secured to the housing 1014 can be closed. Wiring and electrical components such as a dome switch that can be actuated by the activation button 1036, are further shown in FIG. 19. In some examples, the activation button 1036 or the electronic circuitry may reside outside the housing 1014 but may be operably coupled to the housing 1014 and the end effector 1002. In some examples, activation of the forceps 1000 can be accomplished by a foot or knee actuated switch.

As shown in the exploded view of a portion of the forceps 1000 in FIG. 2, the forceps 1000 can include the handpiece 1001 having components for an actuation system, the end effector 1002, the intermediate portion 1006, the jaws 1012, the housing 1014 (including the first housing portion 1016, the second housing portion 1018, the handle portion 1020A and 1020B, the stabilizing flange 1021, and a recess or opening 1021A), the handle locking mechanism 1022, the lever 1024, the drive shaft 1026 (including the first horizontal slot 1069A and the second horizontal slot 1069B, the outer shaft 1028, the rotational actuator 1030, the blade shaft 1032, the blade 1032A the trigger 1034, and the activation button 1036, a first pin 1038, a lever return spring 1040, a coupling link 1042, a second pin 1044, a drive link 1046, a third pin 1048, a fourth pin 1050, a drive shaft motion transfer body 1052 (hereinafter, drive body 1052 or slider block), a force-limiting spring 1054, a clip 1056, an O-ring 1058, an outer hub 1060, a nose 1062, a spool 1064 (e.g., cut block or second drive shaft motion transfer body), a cross pin 1066 (e.g., a blade pin), and a trigger return spring 1068. The handle locking mechanism 1022 can be, for example, of the type described in U.S. patent application Ser. No. 15/941,205 to Boone, titled "Forceps Including a Pre-loaded Handle Latch" filed on Mar. 30, 2018, the disclosure of which is incorporated by reference in its entirety. Furthermore, the components which make up the actuation system can be, for example, of the type described in U.S. patent application Ser. No. 15/839,218 to Butler titled "Laparoscopic Forceps Assembly with An Operable Mechanism" filed on Dec. 12, 2017, the disclosure of which is incorporated by reference in its entirety.

As a general overview of the component interaction of the handpiece 1001 of the forceps 1000, the forceps 1000 can include the drive body 1052 being constrained to the drive shaft 1026 to transfer motion to the drive shaft 1026, thereby operating the jaws 1012. However, in a force limiting state (e.g., position), the drive body 1052 can be slidable with respect to the drive shaft 1026. Thus, the forceps 1000 can be configured to limit a force on the jaws 1012 to protect the jaws 1012 from damage when the lever 1024 is being closed with the jaws 1012 stuck in an open or partially open position. An example of the jaws 1012 stuck in such a position is shown in FIG. 13C.

As further shown and described here and elsewhere in the disclosure, the drive body 1052 along with the clip 1056 can lock the drive shaft 1026 to the rotational actuator 1030 such that the drive shaft 1026 and the outer shaft 1028 are rotationally locked (e.g., rotationally constrained) together at a proximal portion of the drive shaft 1026 and the outer shaft 1028 proximate the rotational actuator 1030. Further, the forceps 1000 can include the trigger 1034, the spool 1064 proximal to the drive body 1052 and connected to the trigger 1034, and a trigger return spring 1068 positioned between the drive body 1052 and the spool 1064 to bias the blade shaft 1032 with blade 1032A proximally but allow movement of the blade 1032A distally to perform a cut, while improving the design of the forceps.

FIGS. 3A, 3B, 3C, 3D and 3E focus on the clamping and rotational aspects of the forceps and will be described together with support from FIGS. 1A, 1B and 2. Many of these components are introduced here, but also shown and described in further detail in other figures herein. Some components related to the cutting functions of the forceps of FIG. 1A are absent in FIGS. 3A, 3B and 3C to provide better visibility of other components. While FIGS. 3A, 3B, 3C, 3D and 3E illustrate components that make up the actuation system of the handpiece 1001, the function and interrelationship of the components are described throughout this disclosure.

Figure 3A:
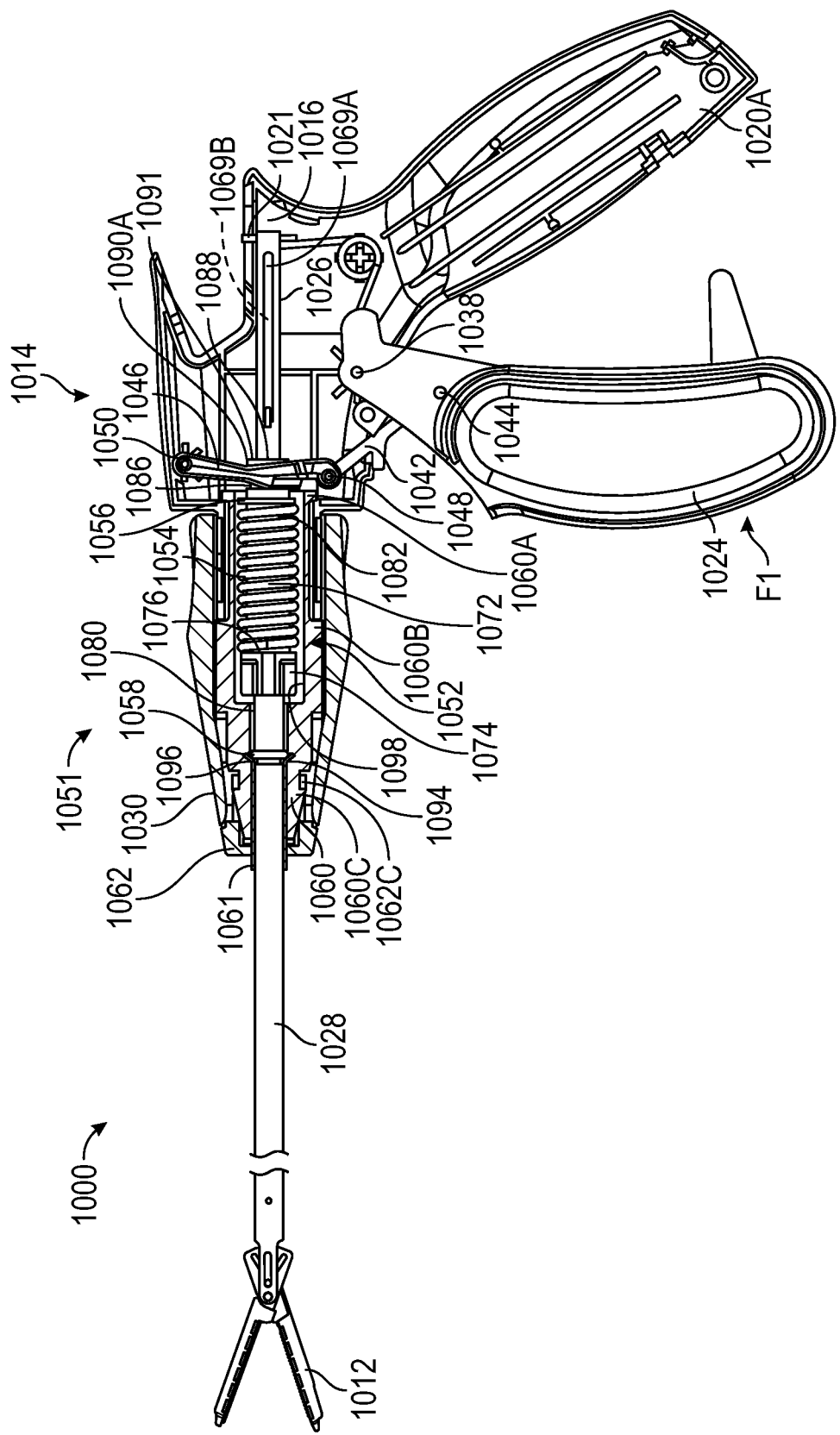
FIG. 3A illustrates a first partial cross-section view of a portion of the forceps of FIG. 1A.
Figure 3B:
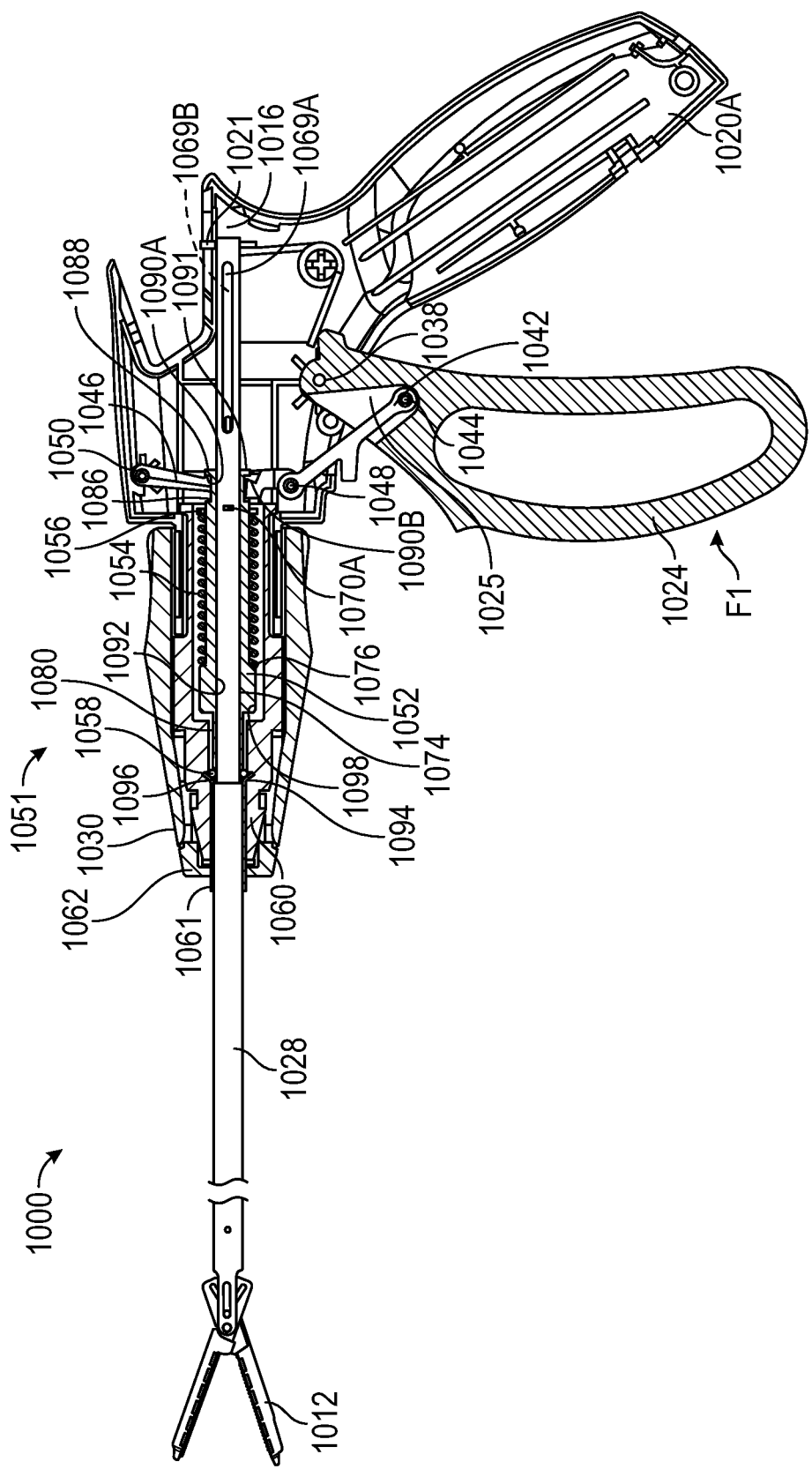
FIG. 3B illustrates a second partial cross-section view of a portion of the forceps of FIG. 1A.
Figure 3C:
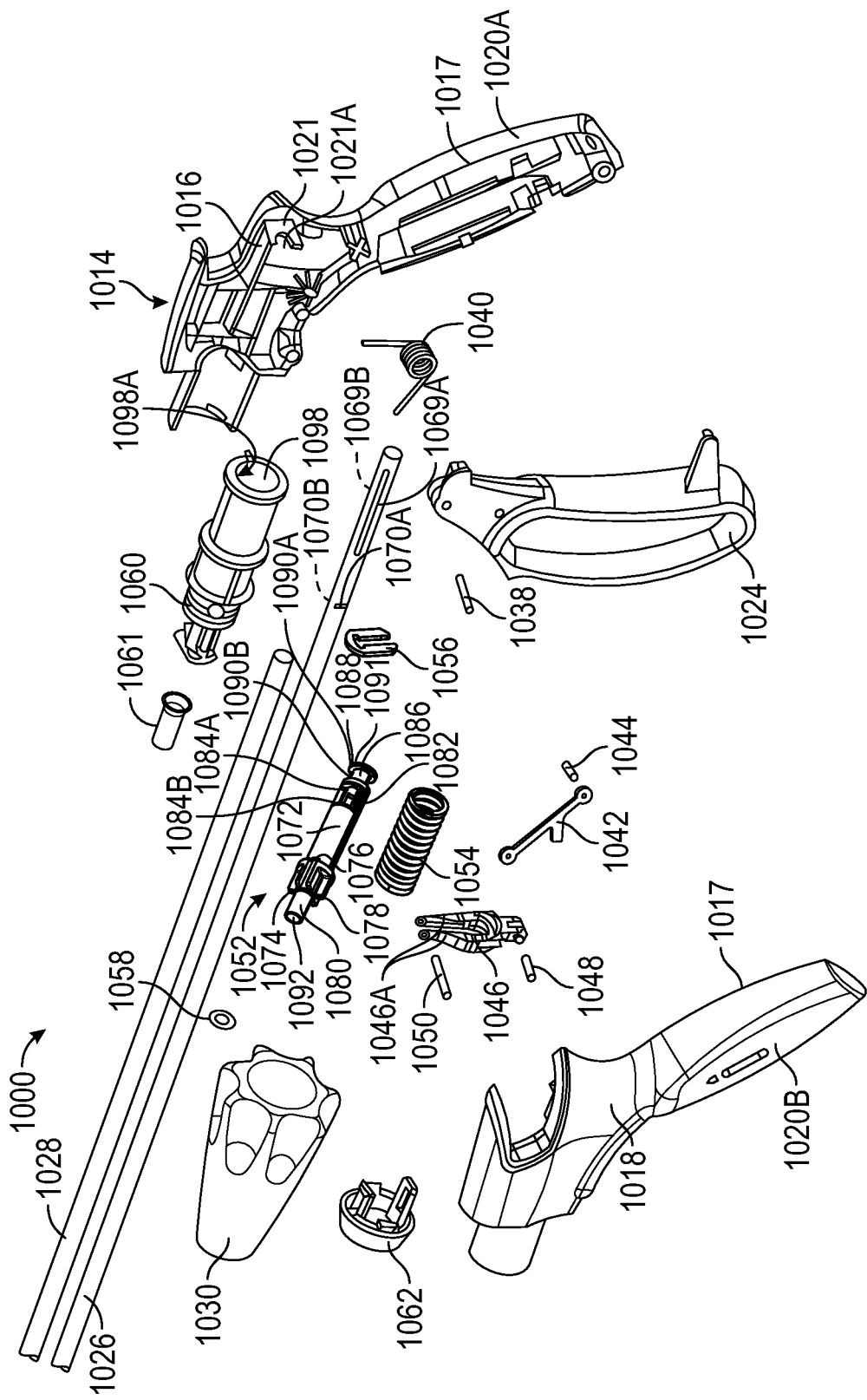
FIG. 3C illustrates a close-up exploded view of a portion of the forceps of FIG. 1A.
Figure 3D:
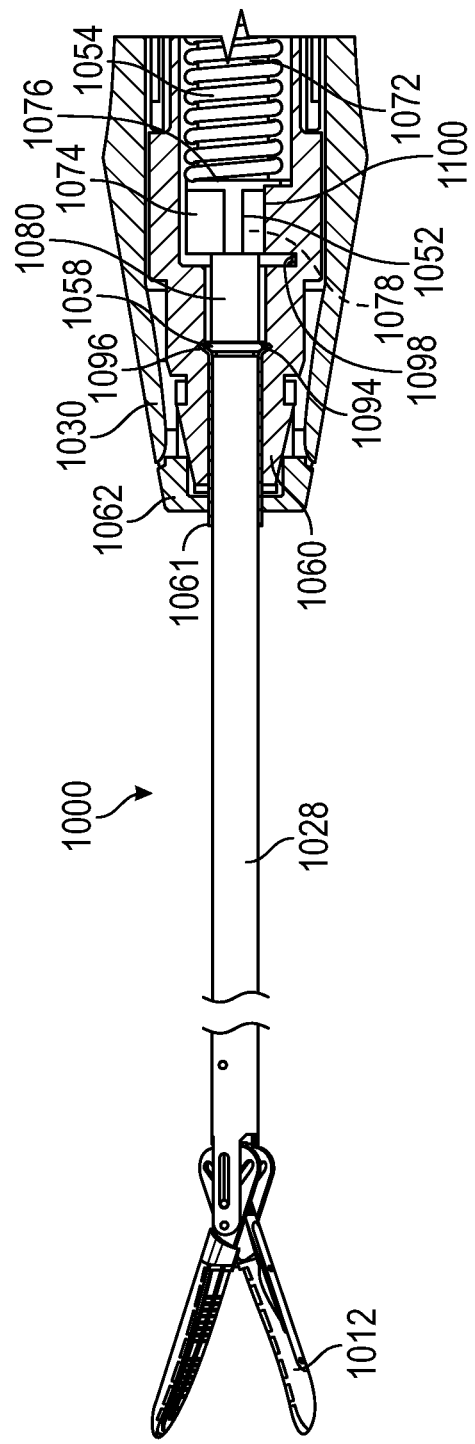
FIG. 3D illustrates a third partial cross-section view of the forceps of FIG. 3A showing a drive shaft motion transfer body in a rotated position.
Figure 3E:
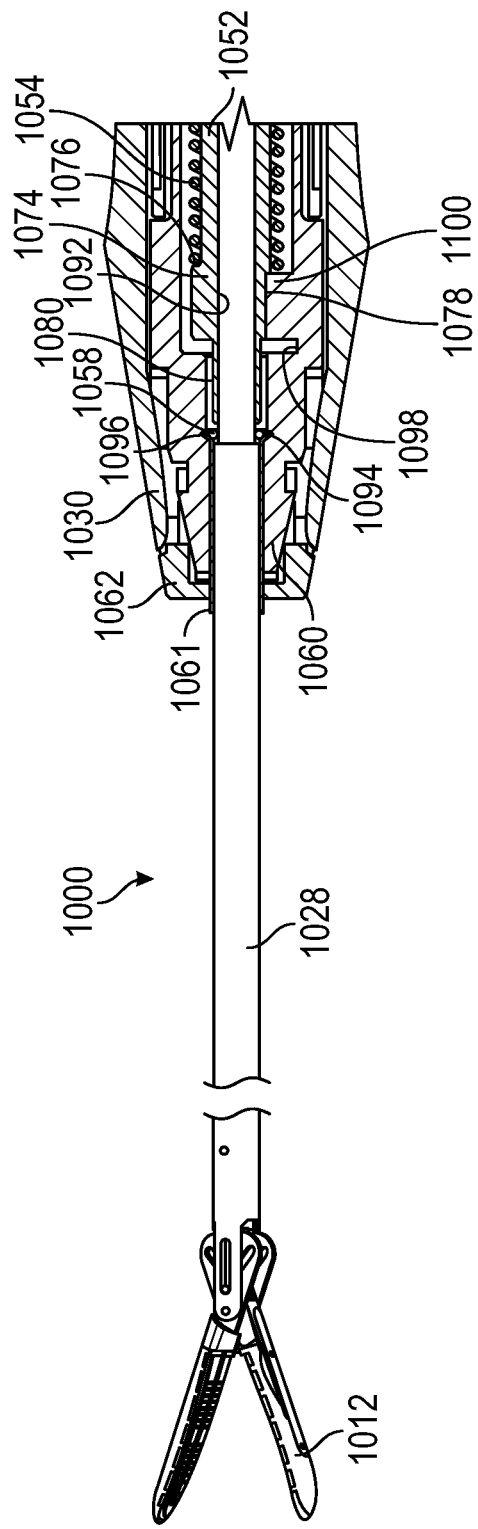
FIG. 3E illustrates a fourth partial cross-section view of the forceps of FIG. 3A showing the drive shaft motion transfer body in the rotated position of FIG. 3D.

FIG. 3A illustrates a first partial cross-section view of a portion of the forceps 1000 of FIG. 1A, FIG. 1B and FIG. 2, in accordance with at least one example. The lever 1024, the drive shaft 1026, the drive body 1052, the force-limiting spring 1054, the clip 1056, the O-ring 1058 and the outer shaft 1028 are not shown in cross section. FIG. 3B illustrates a second partial cross-section view of a portion of the forceps 1000, in accordance with at least one example. The drive shaft 1026 and the outer shaft 1028 are not shown in cross-section. FIG. 3C illustrates a close-up exploded view of a portion of the forceps 1000 of FIG. 1A, in accordance with at least one example. FIG. 3D illustrates a third partial cross-section view of the forceps 1000 of FIG. 3A showing the drive body 1052 in a rotated position, in accordance with at least one example. The drive body 1052, the force-limiting spring 1054, the O-ring 1058, and the outer shaft 1028 are not shown in cross-section. FIG. 3E illustrates a fourth partial cross-section view of the forceps 1000 of FIG. 3A showing the drive body 1052 in the rotated position of FIG. 3D, in accordance with at least one example. The outer shaft 1028 is not shown in cross section.

FIGS. 3A, 3B, 3C, 3D and 3E, described together with most components shown in the exploded view of FIG. 3C, include the housing 1014 (including the first housing portion 1016, the handle portion 1020A, and stabilizing flange 1021), the lever 1024, the first pin 1038, the drive shaft 1026, the lever return spring 1040, the coupling link 1042 can reside within a lever recess 1025, the second pin 1044, the drive link 1046, the third pin 1048, the fourth pin 1050, a drive motion transfer assembly 1051, the drive body 1052, the force-limiting spring 1054, the clip 1056, the O-ring 1058, the outer shaft 1028, the outer hub 1060, a sleeve 1061, the rotational actuator 1030, and the nose 1062. The drive shaft 1026 includes the first horizontal slot 1069A, the second horizontal slot 1069B, a first vertical slot 1070A, and a second vertical slot 1070B, which can be an opening extending through the drive shaft 1026, or a recess or deformation in the drive shaft 1026. The drive body 1052 (shown in further detail in other drawings herein as well) can include a body portion 1072, an anchor portion 1074 (including a distal spring seat 1076 and a rotational keying slot 1078), a cylindrical portion 1080, a window portion 1082 (including a first window 1084A and a second window 1084B, see FIG. 3C), a neck portion 1086, a collar 1088 (such as proximal collar 1088 including a drive surface 1090A and a second distal spring seat 1091, see FIGS. 3B and 3C, as well as FIG. 5A for a close-up view), and a passageway 1092 (e.g. a channel, a bore, a recess, or an aperture extending therethrough). The sleeve 1061 can include a flange 1094. In some examples, such as an example where the sleeve 1061 is omitted, the outer shaft 1028 can include the flange 1094. The outer hub 1060 can include groove 1096, interior surface 1098, and the anti-rotation key 1100 (FIGS. 3D and 3E).

The first and second horizontal slots 1069A, 1069B can extend longitudinally along the drive shaft 1026, in an axial direction, parallel to longitudinal axis A1 (FIG. 1B). In other words, the first and second horizontal slots 1069A, 1069B can be described as extending horizontally when the drive shaft 1026 is held level. In some examples, the first and second vertical slots 1070A may extend along or within a plane perpendicular to the longitudinal axis A1.

The drive shaft 1026 can include the first vertical slot 1070A on a first side and the second vertical slot 1070B on a second side (FIG. 3B, 3C, further shown and described in FIGS. 5A-5C and 6A-6C). The vertical slots 1070A and 1070B can be perpendicular to the longitudinal axis A1 (FIG. 1B) of drive shaft 1026. The first vertical slot 1070A and second vertical slot 1070B can extend into the drive shaft 1026 from an exterior surface of the drive shaft 1026. The first vertical slot 1070A and the second vertical slot 1070B can be sized to accept the clip 1056. In some examples, the clip 1056 can be ridged and can be accepted onto the drive shaft 1026 without distorting the shape of the clip 1056. In some examples, the drive shaft 1026 can have a single vertical slot 1070A or 1070B. The first and second vertical slots 1070A, 1070B can be provided as an opening/aperture or as a deformation with or without an opening through the drive shaft 1026.

As shown in the combination of FIGS. 3A-3E, and in close-up views of FIGS. 5A-5C and 6A-6C, the drive body 1052 can include the body portion 1072 and the anchor portion 1074 connected, or integrally formed, at distal end of the body portion 1072. The anchor portion 1074 can extend outwardly from an outer surface of body portion 1072. As such, the anchor portion 1074 can include the distal spring seat 1076 at a proximal end surface of the anchor portion 1074. The distal spring seat 1076 can be connected to a distal end of the body portion 1072.

Figure 5A:
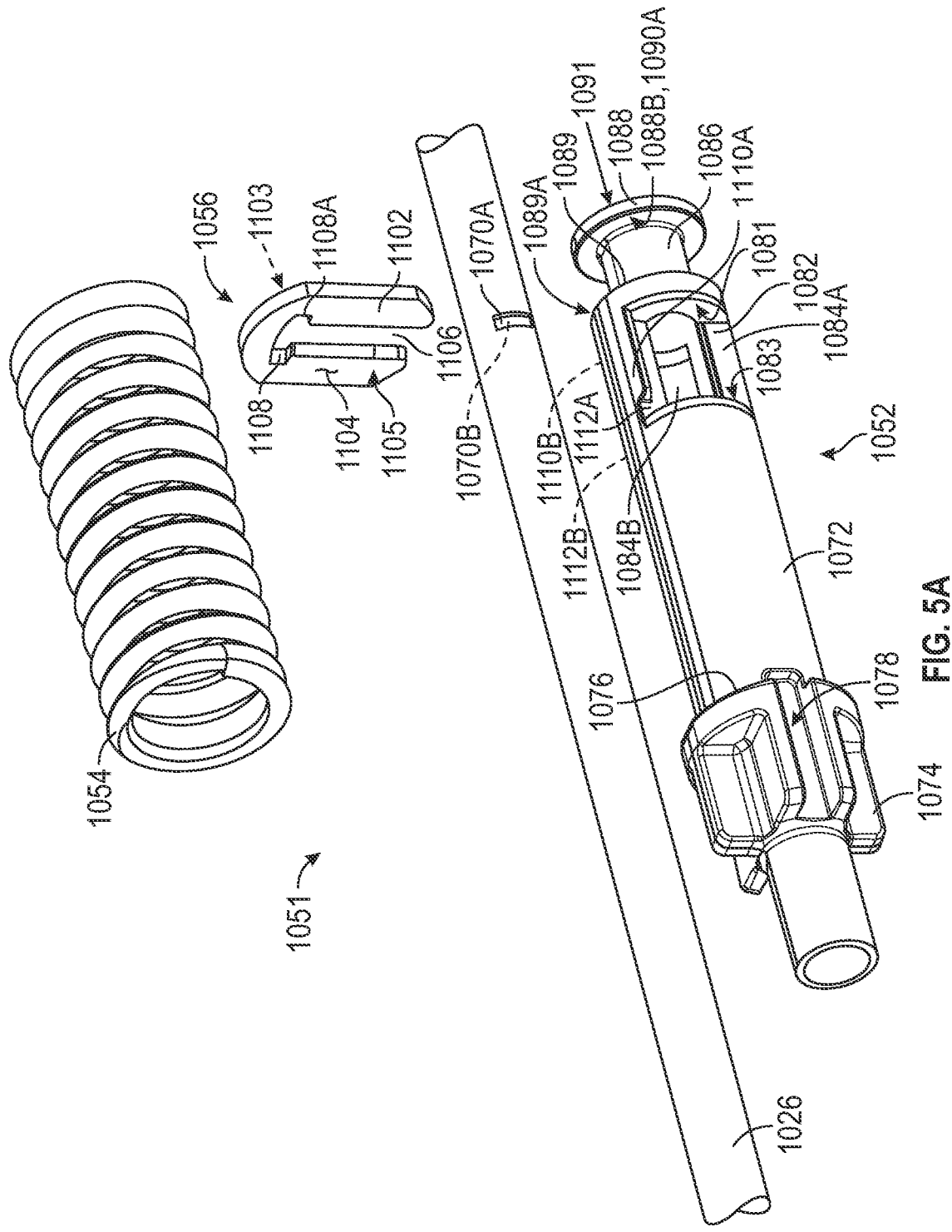
FIG. 5A illustrates an exploded view of a portion of the forceps of FIG. 1A including a drive shaft motion transfer assembly including a drive shaft motion transfer body, a clip, a drive shaft and a spring.

As shown in FIGS. 3C, 3D and 3E, and as shown in further detail in other figures herein, including some features shown close-up in FIG. 5A, the anchor portion 1074 can include the rotational keying slot 1078. The rotational keying slot 1078 is also shown close-up in FIG. 5A. The rotational keying slot 1078 can be horizontal slot, or a slot extending parallel to the longitudinal axis A1 of the drive shaft 1026 (A1 is shown in FIG. 1B). The rotational keying slot 1078 can extend into a side of the body portion 1072. In alternate examples, the drive body 1052 may have any number of the rotational keying slot(s) 1078. In some examples, the rotational keying slot 1078 can be any other suitable keying interface known in the art and are not necessarily provided as a slot. The interaction between the rotational keying slot 1078 and an anti-rotation key 1100 of the outer hub 1060 is further described herein. The rotational keying slot 1078 and the anti-rotation key 1100 on the outer hub 1060 can be any type of interface that limits relative rotation between the drive body 1052 and the outer hub 1060. For example, the rotational keying slot 1078 can be a protrusion instead of a slot to be received by the anti-rotation key 1100 that is a slot, recess or groove of the outer hub 1060 in order to provide the relative anti-rotation features between the drive body 1052 and the outer hub 1060.

The cylindrical portion 1080 of the drive body 1052 can be connected to, or integrally formed with, the distal end of the anchor portion 1074. The cylindrical portion 1080 can be sized to accept the O-ring 1058.

As shown in the exploded view of FIG. 3C, and in additional detail in other figures herein, the window portion 1082 can include the first window 1084A extending through the first side of body portion 1072 and the second window 1084B opposite the first window 1084A and extending through the second side of body portion 1072. Although described as a window, in some examples the window portion 1082 may be provided as a track, such a window or track need not necessarily be bounded on all sides, and sections of the window or track may not extend entirely through the body portion 1072.

As shown in FIGS. 3A, 3B and 3C, with some features shown close-up in FIG. 5A, the neck portion 1086 of the drive body 1052 can be connected to a proximal end of the body portion 1072. The neck portion 1086 can have an outer diameter smaller than the outer diameter of the body portion 1072 (e.g., a minor diameter surface). The collar 1088 can be connected to a proximal end of the neck portion 1086. The collar 1088 can have an outer diameter greater than the outer diameter of the neck portion 1086 and less than an inner diameter of the force-limiting spring 1054.

The collar 1088 can include the drive surface 1090A at a distal end surface of the collar 1088 and the second distal spring seat 1091 at a proximal end of the collar 1088, or a proximal end of the drive body 1052. As such, the drive surface 1090A can be fixedly connected to or integrally molded to the proximal end of the neck portion 1086. Although the neck portion 1086 and associated flanges, such as drive surface 1090A and the second distal spring seat 1091 are shown and described as being located or connected to a proximal end of the body portion 1072, they could be located elsewhere on the drive body 1052, such as along a central portion or distal portion of the drive body 1052, such as distal of the distal spring seat 1076.

The passageway 1092 in the drive shaft 1026 (FIG. 3B, 3C) can be shaped to accept the drive shaft 1026. The passageway 1092 can be a cylindrical or non-cylindrical aperture extending through the cylindrical portion 1080, the anchor portion 1074, the body portion 1072, the window portion 1082, the neck portion 1086, and the collar 1088.

The drive shaft 1026 can extend through the passageway 1092 (FIG. 3B) of the drive body 1052 such that the drive body 1052 can be positioned around at least a portion of the drive shaft 1026. The force-limiting spring 1054 can be positioned on the body portion 1072 and over the window portion 1082 of the drive body 1052. A distal end of the force-limiting spring 1054 can contact the distal spring seat 1076. The clip 1056 can be positioned on the window portion 1082 of the drive body 1052 and can connect to drive shaft 1026 at the first vertical slot 1070A and the second vertical slot 1070B. Examples of clips and windows are described further herein, and for example, in FIGS. 4A, 4B, 4C, 5A, 5B, 5C, 6A, 6B, 6C, 7A, 7B, 8A, 8B, 9A and 9B.

As shown in FIGS. 3A and 3B, and with support for some features shown close-up in FIGS. 5A, 5B, 5C, 6A, 6B, 6C, a proximal end of the force-limiting spring 1054 can contact a distal end surface of the clip 1056. As such, the force-limiting spring 1054 can be positioned on the drive body 1052 between the distal spring seat 1076 of anchor portion 1074 and the clip 1056. In this arrangement, the clip 1056 is fixed to the drive shaft 1026 but can be longitudinally movable with respect to the drive body 1052 within and along window portion 1082 (FIGS. 4A, 4B, 4C) when a preload on the force-limiting spring 1054 is exceeded by the force applied to the lever 1024. As shown close-up in FIG. 5A, a clip support surface 1081 of the body portion 1072 can be adjacent a proximal end of the window portion 1082, and a distal support surface 1083 of the body portion 1072 can be adjacent a distal end of the window portion 1082. In some examples, the clip support surface 1081 and the distal support surface 1083 can function as longitudinal stops for the clip 1056 and impose the preload on the force-limiting spring 1054. In an example, the preload can be in a range between 50-150 Newtons. In a possibly more preferred examples, to improve user experience, the preload can be in a range between 70-90 Newtons, or 135-155 Newtons, depending on the design. Unlike conventional clips, the clip 1056 can be configured to support such high preloads in combination with features of the clip 1056 that couple the clip 1056 to the drive body 1052 and the drive shaft 1026. One of the benefits of such ranges in combination with the forceps 1000 design, including the clip design 1056, is that such preloads can provide adequate jaw 1012 sealing pressure on a tissue, without requiring an excessive input Force F1 to actuate lever 1024. Furthermore, a single actuating jaw can deliver roughly twice the sealing pressure at the jaws 1012 than a dual-actuating jaw, given the same preload on the force-limiting spring 1054.

To cause driving of the jaws 1012 between the open and closed positions shown in FIGS. 1A and 1B, the lever 1024 is moved proximally or distally which moves the drive body 1052 proximally or distally. The drive link 1046 can be operably coupled to the housing 1014 and the drive body 1052 such that the drive link 1046 is configured to transfer a force received at the lever 1024 into a linear motion of the drive body 1052 and the drive shaft 1026 relative to the housing 1014. For example, the drive link 1046 can be connected to the drive body 1052 at the neck portion 1086. The legs 1046B of drive link 1046, shown in FIG. 3C, can fit around the neck portion 1086. When the lever 1024 is moved proximally, the drive link 1046 can contact and push against the drive surface 1090A of the collar 1088. The location of the drive surface 1090A is shown generally in the cross-sectional view of FIGS. 3B and 3C and close-up in FIG. 5A. In contrast, when the lever 1024 is moved distally, the drive link 1046 can move distally, contacting and pushing against a proximal end surface 1090B of body portion 1072 of drive body 1052, also shown in close-up of FIG. 5A.

Figure 31A:
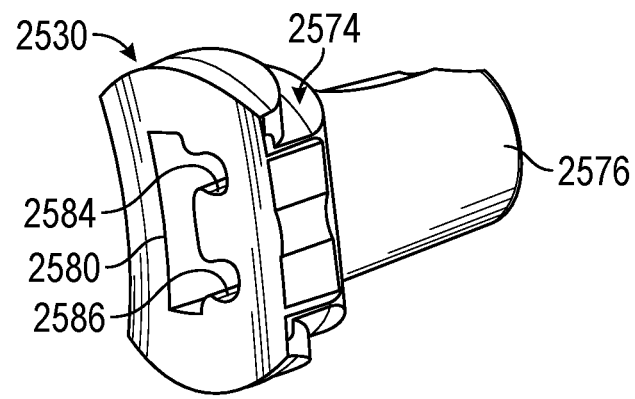
FIG. 31A illustrates an end view of a guide plug of a forceps.

During a surgical procedure, carbon dioxide or other gas may be used for insufflation, which introduces a pressure differential between the body cavity and the external environment. As shown in FIGS. 3A-3E, to prevent leakage, the O-ring 1058 can create a seal between the drive shaft 1026 and the outer hub 1060 so that the pressure differential between the body cavity in which the distal portion of forceps 1000 is positioned and the external environment in which the proximal portion of forceps 1000 is located, is maintained (e.g., pneumatically sealed, substantially pneumatically sealed). In some examples, the O-ring 1058 can be positioned adjacent and distal to the cylindrical portion 1080. Likewise, sealing features within the drive shaft 1026, which can be a hollow tube, can provide similar sealing capabilities to prevent the leakage of air from the body cavity to the external environment in which the proximal portion of forceps 1000, is located. Such sealing features can include a guide plug 2530, such as is shown in FIG. 31A.

The sleeve 1061 or the outer shaft 1028 can include the flange 1094 at a proximal end of the sleeve 1061 or the outer shaft 1028. In the example shown, the sleeve 1061 includes the flange 1094. In some examples, the flange 1094 can be welded to, or formed in, the sleeve 1061 or the outer shaft 1028. The flange 1094 can fit within the groove 1096 of outer hub 1060. The flange 1094 can improve the ability to affix the sleeve 1061 or outer shaft 1028 to the outer hub 1060. For example, the flange 1094 can fit in the groove 1096 in the outer hub 1060. The groove 1096 can form a ring in the interior surface 1098 of the outer hub 1060. In some examples, the outer hub 1060 can be molded to the outer shaft 1028. In another example, the outer hub 1060 can be overmolded on to the sleeve 1061. In such a case, there is not necessarily a groove 1096, but the shape of the outer hub 1060 that accepts the flange 1094 can be formed by the overmolding of the outer hub 1060 onto the flange 1094.

To rotationally fix the outer hub 1060 to the drive body 1052, as shown in FIGS. 3D and 3E, the anti-rotation key 1100 can include a ridge that extends out of the interior surface 1098 of the outer hub 1060 into a channel of the outer hub 1060. For example, the anti-rotation key 1100 can be sized to fit within the rotational keying slot 1078 of the anchor portion 1074. The rotational keying slot 1078 can accepts the anti-rotation key 1100, which can be positioned within the rotational keying slot 1078 such that the rotational keying slot 1078 can be linearly translated, or longitudinally moved, along the anti-rotation key 1100. These features are shown in further detail in FIGS. 11A and 11B.

The flange 1094 and the groove 1096 or other formation can connect and lock the outer shaft 1028 to the outer hub 1060. The anti-rotation key 1100 and rotational keying slot 1078 can connect and rotationally lock the outer hub 1060 and the drive body 1052. Also, the drive shaft 1026 can be rotationally locked to the drive body 1052 by the clip 1056. Thus, rotating rotational actuator 1030 rotates the outer hub 1060, which rotates both the outer shaft 1028 and the drive shaft 1026. The connection between the outer hub 1060, the drive body 1052 and the rotational actuator 1030 is shown and described in further detail with reference to FIGS. 10A, 10B, 11A and 11B. Alternate examples of connections between the outer hub 1060, the drive body 1052 and a rotational actuator 1030 are described with reference to FIG. 12.

As shown in FIG. 3C, to improve stabilization of the drive shaft 1026 while allowing one or both of rotation and longitudinal motion, the first housing portion 1016 can include the stabilizing flange 1021 including a recess or the opening 1021A through which a proximal end of the drive shaft 1026 can extend into or through.

To provide articulation of the lever 1024, the lever 1024 can be operably coupled to the housing 1014 via the first pin 1038. The lever 1024 can be movable about the first pin 1038 by a pivoting motion. In the example, the first pin 1038 is retained in the housing 1014. In other examples, the first pin 1038 may be retained by the lever 1024 or may be part of the lever 1024. As shown in FIG. 3A, the lever 1024 can be biased to a default position (FIG. 1A) by lever return spring 1040. In the example, lever return spring 1040 can be constrained between the housing 1014 and the lever 1024. In some examples, the lever return spring 1040 can be provided as any suitable type of biasing element, such as a helical spring, an elastomeric component, an elastomeric band, or an elastomeric block arranged to bias the lever to a default position. Such a biasing element can be strained, for example by compression, extension, torsion or deflection, and elastically return to its original form, or substantially original form.

As a general overview, to transmit an input motion (e.g., input force F1) received at the lever 1024, a first end of the coupling link 1042 can be connected to the lever 1024 via the second pin 1044. A second end of the coupling link 1042 can be connected to a first end of the drive link 1046 via the third pin 1048. As such, the coupling link 1042 can connect the lever 1024 to the drive link 1046. A second end of the drive link 1046 can be connected to the housing 1014 via the fourth pin 1050. The drive link 1046 can be formed as a yoke. For example, as shown in FIG. 3C, the drive link 1046 can include a base 1046A between the first end and the second end of the drive link 1046. A pair of spaced apart legs 1046B can extend from the base 1046A of drive link 1046 such that the ends of the legs 1046B form the second end of drive link 1046 (also see FIG. 14B).

The illustrative forceps 1000 includes a drive shaft motion transfer assembly 1051 coupled to the housing 1014. The drive shaft motion transfer assembly 1051 can include the drive body 1052 which functions to transmit an input force F1 from the lever 1024 to the drive shaft 1026 to retract or extend the drive shaft 1026 (e.g., to open or close jaws 1012).

In addition to transmitting the input force F1 from the lever 1024 to the drive shaft 1026, in some examples, and as shown in the example forceps 1000, the drive shaft motion transfer assembly 1051, including the drive body 1052 can also transmit a rotational motion from the rotational actuator 1030, through the outer hub 1060, to both the drive shaft 1026 and the outer shaft 1028. However, not all examples of the drive body 1052 require that the drive body 1052 transmit both a longitudinal motion and a rotational motion to the drive shaft 1026. In some examples, the drive body 1052 may only be configured to transmit one or the other of a longitudinal motion and a rotational motion through the drive body 1052 to the drive shaft 1026. For example, some medical devices may employ the extension or retraction features of forceps 1000 but without rotation; and vice versa, other medical devices may employ the rotation features without the extension or retraction features.

In the illustrative drive shaft motion transfer assembly 1051, the drive body 1052 can be positioned around the drive shaft 1026. The drive shaft 1026 can extend through a passageway 1092 in the drive body 1052 (FIG. 3B, FIG.

3C). In some examples, the passageway 1092 may be formed as a center bore, though in some examples, the passageway 1092 does not need to be central and/or does not need to be provided as a circular bore. In other examples, the passageway 1092 can be square, polygonal, irregular, or include a notch. In some examples, the passageway 1092 can include a channel. In some examples the passageway 1092 may not surround the drive shaft 1026.

The drive body 1052 can be located distal with respect to the lever 1024 and can be coupled to the lever 1024. In the example, the drive body 1052 is coupled to the lever 1024 indirectly through a series of linkages. The drive body 1052 can be connected to and receive an input force F1 from the lever 1024 via the drive link 1046 to retract or extend the drive shaft 1026 relative to the housing 1014 and the outer shaft 1028 (thereby closing or opening the jaws 1012). The drive body 1052 can be positioned within the yoke formed by the drive link 1046 to receive the input from the drive link 1046.

The drive shaft motion transfer assembly 1051 can include the force-limiting spring 1054 and the clip 1056. The force-limiting spring 1054 can be positioned around the drive body 1052. The clip 1056 can be positioned on the drive body 1052 adjacent and end of the force-limiting spring 1054. The clip 1056 can be fixed to the drive shaft 1026. In some examples, the force-limiting spring 1054 can be any suitable type of biasing element such as an elastomeric component, an elastomeric band, or an elastomeric block that can be elastically deformed and return to its original state, or substantially original state. In some examples, clip 1056 may be inserted onto the drive shaft 1026 via one or more slots (such as vertical slots 1070A and 1070B). In some examples the clip can be flat, while in other examples, the clip may be non-planar or have irregular, non-flat surfaces.

In some examples, the drive shaft motion transfer assembly 1051 can include the outer hub 1060 which can be connected to the drive body 1052. The outer hub 1060 can include an interior surface 1098 within which the drive body 1052, the force-limiting spring 1054, and the clip 1056 (FIG. 3A, FIG. 3C) can translate longitudinally together.

The rotational actuator 1030 can be positioned around and connected to the outer hub 1060. The rotational actuator 1030 can be rotationally constrained to the outer hub 1060 and axially constrained to the outer hub 1060. The rotational actuator 1030 can also be axially constrained with respect to the housing 1014. The nose 1062 can be connected to a distal end of the outer hub 1060, for example, by a snap fit, adhesive or threaded connection. The drive shaft 1026 and the outer shaft 1028 can extend through and out of nose 1062. In some examples the rotational actuator 1030 and/or the nose 1062 can be omitted and the outer hub 1060 can act as the rotational actuator 1030 and/or the nose 1062 to receive a rotation input directly from a user. In some examples, instead of the nose 1062 being connected to a distal end of the outer hub 1060, the nose 1062 can be connected directly to the rotational actuator 1030, for example, by a snap fit, adhesive or threaded connection.

In the example of FIG. 3A, axial retention of the rotational actuator 1030 relative to housing 1014 can be provided by axially constraining the rotational actuator 1030 between the housing 1014 and the nose 1062. A connection between a first snap fit connector 1060C on the outer hub 1060 and a second snap fit connector 1062C on the nose 1062 can constrain the rotational actuator 1030 from moving distally. The first and second snap fit connectors are shown merely as an example, any type of snap fit connectors, or otherwise, may be provided. In this arrangement, the outer hub 1060 can be axially constrained with respect to the housing 1014 by a proximal housing flange 1060A and a distal flange 1060B of the outer hub 1060, which can be captured by surfaces of the housing 1014 that interface with the proximal housing flange 1060A and the distal flange 1060B. Furthermore, since the nose 1062 is axially constrained to the outer hub 1060, the rotational actuator 1030 can also be axially constrained to the outer hub 1060, the nose 1062 and the housing 1014 by being captured between the nose 1062 and the housing 1014. In other words, the nose 1062 engages the outer hub 1060 in an axial direction to provide axial retention of both the nose 1062 as well as the rotational actuator 1030.

Figure 4A:
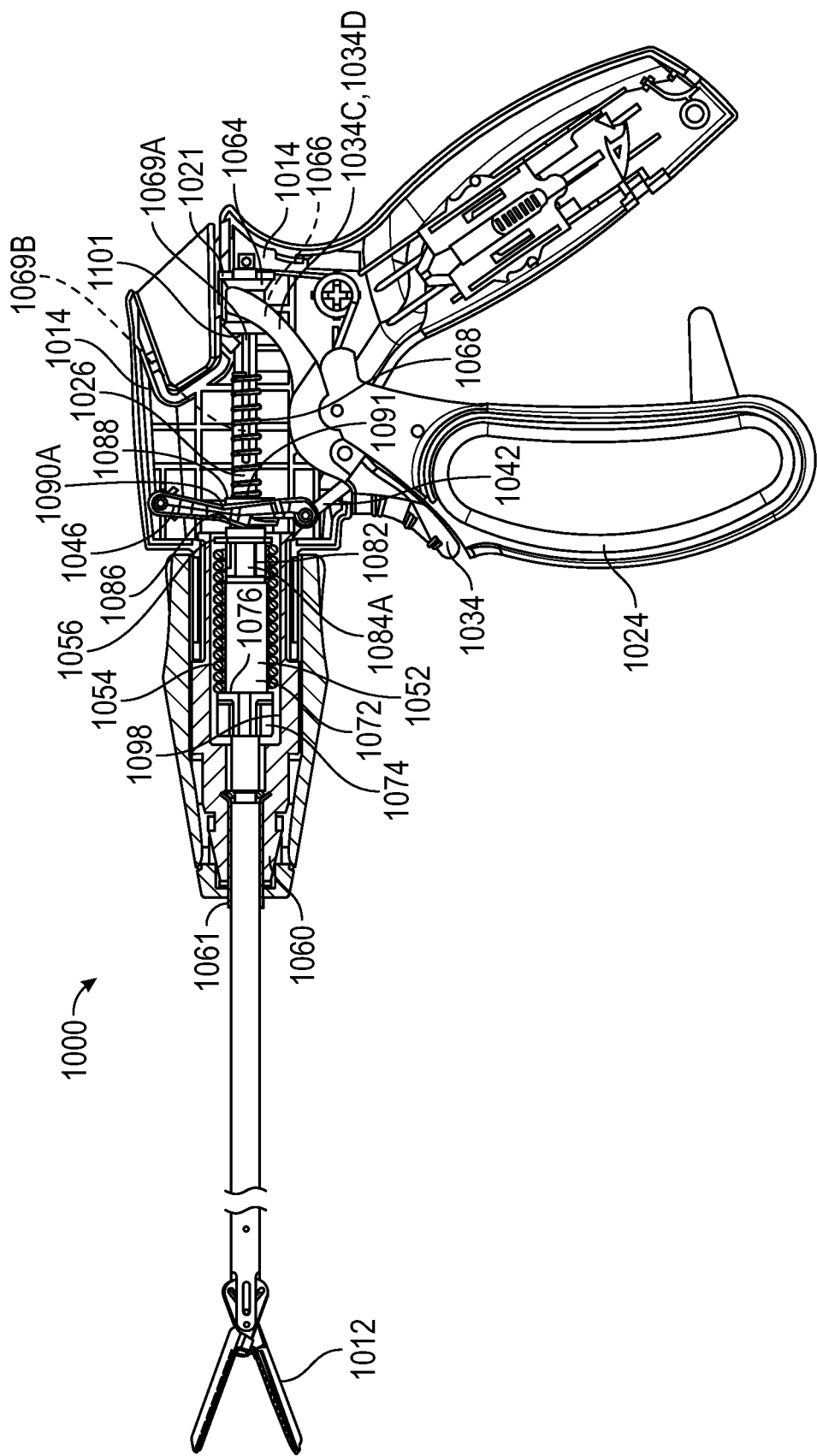
FIG. 4A illustrates a partial cross-sectional view of the forceps of FIG. 1A showing a lever in a distal position (e.g., unactuated position).
Figure 4B:
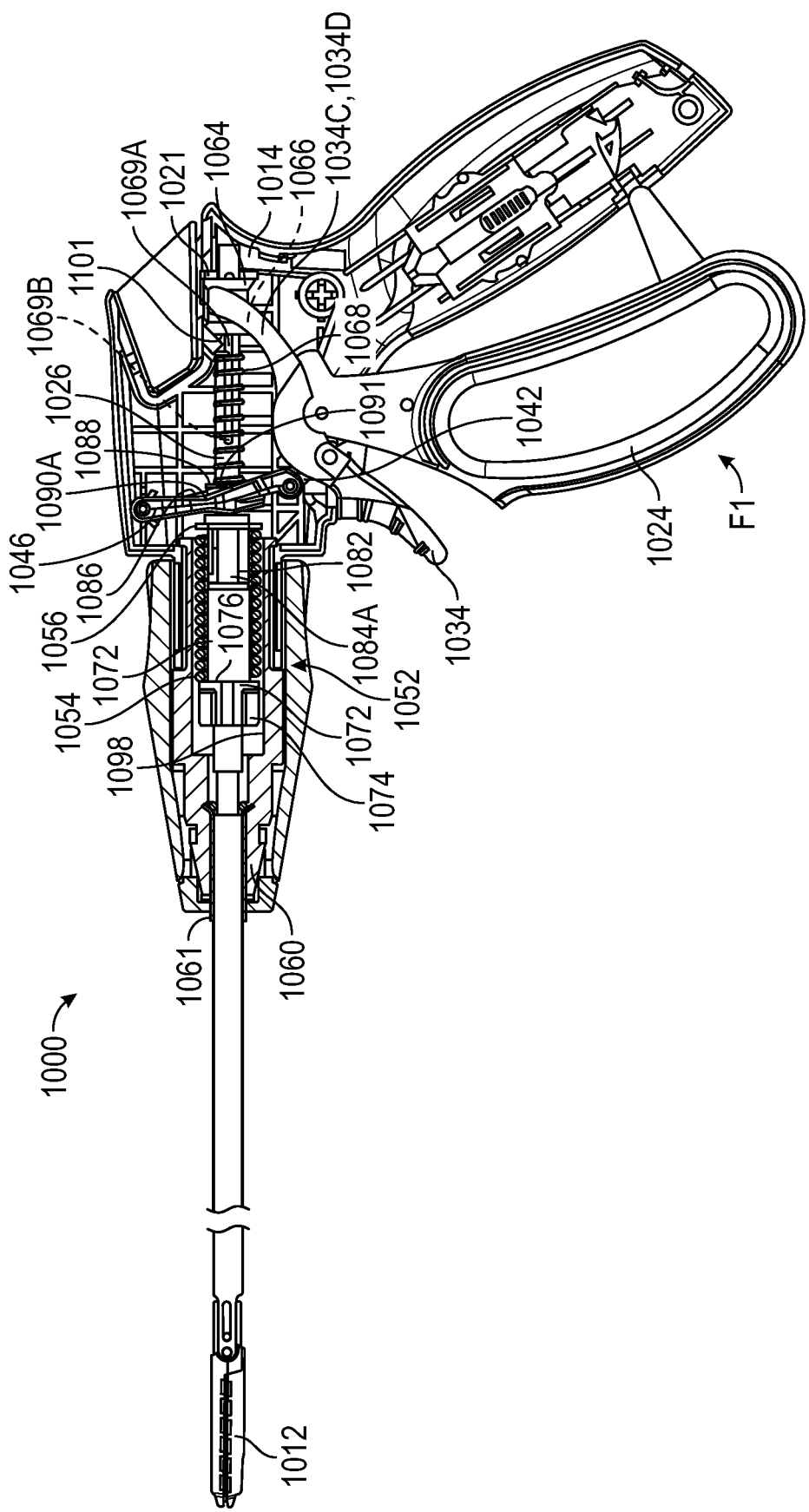
FIG. 4B illustrates a partial cross-sectional view of the forceps of FIG. 1A showing the lever moved proximally (e.g., an actuated position).
Figure 4C:
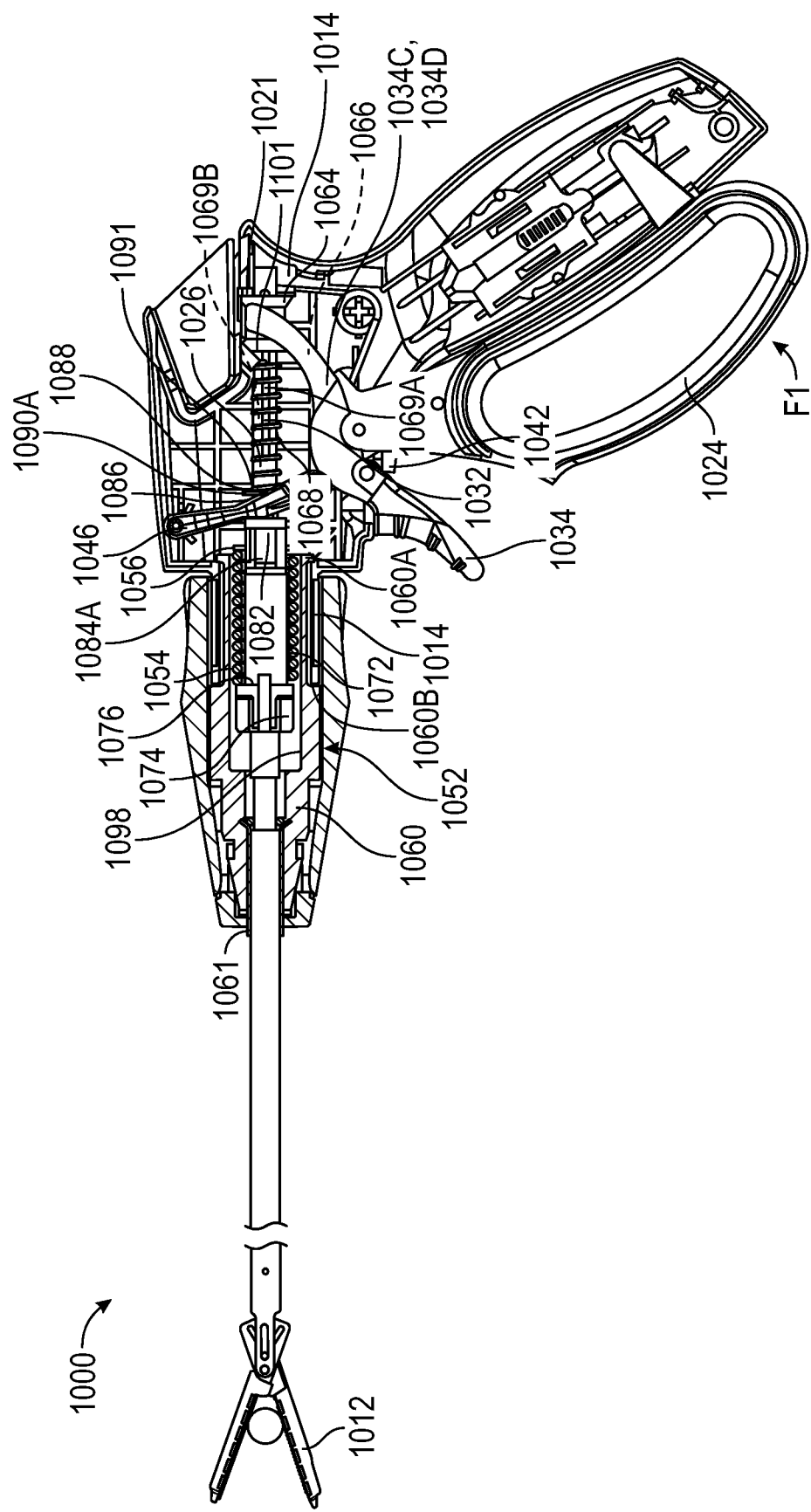
FIG. 4C illustrates a partial cross-sectional view of the forceps of FIG. 1A showing the lever moved further proximally (e.g., a force limiting state, an over-travel position).

FIG. 4A illustrates a partial cross-sectional view of the forceps 1000 of FIG. 1A showing the lever 1024 in a distal position (e.g., an unactuated position), in accordance with at least one example. FIG. 4B illustrates a partial cross-sectional view of the forceps 1000 of FIG. 1A showing the lever 1024 being moved proximally (e.g., an actuated position, one of a plurality of actuated positions or user positions), in accordance with at least one example. FIG. 4C illustrates a partial cross-sectional view of the forceps 1000 of FIG. 1A showing the lever 1024 moved further proximally (e.g., into a further actuated position, which in some examples can be a fully-actuated position, and in this case, into a force limiting or over-travel state), in accordance with at least one example. Note that a force limiting state is a position of the drive body 1052 that occurs when a force applied to the lever 1024 and transferred to the drive body 1052 exceeds a predetermined force that is based on a preload of the force-limiting spring 1054. Force limiting can occur in other actuated positions whenever the predetermined force is exceeded.

FIG. 4A, FIG. 4B, and FIG. 4C will be discussed together and provide a general illustration of how the drive body 1052, the force-limiting spring 1054, and the clip 1056 can function on the drive shaft 1026 in response to the lever 1024 providing an input to a linkage between the lever 1024 and the drive body 1052. The components of the forceps 1000 shown in FIG. 4A, FIG. 4B, and FIG. 4C include the housing 1014 having stabilizing flange 1021, the lever 1024, the drive shaft 1026, the trigger 1034, the coupling link 1042, the drive link 1046, the drive body 1052, the force-limiting spring 1054, the clip 1056, the outer hub 1060, a spool 1064, the cross pin 1066, and the trigger return spring 1068. The drive shaft 1026 can include the first horizontal slot 1069A, the second horizontal slot 1069B, the first vertical slot 1070A, and the second vertical slot 1070B (hidden here, but viewable in FIG. 3C). The drive body 1052 includes the body portion 1072, the anchor portion 1074 (including distal spring seat 1076), the window portion 1082 (including the first window 1084A and the second window 1084B, the neck portion 1086, and the collar 1088 (including the drive surface 1090A and the second distal spring seat 1091, also shown in FIG. 3C, and close-up in FIG. 5A). The outer hub 1060 includes the interior surface 1098. The spool 1064 can include a proximal trigger return spring seat 1101. The spool 1064 is shown as one example of a motion transfer body designed to transmit motion received from an actuator to a shaft (e.g., received from trigger 1034 and transmitted to blade shaft 1032). In other examples a motion transfer body within this disclosure need not be spool-shaped, such as in examples where the spool 1064 does not need to be rotatable.

As shown in FIG. 4A, when the lever 1024 is in a distal position (e.g., default position, open position of jaws 1012), the drive body 1052 is positioned within the channel formed by interior surface 1098 of outer hub 1060. Most of the body portion 1072 of the drive body 1052 is within the channel of the outer hub 1060. The drive shaft 1026 is in a first position with respect to housing 1014 as it is not being pulled proximally (e.g., unactuated position, non-retracted position) by clip 1056 and is within the opening in the stabilizing flange 1021. As a result, the jaws 1012 are in an open position as shown in FIG. 1A.

As shown in FIG. 4B, when the lever 1024 is being moved proximally, the lever 1024 pulls the bottom end of the drive link 1046 in a proximal direction with respect to housing 1014 via the coupling link 1042. The drive link 1046 is connected to the drive body 1052 at the neck portion 1086 and pushes on the drive surface 1090A of the collar 1088, causing the drive body 1052 to move in a proximal direction longitudinally with respect to the housing 1014 (see FIG. 5A for a closeup view of the drive body 1052). As a result, a greater portion of the body portion 1072, including the window portion 1082, of the drive body 1052 moves out the channel of the outer hub 1060. When the drive body 1052 is pulled proximally, the force-limiting spring 1054 and the clip 1056 move along with the drive body 1052 in the same positions with respect to the drive body 1052.

In other words, the distal spring seat 1076 drives the force-limiting spring 1054, which drives the clip 1056, along with the drive body 1052. When the drive force supplied by the drive link 1046 is less than the preload force in the force-limiting spring 1054, the force-limiting spring 1054 acts like a rigid body and the ends of the force-limiting spring 1054 move together. As such, the drive body 1052 moves proximally with respect to the housing 1014 and the clip 1056 moves proximally with respect to the housing 1014. Because the clip 1056 is longitudinally locked to the drive shaft 1026 at the first vertical slot 1070A and the second vertical slot 1070B, the drive shaft 1026 also moves proximally with respect to the housing 1014. As the drive shaft 1026 moves proximally (e.g., is retracted), the end effector 1002 becomes actuated. In this example, actuating the end effector 1002 includes the jaws 1012 beginning to close.

In other words, in the situation of FIG. 4B, the lever 1024 may be closed due to user input to close jaws 1012. Movement of the lever 1024 causes movement of drive body 1052. Closing lever 1024 causes the coupling link 1042 to pull drive link 1046 proximally with respect to housing 1014, which causes longitudinal translation of drive body 1052 in the proximal direction. Moving the drive body 1052 proximally causes longitudinal translation of the drive shaft 1026 in the proximal direction because the drive body 1052 and the drive shaft 1026 are connected via the clip 1056. As a result of the movement of the drive shaft 1026, a mechanism on the jaws 1012 is actuated, closing the jaws 1012. As shown in the illustrative example, while the drive link 1046 drives the drive body 1052 longitudinally, the drive body 1052 can still be free to rotate inside the yoke of the drive link 1046 and can rotate relative to the drive link 1046. However, in some examples, the rotation aspect may be omitted.

In the illustrative example, at any time during use, regardless of whether the jaws 1012 are opened or closed, the jaws 1012 can be rotated. For example, rotation of the rotational actuator 1030 rotates the outer hub 1060, which beneficially transfers rotational motion to rotate the outer shaft 1028 and the drive body 1052. Because drive body 1052 is locked (e.g., constrained) to the drive shaft 1026 via the clip 1056, the drive shaft 1026 can also rotate with the outer shaft 1028.

Figure 20A:
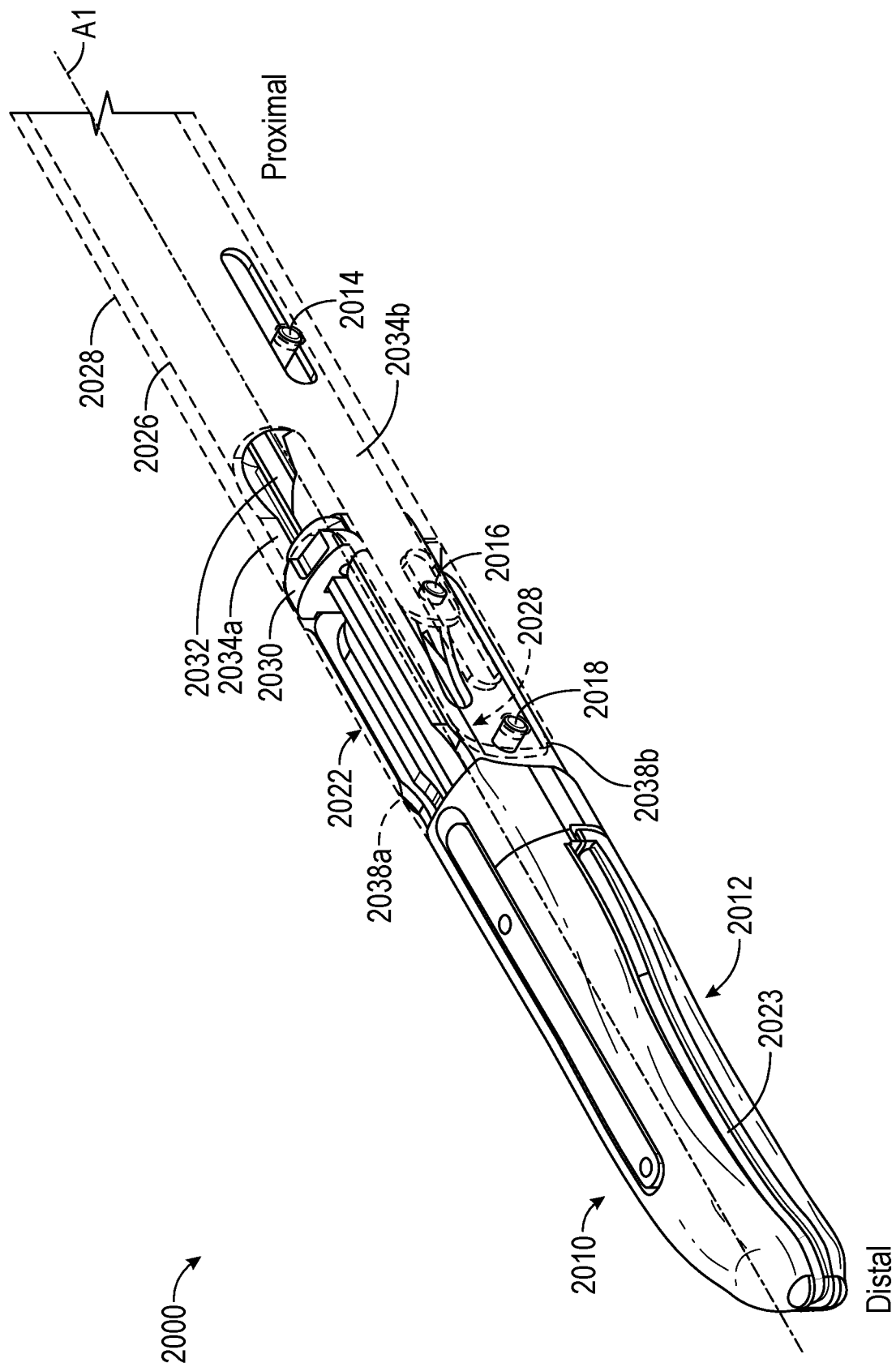
FIG. 20A illustrates an isometric view of a portion of a forceps in a closed position.

Thus, the outer shaft 1028 and the drive shaft 1026 can be rotationally locked together (e.g., rotationally constrained) at a proximal end of forceps 1000, and as is described further herein, the outer shaft 1028 and the drive shaft 1026 can also be rotationally locked or constrained together at a distal end of the forceps 1000 (such as by guide 2014 shown in the forceps 2000 of FIG. 20A, described further herein).

Further, first horizontal slot 1069A and second horizontal slot 1069B in drive shaft 1026 can engage and rotate cross pin 1066 when the drive shaft 1026 is rotated, to rotate blade shaft 1032 and spool 1064. Thus, the drive shaft 1026 and blade assembly (1032, 1032A) can be rotationally constrained (e.g., fixed, locked together) at a proximal end of forceps 1000 via cross pin 1066 (FIG. 2, FIG. 4A). In other words, the blade assembly (1032, 1032A) can be rotationally constrained to the drive shaft 1026 at a longitudinal location along the longitudinal axis A1 (FIG. 1B) that is proximal of the jaws 1012 and proximal of the drive body 1052.

If actuation is complete, to return the jaws 1012 to the unactuated state of FIG. 4A, the lever return spring 1040 can act on the lever 1024 to return (e.g., bias) the lever 1024 to the default position (e.g., distal position). Since the lever 1024 is coupled to the drive shaft 1026 by a series of linkages, described herein with reference to at least FIGS. 15A and 15B, the lever return spring 1040 also returns the drive shaft 1026 and thereby the jaws 1012 to a default position (FIG. 15A), which in the present example is an open position. As shown in the condition of FIG. 4C, it is possible that jaws 1012 may become stuck or caught on an anatomical feature or another medical device in the patient when the lever 1024 is being moved proximally. In such a situation, the jaws 1012 may not be able to close completely. However, the drive motion transfer assembly 1051 of forceps 1000 includes a force limiting feature that prevents the drive shaft 1026 from being retracted to the point where the jaws 1012 become damaged by the additional input force F1 from the user being transmitted to the jaws 1012. The forceps 1000 can be capable of achieving a force limiting state (e.g., an over-travel state) in instances where the lever 1024 is being moved proximally and the jaws 1012 get stuck in an open or partially open position and the user continues to apply a force to the lever 1024.

To prevent damage to the jaws 1012, the force-limiting spring 1054 can be configured to absorb excess force applied to the lever 1024 instead of transferring the excess force to the jaws. For example, the force-limiting spring 1054 can extend from a first end portion to a second end portion and can be in a preloaded state between the distal spring seat 1076 and a distal end surface 1105 of the clip 1056. The force-limiting spring 1054 can push the clip 1056 in a proximal direction such that the clip 1056 contacts and is supported by a clip support surface (e.g., clip support surface 1081, FIG. 5A) of the body portion 1072 adjacent a proximal end of the window portion 1082. The clip support surface (1081, FIG. 5A) can function as a proximal stop for the clip 1056. With the force-limiting spring 1054 in compression, the distal spring seat 1076 can be configured to receive a first spring force from the distal end portion of the force-limiting spring 1054, and the clip 1056 can be configured to receive a second spring force from the proximal end portion of the force-limiting spring 1054. The drive body 1052 can include the clip support surface 1081 configured to transmit the first force to the second surface (e.g., proximal end surface 1103) of the clip 1056 when the force-limiting spring 1054, under a load, such as a preload, drives the clip 1056 against the clip support surface 1081.

With continued reference to FIG. 4C, in an example of force limiting, the lever 1024 is moved to a proximal position by the user, exerting force on the drive link 1046 and pulling the bottom end of drive link 1046 further in a proximal direction, although the jaws 1012 are blocked from closing further. Consequently, the drive link 1046 exerts more force on the drive surface 1090A of the collar 1088, moving the drive body 1052 further proximally with respect to housing 1014 and the drive body 1052 moves farther proximally out of the interior surface 1098 that forms a passageway 1098A (FIG. 3C) of the outer hub 1060. The outer hub 1060 can be constrained from axial movement with respect to the housing 1014 by proximal housing flange 1060a and distal flange 1060B of the outer hub 1060 which can be captured by a portion of housing 1014. As the drive body 1052 moves proximally, the distal spring seat 1076 of the anchor portion 1074 of the drive body 1052 pushes on a distal end of the force-limiting spring 1054. However, because the jaws 1012 are unable to close further, the drive shaft 1026 cannot move proximally along with the drive body 1052. Further, because the clip 1056 is locked to drive shaft 1026, the clip 1056 cannot move proximally with respect to housing 1014 either. Thus, the drive body 1052 moves proximally relative to the clip 1056 and the drive shaft 1026 by sliding (e.g., linear motion, longitudinal motion or translating) proximally relative to the clip 1056.

The clip 1056, by remaining fixed with respect to the drive shaft 1026, effectively moves distally relative to the drive body 1052 within the first window 1084A and the second window 1084B of the window portion 1082. As such, the force-limiting spring 1054 becomes more compressed between the distal spring seat 1076 and the distal end surface of the clip 1056 when the force exerted on the drive link 1046 is greater than a preload of the force-limiting spring 1054. The user can feel this force limiting feature as an increase in force on the lever 1024 due to the additional compression of the force-limiting spring 1054 over the preloaded state, however, the lever 1024, which is no longer transferring motion to the drive shaft, is still movable.

In other words, the lever 1024 can be fully moved into a proximal position, moving the drive body 1052 proximally in the housing 1014 as far as the drive shaft 1026 will go. At the same time, the jaws 1012 can become locked in an open position (e.g., caught on something), preventing the drive shaft 1026 from moving even though the lever 1024 is being moved proximally. Because the drive shaft 1026 cannot move proximally in the housing 1014, the clip 1056 cannot move proximally with respect to the housing 1014. However, because the clip 1056 can slide within the window portion 1082, the drive body 1052 is able to move (e.g., slide, translate) proximally with respect to the clip 1056, changing the position of the clip 1056 within the window portion 1082. As the drive body 1052 moves with respect to the clip 1056, the force-limiting spring 1054 compresses and absorbs the force exerted on the lever 1024. Because moving the drive shaft 1026 causes the jaws 1012 to close, the ability to prevent the drive shaft 1026 from moving when the jaws 1012 are unable to close prevents the jaws 1012 from becoming damaged when a user is unaware of the jaws 1012 being stuck open and the user continues to pull the lever 1024 proximally to close the jaws 1012.

In addition to the clamping system shown and described in FIGS. 4A, 4B and 4C, FIGS. 4A, 4B and 4C also illustrate components that can be used to actuate another system, such as, but not limited to, a cutting system for actuating a blade assembly (e.g., blade shaft 1032, FIG. 3C). Additional aspects of the cutting system are further described throughout this disclosure and in FIGS. 15A, 15B, 16A, 16B in particular.

As shown in the illustrative example of FIGS. 4A, 4B and 4C, the spool 1064 can be positioned around a proximal end of the drive shaft 1026 proximal to the drive body 1052 and can be connected to a proximal end of the blade shaft 1032 via cross pin 1066. Thus, the blade assembly (1032, 1032A) is attached to a proximal end of the drive shaft 1026 via the cross pin 1066 extending through the first horizontal slot 1069A and the second horizontal slot 1069B. The spool 1064 can be within the housing 1014 distal to the stabilizing flange 1021. The spool 1064 can be axisymmetric and can be longitudinally movable with respect to the drive shaft 1026. In an alternate example, where the drive shaft 1026 and blade shaft 1032 do not need to rotate, the spool 1064 can be a non-spool shaped body.

The trigger 1034 can be connected to the spool 1064. A proximal end of the trigger 1034 can include one or more legs, in this example, two legs forming a yoke, that fit around and can be connected to the spool 1064. The spool 1064 can rotate relative to trigger 1034 to allow the drive shaft 1026 to rotate. The trigger return spring 1068 can be a helical compression spring positioned on the drive shaft 1026 between a distal end of spool 1064 and a proximal end of drive body 1052. The trigger return spring 1068 can be assembled by loading the trigger return spring 1068 onto the drive shaft 1026 and then positioning the spool 1064 onto the drive shaft 1026 to connect trigger 1034 to the blade shaft 1032. In some examples, the trigger return spring 1068 can be any suitable biasing element such as an elastomeric component, elastomeric band or elastomeric block that can be strained and elastically return to its original form, or substantially original form.

To facilitate extension and retraction of the blade shaft 1032, the cross pin 1066 can move within the first horizontal slot 1069A and the second horizontal slot 1069B of the drive shaft 1026. In some examples, the dimensioning of first horizontal slot 1069A and the second horizontal slot 1069B can be such that they act as guide rails for the cross pin 1066 to control longitudinal reciprocation of spool 1064. In such an example, the spool 1064 can be guided by the drive shaft 1026. The first horizontal slot 1069A can extend into a first side of the drive shaft 1026, and the second horizontal slot 1069B can extend into a second side of the drive shaft 1026 across from or opposing the first horizontal slot 1069A. The first horizontal slot 1069A and the second horizontal slot 1069B are near a proximal end of the drive shaft 1026. As such, the cross pin 1066 can extend through the spool 1064, the first horizontal slot 1069A of the drive shaft 1026, the blade shaft 1032, and the second horizontal slot 1069B of the drive shaft 1026. The second arm 1034D is hidden in FIGS. 4A, 4B and 4C. The spool 1064 can include a proximal trigger return spring seat 1101 at a distal end of the spool 1064. As such, the trigger return spring 1068 can be positioned on the drive shaft 1026 between a proximal end of the drive body 1052, or the second distal spring seat 1091, and a distal end of the spool 1064, or proximal trigger return spring seat 1101. In an alternate example, a second passageway 1064A (FIG. 2) in the spool 1064 can ride on the drive shaft 1026 and be guided for longitudinal movement along the drive shaft 1026.

The cutting system is further illustrated and further described in FIGS. 15A, 15B, 16A, 16B, however, as a general overview, the cutting system can operate as described in the following manner. Compressing a distal end of the trigger 1034 can move a proximal end of the trigger 1034 in a distal direction with respect to the housing 1014, which can cause the spool 1064 to move distally. The spool 1064 can push against a proximal end of the trigger return spring 1068. The preload of the trigger return spring 1068 can be overcome such that trigger return spring 1068 compresses. The spool 1064, connected to the blade shaft 1032 by the cross pin 1066, can cause the blade shaft 1032 to move longitudinally in a distal direction via the cross pin 1066 traveling along, or within, the first horizontal slot 1069A and the second horizontal slot 1069B of the drive shaft 1026, causing blade 1032A (FIG. 2) to protrude from a distal end of the drive shaft 1026. When the trigger 1034 is not compressed, the trigger return spring 1068 can expand, pushing the spool 1064 and the blade shaft 1032 in a proximal direction to a position in which the blade 1032A (FIG. 2) does not protrude from the drive shaft 1026.

Figure 5B:
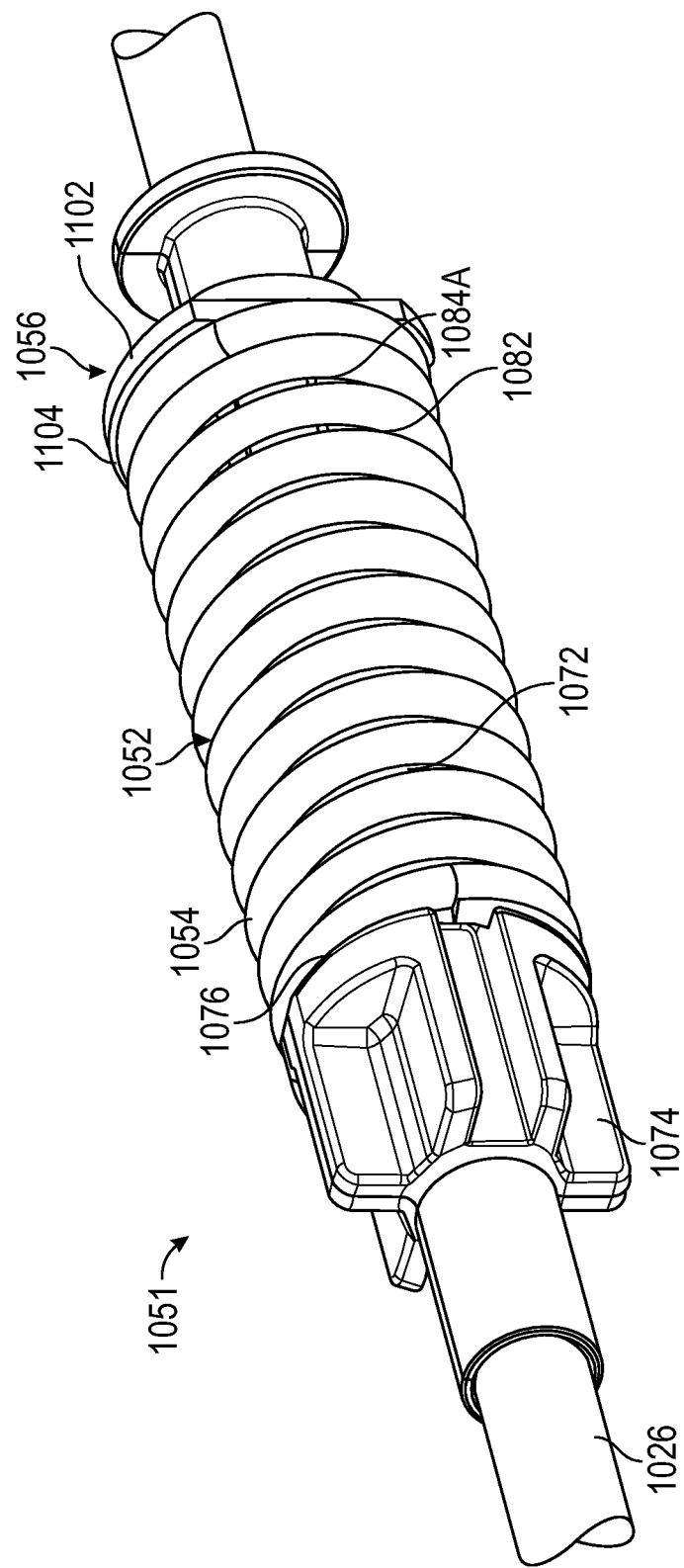
FIG. 5B illustrates an isometric view of the drive shaft motion transfer body of FIG. 5A in the assembled state.
Figure 5C:
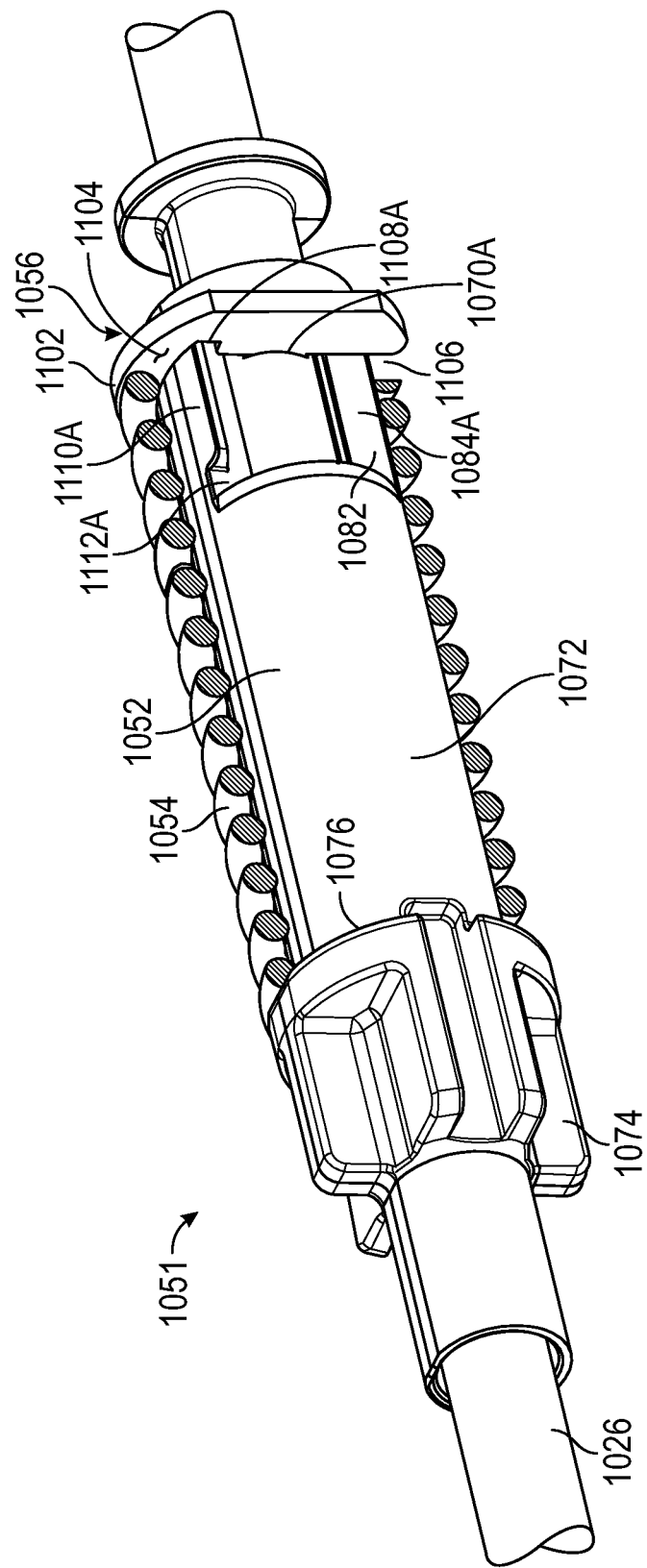
FIG. 5C illustrates an isometric view of the drive shaft motion transfer assembly of FIG. 5A in an assembled state (with the spring in a compressed, pre-loaded position).

FIG. 5A is an isometric view of an example drive shaft motion transfer assembly 1051 that can be used in the forceps 1000 of FIG. 1A, including the drive body 1052, the force-limiting spring 1054, the clip 1056 and the drive shaft 1026. FIG. 5B is an isometric view of the drive body 1052 and the clip 1056 on the drive shaft 1026 with the force-limiting spring 1054 in cross-section. FIG. 5C is an exploded view of the drive body 1052, the clip 1056, and the drive shaft 1026. FIGS. 5A, 5B, and 5C will be discussed together. The motion transfer assembly 1051 serves to transfer a force input F1 (FIG. 1B) applied by a user at lever 1024 and/or a rotational input R1 applied by a user at rotational actuator 1030, to the end effector 1002 (FIG. 1B).

The motion transfer assembly 1051 of the example of FIGS. 5A and 5B is described as follows. The drive shaft 1026 can include the first vertical slot 1070A and the second vertical slot 1070B. The drive body 1052 can include the body portion 1072, the anchor portion 1074 (including the distal spring seat 1076), and the window portion 1082 (including the first window 1084A and the second window 1084B), surfaces to interface with the drive link 1046, including the collar 1088, the neck portion 1086 and the distal collar 1089 (e.g. a distal surface, a proximally-facing distal face). The clip 1056 can include a clip body 1102 having a proximal end surface 1103 and a distal end surface 1105 (e.g., a proximal spring seat 1104), a clip slot 1106, clip notches 1108A and 1108B (including a first clip notch 1108A and a second clip notch 1108B). The window portion 1082 can further include retaining ribs 1110A and 1110B (including a first retaining rib 1110A and a second retaining rib 1110B) and window notches 1112A and 1112B (including a first window notch 1112A and a second window notch 1112B). The drive shaft 1026, drive body 1052, force-limiting spring 1054, and the clip 1056 can have the same structure and function as described with respect to FIGS. 1A-4C.

The clip 1056 can have the clip body 1102 having the proximal end surface 1103 opposite a distal end surface 1105. The distal end surface 1105 of the clip body 1102 can provide the proximal spring seat 1104 for supporting the force-limiting spring 1054. The clip slot 1106 can be a slot that extends into the clip body 1102 from a bottom of the clip body 1102. The clip slot 1106 can have a width about equal to or slightly wider than the length from first vertical slot 1070A to second vertical slot 1070B of the drive shaft 1026. In an alternate example where the clip 1056 is flexible, the clip slot 1106 may have a width slightly narrower than the length from first vertical slot 1070A to second vertical slot 1070B of the drive shaft 1026. The clip notches 1108A and 1108B can extend into the clip body 1102 from the clip slot 1106. The first clip notch 1108A can extend into the clip body 1102 from a first side of the clip slot 1106 at a top of the clip slot 1106, and the second clip notch 1108B can extend into the clip body 1102 from a second side of the clip slot 1106 at the top of the clip slot 1106. As such, the second clip notch 1108B can extend into the clip body 1102 from the clip slot 1106 opposite first the clip notch 1108A.

The window portion 1082 can include the first window 1084A extending through a first side of body portion 1072 and the second window 1084B extending through a second side of the body portion 1072 opposite the first window 1084A. The first retaining rib 1110A can extend into the first window 1084A from a top of the body portion 1072. The first retaining rib 1110A can extend from an upper portion of the top of the body portion 1072 such that the first retaining rib 1110A forms a first lip at the top of the body portion 1072. The second retaining rib 1110B can extend into the second window 1084B from a top of the body portion 1072. The second retaining rib 1110B can extend from an upper portion of the top of the body portion 1072 such that the second retaining rib 1110B forms a second lip at the top of body portion 1072. The first window notch 1112A can be included as part of the first window 1084A at a distal end of the first retaining rib 1110A. The second window notch 1112B be included in as part of the second window 1084B at a distal end of the second retaining rib 1110B. In alternate examples, the first window notch 1112A and the second window notch 1112B can be positioned anywhere along the first retaining rib 1110A and the second retaining rib 1110B, respectively. In a potentially beneficial example, placement of the first and second window notches 1112A and 1112B may be far enough distal such that the clip 1056 never aligns with the window notches 1112A and 1112B as assembled, even when the force limiting spring 1054 is compressed. Preventing the clip 1056 from aligning with the window notches 1112A and 1112B prevents the clip 1056 from egressing out of the window notches 1112A and 1112B.

When the drive body 1052 is on the drive shaft 1026, the clip 1056 can be positioned on the window portion 1082 of the drive body 1052. The clip slot 1106 can fit around drive body 1052 at the window portion 1082 and can fit around the drive shaft 1026 at the first vertical slot 1070A and the second vertical slot 1070B such that the clip 1056 fits within and is accepted by the first vertical slot 1070A and the second vertical slot 1070B of the drive shaft 1026. A proximal end of the force-limiting spring 1054 can contact the proximal spring seat 1104 of the clip 1056. A distal end of the force-limiting spring 1054 can contact the distal spring seat 1076. The distance between the proximal spring seat 1104 and the distal spring seat 1076, being less than a length of the force-limiting spring 1054, causes the force-limiting spring 1054 to be compressed and places a preload upon the force-limiting spring 1054. The first clip notch 1108A can fit around first retaining rib 1110A. The second clip notch 1108B can fit around second retaining rib 1110B. The clip 1056 can move longitudinally within the first window 1084A and the second window 1084B at window portion 1082 and along the first retaining rib 1110A and the second retaining rib 1110B.

The first vertical slot 1070A and the second vertical slot 1070B on the drive shaft 1026 longitudinally and rotationally lock the clip 1056 to the drive shaft 1026. The clip notches 1108A and 1108B and the retaining ribs 1110A and 1110B can fit together to retain the clip 1056 to both the drive body 1052 and the drive shaft 1026, preventing the clip 1056 from backing out of first vertical slot 1070A, second vertical slot 1070B, and the window portion 1082, and rotationally lock the clip 1056 to drive body 1052. However, some instances (e.g., a force limiting state), as described herein, the drive body 1052 is still capable of moving longitudinally with respect to the clip 1056 such that the clip 1056 moves longitudinally with respect to drive body 1052 within the first window 1084A and the second window 1084B along the retaining ribs 1110A and 1110B. As a result, the drive body 1052 can move longitudinally relative to the drive shaft 1026 The clip 1056 is prevented from backing out or popping off drive body 1052 and the drive shaft 1026 while drive body 1052 moves longitudinally relative to the clip 1056 and the drive shaft 1026. In the assembled state, the clip 1056 can be misaligned with the window notches 1112A and 1112B but aligned with first and second vertical slots 1070A and 1070B (FIG. 5C).

In this arrangement, the clip 1056 can be fixed to the drive shaft 1026 and slidably coupled to the drive body 1052. The rotational motion can be delivered from the drive body 1052 through the clip 1056 to the drive shaft 1026, and the linear motion can be delivered from the drive body 1052 indirectly through the force-limiting spring 1054 to the clip 1056 and from the clip 1056 to the drive shaft 1026 to translate the drive shaft 1026.

In other words, the clip 1056 can be coupled to the drive body 1052 and the drive shaft 1026 to rotationally fix the drive body 1052 to the drive shaft 1026. The drive body 1052 can be configured to transfer a rotational input received from the rotational actuator 1030 into a rotational motion of the clip 1056, and the clip 1056 can be configured to transfer the rotational motion of the clip 1056 into a rotational motion of the drive shaft 1026.

As shown in FIG. 5A, the input surfaces to receive an input from the drive link 1046 (FIGS. 3A, 3B, 3C) can include the collar 1088 (e.g., first face), the neck portion 1086 (e.g., minor diameter surface) and the distal collar 1089 (e.g., distal face). The collar 1088, the neck portion 1086 and the distal collar 1089 can form a spool portion of the drive body 1052. In some examples, the spool portion (e.g., 1088, 1086 and 1089) can be an axisymmetric spool portion. In some examples, a distal face 1088B of the proximal collar 1088 and a proximal face 1089A of the distal collar 1089 are planar. In some examples, a distal face 1088B of the proximal collar 1088 and a proximal face 1089A of the distal collar 1089 are parallel. In some examples, the spool portion allows for rotational displacement of the drive body 1052 relative to the drive link 1046.

Figure 6A:
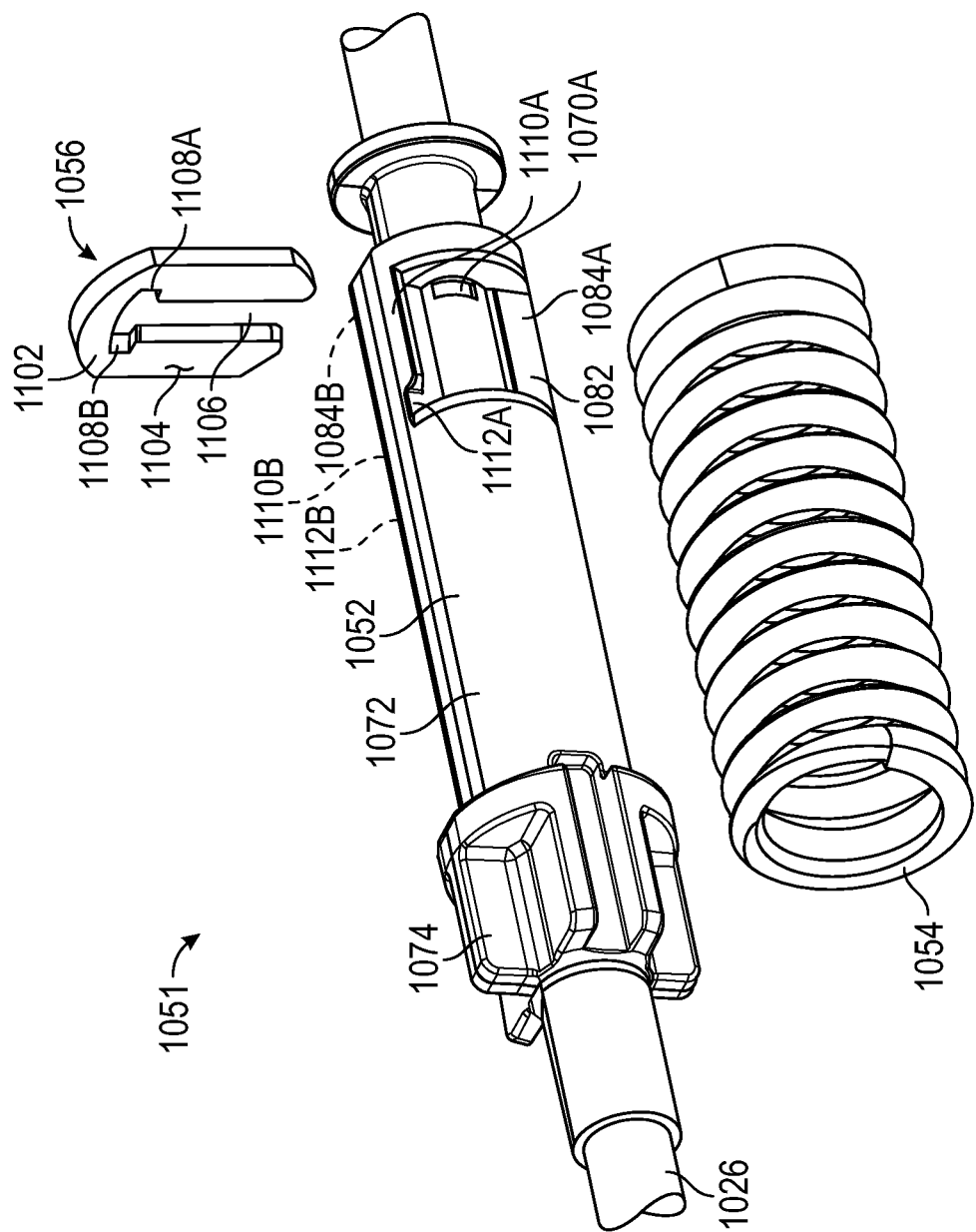
FIG. 6A illustrates a partially exploded view of the drive shaft motion transfer assembly of FIG. 5A showing the drive shaft motion transfer body assembled onto the drive shaft.
Figure 6B:
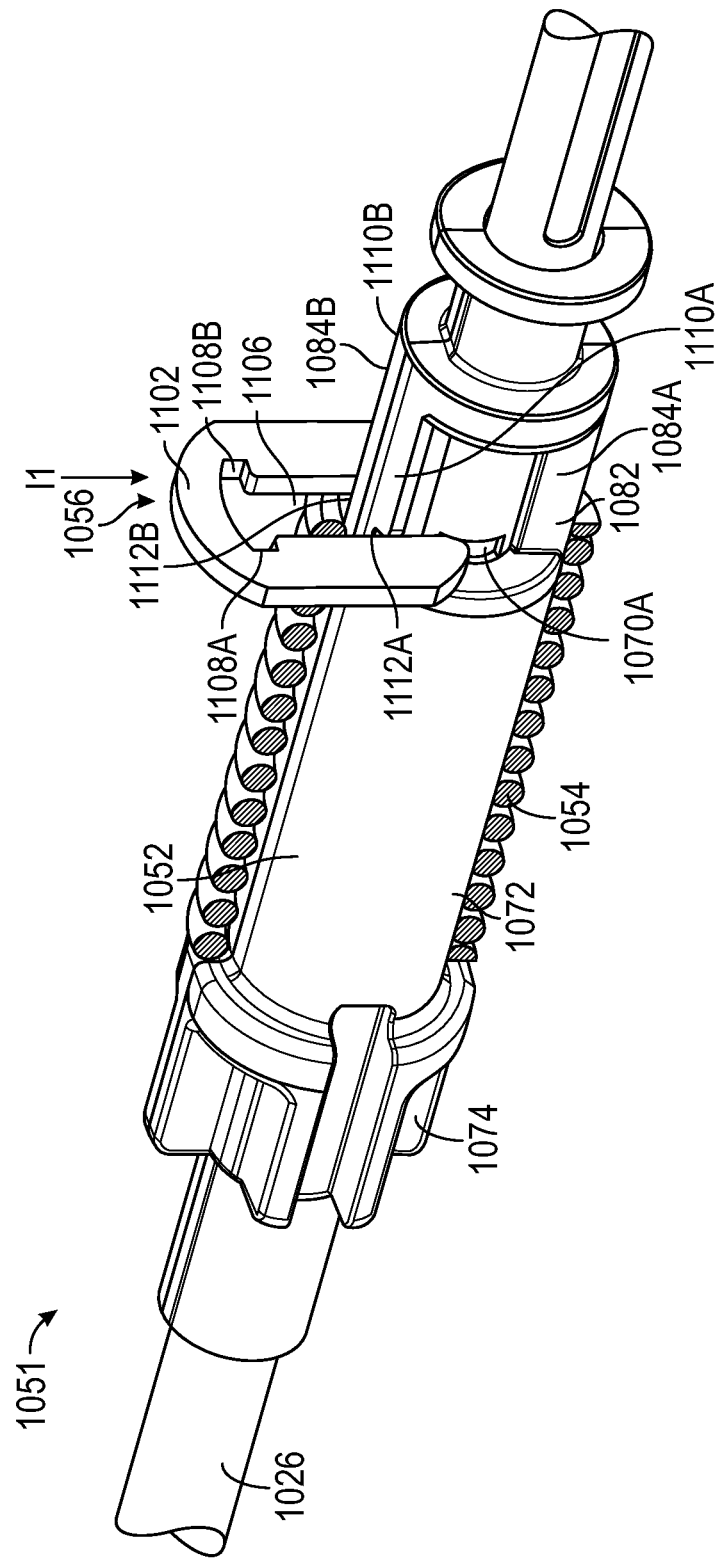
FIG. 6B illustrates an isometric view of the drive shaft motion transfer assembly of FIG. 5A in a partially assembled state, with the spring shown in cross-section.
Figure 6C:
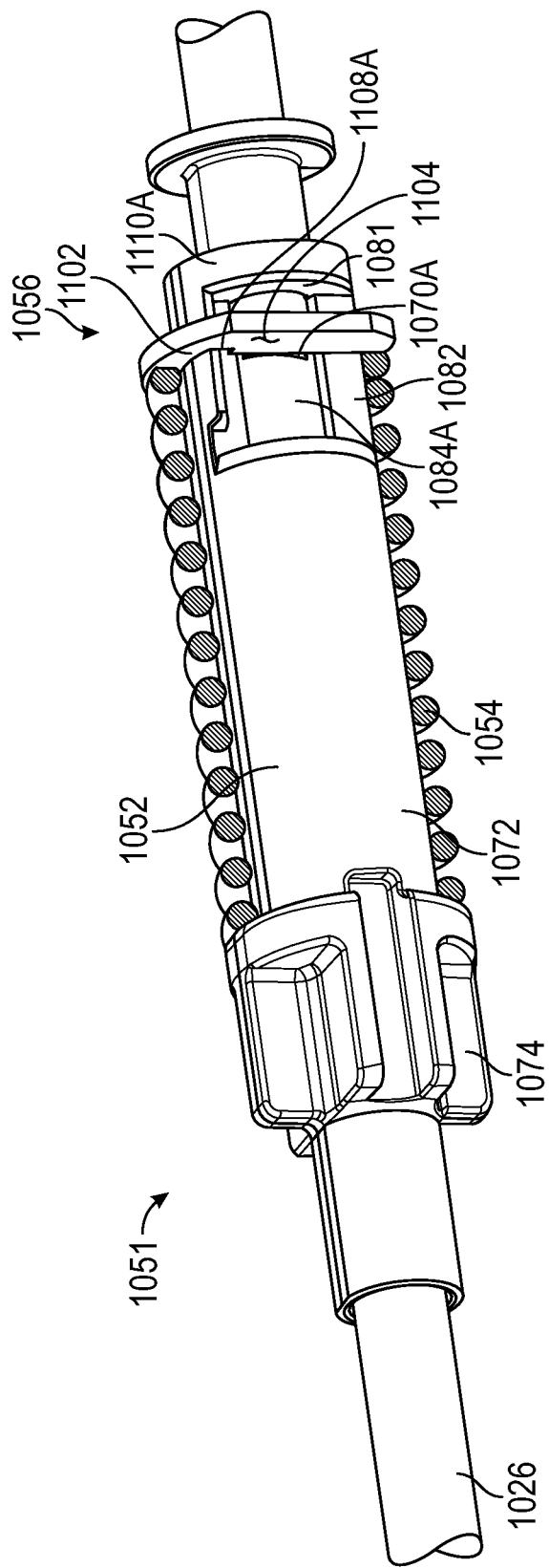
FIG. 6C illustrates an isometric view of the drive shaft motion transfer assembly of FIG. 5A, with the spring shown in cross-section.

FIG. 6A is a partially exploded view of the motion transfer assembly 1051 including the first example of the drive body 1052 and the first example of the clip 1056 showing the drive body 1052 on the drive shaft 1026. FIG. 6B is an isometric view of the first example of the drive body 1052 and the first example of the clip 1056 showing the force-limiting spring 1054 compressed and the clip 1056 being assembled onto the drive shaft 1026 along an insertion direction I1. FIG. 6C is a view of the first example of the drive body 1052 and the first example of the clip 1056 in a force limiting state (e.g., an over-travel position). FIGS. 6A, 6B, and 6C will be discussed together to illustrate how the drive body 1052, the force-limiting spring 1054, and the clip 1056 are assembled onto the drive shaft 1026.

The drive shaft 1026 can include the first vertical slot 1070A and the second vertical slot 1070B. The drive body 1052 can include the body portion 1072, the anchor portion 1074, and the window portion 1082 (including the first window 1084A and the second window 1084B). The clip 1056 can include the clip body 1102, the proximal spring seat 1104, the clip slot 1106, the clip notches 1108A and 1108B (including the first clip notch 1108A and the second clip notch 1108B). The window portion 1082 can further include the retaining ribs 1110A and 1110B (including first retaining rib 1110A and second retaining rib 1110B) and the window notches 1112A and 1112B (including first window notch 1112A and second window notch 1112B). The drive shaft 1026, the drive body 1052, the force-limiting spring 1054, and the clip 1056 can have the same structure and function as described with respect to FIGS. 1A-5C.

To assemble the drive body 1052, the force-limiting spring 1054 and the clip 1056 onto the drive shaft 1026, first the drive body 1052 can be positioned on the drive shaft 1026. Second, the force-limiting spring 1054 can be positioned on the drive body 1052 around the body portion 1072 and the window portion 1082 of drive body 1052. Third, the force-limiting spring 1054 can be slid onto the drive body 1052 from the proximal ends of the drive shaft 1026 and the drive body 1052. Fourth, the force-limiting spring 1054 can be compressed against the anchor portion 1074 such that the force-limiting spring 1054 is not positioned around the window notches 1112A and 1112B, as shown in FIG. 5C. The drive body 1052 can be positioned on the drive shaft 1026 such that first vertical slot 1070A and second vertical slot 1070B in the drive shaft 1026 are aligned with the window notches 1112A and 1112B in the window portion 1082 of the drive body 1052. The first vertical slot 1070A and the second vertical slot 1070B can be visible through the first window 1084A and the second window 1084B when the first vertical slot 1070A and the second vertical slot 1070B are aligned with the window portion 1082. The clip 1056 can then be positioned onto the window portion 1082 of drive body 1052 at the window notches 1112A and 1112B such that the clip 1056 also extends through first vertical slot 1070A and second vertical slot 1070B in the drive shaft 1026, as shown in FIG. 6B. In this method of assembly the clip 1056 does not need to flex, stress or deform during assembly, in order to be installed.

As shown in FIG. 6C, the compression force is then removed from the force-limiting spring 1054, and the force-limiting spring 1054 expands towards a preloaded state between anchor portion 1074 and the clip 1056, pushing the clip 1056 longitudinally within the window portion 1082 until the clip 1056 is against the clip support surface 1081 of body portion 1072 adjacent a proximal end of the window portion 1082, or proximal ends of first window 1084A and second window 1084B.

The clip notches 1108A and 1108B can engage retaining ribs 1110A and 1110B (e.g., or another retention element) as the clip 1056 is moved proximally with respect to the window notches 1112A and 1112B. As shown in FIG. 6C, which also illustrates the position of the clip 1056 relative to the drive body 1052 in the force limiting or over-travel state, the drive body 1052 moves proximally relative to the clip 1056. As such, the clip 1056 can move longitudinally within the first window 1084A and the second window 1084B at the window portion 1082. The clip 1056 can travel within the window portion 1082. The clip 1056 cannot travel longitudinally outside of the window portion 1082 because the body portion 1072 on either side of the window portion 1082 can stop the clip 1056.

The window notches 1112A and 1112B can function as slots that allow the clip 1056 to be assembled onto the retaining ribs 1110A and 1110B. Keeping the clip 1056 within the length of the retaining ribs 1110A and 1110B is desirable as the fit between the clip notches 1108A and 1108B and retaining ribs 1110A and 1110B retains the clip 1056 on the drive body 1052 and the drive shaft 1026. Positioning the clip 1056 onto the window portion 1082 and within first vertical slot 1070A and second vertical slot 1070B rotationally locks the clip 1056 to the drive body 1052 and rotationally and longitudinally locks the clip 1056 to the drive shaft 1026. The fit between the retaining ribs 1110 and 1110B and the clip notches 1108A and 1108B can help to transmit a rotational torque between the drive body 1052 and the clip 1056. Compressing the force-limiting spring 1054 to place the clip 1056 on drive body 1052 provides the force-limiting spring 1054 a preload, which affects the amount of force necessary to initiate the force limiting state (e.g., the over-travel state). The higher the preload on the force-limiting spring 1054, the more force a user must apply before the force limiting state is initiated.

Figure 7A:
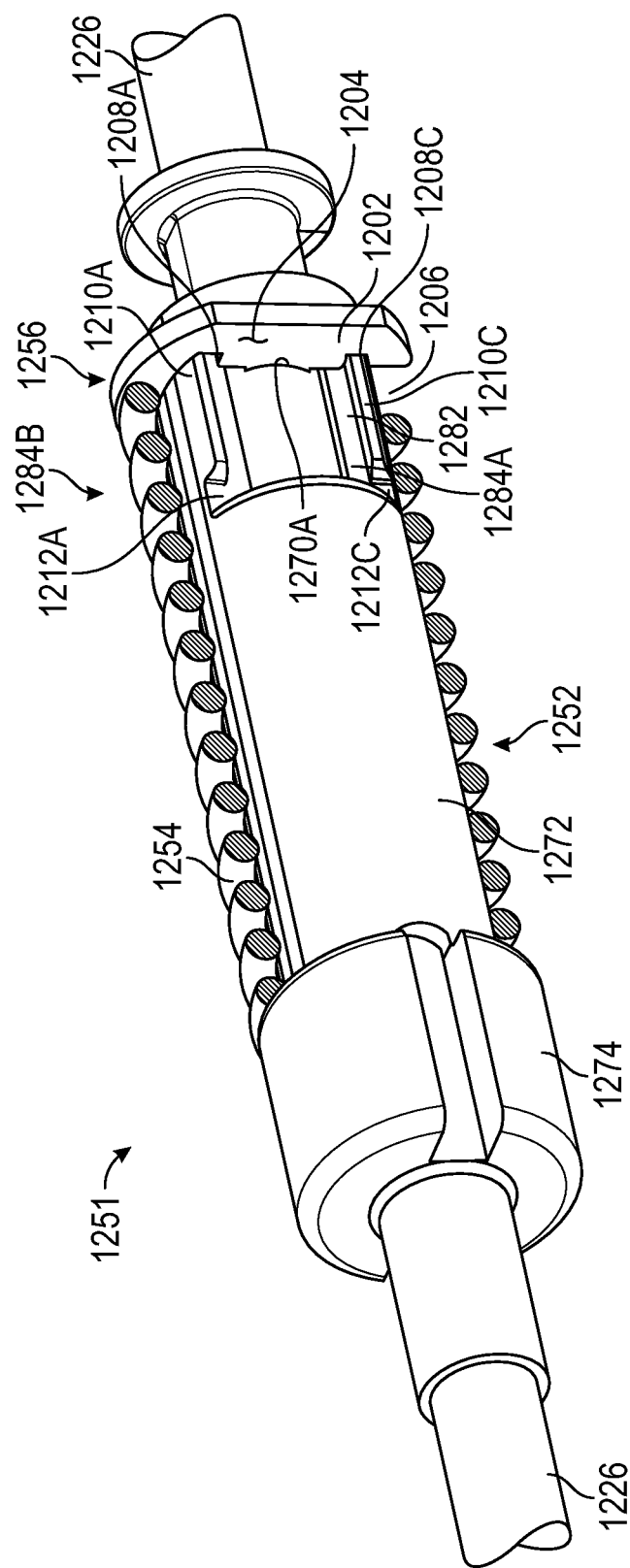
FIG. 7A illustrates an isometric view of a second example of a drive shaft motion transfer assembly that can be used with the forceps of FIG. 1A.
Figure 7B:
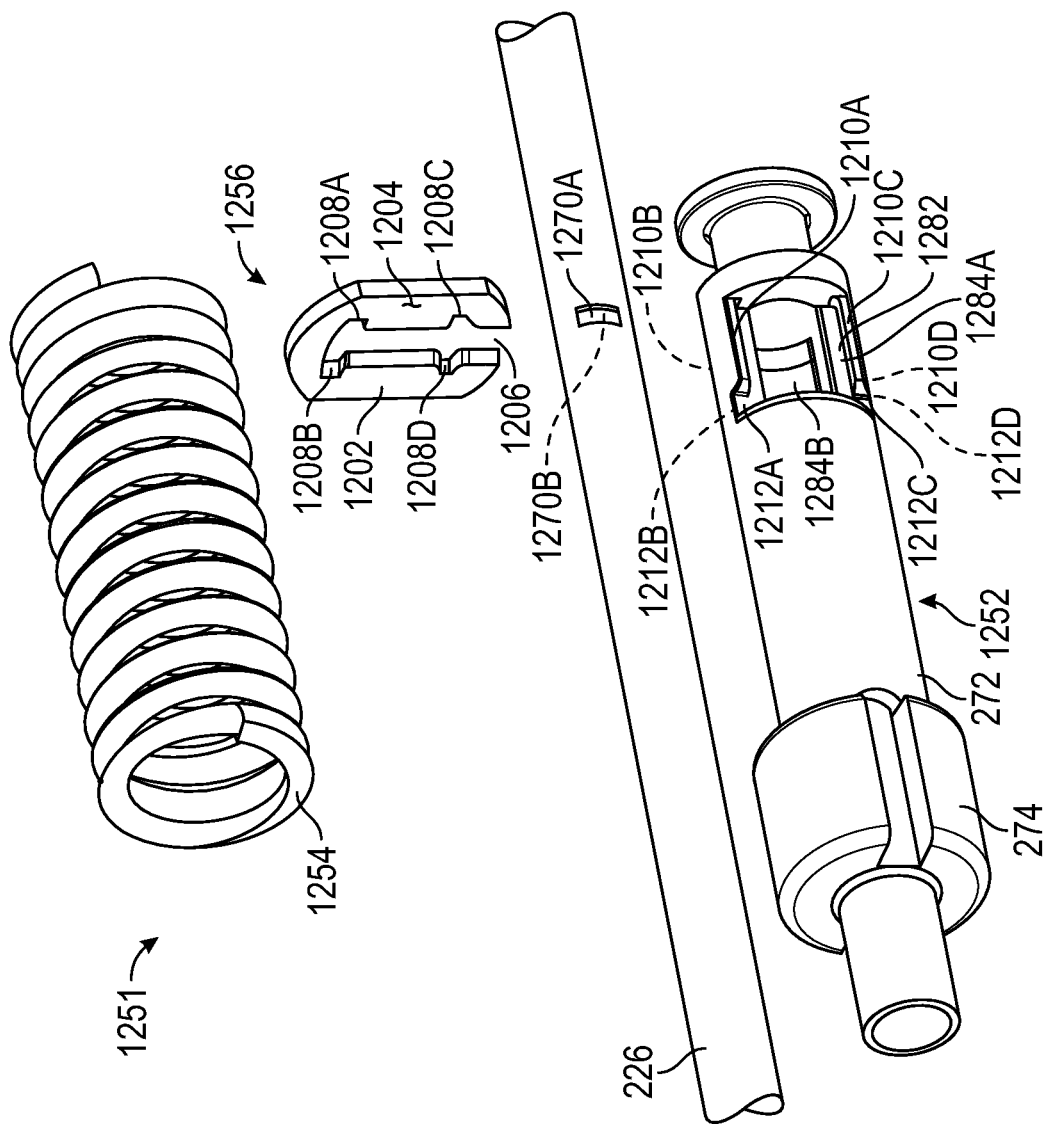
FIG. 7B illustrates an exploded view of the second example of the drive shaft motion transfer assembly of FIG. 7A.

FIG. 7A is an isometric view of a second example of a motion transfer assembly 1251 showing a drive body 1252, a clip 1256, and a cross section of a spring 1254 on a drive shaft 1226. FIG. 7B is an exploded view of the drive body 1252 and the clip 1256, the spring 1254 and the drive shaft 1226. The drive body 1252 can include a body portion 1272, a window portion 1282 and an anchor portion 1274. FIGS. 7A and 7B are discussed together and include features to improve clip 1256 retention to prevent backout of a clip 1256 and for torque transfer from a drive body 1252 to a clip 1256. One benefit of the example of FIGS. 7A and 7B includes a duplication of slots and retaining ribs to increase the surface that facilitates torque transfer and prevents clip 1256 backout.

The window portion can include a first window 1284A, a second window 1284B, a first retaining rib 1210A, a second retaining rib 1210B, a third retaining rib 1210C, a fourth retaining rib 1210D, a first window notch 1212A, a second window notch 1212B, a third window notch 1212C, and a fourth window notch 1212D).

The clip 1256 can include a clip body 1202, a proximal spring seat 1204, a clip slot 1206, a first clip notch 1208A, a second clip notch 1208B, a third clip notch 1208C, and a fourth clip notch 1208D. The drive shaft 1226 includes a first vertical slot 1270A and a second vertical slot 1270B.

The drive body 1252 has the clip 1256 positioned on the drive body 1252 and connected to the drive shaft 1226, which extends through the drive body 1252. The spring 1254 is positioned around the drive body 1252. The drive body 1252 has generally the same structure and function as the drive body 1252 described with respect to FIGS. 1A-6C, including the body portion 1272 and the window portion 1282 having the first window 1284A and the second window 1284B. However, the drive body 1252 has the third retaining rib 1210C, the fourth retaining rib 1210D, the third window notch 1212C, and the fourth window notch 1212D at a bottom of the drive body 1252, and the anchor portion 1274 can be cylindrical.

The first retaining rib 1210A can extend into the first window 1284A from a top of the body portion 1272. The first retaining rib 1210A can extend from an upper portion of the top of the body portion 1272 such that the first retaining rib 1210A forms a first lip at the top of the body portion 1272. The second retaining rib 1210B can extend into the second window 1284B from a top of the body portion 1272. The second retaining rib 1210B can extend from an upper portion of the top of body portion 1272 such that second retaining rib 1210B forms a second lip at the top of the body portion 1272. The first retaining rib 1210A and the second retaining rib 1210B can form a pair of retaining ribs. The third retaining rib 1210C can extend into the first window 1284A from a bottom of the body portion 1272. The third retaining rib 1210C can extend from a lower portion of the bottom of the body portion 1272 such that the third retaining rib 1210C forms a third lip at the bottom of the body portion 1272. The fourth retaining rib 1210D can extend into the second window 1284B from a bottom of the body portion 1272. The fourth retaining rib 1210D can extend from a lower portion of the bottom of the body portion 1272 such that the fourth retaining rib 1210D forms a fourth lip at the bottom of the body portion 1272. The third retaining rib 1210C and the fourth retaining rib 1210D can form a pair of retaining ribs. The first window notch 1212A can be part of the first window 1284A at a distal end of the first retaining rib 1210A. The second window notch 1212B can be part of the second window 1284B at a distal end of the second retaining rib 1210B. The third window notch 1212C can be part of the first window 1284A at a distal end of the third retaining rib 1210C. The fourth window notch 1212D can be part of the second window 1284B at a distal end of the fourth retaining rib 1210D.

The clip 1256 can have generally the same structure and function as the clip 1056 described with respect to FIGS. 1A-6C, including the clip body 1202, the proximal spring seat 1204, and the clip slot 1206. However, in some examples the clip 1256 can further include the third clip notch 1208C and the fourth clip notch 1208D. The first clip notch 1208A can extend into the clip body 1202 from a first side of the clip slot 1206 at a top of the clip slot 1206, and the second clip notch 1208B can extend into the clip body 1202 from a second side of the clip slot 1206 at the top of the clip slot 1206. As such, the second clip notch 1208B can extend into the clip body 1202 from the clip slot 1206 opposite the first clip notch 1208A. The third clip notch 1208C can extend into the clip body 1202 from the first side of the clip slot 1206 near a bottom of the clip slot 1206, and the fourth clip notch 1208D can extend into the clip body 1202 from the second side of the clip slot 1206 near the bottom of the clip slot 1206. As such, the third clip notch 1208C is spaced from the first clip notch 1208A, and the fourth clip notch 1208D can extend into the clip body 1202 from the clip slot 1206 opposite the third clip notch 1208C and is spaced from the second clip notch 1208B. The drive shaft 1226 that receives the clip can be the same as or similar to the drive shaft 1226 described with respect to FIGS. 1A-6C, including the first vertical slot 1270A and the second vertical slot 1270B.

When the drive body 1252 is on the drive shaft 1226, the clip 1256 can be positioned on the window portion 1282 of the drive body 1252. The clip slot 1206 can fit around the drive body 1252 at the window portion 1282 and can fit around the drive shaft 1226 at the first vertical slot 1270A and the second vertical slot 1270B such that the clip 1256 fits within and is accepted by the first vertical slot 1270A and the second vertical slot 1270B of the drive shaft 1226. A proximal end of the spring 1254 can contact the proximal spring seat 1204 of the clip 1256. The first clip notch 1208A can fit around the first retaining rib 1210A such that the first retaining rib 1210A fits within the first clip notch 1208A. The second clip notch 1208B can fit around the second retaining rib 1210B such that the second retaining rib 1210B fits within the second clip notch 1208B. The third clip notch 1208C can fit around the third retaining rib 1210C such that the third retaining rib 1210C fits within the third clip notch 1208C. The fourth clip notch 1208D can fit around the fourth retaining rib 1210D such that the fourth retaining rib 1210D fits within the fourth clip notch 1208D. The clip 1256 can move longitudinally within the first window 1284A and the second window 1284B at the window portion 1282 along the first retaining rib 1210A, the second retaining rib 1210B, the third retaining rib 1210C, and the fourth retaining rib 1210D.

The clip notches 1208A, 1208B, 1208C, and 1208D and the retaining ribs 1210A, 1210B, 1210C, and 1210D can fit together to retain the clip 1256 to the drive body 1252 and the drive shaft 1226 and rotationally lock the clip 1256 to the drive body 1252 while allowing the clip 1256 to move longitudinally within the first window 1284A and the second window 1284B along the retaining ribs 1210A, 1210B, 1210C, and 1210D. As a result, the clip 1256 is prevented from popping off the drive body 1252 and the drive shaft 1226 while being capable of longitudinal movement along axis A1 (FIG. 1B) with respect to the drive body 1252.

Because the drive body 1252 has the third retaining rib 1210C and the fourth retaining rib 1210D that can fit into the third clip notch 1208C and the fourth the clip notch 1208D of the clip 1256, the clip 1256 can more evenly and securely be retained on the drive body 1252 and the drive shaft 1226.

Figure 8A:
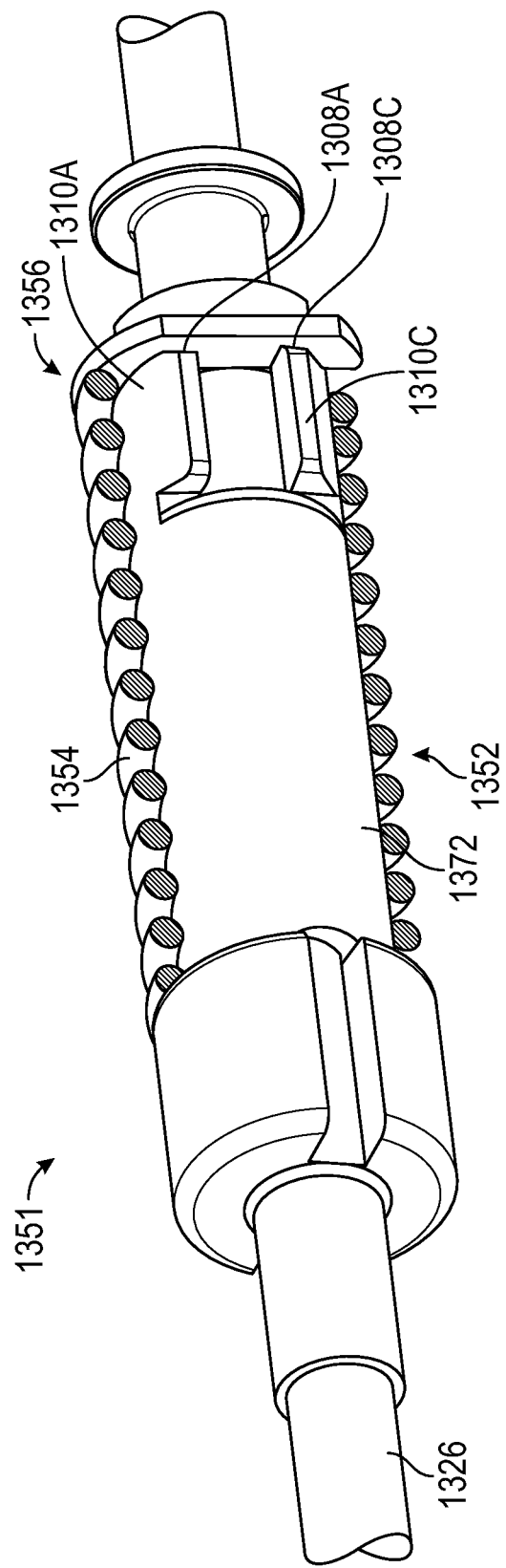
FIG. 8A illustrates an isometric view of a third example of a drive shaft motion transfer assembly that can be used with the forceps of FIG. 1A.
Figure 8B:
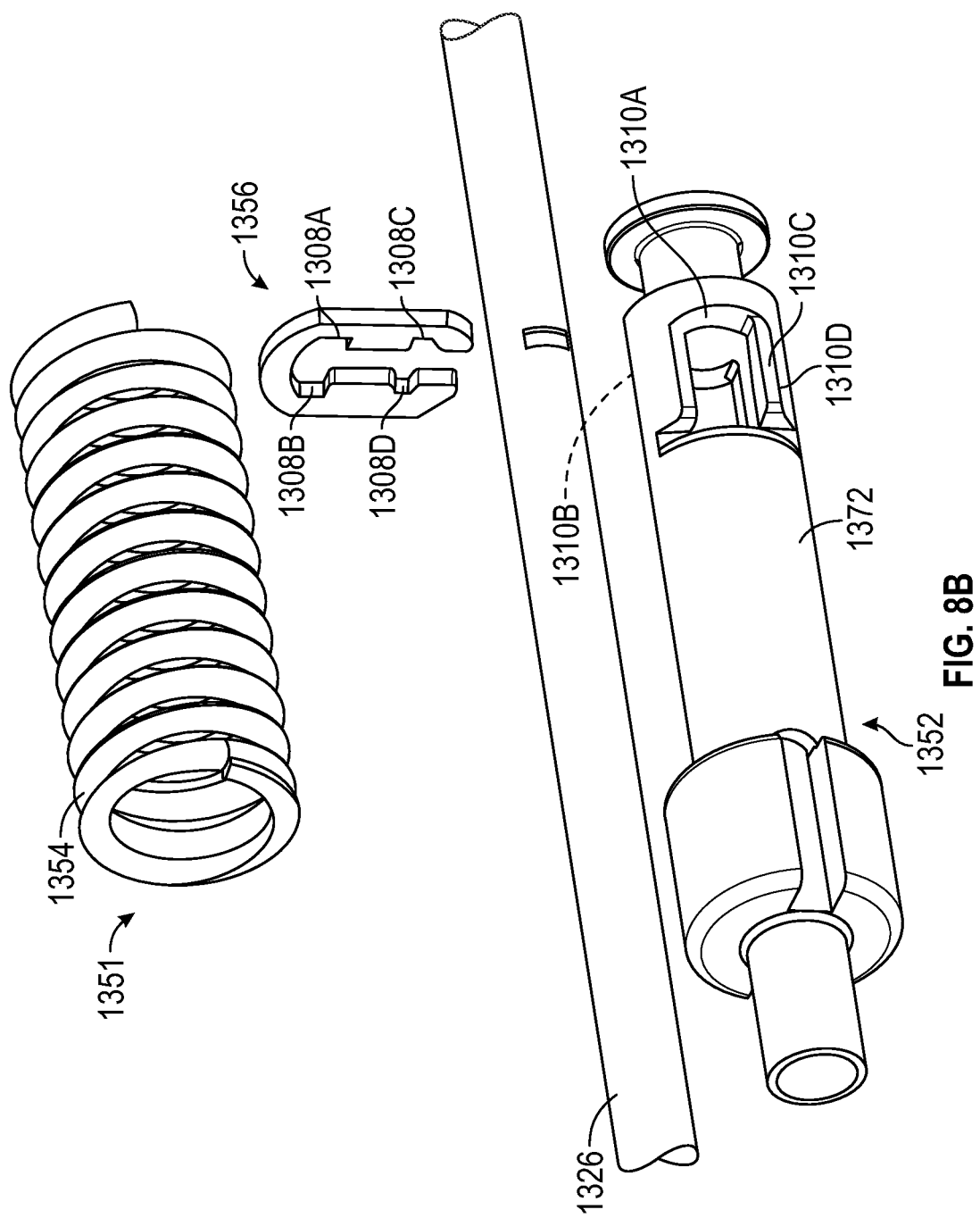
FIG. 8B illustrates an exploded view of the third example of the drive shaft motion transfer assembly of FIG. 8A.

FIG. 8A is an isometric view of a third example of a motion transfer assembly 1351 showing a drive body 1352, a clip 1356 and a cross-section of spring 1354 on a drive shaft 1326. FIG. 8B is an exploded view of the drive body 1352, the clip 1356, the spring 1354 and the drive shaft 1326. The drive body 1352 can include a body portion 1372, a first retaining rib 1310A, a second retaining rib 1310B, a third retaining rib 1310C, and a fourth retaining rib 1310D. The clip 1356 can include a first clip notch 1308A, a second clip notch 1308B, a third the clip notch 1308C, and a fourth the clip notch 1308D. FIGS. 8A and 8B are discussed together and include features to improve clip 1356 retention to prevent backout of a clip 1356 and for torque transfer from a drive body 1352 to a clip 1356. One benefit of the example of FIGS. 8A and 8B includes a duplication of slots and retaining ribs to increase the surface that facilitates torque transfer and prevents clip 1356 blackout.

The drive body 1352 can have the clip 1356 positioned on the drive body 1352 and coupled to the drive shaft 1326. The spring 1354 can be positioned around the drive body 1352. The drive body 1352 can have generally the same structure and function as the drive body 1252 described with respect to FIGS. 7A and 7B, including the body portion 1372. However, the first retaining rib 1310A, the second retaining rib 1310B, the third retaining rib 1310C, and the fourth retaining rib 1310D can be thicker and longer. The first retaining rib 1310A and the second retaining rib 1310B can extend from all or most of a top of the body portion 1372. The third retaining rib 1310C and the fourth retaining rib 1310D can extend from all or most of a bottom of the body portion 1372.

The clip 1356 has generally the same structure and function as the clip 1256 described with respect to FIGS. 7A and 7B. However, the first clip notch 1308A, the second clip notch 1308B, the third clip notch 1308C and the fourth clip notch 1308D can be larger and deeper to accommodate the retaining ribs 1310A, 1310B, 1310C, and 1310D which can be thicker and longer. The drive shaft 1326 can be the same as the drive shaft 1026 described with respect to FIGS. 1A-6C.

The clip notches 1308A, 1308B, 1308C, and 1308D and the retaining ribs 1310A, 1310B, 1310C, and 1310D can fit together to retain the clip 1356 to the drive body 1352 and the drive shaft 1326 and rotationally lock the clip 1356 to the drive body 1352 while allowing the drive body 1352 to move longitudinally relative to the clip 1356 along the retaining ribs 1310A, 1310B, 1310C, and 1310D. As a result, the clip 1356 can be inhibited or prevented from popping off the drive body 1352 and the drive shaft 1326 while being capable of longitudinal movement with respect to the drive body 1352.

Figure 9A:
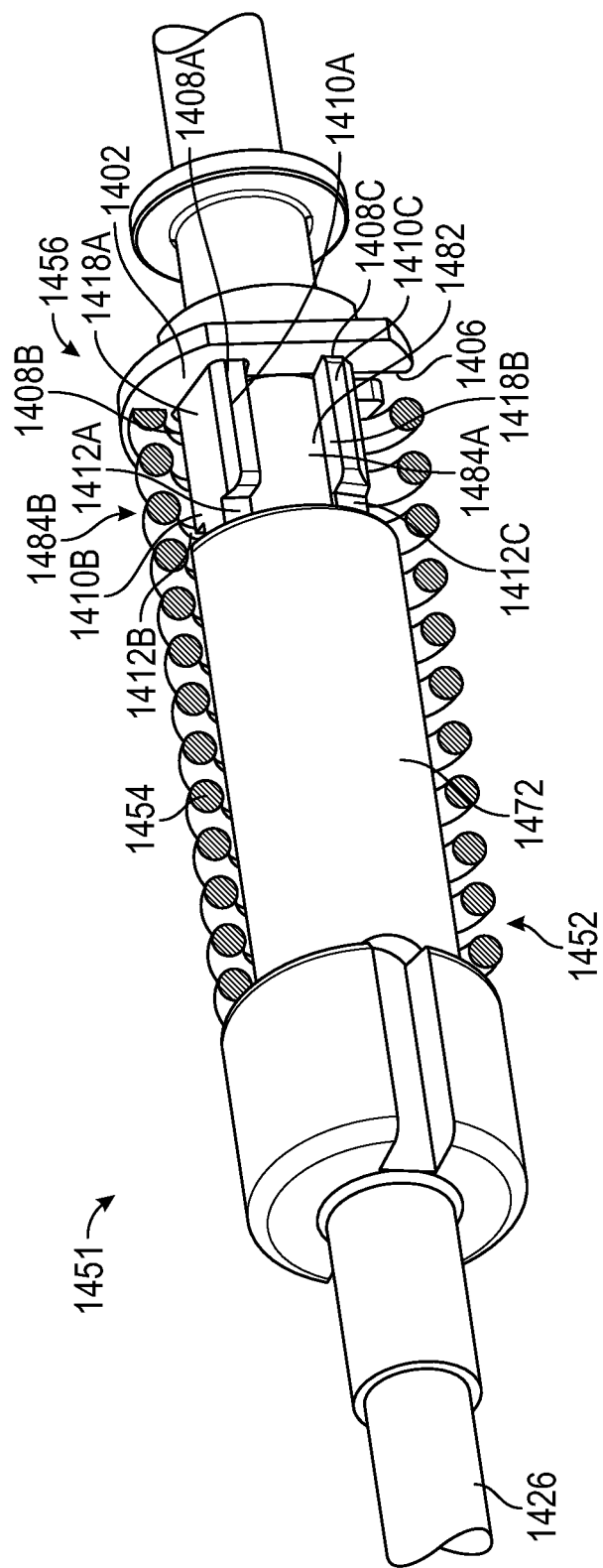
FIG. 9A illustrates an isometric view of a fourth example of a drive shaft motion transfer assembly that can be used with the forceps of FIG. 1A.
Figure 9B:
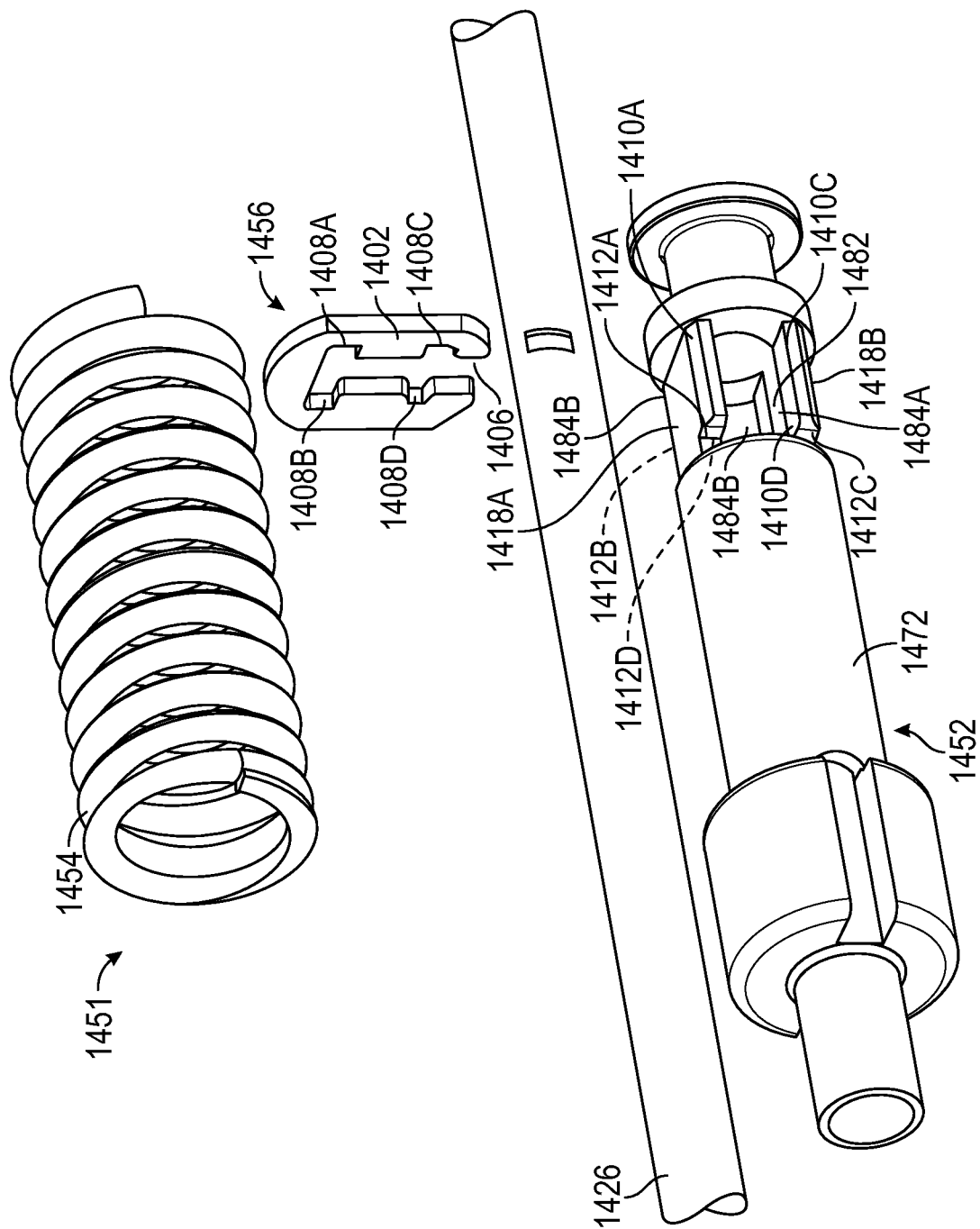
FIG. 9B illustrates an exploded view of the fourth example of the drive shaft motion transfer assembly of FIG. 9A.

FIG. 9A is an isometric view of a fourth example of a motion transfer assembly 451 showing a drive body 1452, a clip 1456 and a cross-section of a spring 1454 on a drive shaft 1426. FIG. 9B is an exploded view of the drive body 1452, the clip 1456, the spring 1454 and the drive shaft 1426. The drive body 1452 can include a body portion 1472, a window portion 1482 and struts 1418. The window portion 1482 can include a first window 1484A, a second window 1484B, a first retaining rib 1410A, a second retaining rib 1410B, a third retaining rib 1410C, a fourth retaining rib 1410D, a first window notch 1412A, a second window notch 1412B, a third window notch 1412C, and a fourth window notch 1412D. The struts 1418 can include a first strut 1418A and a second strut 1418B. The clip 1456 can include a clip body 1402, a clip slot 1406, a first clip notch 1408A, a second clip notch 1408B, a third clip notch 1408C, and a fourth clip notch 1408D. FIGS. 9A and 9B are discussed together and include features to improve clip 1456 retention to prevent backout of a clip 1456 and for torque transfer from a drive body 1452 to a clip 1456. One benefit of the example of FIGS. 9A and 9B includes a duplication of slots and retaining ribs to increase the surface that facilitates torque transfer and prevents clip 1456 backout.

The drive body 1452 has the clip 1456 positioned on the drive body 1452 and connected to the drive shaft 1426, which can extend through drive body 1452. The spring 1454 can be positioned around the drive body 1452.

The drive body 1452 can have generally the same structure and function as the drive body 1352 described with respect to FIGS. 8A and 8B, including the body portion 1472 and the window portion 1482 having the first window 1484A, the second window 1484B, the retaining ribs 1410A, 1410B, 1410C, and 1410D, and the window notches 1412A, 1412B, 1412C, and 1412D. However, the window portion 1482 can include the struts 1418. A top of the body portion 1472 at the window portion 1482 can be flat. When the top of the body portion 1472 at the window portion 1482 is flat, a close connection between a profile of the retaining ribs 1410A, 1410B, 1410C, 1410D and the profile of the respective window notches 1412A, 1412B, 1412C and 1412D can be achieved. As such, the first retaining rib 1410A, the top portion of the body portion 1472, and the second retaining rib 1410B form the first strut 1418A. Likewise, a bottom of the body portion 1472 can be flat. As such, the third retaining rib 1410C, the bottom of the body portion 1472, and the fourth retaining rib 1410D can form the second strut 1418B. Thus, the first window 1484A can be between the first strut 1418A and the second strut 1418B at a first side of the body portion 1472, and the second window 1484B can be between the first strut 1418A and the second strut 1418B at a second side of the body portion 1472.

Although in some examples it may be beneficial that the top of the body portion 1472 at the window portion 1482 are flat, in other embodiments, the top of the body portion 1472 at the window portion 1482 may not be flat or substantially flat. Other shapes may be provided that provide a close connection between the retaining ribs 1410A, 1410B, 1410C, 1410D and the respective window notches 1412A, 1412B, 1412C and 1412D.

The clip 1456 can have generally the same structure and function as the clip 1356 described with respect to FIGS. 8A and 8B, including the clip body 1402, the clip slot 1406, the first clip notch 1408A, the second clip notch 1408B, the third the clip notch 1408C, and the fourth the clip notch 1408D.

However, the clip slot 1406, the first clip notch 1408A, and the second clip notch 1408B can be flat at the top while the third clip notch 1408C and the fourth clip notch 1408D can have flat bottoms to accommodate the struts 1418. The clip slot 1406 can extend into the clip body 1402 to a lesser extent such that the top of the clip slot 1406, between the first clip notch 1408A and the second clip notch 1408B, may be flat.

The drive shaft 1426 can be the same as the drive shaft 1026 described with respect to FIGS. 1A-6C. The clip notches 1408A, 1408B, 1408C, and 1408D and the retaining ribs 1410A, 1410B, 1410C, and 1410D can fit together to retain the clip 1456 to the drive body 1452 and the drive shaft 1426 and rotationally lock the clip 1456 to the drive body 1452 while allowing the drive body 1452 to move longitudinally relative to the clip 1456 along the retaining ribs 1410A, 1410B, 1410C, and 1410D. As a result, the clip 1456 can be prevented from popping off the drive body 1452 and the drive shaft 1426 while being capable of longitudinal movement with respect to the drive body 1452. Further, because the clip slot 1406 may extend into the clip body 1402 to a lesser extent, the clip body 1402 has more surface area to distribute the load from the spring 1454.

Figure 11A:
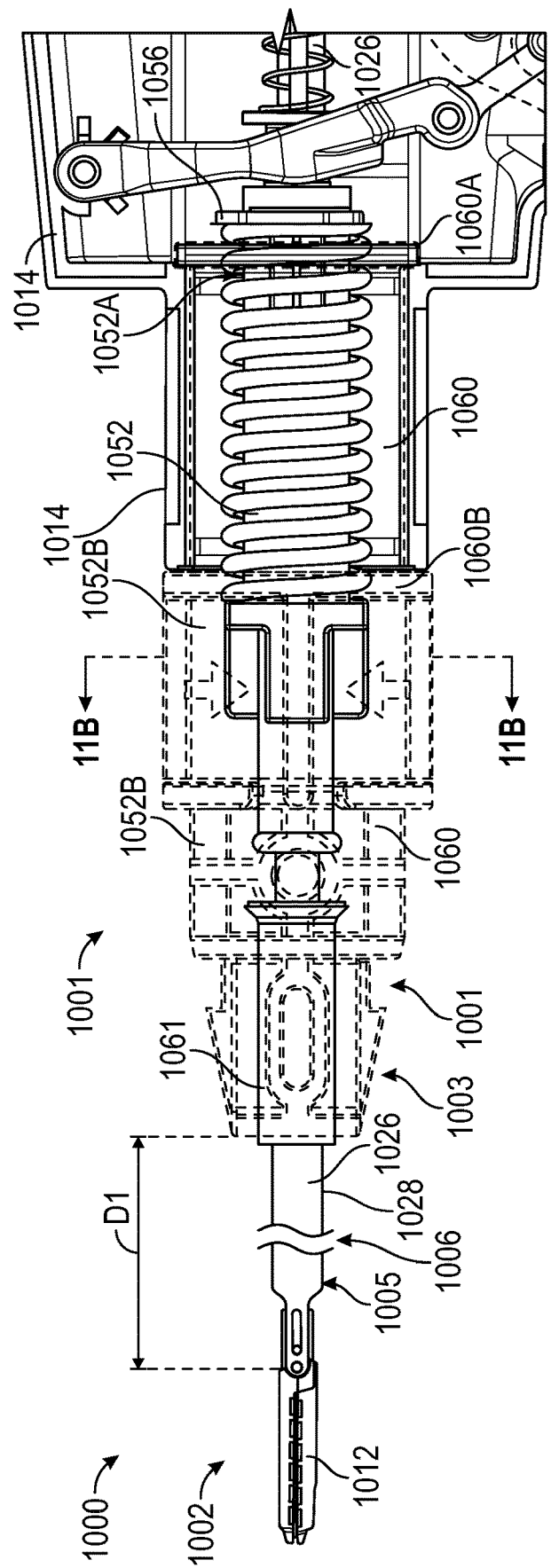
FIG. 11A illustrates a side view of a portion of the forceps of FIG. 1A with the outer hub shown in phantom.
Figure 11B:
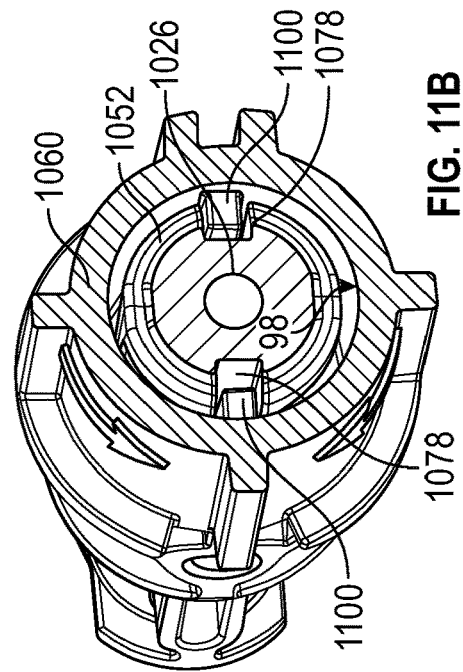
FIG. 11B is a cross-sectional view of the outer hub and the drive body of the shown in FIG. 11A along line 11B-11B' with the outer hub shown in solid.

FIG. 10A, FIG. 10A, FIG. 11A and FIG. 11B illustrate an example of how the drive shaft 1026 and outer shaft 1028 can be constrained to one another and to the outer hub 1060 and rotational actuator 1030. FIG. 10A illustrates a side view of a portion of the forceps of FIG. 1A, in accordance with at least one example. FIG. 10A includes the outer shaft 1028, the outer hub 1060, the housing 1014 and the rotational actuator 1030 (shown in phantom). FIG. 10A is a cross-sectional view of the rotational actuator 1030 and outer hub 1060 of FIG. 10A along line 10A-10A' but with the rotational actuator 1030 shown in solid, in accordance with at least one example.

The outer hub 1060 can be located around at least a portion of the drive body 1052 and the drive shaft 1026. To transfer rotational motion from the outer hub 1060 to the drive shaft 1026, the rotational motion received from the rotational actuator 1030 can be transferred to the outer hub 1060; transferred from the outer hub 1060 to the drive body 1052; transferred from the drive body 1052 to the clip 1056; and transferred from the clip 1056 to the drive shaft 1026. The rotational input received from the rotational actuator 1030 can also be transferred from the outer hub 1060 to the outer shaft 1028 to rotate the outer shaft 1028. In other examples, the clip 1056 can be omitted and/or the passageway 1092 (e.g., bore) in the drive body 1052 can be rotationally keyed to the drive shaft 1026 to transfer the rotational input.

As shown in the combination of FIG. 10A and FIG. 10B, at the proximal portion of the forceps 1000, the rotational actuator 1030 can be constrained to the outer hub 1060 via a keyed interface. For example, the rotational actuator 1030 can include an actuator-hub keyed interface 1033 that is configured to be rotationally constrained to the outer hub 1060 having a complimentary actuator-hub keyed interface 1063. The keyed interface 1033, 1063 can constrain, couple, fix, lock, or limit rotation between the rotational actuator 1030 and the outer hub 1060.

In this arrangement, the outer hub 1060 can be configured to receive a rotational input from the rotational actuator 1030 such that the rotational actuator 1030 and outer hub 1060 can be rotated relative to the housing 1014. In alternate examples, the rotational actuator 1030 can be otherwise attached to the outer hub 1060, such as by integral molding, adhesive, welding, snap-fit, or any other suitable method. In some examples, the rotational actuator 1030 can be omitted and the outer hub 1060 can function as an actuator to receive a rotational input from a user directly. The rotational actuator 1030 is merely shown as one example of a component to receive a rotational input from a user, any suitable rotational input device can be provided.

FIG. 11A illustrates a side view of a portion of the forceps of FIG. 1A including the housing 1014, the drive shaft 1026, the outer shaft 1028, the drive body 1052 (having a first portion 1052A and a second portion 1052B), the force-limiting spring 1054, the drive link 1046, the outer hub 1060 (shown in phantom), the sleeve 1061, and the jaws 1012 in accordance with at least one example. FIG. 11B is a cross-sectional view of the outer hub 1060 and the drive body 1052 of FIG. 11A along line 11B-11B' with the outer hub 1060 shown in solid, in accordance with at least one example.

To rotationally fix the outer hub 1060 to the drive body 1052, the outer hub 1060 and the drive body 1052 can include a hub-body keyed interface. For example, the outer hub 1060 can include the anti-rotation key 1100, and the drive body 1052 can have a complimentary hub-body keyed interface, such as rotational keying slot 1078. The rotational keying slot 1078 can be located at a second portion 1052B of the drive body 1052 (e.g., distal portion). In this arrangement, the drive body 1052 can be configured to receive a rotational input from the outer hub 1060, supplied to the outer hub 1060 by the rotational actuator 1030 (FIG. 10A, 10B).

The anti-rotation key 1100 can include a ridge that extends out of the interior surface 1098 of the outer hub 1060 into the channel formed by the interior surface 1098. The anti-rotation key 1100 can be sized to fit within the rotational keying slot 1078 of the outer hub 1060. The rotational keying slot 1078 can accept the anti-rotation key 1100 such that the rotational keying slot 1078 can be linearly translated, or otherwise longitudinally moved, along the anti-rotation key 1100 in order to allow retraction and extension of the drive body 1052 with respect to the outer hub 1060 and the housing 1014.

In other words, the anti-rotation key 1100 and rotational keying slot 1078 constrain the outer hub 1060 and the drive body 1052 rotationally, but the drive body 1052 can still move (e.g., slide, translate) along the longitudinal axis A1 relative to the outer hub 1060 when the lever 1024 is actuated by a user (FIG. 1B). The longitudinal movement of the outer hub 1060 relative to the drive body 1052 allows the drive body 1052 to retract relative to the outer hub 1060 when the lever 1024 is actuated to close the jaws 1012. Such retraction of the drive body 1052 results in retraction of the drive shaft 1026, up until a specified input force F1 is applied to the lever 1024 (FIG. 13B) that exceeds the preload of the force-limiting spring 1054. When the input force F1 exceeds the specified input force, the drive body 1052 can continue to move proximally with respect to the drive shaft 1026 and without retracting the drive shaft 1026. Thereby protecting the end effector 1002 from receiving an excessive force and becoming damaged.

Traditional forceps sometimes include an outer shaft and an inner shaft that are only rotationally locked together at a distal end near an end effector. In such configurations, a rotational input received at a rotational actuator only rotates a proximal end of an outer shaft, but not the inner shaft, to rotate the jaws. In traditional forceps, only when the jaws rotate, does a distal end of the inner shaft receive the rotational motion from a connection of the outer shaft to the inner shaft proximate the end effector, which eventually causes rotation of the inner shaft at a proximal end. A limitation of such a design is that the inner shaft and the outer shaft can "wind up" relative to each other and become damaged as a result.

In contrast, the illustrative forceps 1000 can rotationally constrain the inner drive shaft 1026 to the outer shaft 1028 at a first longitudinal location and a second longitudinal location. In some examples, the first and second longitudinal locations can include first and second longitudinal regions. In the illustrative example of FIG. 11A, the drive shaft 1026 and the outer shaft 1028 can be rotationally constrained at both a proximal portion 1003 of the forceps 1000 and at a distal portion 1005 of the forceps 1000. In this arrangement, the outer shaft 1028 and the drive shaft 1026 rotate more evenly together and are thus less likely to become damaged when the jaws 1012 are rotated. An example of a connection at the proximal portion 1003 of the forceps 1000 is shown and described with continued reference to FIG. 11A and FIG. 11B. An example of a connection at the distal portion 1005 of the forceps 1000 is shown and described with reference to FIGS. 20A-25.

To provide a rotational constraint between the drive shaft 1026 and the outer shaft 1028 at the proximal portion of the forceps 1000, the drive shaft 1026 and the outer shaft 1028 can be rotationally constrained to each other via the drive body 1052 and the outer hub 1060.

To transfer the rotational motion from the outer hub 1060 to the outer shaft 1028, the outer hub 1060 can be fixedly coupled to the outer shaft 1028. In an example, a sleeve 1061 can be affixed to both the outer hub 1060 and affixed to the outer shaft 1028. The sleeve 1061 can be affixed to an interior surface 1098 of the outer hub 1060, although the sleeve 1061 can be affixed to other portions of the outer hub 1060. In some examples, the sleeve 1061 can be omitted and the outer hub 1060 can be directly or otherwise affixed to the outer shaft 1028.

The outer hub 1060 can be longitudinally constrained to the housing 1014 while remaining rotatable relative to the housing 1014. This can be accomplished, for example, by the outer hub 1060 including the proximal housing flange 1060A and the distal flange 1060B that longitudinally constrains a portion of housing 1014 therebetween.

In the illustrative example, the interface between the proximal housing flange 1060A and the housing 1014 can constrain the outer hub 1060 from moving distally relative to the housing 1014. In a corresponding fashion, the interface between the distal housing flange 1060B and the housing 1014 can constrain the outer hub 1060 from moving proximally relative to the housing 1014. One of the benefits of this arrangement is that the outer hub 1060 is prevented from moving longitudinally with respect to the housing 1014, without impacting the ability of the outer hub 1060 to rotate relative to the housing 1014, thereby rotating the end effector 1002. In other examples, the housing 1014 can also or alternatively include a flange to interface with the outer hub 1060 and thereby provide a similar longitudinal constraint. In some examples, a single flange can provide one or more interfaces with the housing 1014 to constrain the outer hub 1060 longitudinally with respect to the housing. In some examples, instead of the proximal housing flange 1060A and the distal housing flange 1060B, a single flange can provide the interface that constrains the outer hub 1060 longitudinally with respect to the housing 1014. For example, by an interface such as a single flange on the outer hub 1060 or a single flange on the housing 1014 that is bounded proximally and distally by the other of the outer hub 106 and the housing 1014. Such alternate geometries are within the scope of this disclosure.

To transfer the rotational motion from the outer hub 1060 to the drive shaft 1026, the transfer can occur from the outer hub 1060 through the clip 1056 to the drive body 1052 and the drive shaft 1026. To transfer the rotational motion from the outer hub 1060 to the outer shaft 1028, the outer hub 1060 can be fixedly coupled to the outer shaft 1028. Examples of attachment of an outer hub to an outer shaft are shown and described in FIGS. 9 and 10.

By rotationally constraining the drive shaft 1026 and the outer shaft 1028 to the outer hub 1060 at the proximal end, along with rotationally constraining the drive shaft 1026 to the outer shaft 1028 at the distal end proximate the end effector (e.g., jaws 1012), the forceps 1000 can be less susceptible to torsion of the drive shaft 1026 relative to the outer shaft 1028 along the intermediate portion 1006 between the handpiece 1001 and the end effector 1002 (FIG. 1B). Reducing torsion in the drive shaft 1026 and the outer shaft 1028 reduces "wind up" of the drive shaft 1026 relative to the outer shaft 1028. Limiting "wind up" can improve the ability of the user to control the end effector 1002, thereby limiting undesirable movements (e.g., unwinding, spring back) of the end effector 1002. Examples illustrating constraining rotation at the distal end of the forceps (e.g., distally of the outer hub 1060, proximal of the end effector 1002) are described further herein with respect to FIGS. 20A-25.

In some examples, the first longitudinal location (e.g., 1003) can be closer to the handpiece 1001 than to the end effector 1002 and the second longitudinal location (e.g., 1005) can be closer to the end effector 1002 than to the handpiece 1001. The second longitudinal location (e.g., 1005) can be distal of the first longitudinal location (e.g., 1003). The second longitudinal location (e.g., 1005) can be proximal of the end effector 1002. The second longitudinal location (e.g., 1005) can be proximal of the end effector 1002 coupling to the drive shaft 1026 or the outer shaft 1028.

The outer shaft 1028 can extend from a proximal end proximate the handpiece 1001 to a distal end proximate the end effector 1002. In some examples, the second longitudinal location (e.g., 1005) can be located in a range between 75%-95% of a distance D1 from the proximal end to the distal end of the outer shaft 1028.

Figure 12:
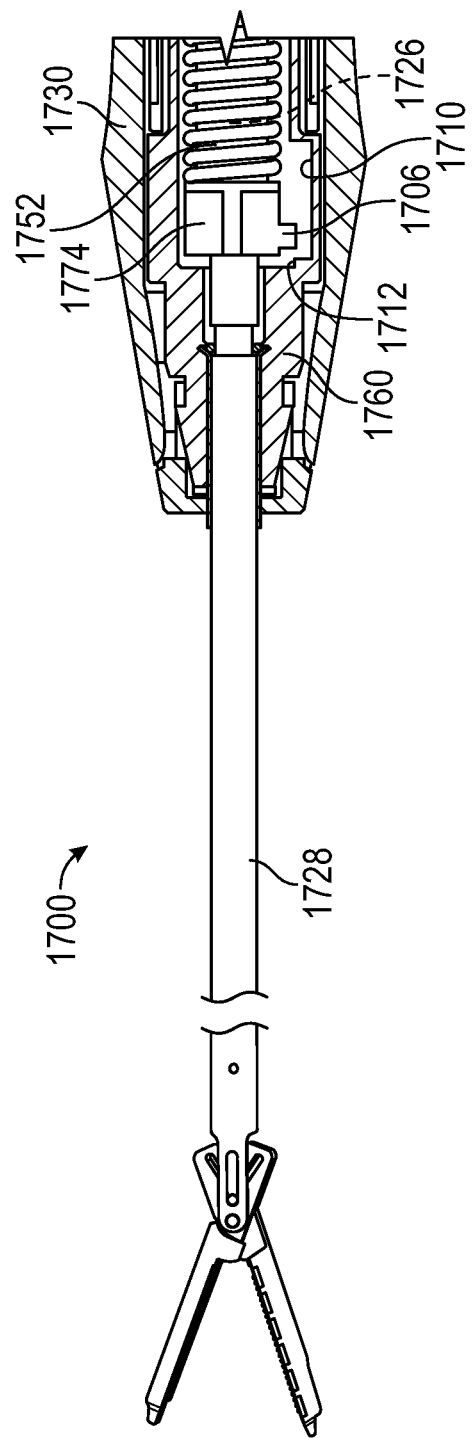
FIG. 12 illustrates a partial cross-sectional view of another example of a drive shaft motion transfer body with an anchor portion including an anti-rotation key and an outer hub including a rotational keying slot.

FIG. 12 is a partial cross-sectional view of a portion of an example forceps 1700 showing another example of a hub-body interface. FIG. 12 shows a drive body 1752 with an anchor portion 1774 including another example of an anti-rotation key 1706 and a hub 1760 including a rotational keying slot 1710. The drive body 1752, an outer shaft 1728, and a drive shaft 1726 are not shown in cross-section. The forceps 1700 can include the drive body 1752 (including the anchor portion 1774 having the anti-rotation key 1706), the hub 1760 (including the rotational keying slot 1710 and an interior surface 1712), a rotation knob 1730 (e.g., rotational actuator), an outer shaft 1728, and the drive shaft 1726.

Forceps 1700 can have generally the same structure and function as forceps 1000 described with respect to FIGS. 1A-6C and FIGS. 10A-11B; however, the drive body 1752 can include the anchor portion 1774 (e.g., distal portion) that has the anti-rotation key 1706, and the hub 1760 has the rotational keying slot 1710. The anti-rotation key 1706 can be a protrusion or ridge that extends out of a side of the anchor portion 1774. The anti-rotation key 1706 can be sized to fit within the rotational keying slot 1710 of the hub 1760.

The hub 1760 can have the rotational keying slot 1710 extending into the hub 1760 from the interior surface 1712.

The rotational keying slot 1710 can accept the anti-rotation key 1706, which is positioned within the rotational keying slot 1710. The anti-rotation key 1706 can have a length shorter than a length of rotational keying slot 1710 such that the anti-rotation key 1706 and the drive body 1752 can be linearly translated along the rotational keying slot 1710 and the hub 1760. In other words, while the anti-rotation key 1706 and the rotational keying slot 1710 prevent relative rotation between the hub 1760 and the drive body 1752, the anti-rotation key 1706 can act, at in least in part, as a guide for longitudinal movement of the drive body 1752 relative to the hub 1760.

The anti-rotation key 1706 and the rotational keying slot 1710 can connect and rotationally lock the hub 1760 and the drive body 1752. Thus, rotating the rotation knob 1730 rotates the hub 1760, which rotates the drive body 1752. As a result, rotating the rotation knob 1730 rotates both the outer shaft 1728 and the drive shaft 1726 together.

In some examples, any of the anti-rotation interfaces described herein can have the geometries of the keyed interfaces swapped, or the keyed interfaces can include different interface geometries.

Figure 13A:
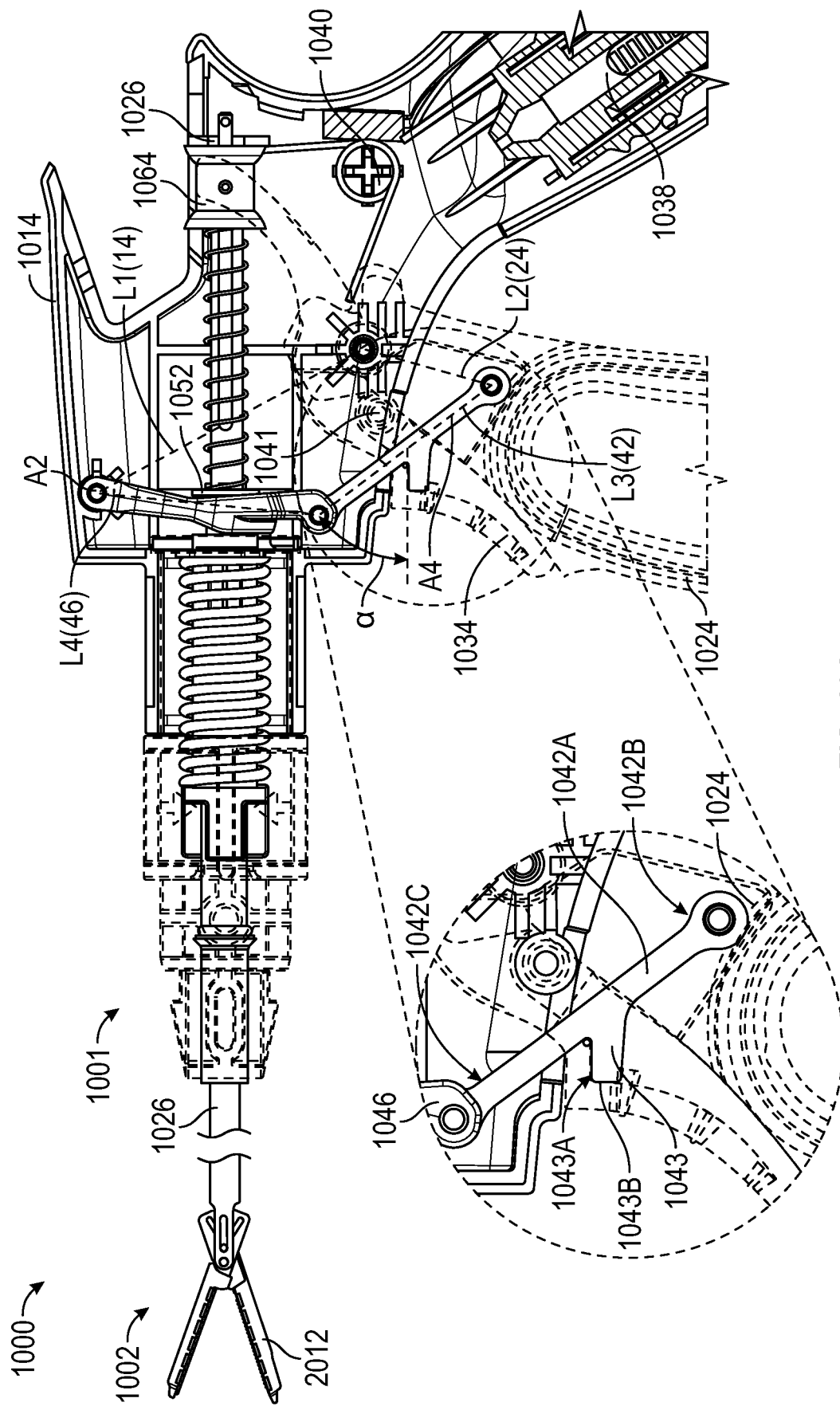
FIG. 13A illustrates a side view of a portion of the forceps of FIG. 1A with a lever in an unactuated position (e.g., retracted).
Figure 13B:
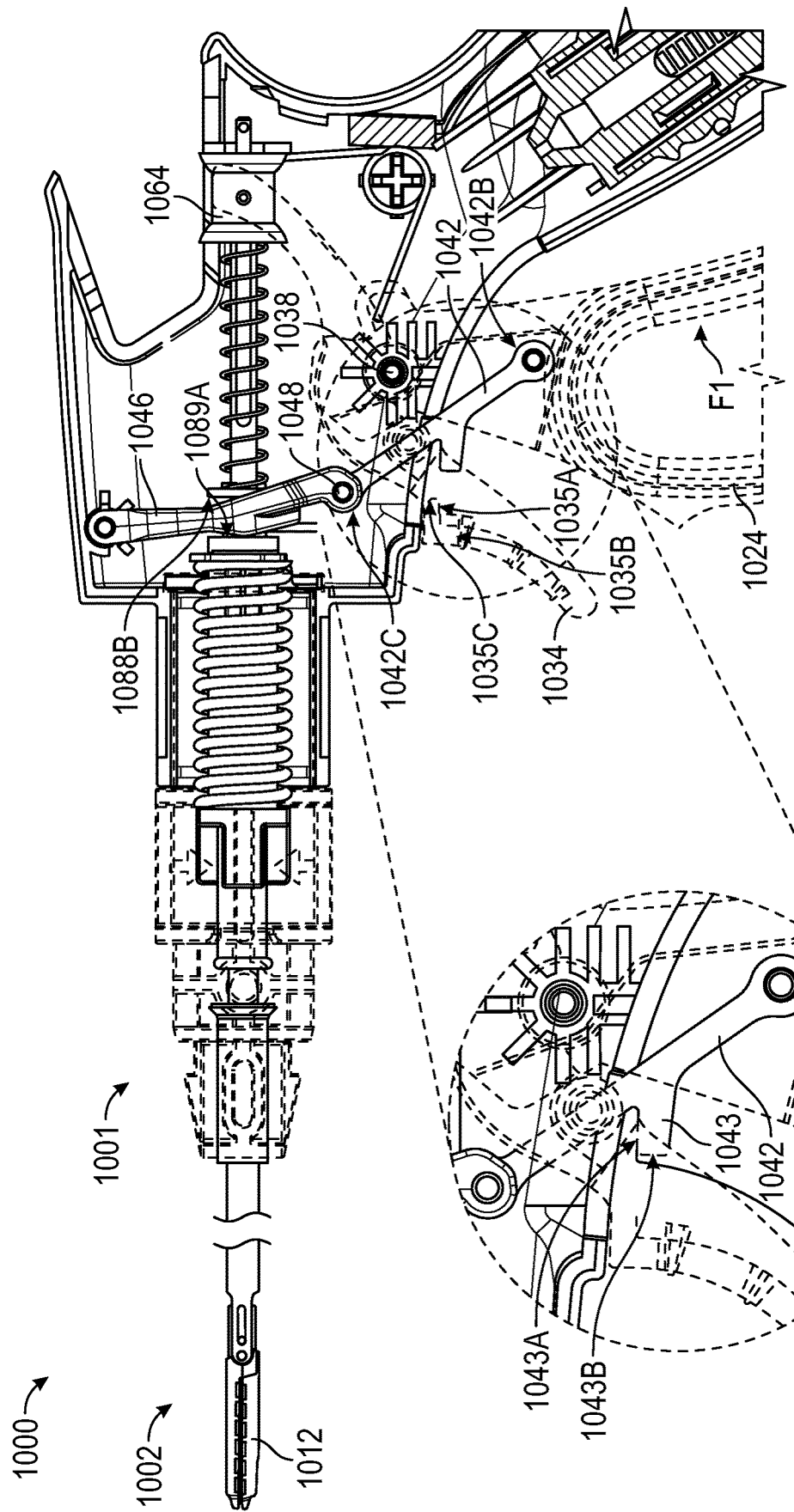
FIG. 13B illustrates a side view of the portion of the forceps of FIG. 1A, with the lever in an actuated position.
Figure 13C:
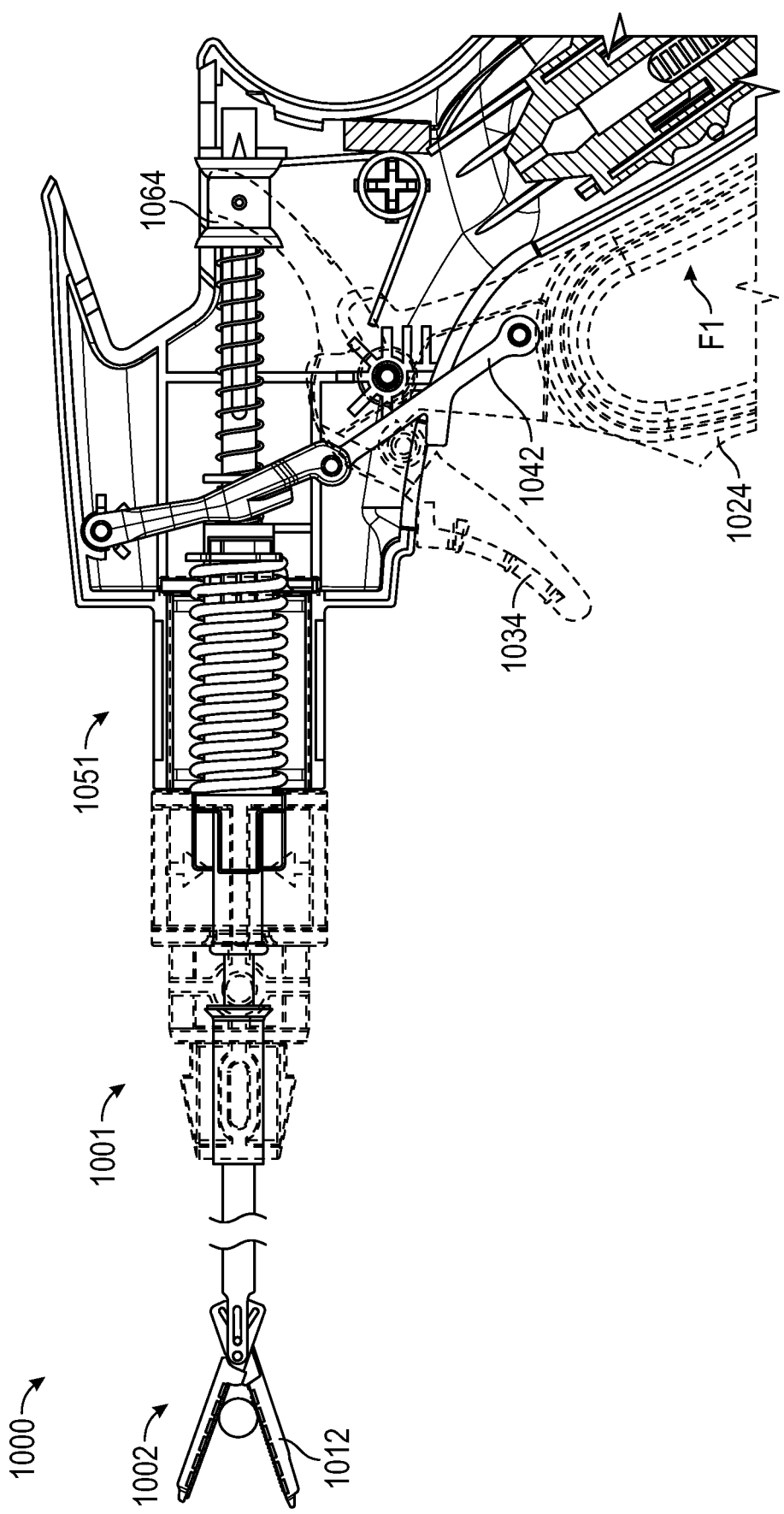
FIG. 13C illustrates a side view of the portion of the forceps of FIG. 1A, with the lever in a force limiting state (e.g., an over-travel position).

FIG. 13A illustrates a side view of a portion of the forceps 1000 of FIG. 1A with the lever 1024 in an unactuated position (e.g., drive shaft 1026 not retracted, jaws 1012 open), in accordance with at least one example. FIG. 13B illustrates a side view of a portion of the forceps 1000 of FIG. 1A, with the lever 1024 in an actuated position (e.g., drive shaft retracted, jaws closed), in accordance with at least one example. FIG. 13C illustrates a side view of a portion of the forceps 1000 of FIG. 1A, with the lever 1024 in a force limiting state (e.g., jaws stuck open, an over-travel position), in accordance with at least one example. While FIGS. 13A, 13B and 13C show the lever 1024 in various positions of actuation, in all of FIGS. 13A, 13B and 13C, the trigger 1034 is in an unactuated position. FIGS. 13A, 13B, 13C illustrate close-up views of a portion of the handpiece 1001 shown and described with respect to FIGS. 4A, 4B and 4C. The outer hub 1060, the lever 1024 and the trigger 1034 are shown in phantom so that some hidden portions within the handpiece 1001 are visible.

FIG. 13A shows the lever 1024 and the trigger 1034 in their unactuated positions. As shown in FIG. 13B, moving the lever 1024 in a proximal direction (by force F1) actuates a linkage, which in this example is a four-bar type mechanism that can indirectly cause the drive shaft 1026 to be retracted. The four links can include a first link L1 (e.g., a ground link), a second link L2, a third link L3 and a fourth link L4. The first link L1 can be the housing 1014 which provides the grounding for the linkage. The second link L2 can be provided by a portion of the lever 1024. The third link L3 can be the coupling link 1042 that is connected between the second link L2 and the fourth link L4, and the fourth link L4 can be the drive link 1046. Note that while the ground link L1 is provided by the housing 1014, the ground link L1 could also be a frame, or a separate link fixed to the housing 1014 or frame.

The second link L2 (e.g., lever 1024) can be pivotably coupled to the ground link L1 (e.g., first link, housing 1014, frame). A first movable element such as the drive body 1052 can be operatively coupled to the second link L2 (e.g., lever 1024) by a linkage including the third link L3 (e.g., coupling link 1042) and the fourth link L4 (e.g., drive link 1046). Actuating the second link L2 (e.g., lever 1024, a movable handle or another actuator) provides input to the linkage (L1, L2, L3, L4) to cause the drive body 1052 to move with respect to the ground link L1 (e.g., housing 1014).

In other words, moving the lever 1024 in a proximal direction can cause the drive link 1046 of the four-bar mechanism to pivot about drive link pivot axis A2, or another articulation mechanism, to provide an input to the drive body 1052 to retract the drive shaft 1026. In the example forceps 1000, this action closes the jaws 1012 as shown in FIG. 13B. In some examples, retraction of the drive shaft 1026 can cause a different effect besides closing jaws 1012 when used with a different end effector. In some examples there may be fewer or more than four links in the mechanism, such as a five bar, six bar or more than six bar mechanism. Applying the linkage (L1, L2, L3, L4) to the non-limiting example of FIGS. 13A, 13B and 13C, the lever 1024 is pivotably coupled to the housing 1014, and the drive link 1046 is pivotably coupled to the housing 1014.

Described yet another way, and as labeled in FIG. FIG. 13B, moving the actuatable end of the lever 1024 proximally causes the lever 1024 to rotate with respect to the housing 1014 about first pin 1038, which causes the first portion 1042B of coupling link 1042 to move proximally. By this motion, the second portion 1042C of coupling link 1042 is also moved proximally. The drive link 1046 is thereby caused to pivot with respect to the housing 1014 such that the portion of the drive link 1046 that is coupled to the coupling link 1042 at third pin 1048 and the portion of the drive link 1046 that engages the drive body 1052 at the distal face 1088B (FIG. 13B), move proximally. Consequently, when the lever 1024 is reversed and allowed to move distally, all these actions are reversed by the lever return spring 1040 which, in some cases, can also result in causing the drive link 1046 to engage the drive body 1052 at the proximal face 1089A (FIG. 13B).

In a situation where the lever 1024 is pulled proximally and the jaws 1012 encounter some resistance, the drive shaft is placed under a tensile load. This can occur if there is an impediment between the jaws 1012, such as if there is tissue or another medical device located between the jaws 1012, or if the jaws 1012 are fully closed and the lever 1024 continues to be actuated. In this tensile state, there can be a tensile load in the drive link 1046 and also a tensile load in the coupling link 1042. A benefit of such a tensile state is that relatively thin components can be used in a mechanism and such thin components are more stable under tension than under compression, which can result in the lever 1024 operating more smoothly than in a device that relies on creating a compressive state in the components.

As shown in the inset of FIG. 13A, the coupling link 1042 can have a main body 1042A extending from a first portion 1042B pivotably coupled to the lever 1024, to a second portion 1042C pivotably coupled to the drive link 1046. The coupling link 1042 can include a tab 1043 (or multiple tabs) extending away from the main body 1042A. The coupling link 1042 can reside within the lever recess 1025 in the lever 1024 (see cross-sectional view of lever 1024 in FIG. 3B).

The tab 1043 can provide one or more functions, including serving as a blocking tab to prevent the trigger 1034 from being prematurely or inadvertently actuated until the lever 1024 is at least partially actuated. The tab 1043 can include one or more blocking tab portions. The tab 1043 can extend away from a mid-portion of the main body 1042A located between the first portion and the second portion. The tab 1043 can include first blocking tab portion 1043A extending away from the main body 1042A at an acute angle α relative to an axis A4 of the main body in a direction towards the trigger 1034. The first blocking tab portion 1043A can include a shelf that extends in a proximal-distal direction to receive the trigger 1034.

The trigger 1034 can be operatively coupled to the housing 1014, such as by a pivotable coupling 1041. The trigger 1034 can serve as a second lever or second actuator for actuating functions of the end effector 1002. The trigger 1034 can be operatively coupled to a second movable element, such as, but not limited to the spool 1064 (e.g., a second motion transfer body or cut block). When actuated, the trigger 1034 can cause the spool 1064 to move with respect to the housing 1014. The trigger 1034 can include a blocking surface 1035 having one or more blocking surface portions, an example of which is labeled in FIG. 13B.

As illustrated in FIG. 13A, the tab 1043 on the coupling link 1042 can be positioned to engage with at least a portion of the blocking surface 1035 of the trigger 1034 to limit movement of the trigger 1034 until the lever 1024 is at least partially actuated. In an example where the trigger 1034 extends a blade shaft 1032 to operate a cutting operation of the blade 1032A (FIG. 2), this prevents actuation of the blade 1032A until the jaws 1012 are at least partially closed or closed.

As illustrated in FIG. 13B, when the lever 1024 is at least partially actuated, the tab 1043 can move such that a clearance is created between the tab 1043 and the blocking surface 1035, allowing the trigger 1034 to be at least partially actuated. The blocking surface 1035 can include multiple blocking surfaces such as a first blocking surface portion 1035A and a second blocking surface portion 1035B.

In the illustrative example, as shown in the combination of FIGS. 13A and 13B, and starting in the unactuated position of FIG. 13A, the first blocking tab portion 1043A can engage the first blocking surface portion 1035A and/or the second blocking tab portion 1043B can engage the second blocking surface portion 1035B.

In the transition between the blocked position of FIG. 13A (e.g., engaged position, unactuated lever 1024) and the unblocked position of FIG. 13B (e.g., disengaged position, actuated position of the lever 1024), different portions of the tab 1043 can engage and support different portions of the blocking surface 1035 throughout the kinematics of the linkage L1, L2, L3, L4. This is because as the coupling link 1042 orientation changes with respect to the lever 1024 and the drive link 1046, the orientation of the tab 1043 with respect to the trigger 1034 can also change. The kinematics can affect which portion(s) of the tab 1043 are engaging and supporting which portion(s) of the blocking surface 1035.

For example, as the lever 1024 is pulled and the tab 1043 transitions from the blocked position in FIG. 13A to the unblocked position in FIG. 13B, the first blocking tab portion 1043A may provide less engagement with the first blocking surface portion 1035A, while the second blocking tab portion 1043B can play a larger role in inhibiting or limiting the actuation of the trigger 1034. In some examples, prior to disengagement, the second blocking tab portion 1043B can move and engage the first blocking surface portion 1035A or a third blocking surface portion 1035C, before completely disengaging from the trigger 1034, allowing the trigger 1034 to be actuated, or at least partially actuated.

FIGS. 13B and 13C show two different unblocked positions, with FIG. 13B showing the lever 1024 in an actuated position, and FIG. 13C showing the lever 1024 in a second actuated position where the force F1 being applied to the lever 1024 is high enough that the force limiting aspects of the motion transfer assembly 1051 are actuated. As shown in FIGS. 13B, as the lever 1024 is moved through its range of motion by force F1 applied by a user, the tab 1043 moves out of the way of trigger 1034 such that the tab 1043 does not engage the blocking surface 1035 further, and the trigger 1034 can be actuated. In the unblocked position, the first blocking tab portion 1043A may not engage the first blocking surface portion 1035A, the second blocking surface portion 1035B or the third blocking surface portion 1035C; and the second blocking tab portion 1043B may not engage any of the first blocking surface portion 1035A, the second blocking surface portion 1035B, or the third blocking surface portion 1035C.

The example forceps 1000 presents merely one example of actuation system components coupled to a housing 1014. In various examples, the components may be located within or outside of the housing 1014. For example, at least a portion of the second link L2 (e.g., lever 1024) can be located within or outside the housing 1014. At least a portion of the fourth link L4 (e.g. drive link 1046) can be located within or outside the housing 1014. At least a portion of the trigger 1034 can be located within or outside the housing 1014. At least a portion of the third link L3 (e.g., coupling link 1042 can be located within or outside the housing 1014. In some examples, at least a portion of the third link L3 (e.g., coupling link 1042) can be external of the housing 1014 for a full range of travel of the third link L3.

Figure 14C:
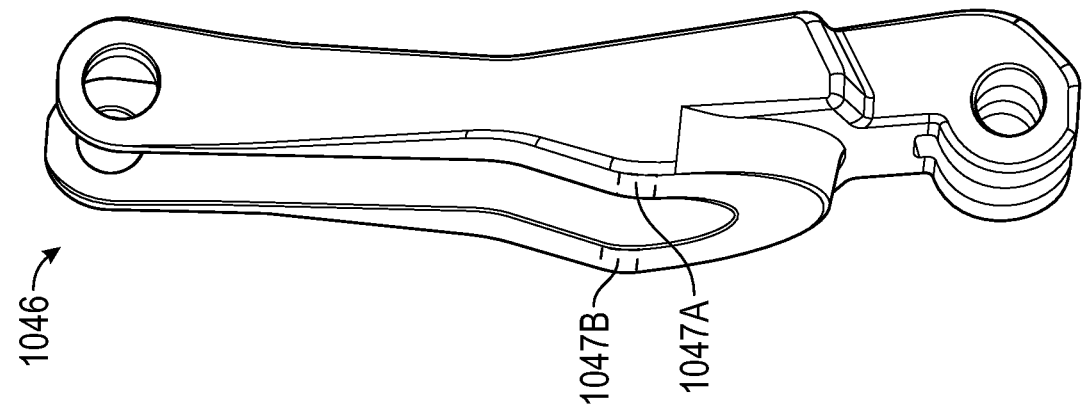
FIG. 14C illustrates a distal isometric view of the drive link of the forceps of FIG. 1A.
Figure 14B:
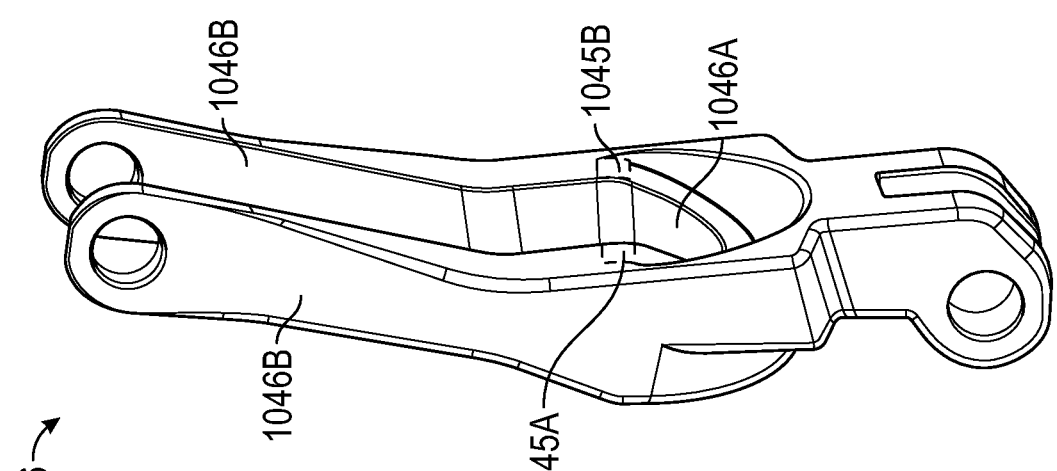
FIG. 14B illustrates a proximal isometric view of the drive link of the forceps of FIG. 1A.
Figure 14A:
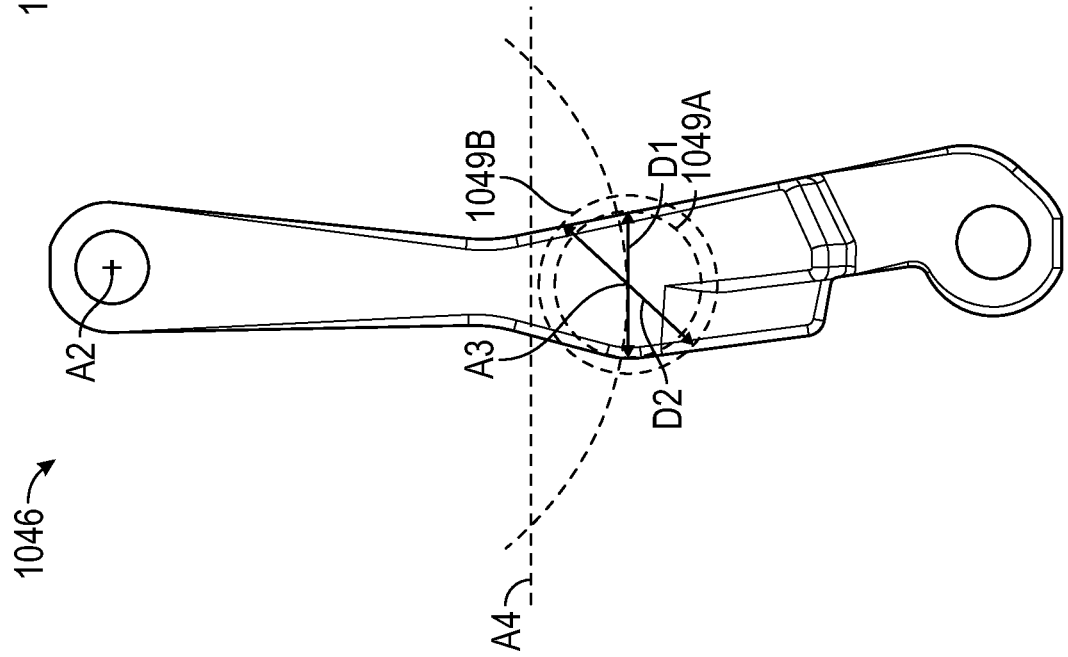
FIG. 14A illustrates a side view of a drive link of the forceps of FIG. 1A.

FIG. 14A illustrates a side view of an example drive link 1046 of the forceps of FIG. 1A, in accordance with at least one example. FIG. 14B illustrates a proximal isometric view of the drive link 1046 of the forceps of FIG. 1A, in accordance with at least one example. FIG. 14C illustrates a distal isometric view of the drive link 1046 of the forceps of FIG. 1A, in accordance with at least one example.

FIGS. 14A, 14B and 14C illustrate example surfaces of the drive link 1046 and will be described together. As previously described with respect to FIGS. 4A, 4B, 4C, 13A, 13B and 13C, the drive link 1046 is operably coupled to the housing 1014. The drive link 1046 can be configured to transfer an input force F1 received from an actuator, such as the lever 1024, into a linear motion of the drive body 1052 and the drive shaft 1026. The drive link 1046 can transfer force to the drive body 1052 via one or more cam surfaces of the drive link 1046. As illustrated in the combination of FIGS. 14A, 14B and 14C, the drive link 1046 can include one or more proximal cam surface(s) 1045A, 1045B formed on a proximal side of the drive link 1046 and one or more distal cam surface(s) 1047A, 1047B formed on a distal side of the drive link 1046. The proximal cam surfaces 1045A and 1045B can be arranged opposite the distal cam surfaces 1047A, 1047B in the longitudinal direction of the forceps 1000 such that the proximal surface 1045A faces away from the distal cam surface 1047A and such that the proximal cam surface 1045 B faces away from the distal cam surface 1047B. To drive the drive body 1052 (FIG. 5A) in a proximal direction (e.g., to retract the drive shaft 1026 and close the jaws 1012), the proximal cam surfaces 1045A, 1045B can be configured to interface with the collar 1088 shown in FIG. 5A. To drive the drive body 1052 (FIG. 5A) in a distal direction (e.g., to extend the drive shaft 1026 and open the jaws 1012), the distal cam surfaces 1047A, 1047B can be configured to interface with a distal surface or collar 1089 shown in FIG. 5A.

To improve the user's ergonomic experience and maximize space efficiency in the handpiece 1001 and to minimize the overall length of the forceps 1000, particularly in a longitudinal direction (L1, FIG. 1B), the cam surfaces 1045A, 1045B, 1047A and 1047B can be formed as portions of concentric cylinders. For example, in FIG. 14A, the portions of concentric cylinders 1049 is shown as being portions of cylinders of equal diameter (e.g., as in D1), however, this is not required. The proximal cam surfaces 1045A, 1045B can be of a different diameter than the distal cam surfaces 1047A, 1047B, but still remain concentric with one another about a common axis A3. For example, at least one of the proximal cam surfaces 1045A, 1045B can be formed as at least a portion of a first cylindrical surface 1049A having a diameter D1, while at least one of the distal cam surfaces 1047A, 1047B can be formed as at least a portion of a second cylindrical surface 1049B having a diameter D2, such that the at least a portion of the first cylindrical surface 1049A and such that at least a portion of the second cylindrical surface 1049B are concentric about a common axis A3.

In some examples, during the range of motion of the drive link 1046, the common axis A3 of the proximal cam surfaces 1045A, 1045B and the distal cam surfaces 1047A, 1047B is configured to pass below the drive link pivot axis A2. In some examples, the common axis A3 is configured to pass through a plane perpendicular to a translation axis A4 of the drive body 1052 and which passes through the drive link pivot axis A2. In some examples, during the range of motion of the drive link 1046, the common axis A3 is configured to pass through an axis of translation A4 of the drive body 1052 twice. The axis of translation A4 can be an axis coincident or parallel to the longitudinal axis A1 shown in FIG. 1B.

In some examples, because the proximal and distal cam surfaces 1045A, 1045B, 1047A, 1047B can be formed by portions of cylindrical surfaces (e.g., 1049A and/or 1049B), the surface of the drive body 1052 that drives the cam surfaces 1045A, 1045B, 1047A, 1047B is arranged at a position tangent to the relevant cam surface throughout the range of travel. For example, as illustrated in the combination of FIGS. 5A and 14A, because the proximal cam surfaces 1045A, 1045B include a circular shape, a distal face 1088B of the proximal collar 1088 can contact the proximal cam surfaces 1045A, 1045B at a position tangent to the proximal cam surfaces 1045A, 1045B over a range of motion of the drive link 1046. The range of movement of the drive link 1046 can correspond to the jaws 1012 being displaced from an open position to a closed position (jaw 1012 positions shown in FIGS. 1A and 1B). One benefit of this arrangement is that the distance from the proximal cam surface 1045A to the distal cam surface 1047A remains the same throughout rotation of the drive link 1046. Because of this constant distance between the proximal cam surface 1045A and the distal cam surface 1047B (and likewise between cam surfaces 1047A and 1047B), the distance between the distal face 1088B of the proximal collar 1088 and the proximal face 1089A of the distal collar 1089 can be reduced to a set distance. This is more space efficient compared to conventional forceps and provides a smooth motion.

While the cam surfaces 1045A, 1045B, 1047A, 1047B are shown and described with reference to a drive link 1046 having a yoke and two proximal cam surfaces 1045A, 1045B and two distal cam surfaces 1047A, 1047B, any number of cam surfaces may be provided. In some examples, a drive link 1046 can include two or more cam surfaces without necessarily being yoke shaped. For example, a drive link can have only one leg and may include a single proximal cam surface 1045A and a single distal cam surface 1047A. In other examples, a drive link can have an uneven number of cam surfaces, such as a single proximal cam surface 1045A and two distal cam surfaces 1047A, 1047B, or vice-versa. In some examples, there can be any combination of two or more cam surfaces (e.g., 1045A, 1045B, 1047A, 1047B) such that at least two opposing cam surfaces each include a portion of a cylindrical surface, and that the portions of the cylindrical surfaces are concentric about the common axis A3.

In some examples, the drive link 1046 can include one or more cam surfaces. In such an example, the drive body 1052 can include a face (e.g., distal face 1088B of collar 1088, FIG. 5A) to receive the drive surface (e.g., cam surface 1045A) of the drive link 1046. In such an example, the drive surface can include a portion of a cylinder having an axis (e.g., A3) that is configured to pass below the drive link pivot axis A2 when the drive link 1046 passes through its range of motion and/or pass through a longitudinal axis A1 of the translation of the drive body 1052 when the drive link 1046 passes through its range of travel. One benefit of such kinematics is that the distance the proximal collar 1088 or distal collar 1089 has to be driven for the lowest amount of lever force F1 is optimized.

The common axis A3 can be perpendicular to a plane through the longitudinal axis A1 (FIG. 1B) along which the drive body 1052 translates and which intersects the drive link 1046. The common axis A2 can be parallel to the drive link pivot axis A2 of the drive link 1046 to the housing 1014.

Figure 15A:
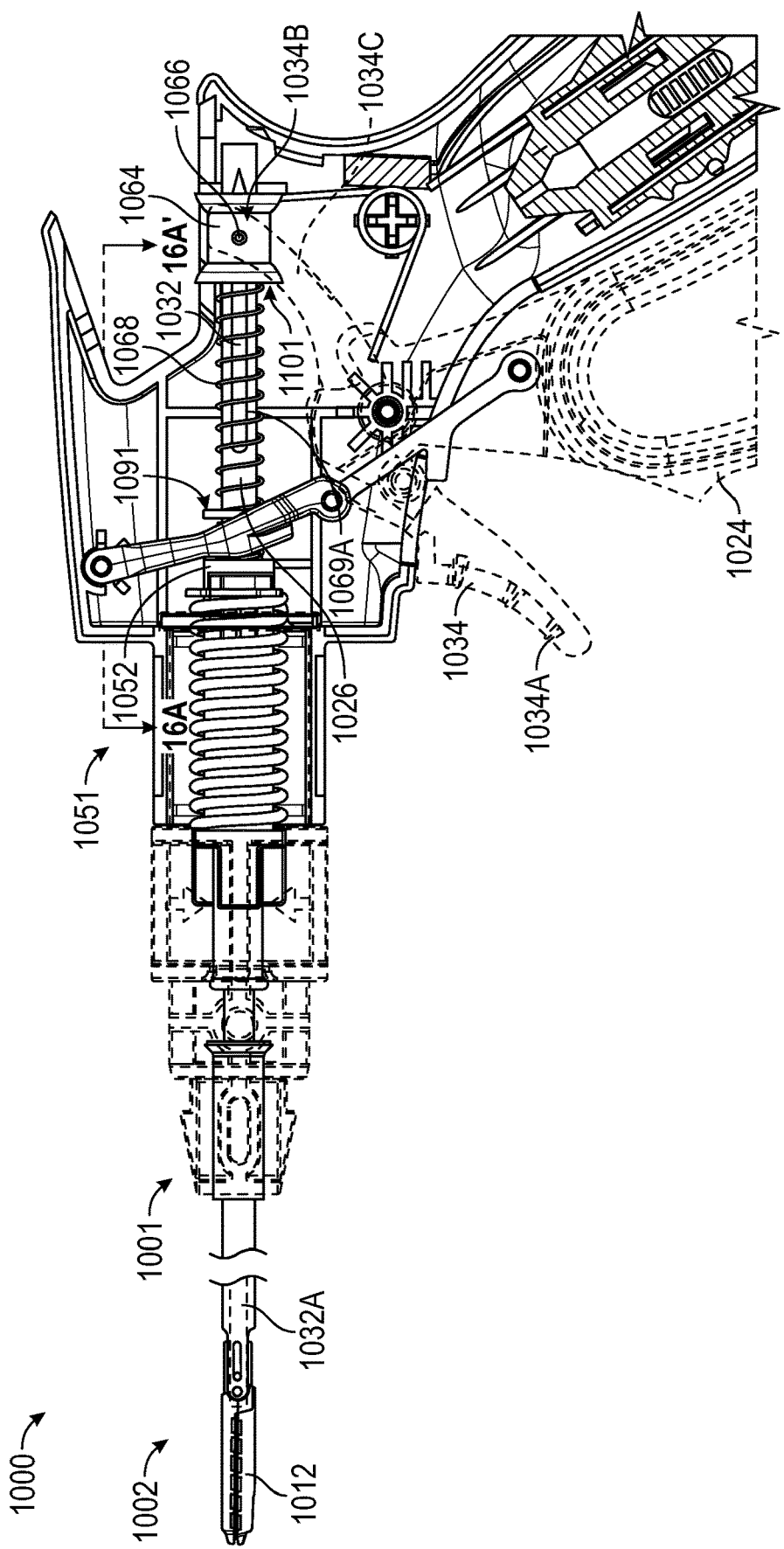
FIG. 15A illustrates a side view of a portion of the forceps of FIG. 1A with a first lever in an actuated position and a trigger in an unactuated position.

FIG. 15A illustrates a cross-sectional view of a portion of the forceps 1000 of FIG. 1A with the lever 1024 in an actuated position and the trigger 1034 in an unactuated position, in accordance with at least one example. FIG. 15A is similar to FIG. 13C, illustrating a position where the clamping function is actuated by the lever 1024 such that the jaws 1012 are closed by the action of the first motion transfer assembly 1051 causing retraction of the drive body 1052 and the drive shaft 1026, but the blade 1032A is not yet actuated.

Figure 15B:
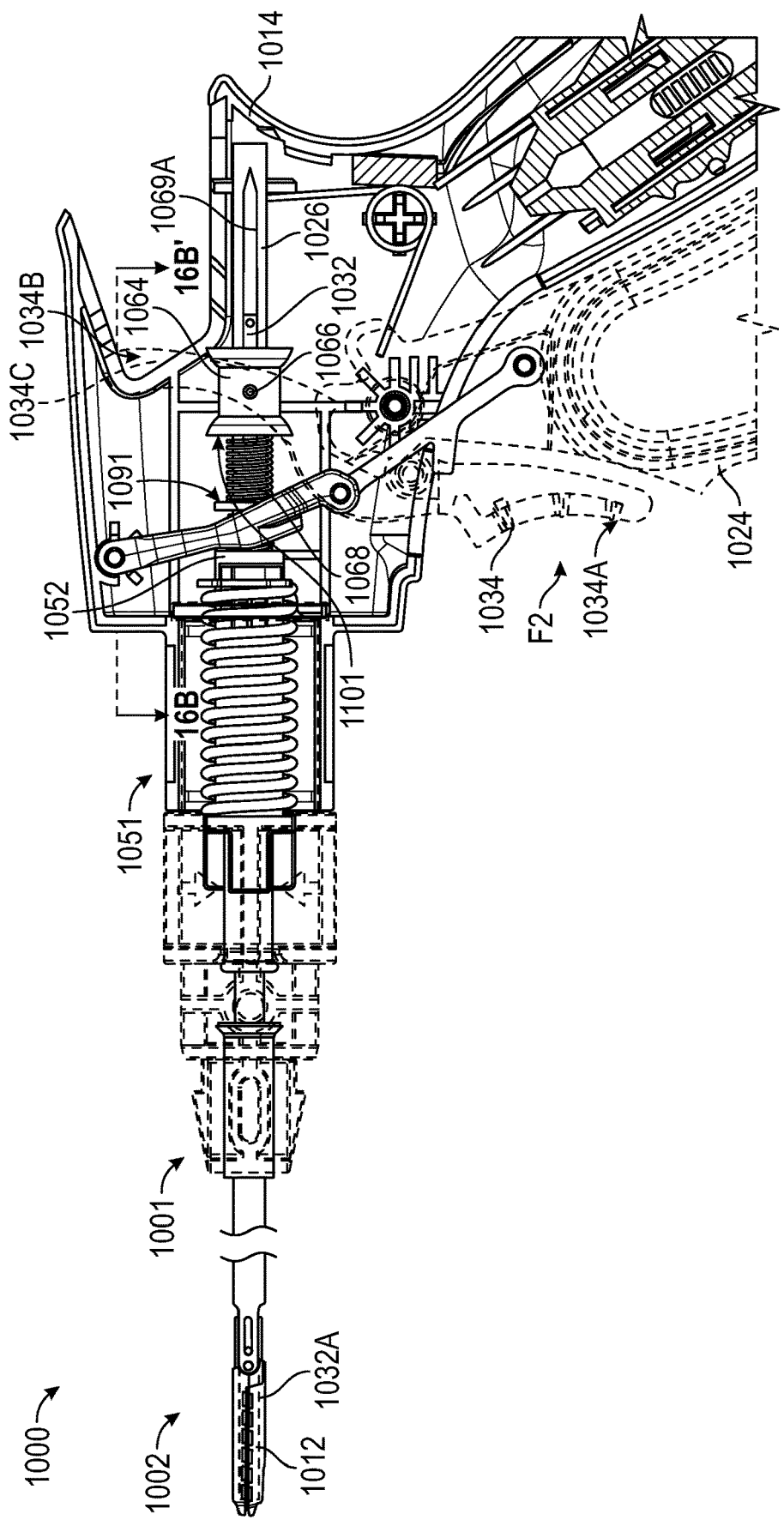
FIG. 15B illustrates a side view of the portion of the forceps of FIG. 1A with the first lever in an actuated position and the second actuator in an actuated position.

FIG. 15B illustrates a cross-sectional view of the portion of the forceps 1000 of FIG. 1A with the lever 1024 in an actuated position and the trigger 1034 in an actuated position (e.g., blade 1032A extended), in accordance with at least one example. In some examples, the trigger 1034 does not have to be a trigger specifically, it can be a second lever or another type of second actuator.

As shown in FIG. 15A, the trigger return spring 1068 biases the trigger 1034 to a first position (e.g., default position, unactuated position, retracted position) such that the blade shaft 1032 remains in a retracted state until the trigger 1034 is compressed and moved proximally to actuate the blade 1032A (FIG. 2). In the first, unactuated position, the spool 1064 is in a proximal position on the drive shaft 1026. The cross pin 1066 is in a proximal position within first horizontal slot 1069A and second horizontal slot 1069B. As such, the trigger return spring 1068 is in a relaxed state floating between the drive body 1052 and the spool 1064, or the second distal spring seat 1091 and the proximal trigger return spring seat 1101. The blade shaft 1032 is in a proximal position such that blade shaft 1032 is retracted.

To facilitate extension and retraction of the blade shaft 1032 and blade 1032A (FIG. 2), the cross pin 1066 can move within one or more aperture(s) (e.g., elongate aperture) in the drive shaft 1026, such as the first horizontal slot 1069A and the second horizontal slot 1069B (hidden). The first and second horizontal slots 1069A and 1069B can act as guide rails for the longitudinal reciprocation of the spool 1064. As such, the spool 1064 can be guided along and by the drive shaft 1026. The first horizontal slot 1069A can extend into a first side of the drive shaft 1026, and the second horizontal slot 1069B can extend into a second side of the drive shaft 1026 across from or opposing the first horizontal slot 1069A.

The first horizontal slot 1069A and the second horizontal slot 1069B can be in a proximal portion of the drive shaft 1026 or near a proximal end of the drive shaft 1026 and can extend along the longitudinal axis A1 (FIG. 1B) of the drive shaft 1026. As such, the cross pin 1066 can extend from a first arm 1034C of the trigger 1034 to a second arm 1034D (hidden) of the trigger 1034 through the spool 1064, the first horizontal slot 1069A of the drive shaft 1026, the blade shaft 1032, and the second horizontal slot 1069B of the drive shaft 1026. The spool 1064 can include a proximal trigger return spring seat 1101 at a distal end of the spool 1064. As such, the trigger return spring 1068 can be positioned on the drive shaft 1026 between a proximal end of the drive body 1052, or the second distal spring seat 1091, and a distal end of the spool 1064, or proximal trigger return spring seat 1101.

As shown in FIG. 15B, to extend the blade 1032A, a user can apply an actuation force input F2 to the trigger 1034. The trigger 1034 can be configured to receive the force input F2 from a user and transfer the force input to the spool 1064 via at least one arm 1034C of the trigger 1034. When the trigger 1034 is compressed (and a distal portion of the trigger 1034 is moved proximally) to a second, actuated position, the trigger 1034 moves the spool 1064 distally with respect to the housing 1014 and the cross pin 1066 translates distally within the first horizontal slot 1069A and the second horizontal slot 1069B. The spool 1064, such as the proximal trigger return spring seat 1101 of the spool 1064, can push the trigger return spring 1068 against the second distal spring seat 1091 until the preload of the trigger return spring 1068 is overcome and the trigger return spring 1068 compresses, allowing the spool 1064 to continue moving distally. The cross pin 1066 can be constrained to the blade shaft 1032, such as by extending through a bore 1032B (FIG. 2) in the blade shaft 1032, thereby constraining the cross pin 1066 to the blade shaft 1032. As a result, the blade shaft 1032 can move distally into an extended position such that the blade 1032A (FIG. 2) can be visible at a distal end of forceps 1000 or can be extended distally between the closed jaws 1012 and is not necessarily visible. When the trigger 1034 is released from the second position, the trigger return spring 1068 can expand, pushing against the proximal trigger return spring seat 1101 and driving the spool 1064 proximally with respect to the housing 1014. As such, the cross pin 1066 can move proximally within the first horizontal slot 1069A and the second horizontal slot 1069B, moving the blade shaft 1032 proximally to a retracted position such that the blade 1032A (FIG. 2) is no longer visible at a distal end of the forceps 1000. Without a force on the trigger 1034, the trigger 1034 returns to the first position (FIG. 15A).

Figure 17B:
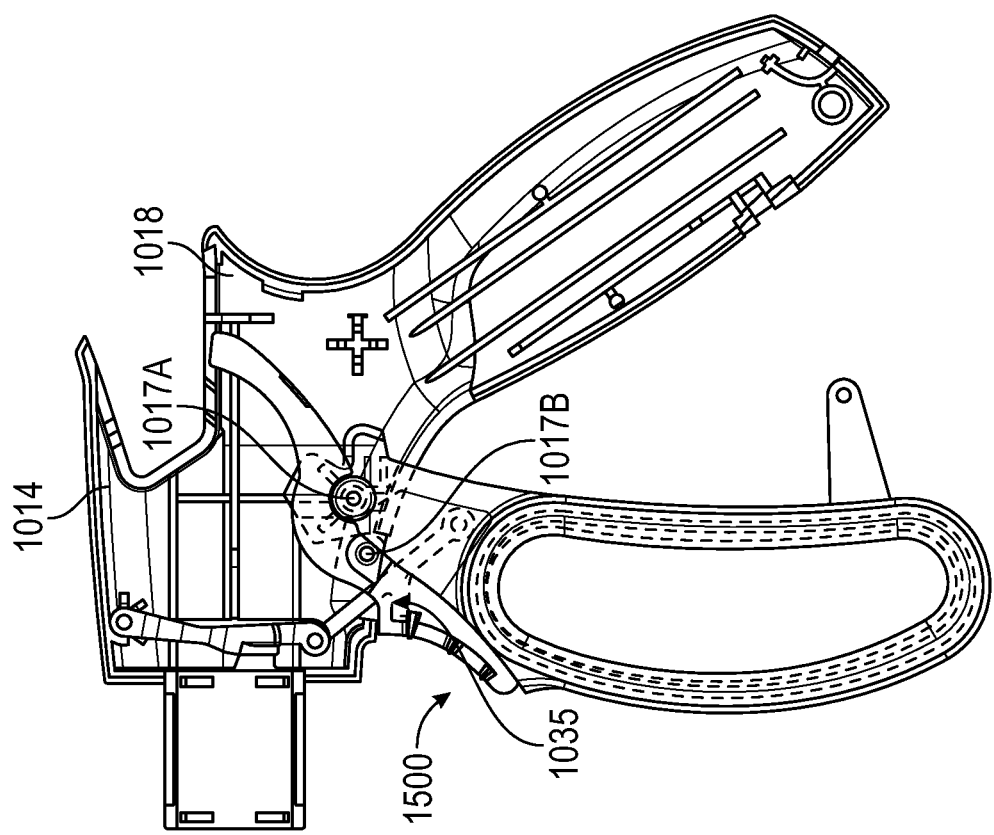
FIG. 17B illustrates a side view of the subassembly of FIG. 17A being inserted into a first housing portion with some portions shown in phantom.
Figure 17A:
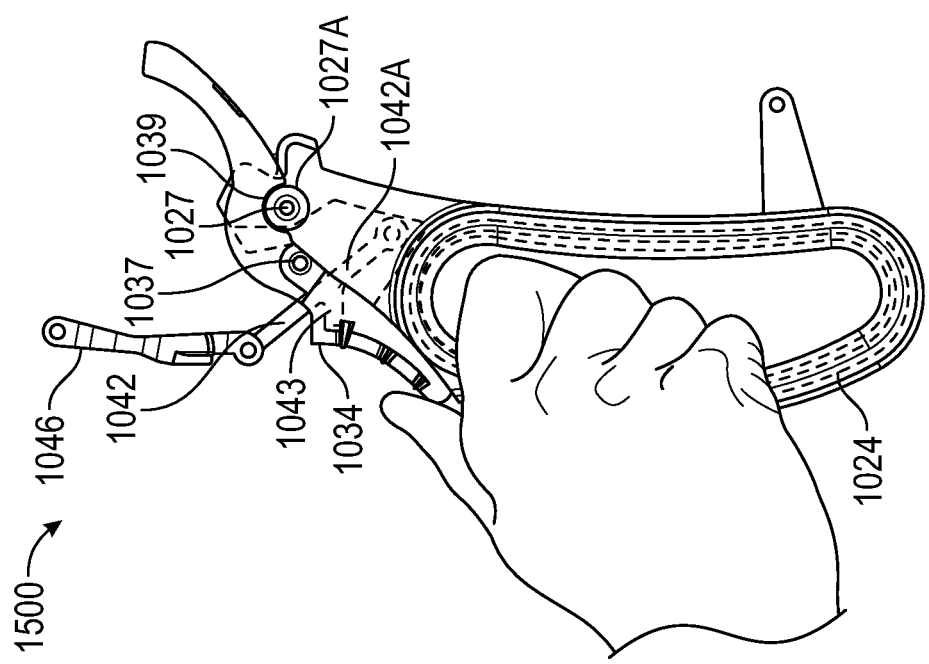
FIG. 17A illustrates a side view of a subassembly of the forceps of FIG. 1A held in a hand during assembly with some portions shown in phantom.
Figure 17D:
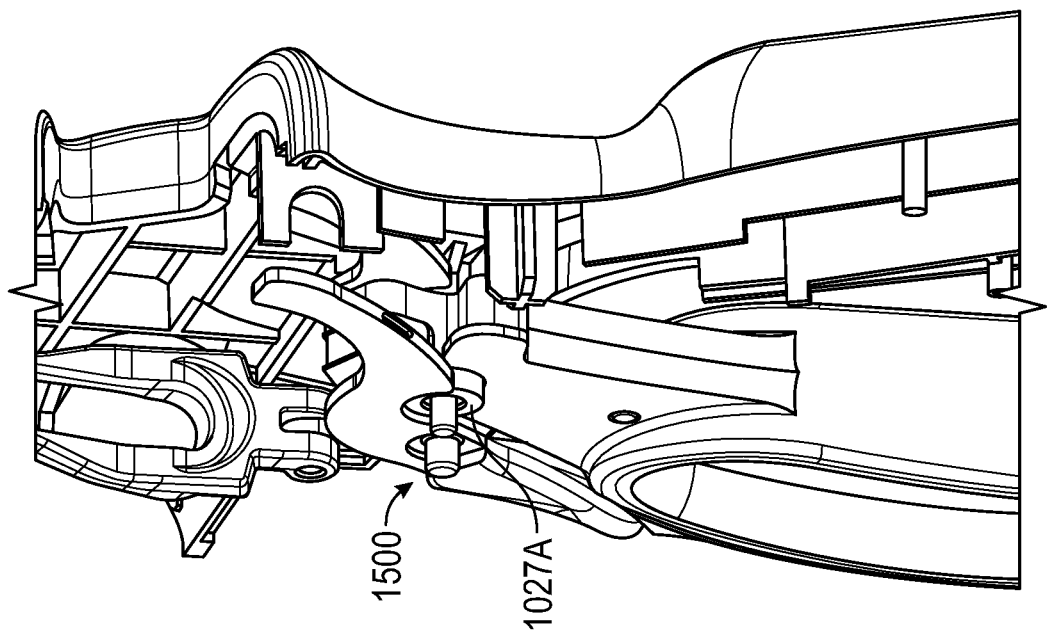
FIG. 17D illustrates a proximal isometric view of the subassembly and housing of FIG. 17C.

The proximal portion 1034A of the trigger 1034 can include the one or more arms 1034C, 1034D (more visible in FIG. 17D). In the example, the first arm 1034C can be laterally spaced apart from the second arm 1034D forming a yoke that receives the spool 1064 while the spool 1064 is connected to the drive shaft 1026 by cross pin 1066 extending therethrough. Thus, because of the spool's 1064 cylindrical shape, and because the spool 1064 is not fixedly coupled to the arms 1034C, 1034D, the spool 1064 can rotate relative to the arms 1034C, 1034D of the trigger 1034 to allow the drive shaft 1026 to rotate. In other words, the spool 1064 is rotatable with the drive shaft 1026 and is not inhibited by the arms 1034C, 1034D of the trigger 1034. This trigger 1034 to spool 1064 interface can be described as a yoke-and-spool cam connection (similar to the drive link 1046 to drive body 1052 connection). The yoke-and-spool cam connections allows the drive shaft 1026 and the blade shaft 1032 within to rotate while still allowing the trigger 1034 to engage the spool 1064 to impart movement of the spool 1064 along the longitudinal axis A1 (FIG. 1B).

The spool 1064 provides a beneficial shape that allows the trigger 1034 to extend the blade shaft 1032 while still permitting the drive shaft 1026, which extends through the spool 1064 to rotate under an input of the rotational actuator 1030. As illustrated in the combination of the retracted position of the blade 1032A in FIG. 15A and the extended position of the blade 1032A in FIG. 15B, a body, such as but not limited to the illustrative spool 1064, can be configured to be guided by the drive shaft 1026 to displace the blade shaft 1032, and thereby the blade 1032A, between the retracted position and the extended position.

It is not required that the spool 1064 be provided as an axisymmetric spool or as having a cylindrical body that allows for rotation of the spool 1064 relative to the trigger 1034. The spool 1064 can alternatively include a non-cylindrical body such as a cuboid or irregular shape, such as in examples that do not include a rotatable drive shaft. For example, as when a drive shaft can be rotatably fixed with respect to a housing to translate with respect to the housing. In some examples, the spool 1064 can be described as a body, a second body, a second motion transfer body, a cut body, or a second drive body.

As illustrated in FIGS. 15A and 15B, the drive shaft 1026 can extend from a location proximal of the drive body 1052, through the spool 1064 and towards a proximal end of the housing 1014. A benefit of the drive shaft 1026 extending through a second passageway 1064A (FIG. 2) in the spool 1064, and proximally past the spool 1064 to a proximal end of the housing 1014 where it is supported by the stabilizing flange 1021, is that the drive shaft 1026, in addition to providing actuation functions to the jaws 1012, can also serve as a guide or rail for the spool 1064 to ride along. In some examples, the drive shaft 1026 may extend through the stabilizing flange 1021.

With the spool 1064 located on or around the drive shaft 1026, the spool can move longitudinally along the drive shaft 1026, and although an axisymmetric spool 1064 is shown, other examples of a second motion transfer body can be provided that are not specifically a spool. In some such examples, such a second motion transfer body can be guided by the drive shaft 1026, but the second motion transfer body does not necessarily need to surround the drive shaft 1026 and may not spool-shaped or rotatable. The spool 1064 is shown as one example of a motion transfer body designed to transmit motion received from an actuator to a shaft (e.g., received from trigger 1034 and transmitted to blade shaft 1032). In other examples, a motion transfer body of this disclosure need not be spool-shaped, such as in examples where the spool 1064 does not need to be rotatable.

The trigger return spring 1068 can be a helical compression spring positioned on the drive shaft 1026 between a distal end of spool 1064 and a proximal end of drive body 1052. Conventional trigger return springs have disadvantages in that they are generally backed up against a fixed flange on a housing. The illustrative trigger return spring 1068 being a floating spring that is positioned between the spool 1064 and the drive body 1052 has advantages in that there is no need to design in a flange in the housing 1014 that has to interface with the trigger return spring 1068. The axial stack-up along the direction of the longitudinal axis A1 (FIG. 1B) of the forceps can be reduced, shortening the length of the forceps 1000, improving ergonomics. In addition, the trigger return spring 1068 can be easily assembled by loading it onto the drive shaft 1026, hence, in contrast to conventional forceps, there is no additional assembly step of securing a spring end to a flange in a housing.

Figure 16A:
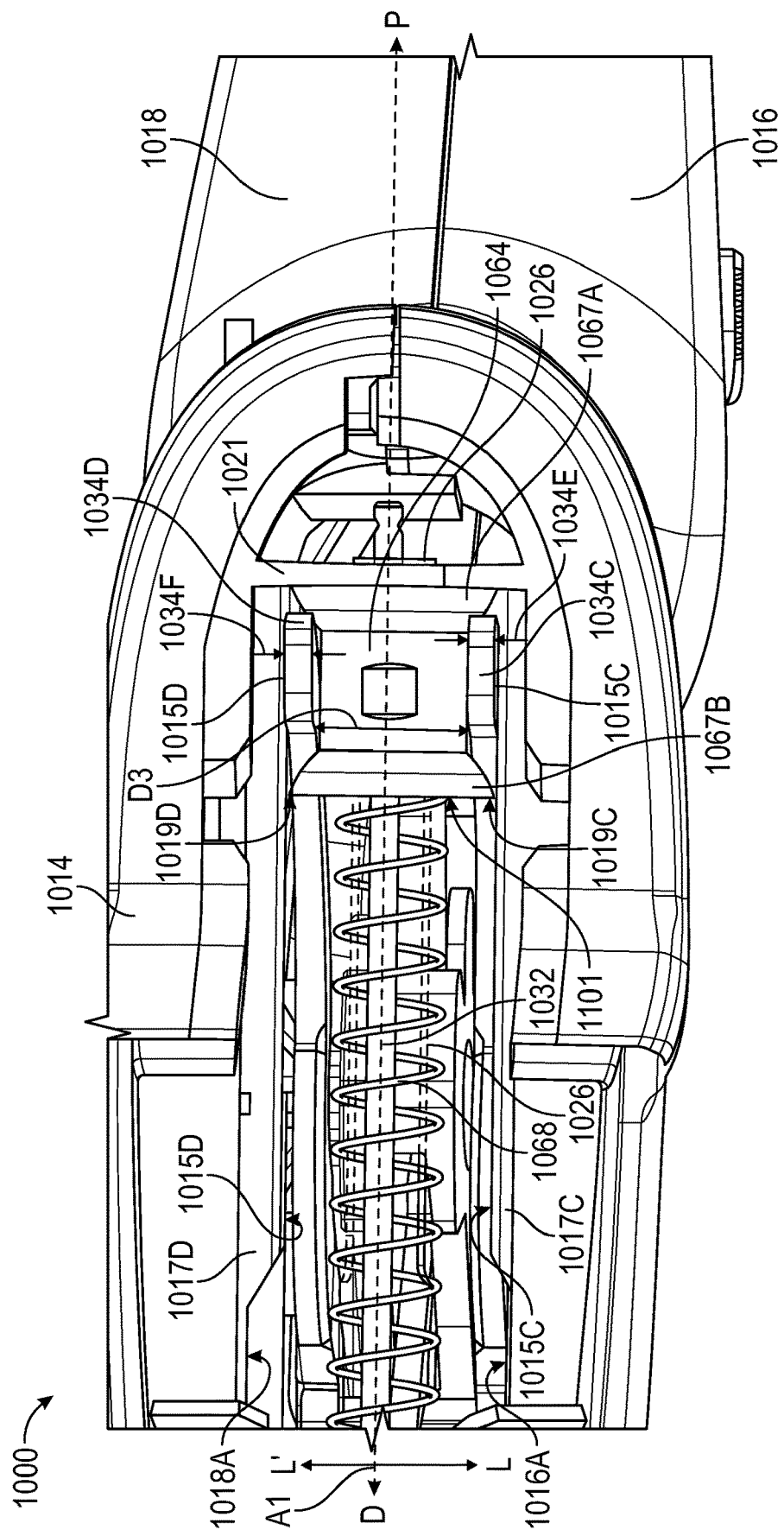
FIG. 16A illustrates cross-sectional view of a portion of the forceps of FIG. 1A along line 16A-16A' in FIG. 15A, and with the trigger in the unactuated position of FIG. 15A.
Figure 16B:
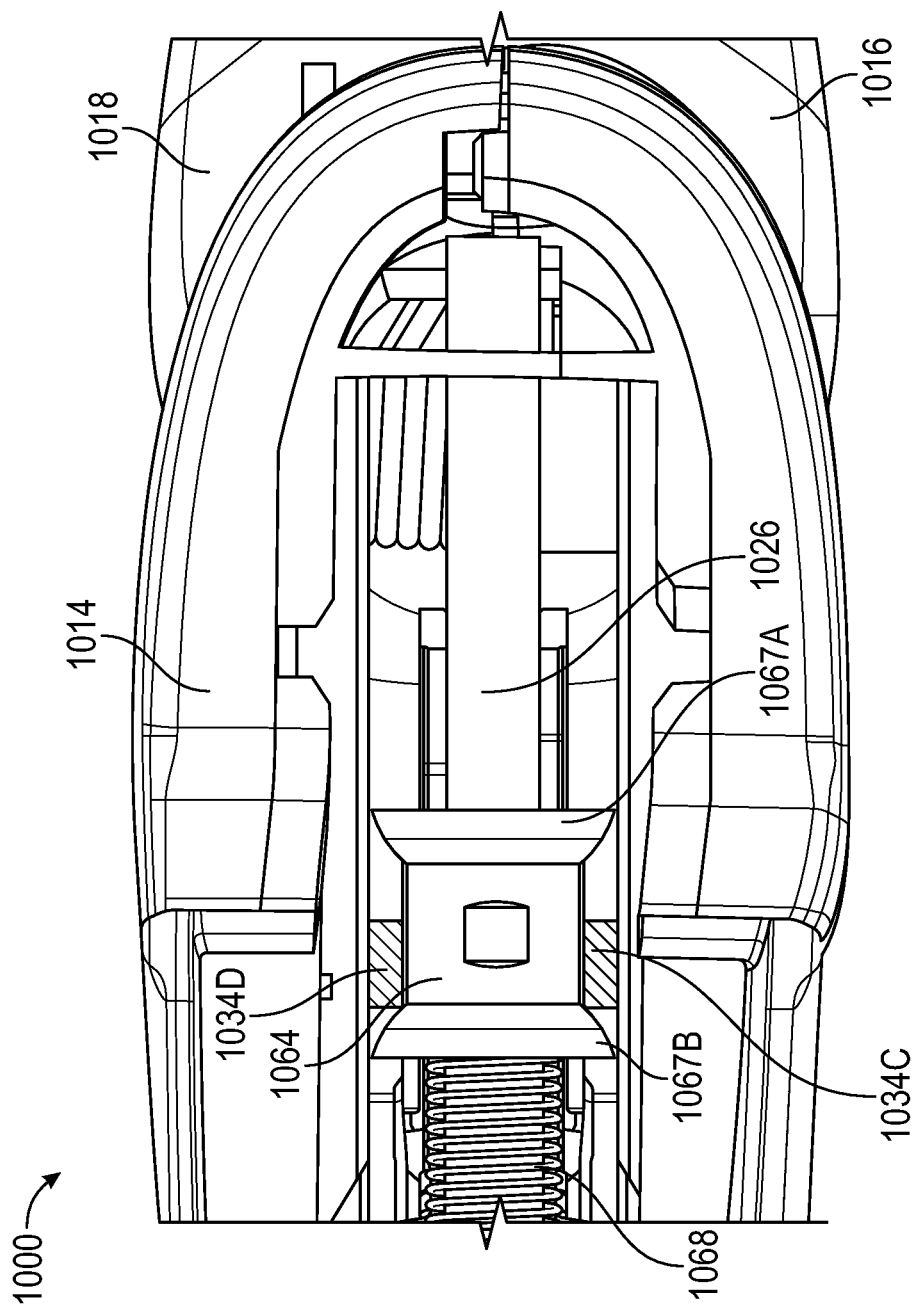
FIG. 16B illustrates a cross-sectional view of the portion of the forceps of FIG. 1A along line 16B-16B' in FIG. 15B, and with the trigger in the actuated position of FIG. 15B.

FIG. 16A is cross-sectional view of a portion of the forceps 1000 along line 16A-16A' in FIG. 15A with the trigger 1034 in the unactuated position of FIG. 15A, in accordance with at least one example. FIG. 16B is a cross-sectional view of the portion of the forceps 1000 along line 16B-16B' in FIG. 15A with the trigger 1034 in the actuated position of FIG. 15B, in accordance with at least one example. FIGS. 16A and 16B will be described together.

As shown in FIG. 16A, the spool 1064 can extend from a proximal end portion to a distal end portion and can include one or more peripheral flanges (e.g., 1067A, 1067B) extending outward from a minor diameter D3 towards the housing 1014. In the example, the spool 1064 includes a proximal flange 1067A, a distal flange 1067B and the minor diameter D3 extending therebetween along the longitudinal axis A1.

When a distal portion 1034B of the trigger 1034 is moved proximally, the arms 1034C, 1034D of the trigger 1034 slide along the minor diameter D3 of the spool 1064 until the arms 1034C, 1034D come into contact with the distal flange 1067B of the spool 1064. Once the arms 1034C, 1034D are in contact with the distal flange 1067B, the arms 1034C, 1034D can push against the distal flange 1067B of the spool 1064. As the distal portion 1034B of the trigger 1034 continues to be actuated proximally, the arms 1034C, 1034D, pushing against the distal flange 1067B cause the spool 1064 to slide distally along the drive shaft 1026 relative to the housing 1014, thereby extending the blade assembly including the blade shaft 1032 relative to the housing 1014.

When a user is finished actuating the blade 1032A and releases the actuation force input F2 on the trigger 1034, the distal portion of the trigger 1034 can be moved distally by the force of the compressed trigger return spring 1068 unloading. As the arms 1034C, 1034D of the trigger 1034 slide along the minor diameter D3 of the spool 1064 the arms 1034C, 1034D can eventually come into contact with the proximal flange 1067A of the spool 1064. Once the arms 1034C, 1034D are in contact with the proximal flange 1067A, the arms 1034C, 1034D can push, by the force of the compressed trigger return spring 1068, against the proximal flange 1067A of the spool 1064 to return the spool 1064, by sliding proximally along the drive shaft 1026 to the default proximal position of FIG. 15A, thereby retracting the blade shaft 1032 relative to the housing 1014.

With continued reference to FIGS. 16A and 16B, one or both of the proximal flange 1067A and the distal flange 1067B can be tapered flanges, such as dual-acting tapered flanges. This allows for better angles between the components in the handpiece 1001, improved kinematics and ease of use. However, it is possible that if an excessive force is applied by a user to move the trigger 1034 proximally, the arms 1034C, 1034D of the trigger 1034 can be caused to splay, deflect or bend outward laterally away from the longitudinal axis A1 and cause the arms 1034C, 1034D of the trigger 1034 to disengage from the spool 1064. In other words, the magnitude of the actuation input force F2 (FIG. 16B) is such that it causes at least one of the arms 1034C, 1034D to be deformed outward laterally in the direction L or L'.

To manage the splay of one or more of the arms 1034C, 1034D, the housing 1014 can include one or more control surfaces 1015C, 1015D configured to prevent splaying of the one or more arms. Splay is most likely to occur when the arms 1034C, 1034D apply a force to the distal flange 1067B at the distal end of travel of the arms 1034C, 1034D. Splay may also occur, though less likely, when the arms 1034C, 1034D apply a force to the proximal flange 1067A at the proximal end of travel of the arms 1034C, 1034D. For example, a first control surface 1015C can extend towards a first arm 1034C such that lateral splay of the first arm 1034C is controlled by the first control surface 1015C. Likewise, a second control surface 1015D can extend towards a second arm 1034D such that lateral splay of the second arm 1034D is controlled by the second control surface 1015D.

In some examples, the control surfaces 1015C, 1015D can be coupled to or integrally formed in the first housing portion 1016 or the second housing portion 1018. As shown in the example of FIGS. 16A, 16B, the one or more control surfaces 1015C, 1015D can be provided as rib(s) 1017C, 1017D formed on the inside of the first housing portion 1016 and the second housing portion 1018 that extend inward towards the arms 1034C, 1034D. The first rib 1017C can be arranged opposite or facing the second rib 1017D. The first rib 1017C can extend inward from a first inner surface 1016A of the first housing portion 1016 and along a proximal-distal direction. The second rib 1017D can extend inward from a second inner surface 1018A of the second housing portion 1018 and along a proximal-distal direction. With the arms 1034C, 1034D that form the yoke located about the spool 1064, the arms 1034C, 1034D can be constrained between the first rib 1017C and the second rib 1017D. In this arrangement, if one of the arms 1034C, 1034D pushing against one of the ribs 1017C, 1017D tries to splay outward, the arm 1034C or 1034D will be restrained by the rib 1017C or 1017D and kept inward such that the arm 1034C or 1034D maintains contact with the spool 1064 to transmit force from the yoke of trigger 1034 to the spool 1064. In some examples, the trigger 1034 may include only one arm and the housing only one rib or other control surface.

In other examples, the control surfaces 1015C, 1015D that prevent (e.g., inhibit, limit, constrain) splaying of the arms 1034C, 1034D may not be provided as ribs 1017C, 1017D, but rather can include an inner surface 1016A, 1018A of the housing 1014 formed in a particular shape, arranged in a manner, or positioned relative to at least one arm 1034C, 1034D to restrict lateral splaying of the arm 1034C, 1034D, thereby preventing disengagement of the arm 1034C, 1034D from the proximal or distal flanges 1067A, 1067B of the spool 1064. In some examples, the respective arm 1034C, 1034D and control surface 1015C, 1015D can be in contact with one another along at least a portion of a full range of travel of the arm 1034C, 1034D. For example, the travel of the arms 1034C, 1034D between the unactuated position of FIG. 16A and the actuated position of 16B.

To manage lateral splaying of the arms 1034C, 1034D, a gap 1019C, 1019D or no gap can be provided between the first arm 1034C and the first control surface 1015C, and between the second arm 1034D and the second control surface 1015D. For example, as shown in FIG. 16A, the gap 1019C can be located between the first control surface 1015C and the first arm 1034C along at least a portion of the first control surface 1015C. To prevent the first arm 1034C from splaying outward when the trigger 1034 is actuated to the degree that the first arm 1034C disengages from the distal flange 1067B, the first gap 1019C can have a distance that is less than an arm thickness 1034E of the first arm 1034C. In some examples, a second gap 1019D can have a distance that is less than a second arm thickness 1034F of the second arm 1034D.

In some examples, the arm thickness 1034E or 1034F can be in a range between about 0.5 mm-4 mm, and the respective gap 1019C or 1019D distance can be in a range between about 10-90% of the arm thickness 1034E or 1034F. In another example, the arm thickness 1034E or 1034F can be in a range between about 0.5-3.0 mm and the respective gap 1019C or 1019D can be 10-60% of the arm thickness 1034E or 1034F. In a possibly more preferred example, the arm thickness 1034E or 1034F can be in a range between about 1-2 mm, and the respective gap 1019C or 1019D distance can be in a range between about 10-50% of the arm thickness 1034E or 1034F. In a possibly yet more preferred example, the arm thickness 1034E or 1034F can be in a range between 1.4 mm and 1.7 mm, and the gap 1019C or 1019D distance can be in a range between 0.1 mm and 0.75 mm.

The arrangement of the arm thickness 1034E or 1034F compared to the respective gap 1019C or 1019D distance can also be defined by a ratio of the gap 1019C or 1019D distance compared to the respective arm thickness 1034E or 1034F (e.g. gap-arm ratio). For example, the gap-arm ratio may be between $1/10$ and $9/10$ (e.g., the gap is 10-90% of the arm thickness). However, depending on the device specifics, in possibly more preferred example, the gap-arm ratio may be about 30% plus or minus 25%, or the gap-arm ratio may be in a range between about $1/5$ and $3/5$ (e.g., the gap distance is 20% to 60% of the arm thickness). In some possibly preferred examples, to prevent the arms 1034C and 1034D from splaying, the ratio may be less than $1/2$, or in a range between 10% and 50%.

When the trigger 1034 is actuated, the first arm 1034C and the first rib 1017C can be in contact with one another along at least a portion of a range of travel of the first arm 1034C. Likewise, the second arm 1034D and the second rib 1017D can be in contact with one another along at least a portion of a range of travel of the second arm 1034D.

Figure 17C:
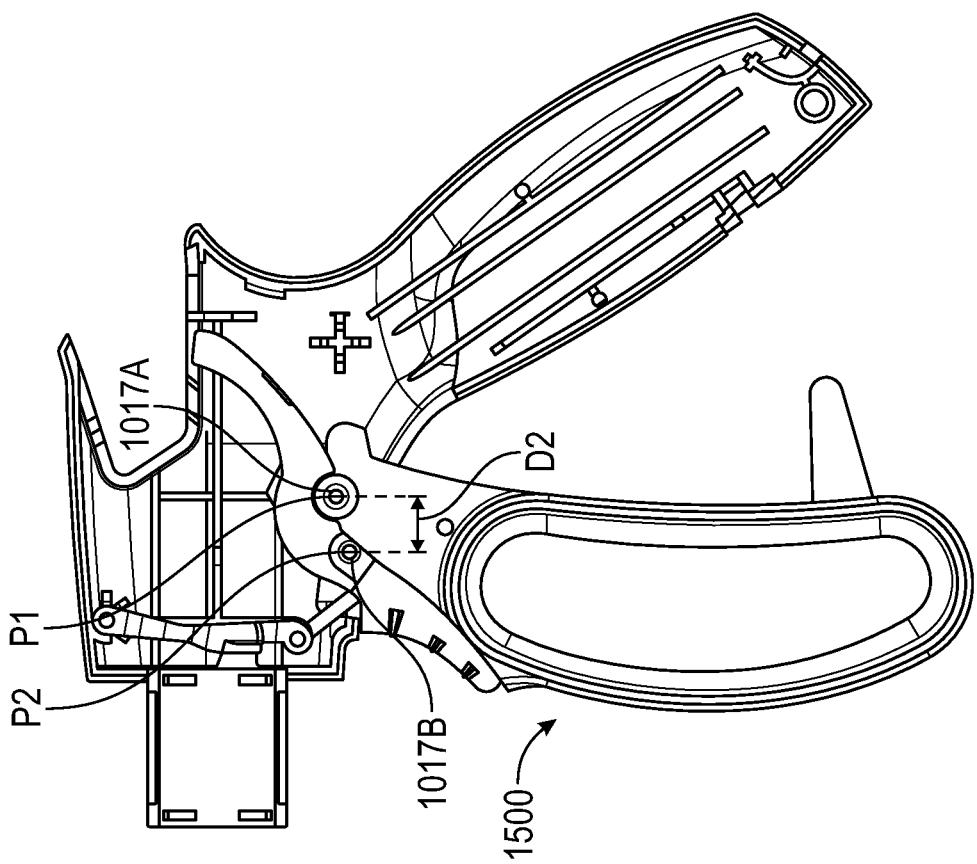
FIG. 17C illustrates a side view of the subassembly and housing of FIG. 17B shown in solid.

FIG. 17A is a side view of a subassembly 1500 of the forceps 1000 of FIG. 1A. The subassembly 1500 held in a hand during assembly, with some components shown in phantom, in accordance with at least one example. FIG. 17B is a side view of the subassembly 1500 of FIG. 17A inserted into the housing (e.g., second housing portion 1018) with some components shown in phantom, in accordance with at least one example. FIG. 17C is a side view of the subassembly 1500 and the second housing portion 1018 of FIG. 17B shown in solid, in accordance with at least one example. FIG. 17D is a proximal isometric view of the subassembly 1500 and the second housing portion 1018 of FIG. 17C, in accordance with at least one example. FIGS. 17A, 17B, 17C and 17D will be described together.

When assembling medical devices such as the forceps 1000, it can be difficult to assemble a set of links onto multiple pivot attachments in a housing. The parts tend to move around making it hard to align multiple pivots with corresponding attachments in the housing. To improve the ease of assembly, the inventors have discovered that the nested subassembly 1500 can be aligned with and inserted into the housing 1014.

The subassembly 1500 of FIG. 17A can be formed and held as a temporary subassembly 1500 in an assembler's hand. For example, the subassembly 1500 can be held together by the support of the user's hand along with the nested arrangement of the lever 1024, the coupling link 1042 and the trigger 1034. Assembly is improved because creating the subassembly 1500 allows both a lever pivot 1027 on the lever 1024 and a trigger pivot 1037 on the trigger 1034 to be aligned with and coupled to the pivot attachments on the second housing portion 1018 in one step (e.g., in one action at the same time).

As shown in the combination of FIGS. 17A-17D, a boss 1027A can extend around at least a portion of the lever pivot 1027. The lever pivot 1027 can interface with the housing 1014 to allow the lever 1024 to rotate about a lever pivot axis P1 (FIG. 17C).

The trigger 1034 can include the arm 1034C having a recess 1039 configured to receive the boss 1027A. The coupling link 1042 pivotably coupled to the lever 1024 can include the main body 1042A and the tab 1043 extending away from the main body 1042A. As shown and described in FIGS. 13A, 13B, 13C, the tab 1043 on the coupling link 1042 can be arranged to provide support to an inner surface (e.g., blocking surface 1035 shown and described in FIGS. 13A, 13B, 13C) of the trigger 1034 when the boss 1027A is seated in the recess 1039. The tab 1043 can extend away from the main body 1042A at an acute angle towards the inner surface (e.g., 1035) of the trigger 1034. In the illustrative example, the tab 1043 can extend away from a mid-portion of the main body 1042A. In other examples, the tab 1043 can extend away from any portion of the main body 1042A, including an end of the main body 1042A.

Figure 18:
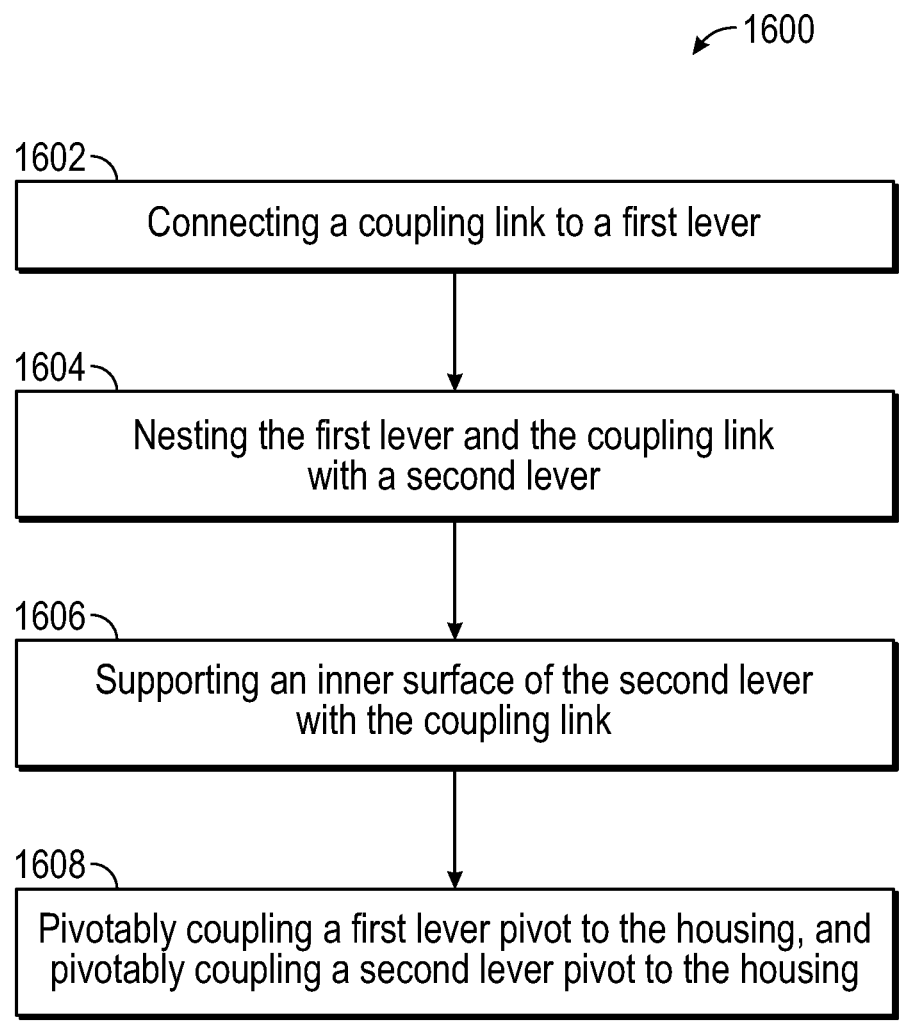
FIG. 18 illustrates a method of assembling a medical device, such as the forceps of FIG. 1A.

FIG. 18 illustrates a method 1800 of assembling a medical device, such as the forceps 1000 including the subassembly 1500 of FIGS. 17A-17D. In operation 1802, the method 1800 can include in pivotably connecting the coupling link 1042 to a first lever, such as the lever 1024. The coupling link 1042 can include the main body 1042A and the tab 1043 extending away from the main body 1042A, and the lever 1024 can include the lever pivot 1027 and the boss 1027A.

Operation 1804 can include nesting the lever 1024 and the coupling link 1042 with a second lever, such as the trigger 1034 having trigger pivot 1037. In the nested position, a recess 1039 in the trigger 1034 can be supported by the boss 1027A. In some examples, the nesting step in operation 1804 can include inserting the coupling link 1042 and the lever 1024 in between the two spaced apart arms 1034C, 1034D of the trigger 1034. Operation 1806 can include supporting the inner surface (e.g., 1035) of the trigger 1034 with the coupling link 1042 to provide a subassembly 1500 held in a sub-assembled state.

With the subassembly 1500 held in a hand of an assembler, operation 1808 can include pivotably coupling the lever pivot 1027 to the housing 1014 (e.g., or a frame) and pivotably coupling the trigger pivot 1037 to the housing 1014. Coupling the lever pivot 1027 and trigger pivot 1037 in operation 1808 can be performed, for example, simultaneously, substantially simultaneously, or in a single motion or step. Pivotably coupling the lever 1024 to the housing 1014 can include aligning the lever pivot 1027 and the boss 1027A with the lever pivot attachment 1017A on the housing 1014. Pivotably coupling the trigger 1034 to the housing 1014 can include aligning the trigger pivot 1037 with the trigger pivot attachment 1017B on the housing 1014.

In some examples, the recess 1039 is supported by the boss 1027A and the inner surface (e.g., 1035) of the trigger 1034 is supported by the tab 1043 such that the lever pivot 1027 can be connected to a lever pivot attachment 1017A of the housing 1014 and the trigger pivot 1037 can be connected to the trigger pivot attachment 1017B of the housing 1014 without dislodging the recess 1039 from the boss 1027A.

In the sub-assembled state, the lever pivot 1027 and trigger pivot 1037 can provide a like distance D2 to the distance between the lever pivot attachment 1017A and the trigger pivot attachment 1017B on the housing 1014. The like distance can include, but is not limited to, the same distance, the same distance within reasonable manufacturing and assembly tolerances, a distance that facilitates assembly of the lever 1024 and the trigger 1034 to the housing 1014 in one step. In some examples, the distance D2 can be measured between the lever pivot axis P1 and the trigger pivot axis P2 as assembled.

Although method 1800 is described with reference to the forceps 1000 of FIG. 1A, the method 1800 can be performed to assemble other medical devices having a frame, a first lever having a first pivot, a second lever having a second pivot (such as but not limited to, a trigger), a coupling link and first and second pivot attachments on the frame.

Figure 19A:
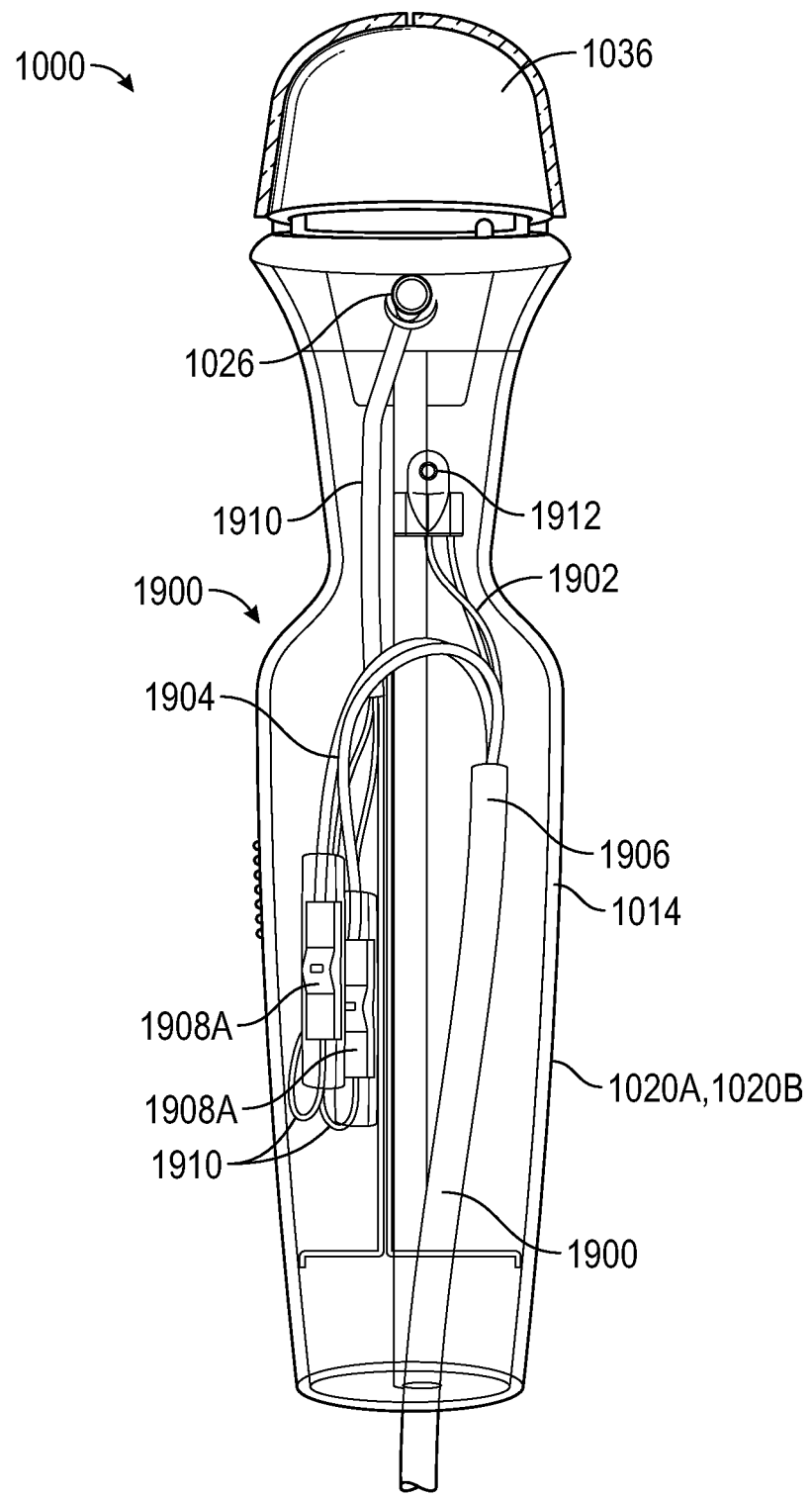
FIG. 19A illustrates a distal end of the forceps 1000 of FIG. 1A including a wire harness routing.
Figure 19B:
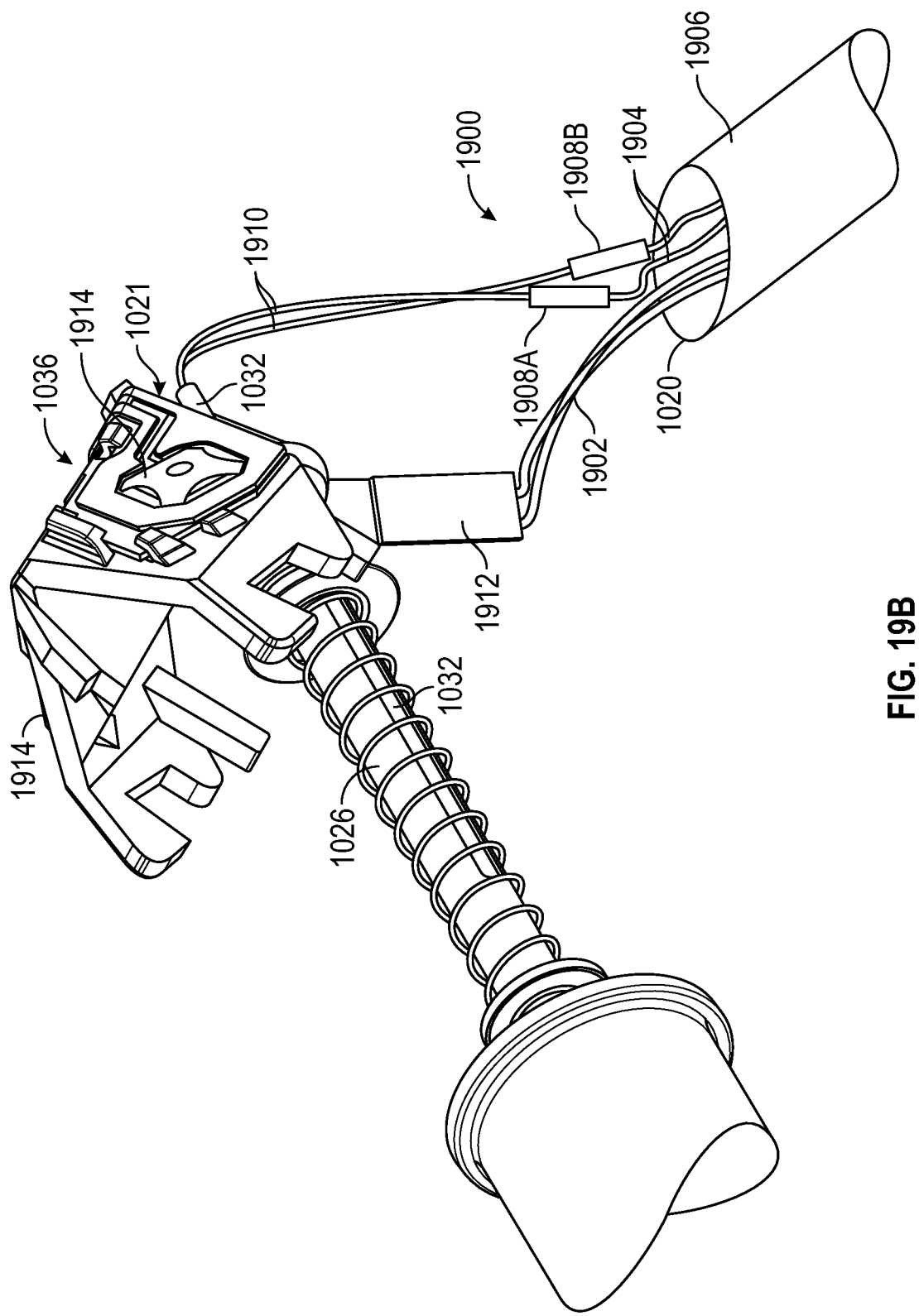
FIG. 19B illustrates a portion of the forceps 1000 of FIG. 1A including the wire harness routing of FIG. 19A.

FIG. 19A illustrates a distal end of the forceps 1000 of FIG. 1A including a wire harness 1900 routing, in accordance with at least one example. FIG. 19B illustrates a portion of the forceps 1000 of FIG. 1A including the wire harness routing 1900 of FIG. 19A, in accordance with at least one example.

Figure 21:
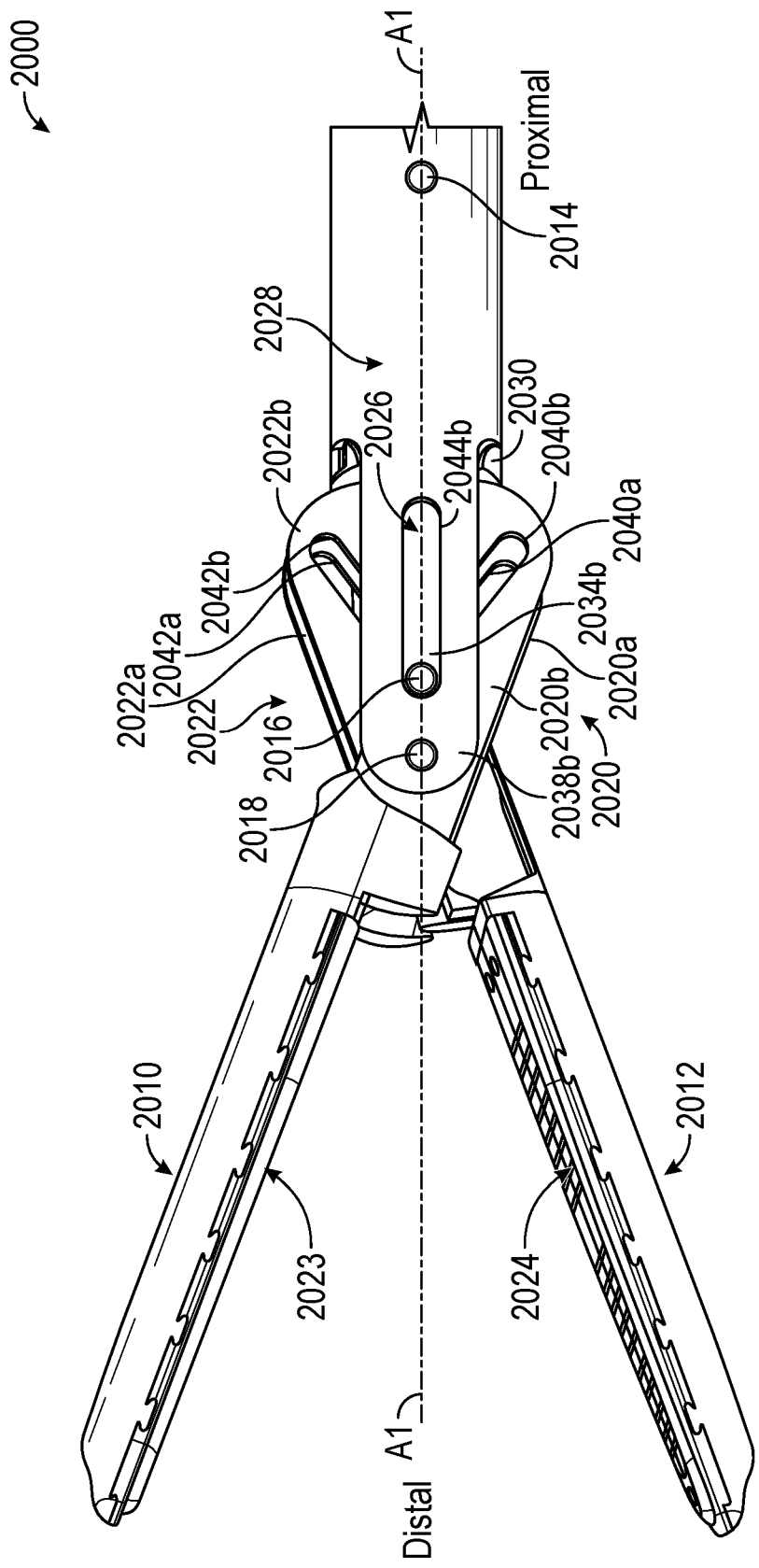
FIG. 21 illustrates a side view of a portion of a forceps in an open position.

The wire harness 1900 can provide electromagnetic energy, for example, to actuate one or more electrodes of the end effector 1002 of FIG. 1A. The wire harness 1900 can enter housing 1014, for example, at the handle portion 1020A, 1020B. The wire harness 1900 can include one or more low voltage wires and one or more high voltage wires. For example, as shown in FIG. 21, the wire harness 1900 can include a pair of low voltage wires 1902 and a pair of high voltage wires 1904 grouped together in a polymeric covering 1906.

As the plurality of high and low voltage wires travel into the housing 1014, the wires can be separated into the pair of low voltage wires 1902 and a pair of high voltage wires 1904. The pair of low voltage wires 1902 can route to one or more switches 1914 via connector 1912 that can form part of a flexible printed circuit board. The one or more switches 1914 can be, for example, dome switches that are actuatable by the activation button 1036. The pair of high voltage wires 1904 can route to one or more electrical couplings 1908A, 1908B that are in electrical communication with the end effector 1002. In an example, the low voltage pair of wires 1902 can carry a 12-volt DC current to the activation button 1036 (FIG. 1A). The activation button 1036 can include or be coupled to the one or more switches, such as a two dome switches by the activation button 1036 that floats above a flexible circuit board with the switches. When the activation button 1036 is pushed, a post or hook on the activation button 1036 can depress the dome switches 1914 to close the circuit.

The activation button 1036 can be a wraparound multi-directional button. The activation button 1036 can be pushed anywhere on the button and in any direction to activate the switch 1914. A feature on the activation button 1036, such as a post or hook formed on an inner surface facing the switches 1914, along with the two dome switches 1914 laterally spaced apart on sides of the handpiece 1001 make it possible to activate the activation button 1036 from many directions. This arrangement makes it easy for a user to activate. In the example, the two switches 1914 are arranged generally symmetrically about the longitudinal axis of the forceps 1000.

The low voltage pair of wires 1902 can include a ground wire and a reference wire forming a closed circuit. In an example, the high voltage pair of wires 1904 can carry 2265-volt, 450,000 Hz, 505 amps of current having waves that are out of phase with each other. The high voltage pair of wires 1904 can carry power to the end effector 1002.

The pair of high voltage wires 1904 can terminate at the electrical coupling 1908 where they can be electrically coupled to a pair of wires 1910 (hereinafter, "drive shaft wires") that travel through the drive shaft 1026. The electrical coupling 1908 and drive shaft wires 1910 facilitates adapting a single wire harness 1900 to accommodate forceps having drive shafts 1026 of different lengths. The pair of drive shaft wires 1910 can enter the proximal end of the of the drive shaft 1026 and can travel through the drive shaft 1026 alongside the blade shaft 1032 and exit out of the distal end of the drive shaft 1026. The pair of drive shaft wires 1910 can be coupled to the end effector 1002 at a distal end of the drive shaft 1026. In some examples the pair of high voltage wires 1904 can provide power to one or more electrodes of the jaws 1012. The routing of the drive shaft wires 1910 proximate the end effector 1002 is further discussed herein.

Figure 20B:
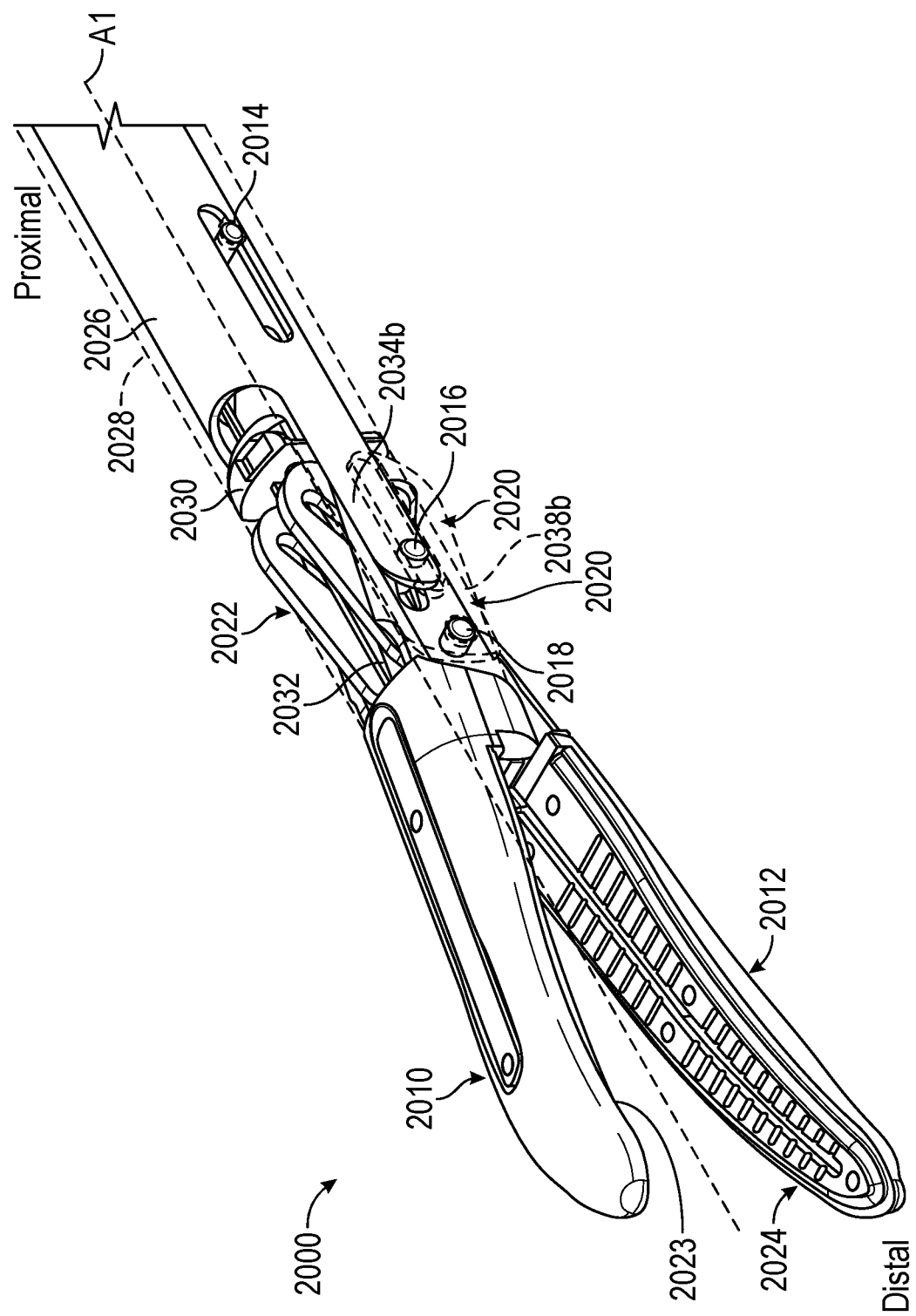
FIG. 20B illustrates an isometric view of a portion of a forceps in a partially open position.
Figure 20C:
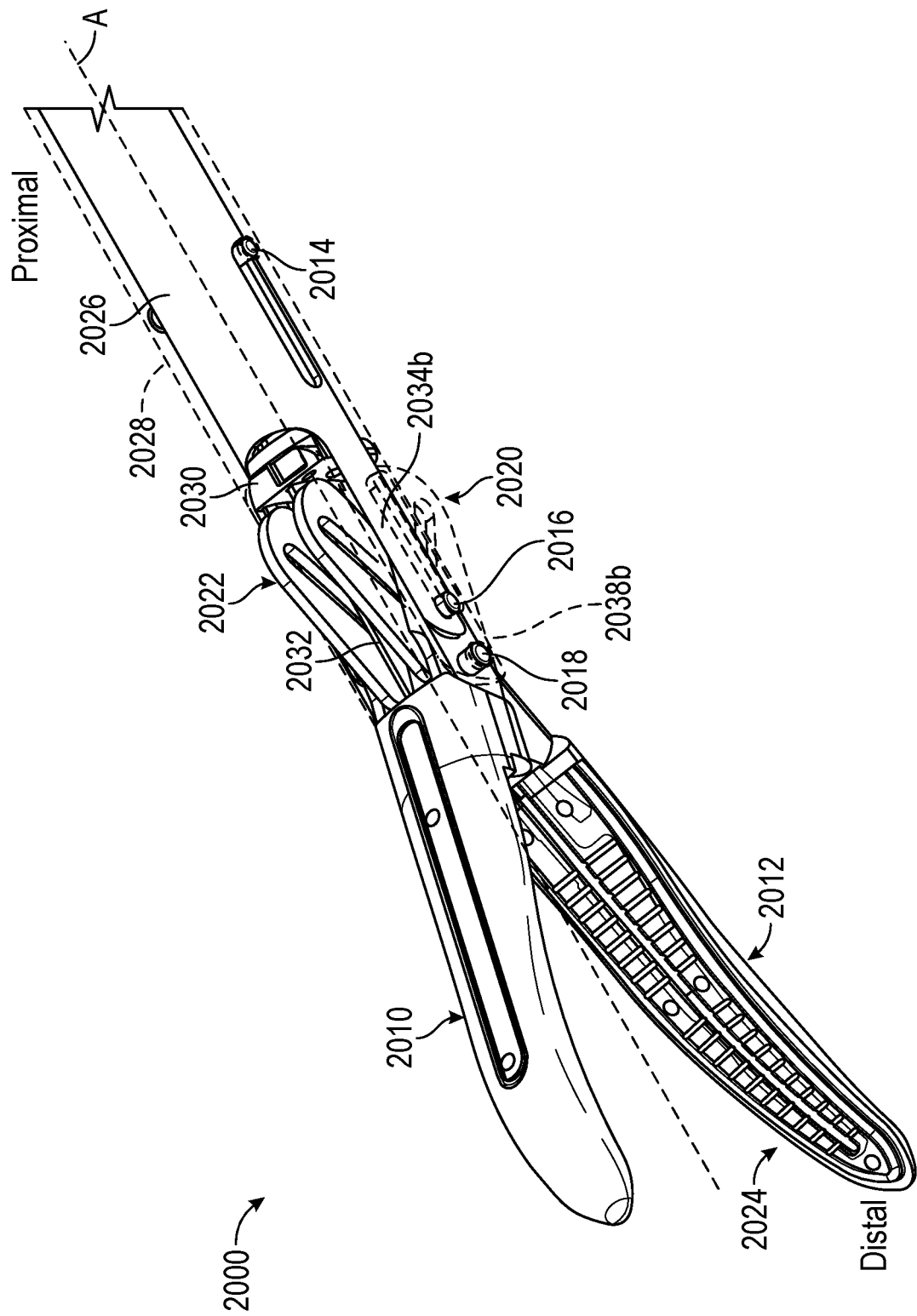
FIG. 20C illustrates an isometric view of a portion of a forceps in an open position.

FIG. 20A illustrates an isometric view of a portion of a forceps 2000 in a closed position, in accordance with at least one example of this disclosure. FIG. 20B illustrates an isometric view of a portion of the forceps 2000 in a partially open position. FIG. 20C illustrates an isometric view of a portion of the forceps 2000 in an open position. FIGS. 20A-20C also show axis A1 and orientation indicators Proximal and Distal. FIGS. 20A-20C are discussed below concurrently.

The forceps 2000 can be surgical forceps consistent with the description above, such that the forceps 2000 can be operated to open and close jaws to grasp tissue, apply electrical energy to the tissue, and/or to cut the tissue, such as may be employed during a surgery, biopsy or treatment procedure. Any of the features of the forceps 2000 or any forceps or end effectors discussed below can be included in the forceps discussed above. Further details of the forceps 2000 are discussed below.

The forceps 2000 can include an upper jaw 2010, a lower jaw 2012, a guide (or proximal pin) 2014, a drive pin 2016, and a pivot pin 2018. The upper jaw 2010 can include flanges 2020a and 2020b (collectively referred to as the flanges 2020) and an upper grip plate 2023; and, the lower jaw 2012 can include flanges 2022a and 2022b (collectively referred to as the flanges 2022) and a lower grip plate 2024. (The flanges 2020 and 2022 can also be referred to as struts herein.) The forceps 2000 can also include an inner shaft 2026 (or inner tube or drive shaft), an outer shaft 2028 (or outer tube), and a distal plug 2030. The inner shaft 2026 can include inner arms 2034a and 2034b (collectively referred to as the inner arms 2034). The outer shaft 2028 can include outer arms 2038a and 2038b (collectively referred to as the outer arms 2038). The flanges 2020a and 2020b can include tracks 2040a and 2040b, respectively (collectively referred to as tracks 2040). The flanges 2022a and 2022b can include tracks 2042a and 2042b, respectively (collectively referred to as tracks 2042). A portion of the forceps 2000 shown in FIGS. 20A-20C can be referred to as an end effector 2002.

The components of the forceps 2000 can each be comprised of materials such as one or more of metals, plastics, foams, elastomers, ceramics, composites, combinations thereof, or the like. Materials of some components of the forceps are discussed below in further detail.

The jaws 2010 and 2012 can be rigid members configured to engage tissue. The jaws 2010 and 2012 can be coupled to the outer shaft 2028, such as pivotably coupled, via the pivot pin 2018. The pivot pin 2018 can extend through a portion of the jaws 2010 and 2012 (such as a bore of each of the jaws 2010 and 2012) such that the pivot pin 2018 can be received by the outer arms 2038 of the outer shaft 2028. In other examples, the jaws 2010 and 2012 can be pivotably coupled to the outer shaft 2028 via a boss (or bosses) of the outer shaft 2028. In another example, the jaws 2010 and 2012 can include a boss (or bosses) receivable in bores of the outer shaft 2028 to pivotably couple the jaws 2010 and 2012 to the outer shaft 2028. In another example, outer shaft 2028 can include a boss (or bosses) receivable in bores of the jaws 2010 and 2012 to pivotably couple the jaws 2010 and 2012 to the outer shaft 2028.

The flanges 2020a and 2020b (which can be a set of flanges, that is, two flanges) can be rigid or semi-rigid members located at a proximal portion of the jaw 2010. Similarly, the flanges 2022a and 2022b can be rigid or semi-rigid members located at a proximal portion of the jaw 2012. In some examples, the flanges 2020 can be positioned laterally outward of the inner flanges 2022. In other examples, the flanges 2020 and 2022 can be interlaced.

The grip plates 2023 and 2024 of the jaws 2010 and 2012 can each be a rigid or semi-rigid member configured to engage tissue and/or the opposing jaw to grasp tissue, such as during an electrosurgical procedure. One or more of the grip plates 2023 and 2024 can include one or more of serrations, projections, ridges, or the like configured to increase engagement pressure and friction between the grip plates 2023 and 2024 and tissue. The flanges 2020 of the upper jaw 2010 can extend proximally away from the grip plate 2023 and 2034, and in some examples, substantially downward when the upper jaw 2010 is in the open and partially open positions (as shown in FIGS. 20B and 20C, respectively). Similarly, the flanges 2022 of the lower jaw 2012 can extend proximally away from the grip plate, and in some examples, substantially upward when the upper jaw 2010 is in the open and partially open positions (as shown in FIGS. 20B and 20C, respectively), such that the jaws 2010 and 2012 and flanges 2020 and 2022 operate to open and close in a scissoring manner. The jaws 2010 and 2012 can each include an electrode configured to deliver electricity to tissue (optionally through the grip plates 2023 and 2024), a frame supporting the electrode, and a blade slot configured to receive a blade between the jaws 2010 and 2012, as discussed in detail below.

The tracks 2040 of the flanges 2020 and the tracks 2042 of the flanges 2022 can each be a track, channel, path, or slot in the flanges 2020 and 2022, respectively. In some examples, the tracks 2040 and 2042 can be located proximally of the pivot pin 2018 when the pivot pin 2018 is coupled to the jaws 2010 and 2012 (and optionally to the outer shaft 2028). The tracks 2040 and 2042 can be shaped to receive the drive pin 2016 therein. In some examples, the tracks 2040 and 2042 can be slots or channels configured to receive the drive pin 2016 therethrough to connect the drive shaft 2026 (such as the inner arm 2034a and/or the inner arm 2034b) to the flanges 2020 and 2022 (and therefore to the jaws 2010 and 2012).

The tracks 2040 and 2042 can be straight in some examples and can be arcuately shaped in some examples. In any example, the tracks 2040 and 2042 can be configured to allow the drive pin 2016 to travel along the tracks 2040 and 2042 simultaneously to open and close the jaws.

Each of the inner shaft 2026 and the outer shaft 2028 can be a rigid or semi-rigid and elongate body having a geometric shape of a cylinder, where the shape of the inner shaft 2026 matches the shape of the outer shaft 2028. In some examples, the inner shaft 2026 and the outer shaft 2028 can have other shapes such as an oval prism, a rectangular prism, a hexagonal prism, an octagonal prism, or the like. In some examples, the inner shaft 2026 and the outer shaft 2028 can be shaped so that the inner shaft 2026 cannot rotate with respect to the outer shaft 2028, but the inner shaft 2026 can still translate with respect to the outer shaft. For example, the inner shaft 2026 and the outer shaft 2028 can be concentric oval prisms. In another example, the inner shaft 2026 and the outer shaft 2028 can be rectangular tubes sized to limit relative rotation of the inner shaft 2026 with respect to the outer shaft 2028. In some examples, the shape of the inner shaft 2026 can be different from the shape of the outer shaft 2028.

The inner shaft 2026 can extend substantially proximally to distally along the axis A1, which can be a longitudinal axis. Similarly, the outer shaft 2028 can extend substantially proximally to distally along the axis A1. In some examples, the axis A1 can be a central axis of one or more of the inner shaft 2026 and the outer shaft 2028. The inner shaft 2026 can include an axial bore extending along the axis A1. The outer shaft 2028 can also include an axial bore extending along the axis A1. The inner shaft 2026 can have an outer dimension (such as an outer diameter) smaller than an inner diameter of the outer shaft 2028 such that the inner shaft 2026 can be positioned within the outer shaft 2028 and can be translatable therein along the axis A1. The inner shaft 2026 can also be referred to as a drive shaft 2026, a cam shaft 2026, or an inner tube 2026. The outer shaft 2028 can also be referred to as an outer tube 2028.

The inner arms 2034a and 2034b (distal arms) of the inner shaft 2026 can extend distally from a distal portion of the inner shaft 2026 and the inner arms 2034a and 2034b can be positioned laterally outward of the flanges 2020 and 2022. In some examples, the inner arms 2034a and 2034b can together form a fork or clevis. The outer arms 2038a and 2038b can extend distally from a distal portion of the outer shaft 2028 to form a fork or clevis. In some examples, the outer arms 2038a and 2038b can extend distally beyond the inner arms 2034a and 2034b to receive the pivot pin 2018 therein to secure the flanges 2020 and 2022 (and therefore the jaws 2010 and 2012) to the outer shaft 2028.

The jaw 2010 can include the flanges 2020a and 2020b and the jaw 2012 can include the flanges 2022a and 2022b. The jaws 2010 and 2012 can each include two flanges to help distribute forces applied to the jaws by the drive pin 2016. For example, use of two flanges per jaw can help to reduce forces applied to the tracks 2040 and 2042 by the drive pin 2016 during opening and closing of the jaws 2010 and 2012. The use of two flanges per jaw can also help to stabilize operation of the jaws because the pin 2016 has multiple contact points on each jaw. That is, the drive pin 2016 contacts each of the flanges 2020a and 2020b and the flanges 2022a and 2022b.

The distal plug 2030 can be a plug positionable within the outer shaft 2028 between the outer arms 2038 such that the inner arms 2034 can translate around the distal plug. The distal plug 2030 can include a blade channel extending therethrough to allow the blade 2032 to extend through (and translate with respect to) the distal plug 2030. The distal plug 2030 can include one or more conduit bores for receiving conduit (connected to the electrodes of the jaws 2010 and 2012) therethrough. The distal plug 2030 is discussed in further detail below.

The blade 2032 can be an elongate cutting member including one or more sharpened edges configured to cut or resect tissue or other items. The blade 2032 can be located within the outer shaft 2028 (and within the inner shaft 2026) and can extend along (and optionally parallel with) the axis A1. The blade 2032 can be translatable with respect to the inner shaft 2026 and the outer shaft 2028 to extend between (or into) the first jaw 2010 and the second jaw 2012. In some examples, the blade 2032 can extend axially through the inner shaft 2026 and can be laterally offset from the axis A1. In some examples, the blade 2032 the blade can extend axially through the flanges 2020 and 2022 such that the blade 2032 is in a position laterally inward of the first set of flanges 2020 and the second set of flanges 2022.

The guide 2014, the drive pin 2016, and the pivot pin 2018 can each be a rigid or semi-rigid pin, such as a cylindrical pin. The guide 2014, the drive pin 2016, and the pivot pin 2018 can have other shapes in other examples, such as rectangular, square, oval, or the like. In some examples, each pin can be the same size (e.g., diameter and length) to simplify manufacturing and reduce cost. Each pin can have a smooth surface to help reduce surface friction between the pins and components of the forceps 2000, such as between the pivot pin 2018 and the outer shaft 2028 or the drive pin 2016 and the flanges 2020 and 2022. In some examples, each of the guide 2014, the drive pin 2016, and the pivot pin 2018 can be other components such as one or more projections, bosses, arms, or the like.

Operation of the forceps 2000 is discussed below in the discussion of FIG. 21 with reference to FIGS. 20A-20C.

FIG. 21 illustrates a side view of a portion of the forceps 2000 in an open position, in accordance with at least one example of this disclosure. FIG. 21 also show the axis A1 and orientation indicators Proximal and Distal. The forceps 2000 of FIG. 21 can be consistent with the forceps discussed with respect to FIGS. 20A-20C; FIG. 21 shows the forceps 2000 with the outer shaft 2028 in phantom.

FIG. 21 also shows outer slots 2044a and 2044b (only slot 2044b is visible win FIG. 21). The outer slots 2044a and 2044b (collectively referred to as the outer slots 2044) can be axial slots extending through opposing portions of the outer shaft 2028. In some examples, the outer slot 2044a can be on the arm 2038a on an opposite side of the outer tube 2028 from the outer slot 2044b on the arm 2038b. The outer slots 2044 can be sized to receive the drive pin 2016 therein such that the drive pin 2016 can translate along the outer slots 2044 (when the inner shaft 2026 translates with respect to the outer shaft 2028) in examples where the drive pin 2016 extends laterally outward from outer surfaces of the inner shaft 2026. In some examples, the outer slots 2044 can be tracks extending into a portion of the outer shaft 2028 (and not entirely through the outer shaft 2028).

In operation of some examples, a handle (such as those discussed above) can be operated to translate the inner shaft 2026 within (and with respect to) the outer shaft 2028. For example, distal translation of the inner shaft 2026 with respect to the outer shaft 2028 can cause the drive pin 2016 to translate distally causing the jaws 2010 and 2012 to move from a closed position (as shown in FIG. 20A) to an intermediate position (as shown in FIG. 20B) to an open position (as shown in FIGS. 20C and 431). Conversely, proximal translation of the inner shaft 2026 can cause the drive pin 2016 to translate proximally to move the jaws 2010 and 20112 to the closed position, such that the drive pin 2016 can translate to cause the jaws 2010 and 2012 to open and close in a scissoring manner. In other examples, the action can be reversed such that distal movement of the inner shaft 2026 can cause the jaws 2010 and 2012 to move toward a closed position and proximal movement of the inner shaft 2026 can cause the jaws 2010 and 2012 toward an open position.

More specifically, in one example, distal translation of the inner shaft 2026 can cause the drive pin 2016 to translate distally within the outer slots 2044 such as to help guide axial translation of the drive pin 2016 by helping to limit rotation of the inner shaft 2026 with respect to the outer shaft 2028 and by helping to limit non-axial movement of the inner shaft 2026 with respect to the outer shaft 2028. As the drive pin 2016 translates distally in the outer slots 2044, the drive pin 2016 can translate distally along (such as within) the tracks 2040 of the flanges 2020 of the upper jaw 2010 and along the tracks 2042 of the flanges 2022 of the lower jaw 2012. Because the tracks 2040 and 2042 can be angled and/or curved along the flanges 2020 and 2022, respectively, and because the tracks 2040 and 2042 can be oppositely oriented with respect to each other, distal translation of the drive pin 2016 can cause the jaws 2010 and 2012 to open in a scissor type movement. That is, the upper jaw 2010 moves upward and its flanges 2020 move downward, and the lower jaw 2012 moves downward and its flanges 2022 move upward, moving the upper jaw 2010 and the lower jaw 2012 toward (and ultimately into) an open position.

Distal translation of the inner shaft 2026 can be limited by contact between the drive pin 2016 and a distal end of each of the outer slots 2044 (as shown in FIG. 21). In some examples, distal translation of the inner shaft 2026 can be limited by contact between the drive pin 2016 and a distal end of each of the tracks 2040 and 2042. In other examples, distal translation of the inner shaft 2026 can be limited by contact between the guide 2014 and a portion of the inner shaft 2026.

To close the jaws, the inner shaft 2026 can be translated proximally to proximally translate the drive pin 2016, which causes the drive pin 2016 to translate proximally within the outer slots 2044. As the drive pin 2016 translates proximally in the outer slots 2044, the drive pin 2016 can translate proximally along (such as within) the tracks 2040 of the flanges 2020 of the upper jaw 2010 and along the tracks 2042 of the flanges 2022 of the lower jaw 2012. Proximal translation of the drive pin 2016 can cause the jaws 2010 and 2012 to close in a scissor type movement. That is, the upper jaw 2010 moves downward and its flanges 2020 move upward, and the lower jaw 2012 moves upward and its flanges 2022 move downward, moving the upper jaw 2010 and the lower jaw 2012 toward (and ultimately into) a closed position.

Proximal translation of the inner shaft 2026 can be limited by contact between the drive pin 2016 and a proximal end of each of the outer slots 2044. In some examples, proximal translation of the inner shaft 2026 can be limited by contact between the drive pin 2016 and a proximal end of each of the tracks 2040 and 2042. In other examples, proximal translation of the inner shaft 2026 can be limited by contact between the guide 2014 and a portion of the inner shaft 2026. In other examples, proximal translation of the inner shaft 2026 can be limited by contact between the jaws 2010 and 2012 (or by the limit to pivotal motion of the clamp lever with respect to the housing, as shown in FIG. 4C)

When the jaws 2010 are in the partially closed position (as shown in FIG. 20B), or when the jaws are not in a fully open position, the blade 2032 can be partially extended into the jaws 2010 and 2012 such as to cut tissue between the jaws 2010 and 2012. The blade 2032 can be extended by operating a trigger of the handle (or another actuator), as discussed above. When the jaws 2010 are in the closed position (as shown in FIG. 20A), the blade 2032 can be fully extended into the jaws 2010 and 2012 such as to cut tissue between the jaws 2010 and 2012. Using these operations, a physician can use the forceps 2000 to grasp tissue using the jaws 2010 and 2012, resect tissue using the blade 2032, and remove tissue of a patient. Further details of the forceps are discussed below.

Figure 22:
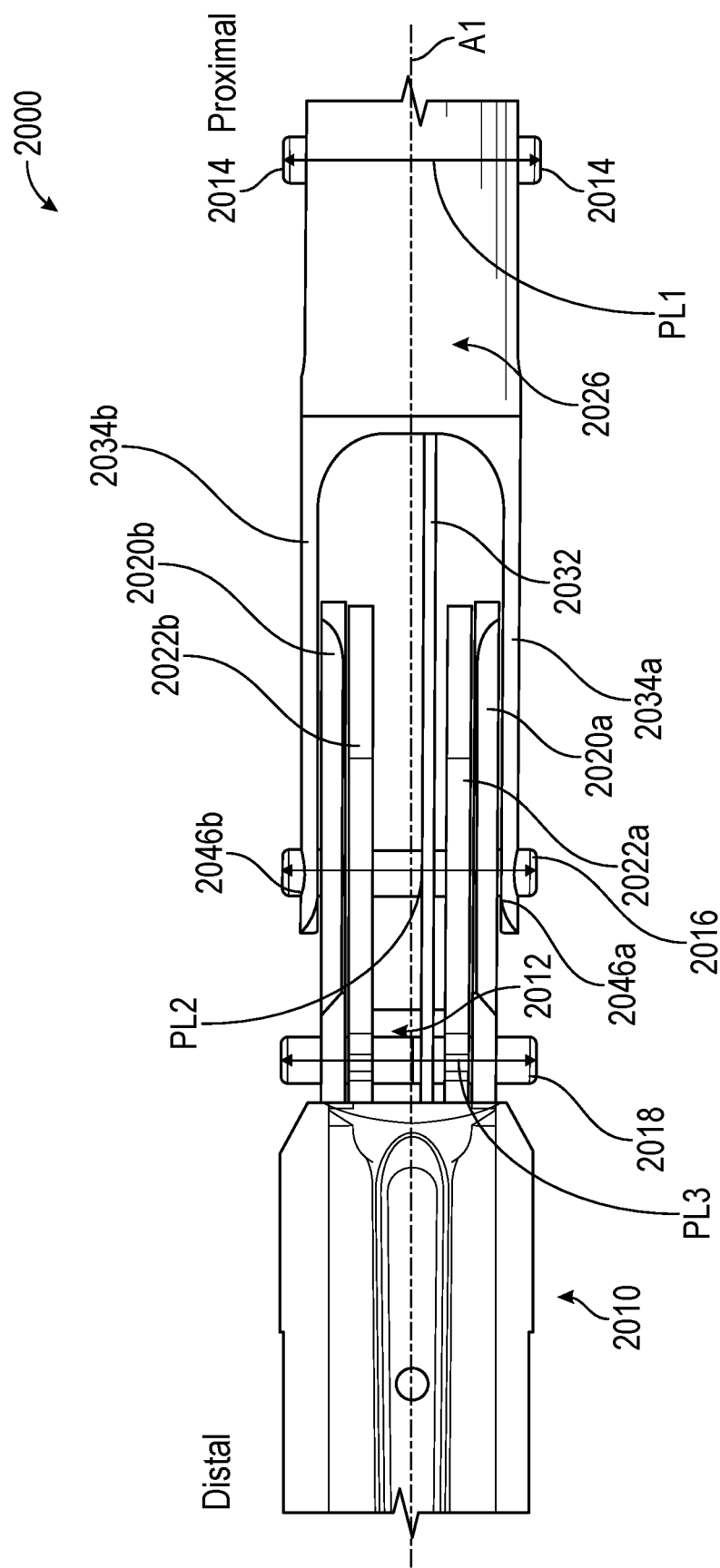
FIG. 22 illustrates a top view of a portion of a forceps in an open position.

FIG. 22 illustrates a top view of a portion of the forceps 2000 in the open position with the outer shaft 2028 removed, in accordance with at least one example of this disclosure. FIG. 22 shows orientation indicators Proximal and Distal and axis A1.

The forceps 2000 of FIG. 22 can be consistent with the forceps 2000 discussed above; further details are discussed with respect to FIG. 22. For example, FIG. 22 shows that the arms 2034a and 2034b of the inner shaft 2026 can include bores 2046a and 2046b, respectively, which can be sized and shaped to receive the drive pin 2016 therein (and therethrough in some examples).

FIG. 22 also shows that the flanges 2020 can be positioned laterally outward of the flanges 2022. FIG. 22 also shows that the flanges 2020 can be positioned laterally inward of the arms 2034 such that a gap exists between the flanges 2022a and 2022b such that the arms 2034 can control an outward lateral position of the flanges 2020 (and therefore the flanges 2022). The blade 2032 can be located between the flanges 2022, which allows the blade 2032 to translate parallel to the axis A1 without contacting the flanges 2022 or 2020. The blade 2032 being located between the flanges 2022 also allows the blade 2032 to be positioned at or near a center of the inner shaft 2026 and the jaws 2010 and 2012 so that the blade 2032 can extend along or near a central portion of the jaws 2010 and 2012 to help improve cutting operations using the blade 2032. In some examples, the flanges 2022 also allow the blade 2032 to be laterally inward of the flanges 2022 while still being offset from the axis A1.

FIG. 22 also shows that the pivot pin 2018 and the drive pin 2016 can extend through the blade 2032. FIG. 22 further shows that the drive pin 2016 can extend through the flanges 2020 and 2022 and the arms 2034. FIG. 22 further shows that the guide 2014 can define a length PL1, the drive pin 2016 can define a length PL2, and the pivot pin 2018 can define a length PL3. In some examples, the lengths PL1, PL2, and PL3 can all be the same to help simplify the bill of materials and construction of the forceps 2000. However, the lengths PL1, PL2, and PL3 can be different in other examples.

Figure 23:
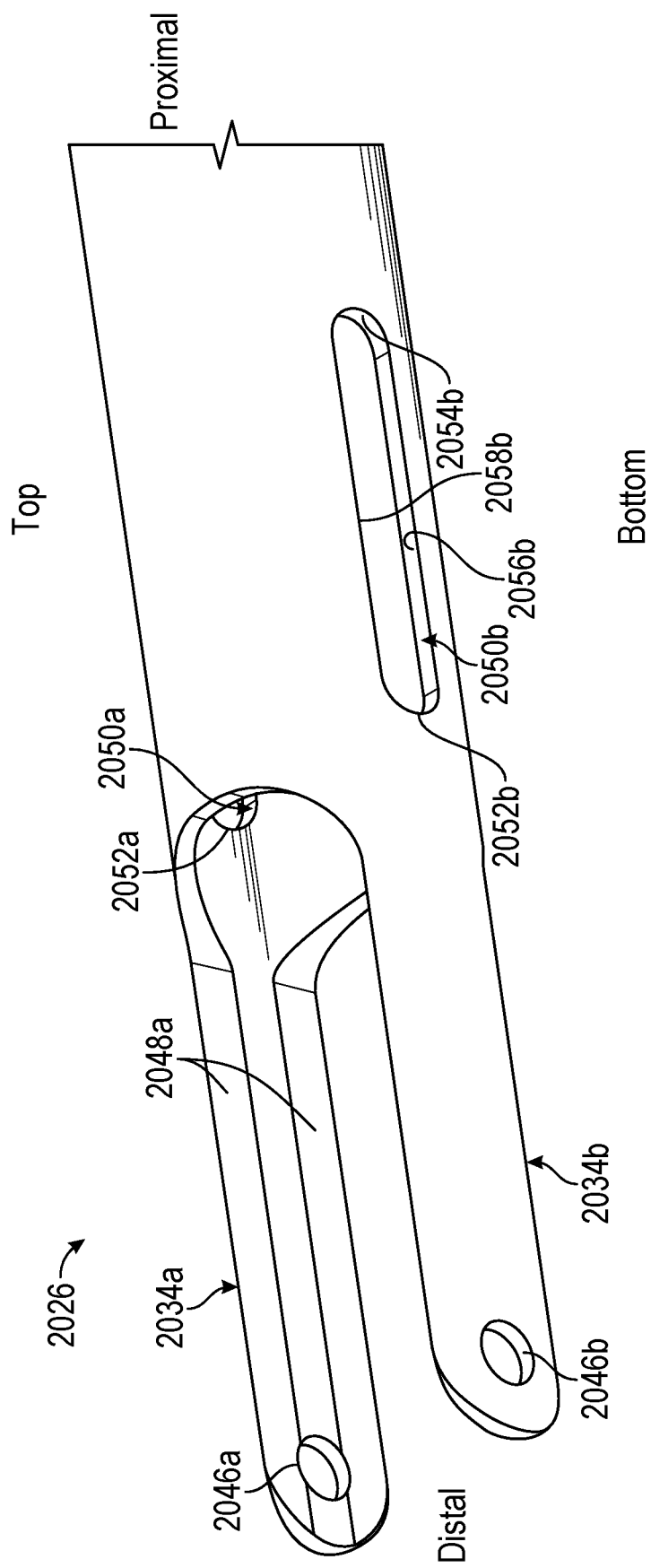
FIG. 23 illustrates an isometric view of a portion of a forceps.

FIG. 23 illustrates an isometric view of the inner shaft 2026 of the forceps 2000, in accordance with at least one example of this disclosure. FIG. 23 also shows orientation indicators Proximal, Distal, Top, and Bottom.

The inner shaft 2026 can be consistent with the description of the inner shaft 2026 above; FIG. 23 shows additional details of the inner shaft 2026 such as the flats 2048a and 2048b (only 2048a is visible in FIG. 23) of the arms 2034a and 2034b, respectively. The flats 2048 can be sized and shaped to allow the flanges 2020 and 2022 to be positioned within the arms 2034 and can be substantially parallel surfaces configured to reduce contact and friction between the flanges 2020 and 2022 and the arms 2034 during opening and closing of the jaws 2010 and 2012.

FIG. 23 also shows axial tracks 2050a and 2050b (collectively referred to as axial tracks 2050) The axial tracks 2050 can also be referred to as axial slots or channels or proximal slots of the inner shaft 2026. The axial tracks 2050 can each be axial slots extending laterally through walls of the inner shaft 2026. In other example, the axial tracks 2050 can be channels, grooves, recesses, or other guides configured to receive a guiding member. In some examples, the axial tracks 2050 do not extend entirely through the inner shaft 2026.

The axial track 2050a (not entirely visible in FIG. 23) can a include a distal edge 2052a, a proximal edge 2054a, a bottom edge 2056a, and a top edge 2058a. The axial track 2050b can a include a distal edge 2052b, a proximal edge 2054b, a bottom edge 2056b, and a top edge 2058b. One or more of the axial tracks 2050 can be sized and shaped to receive the guide 2014 therein (and therethrough in some examples) and can be sized and shaped for the guide 2014 to translate within the axial tracks 2050 between the edges 2054 and 2056. The interaction between the guide 2014 and the axial tracks 2050 is discussed in further detail below.

Figure 24:
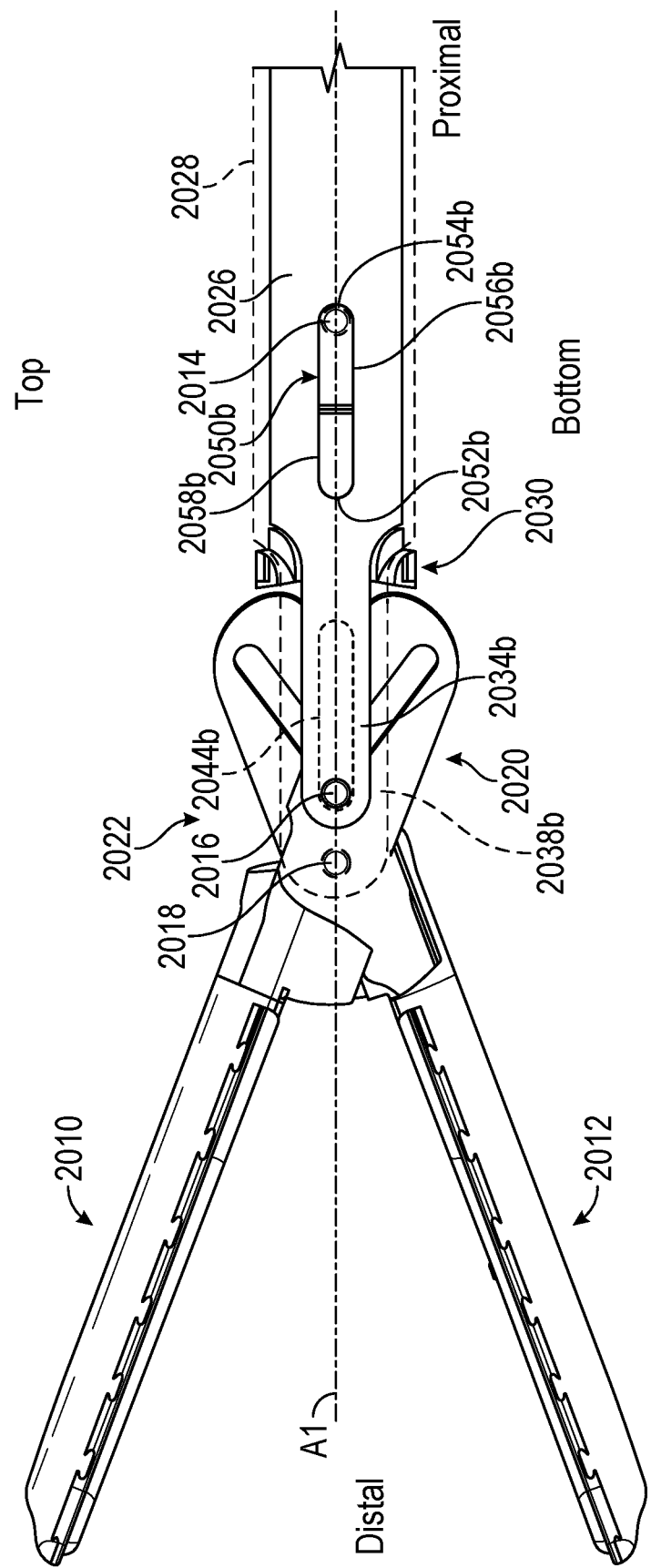
FIG. 24 illustrates a side view of a portion of a forceps in an open position
Figure 25:
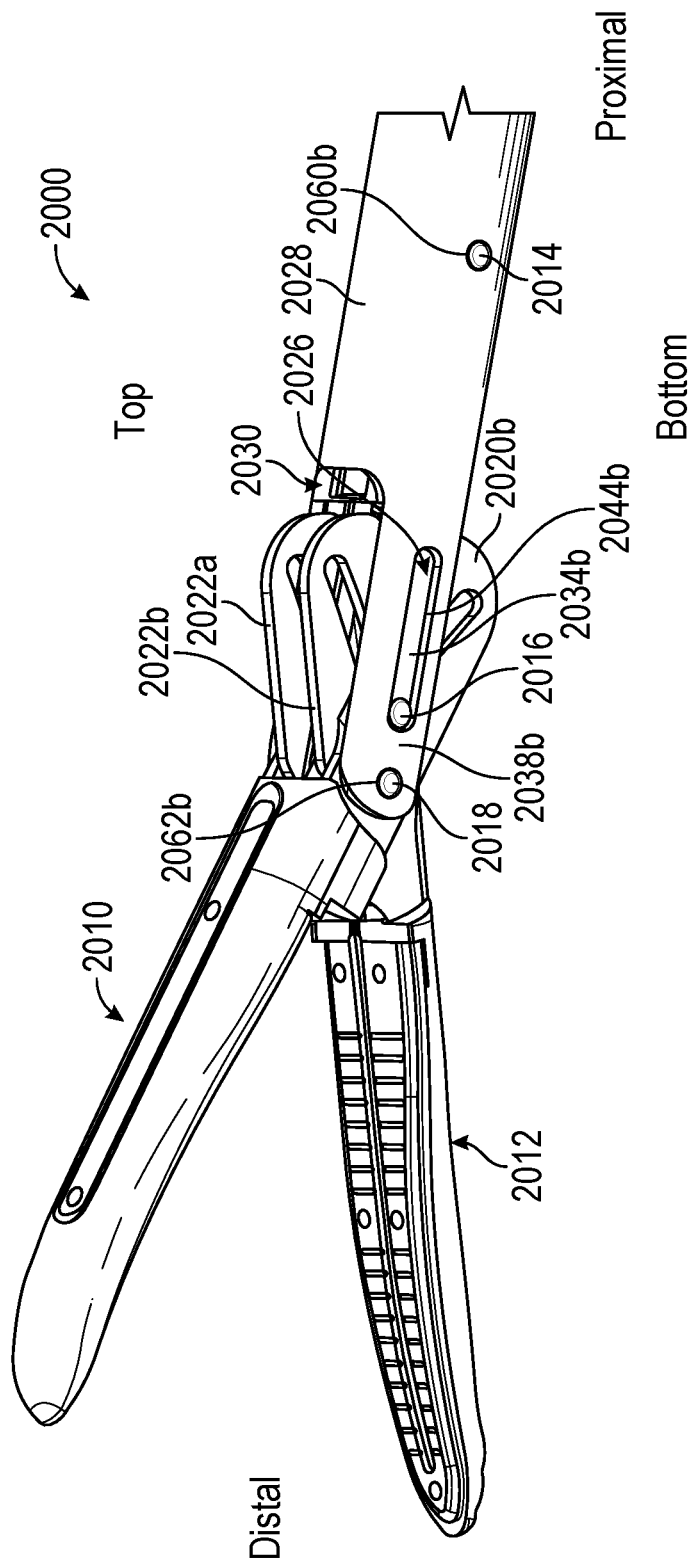
FIG. 25 illustrates a side isometric view of a portion of a forceps.

FIG. 24 illustrates a side view of a portion of the forceps 2000 in an open position with the outer shaft 2028 in phantom, in accordance with at least one example of this disclosure. FIG. 25 illustrates a side isometric view of a portion of the forceps 2000, in accordance with at least one example of this disclosure. FIGS. 24 and 25 are discussed below concurrently. FIGS. 24 and 25 show orientation indicators Proximal, Distal, Top, and Bottom, and FIG. 24 shows axis A1.

FIG. 25 shows that the guide 2014 can be secured to the outer shaft 2028 such as by insertion to bores 2060a and 2060b (only bore 2060b is visible in FIG. 25). The bores 2060 and the guide 2014 can be located at a distal portion of the outer shaft 2028 with respect to the forceps 2000. In some examples, the bores 2060 can be substantially coaxial and can be substantially perpendicular to the axis A1. In such cases, the guide 2014 can be positioned in the bores 2060 and can be on the axis defined by the bores 2060, substantially perpendicular to the axis A1. The bores 2060 can also be substantially centered about the outer shaft 2028 to center the guide 2014. In some examples, the bores 2060 can be offset from the axis A1 (either above, below) and substantially perpendicular to the axis A1. In other examples, the bores 2060 can cross a lateral plane defined in part by the axis A1 such that one bore is above the axis A1 and one is below; the axis defined by the bores 2060 can run through the axis A1 or can be offset therefrom in such a configuration. The axial tracks 2050 can be configured to match the orientation of the guide 2014 to allow the inner shaft 2026 to translate with respect to the guide 2014.

FIG. 25 also shows that the pivot pin 2018 can be positioned in bores 2062a and 2062b (only the bore 2062b is visible in FIG. 25) and can be secured therein. The orientation of the bores 2062a and 2062b can be similar to any of those discussed above with respect to the guide 2014 (aligned with the axis A1, offset of the axis A1, crossing the axis A1, etc.).

The guide 2014 can be affixed to the bores 2060 and the pivot pin 2018 can be affixed to the bores 2062 to help prevent the pins 2014 and 2018 from moving out of the bores 2060 and 2062, respectively. The pins 2014 and 2018 can be secured to the bores 2060 and 2062, respectively, using one or more of a weld (such as a laser weld), a threaded engagement, a fastener, an adhesive, or the like.

In operation of some examples, when the inner shaft 2026 is translated distally with respect to the outer shaft 2028 to move the drive pin 2016 distally to move the flanges 2020 and 2022 to fully open the jaws 2010 and 2012, distal translation of the inner shaft 2026 with respect to the outer shaft 2028 can be limited by contact between the guide 2014 and the proximal edges 2054 of the axial tracks 2050 (as shown in FIG. 24) of the inner shaft 2026 such that the guide 2014 can serve as a distal stop (or distal movement stop) for the inner shaft 2026.

In operation of some examples, when the inner shaft 2026 is translated proximally with respect to the outer shaft 2028 to move the drive pin 2016 proximally and to move the flanges 2020 and 2022 to fully close the jaws 2010 and 2012, proximal translation of the inner shaft 2026 can be limited by contact between the guide 2014 and the distal edges 2052 of the axial tracks 2050 of the inner shaft 2026 such that the guide 2014 can serve as a proximal stop for the inner shaft 2026. In other examples, proximal translation of the inner shaft 2026 can be limited by contact between the jaws 2010 and 2012 (such as the grip plates thereof).

Also, contact between the guide 2014 with one or more of the top edges 2052 can help limit downward movement of the inner shaft 2026. Similarly, contact between the guide 2014 with one or more of the bottom edges 2054 can help limit upward movement of the inner shaft 2026. Contact between the guide 2014 and the top and bottom edges 2052 and 2054, respectively, can also help to limit rotation of the inner shaft 2026 about the axis A1 with respect to the outer shaft 2028 such as when the end effector is rotated at the handle (discussed above). This can help limit winding on the shafts 2028 and 2026, which can improve performance of the forceps 2000 and help prevent breakage thereof.

The guide 2014 can also serve as one or more of a proximal translation stop, a distal translation stop, a vertical movement limiter, and a rotation limiter for the inner shaft 2026 in examples where proximal translation of the inner shaft 2026 opens the jaws 2010 and 2012 and distal translation of the inner shaft 2026 closes the jaws 2010 and 2012. The guide 2014 can be any of the variations discussed above regarding shape, size, and placement. In some examples, the guide 2014 can be engageable with the inner shaft 2026 to limit movement of the drive shaft 2026 with respect to the outer shaft 2028 in a direction not parallel with the guide 2014. In some examples, the guide 2014 can be engageable with the inner shaft 2026 to limit movement of the drive shaft 2026 in a direction perpendicular to the guide 2014. Such a perpendicular limitation of movement by the guide 2014 can limit movement of the shaft 2026 proximally and/or distally and/or vertically up and/or vertically down.

FIG. 26A illustrates a side view of a portion of the forceps 2000 with the inner shaft 2026 and the outer shaft 2028 shown in phantom and with the blade 2032 retracted, in accordance with at least one example of this disclosure. FIG. 26B illustrates a side view of a portion of the forceps 2000 with the inner shaft 2026 and the outer shaft 2028 shown in phantom and with the blade 2032 advanced. FIGS. 26A and 26B also show orientation indicators Proximal, Distal, Top, and Bottom, and axis A1. FIGS. 26A and 7B are discussed below concurrently.

The forceps 2000 of FIGS. 26A and 26B can be consistent with the forceps 2000 discussed above; FIGS. FIGS. 26A and 26B show additional details of the blade 2032. For example, FIGS. 26A and 26B show that the blade 2032 can include an edge 2064, where the edge 2064 can be retracted from the jaws 2010 and 2012 when the blade 2032 is retracted and the edge 2064 can extend into the jaws 2010 and 2012 (along the tracks of the jaws 2010 and 2012) when the blade 2032 is extended.

In operation of some examples, the blade 2032 can be translated distally into tracks of the jaws 2010 and 2012 when the jaws are between the open position and the closed position or when the jaws 2010 and 2012 are in the closed position. The blade 2032 can be used to cut tissue or other items between the jaws 2010 and 2012.

FIG. 26B also shows that the blade 2032 can include a blade track 2066 (or blade channel 2066) that can include a proximal edge 2068, a top edge 2070T, and a bottom edge 2070B. The track 2066 can extend most of a length of the blade 2032 along the axis A1 and can have a height slightly larger than a diameter of the pins (2014, 2016, and 2018) to allow the blade 2032 to translate along the axis A1 past the pins.

The track 2066 can be configured to contact the guide 2014 to limit axial translation of the blade 2032 with respect to the guide 2014 and the outer shaft 2028. For example, the proximal edge 2068 (which can be rounded complimentary to the guide 2014) can be configured to contact the guide 2014 to limit distal translation of the blade 2032 with respect to the inner shaft 2026, the outer shaft 2028, and the jaws 2010 and 2012. In some examples, the blade track 2066 can have a length longer than a length of the outer slots 2044a and 2044b such that the outer slots 2044a and 2044b do not limit translation of the blade 2032 with respect to the inner shaft 2026, the outer shaft 2028, and or the jaws 2010 and 2012.

Also, contact between one or more of the guide 2014, the drive pin 2016, and the pivot pin 2018 with the top edge 2070T can help limit downward and/or upward movement of the blade 2032 with respect to the inner shaft 2026, the outer shaft 2028, and the jaws 2010 and 2012. Such contact can also help limit rotation of the blade 2032, such as about the axis A1. Similarly, contact between one or more of the guide 2014, the drive pin 2016, and the pivot pin 2018 with the bottom edge 2070B can help limit upward movement of the blade 2032 with respect to the inner shaft 2026, the outer shaft 2028, and the jaws 2010 and 2012. Such contact can also help limit rotation of the blade 2032. In some examples, the guide 2014 can be diametrically centered about the outer shaft 2028. In other examples, the guide 2014 can be offset (above, below, and/or laterally) from the axis A1.

Figure 27:
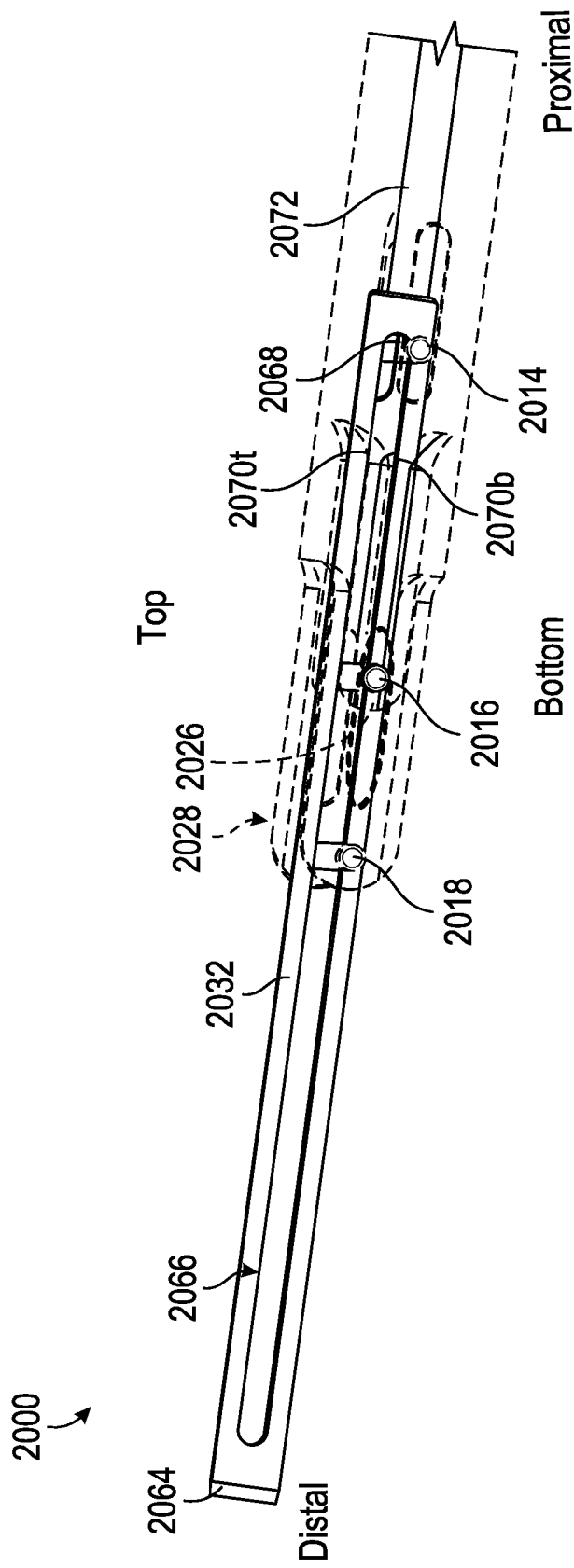
FIG. 27 illustrates an isometric view of a portion of a forceps with an inner shaft and an outer shaft shown in phantom and with jaws removed.

FIG. 27 illustrates an isometric view of a portion of the forceps 2000 with the inner shaft 2026 and the outer shaft 2028 shown in phantom and with the jaws 2010 and 2012 removed, in accordance with at least one example of this disclosure. FIG. 27 also shows orientation indicators Proximal, Distal, Top, and Bottom.

The forceps 2000 of FIG. 27 can be consistent with the forceps 2000 discussed above; additional details of the forceps are discussed with respect to FIG. 27. For example, FIG. 27 shows how the proximal edge 2068 of the blade track 2066 can engage the guide (shaft pin) 2014 to limit distal translation of the blade 2032. FIG. 27 also shows a blade shaft 2072, which can be connected to a proximal portion of the blade 2032 at a location proximal of the guide 2014. The blade shaft 2072 can extend through the outer shaft 2028 and the inner shaft 2026, proximally, from the connection with the blade 2032, where the shaft 2072 can connect to components of the handle, as discussed above.

Figure 28:
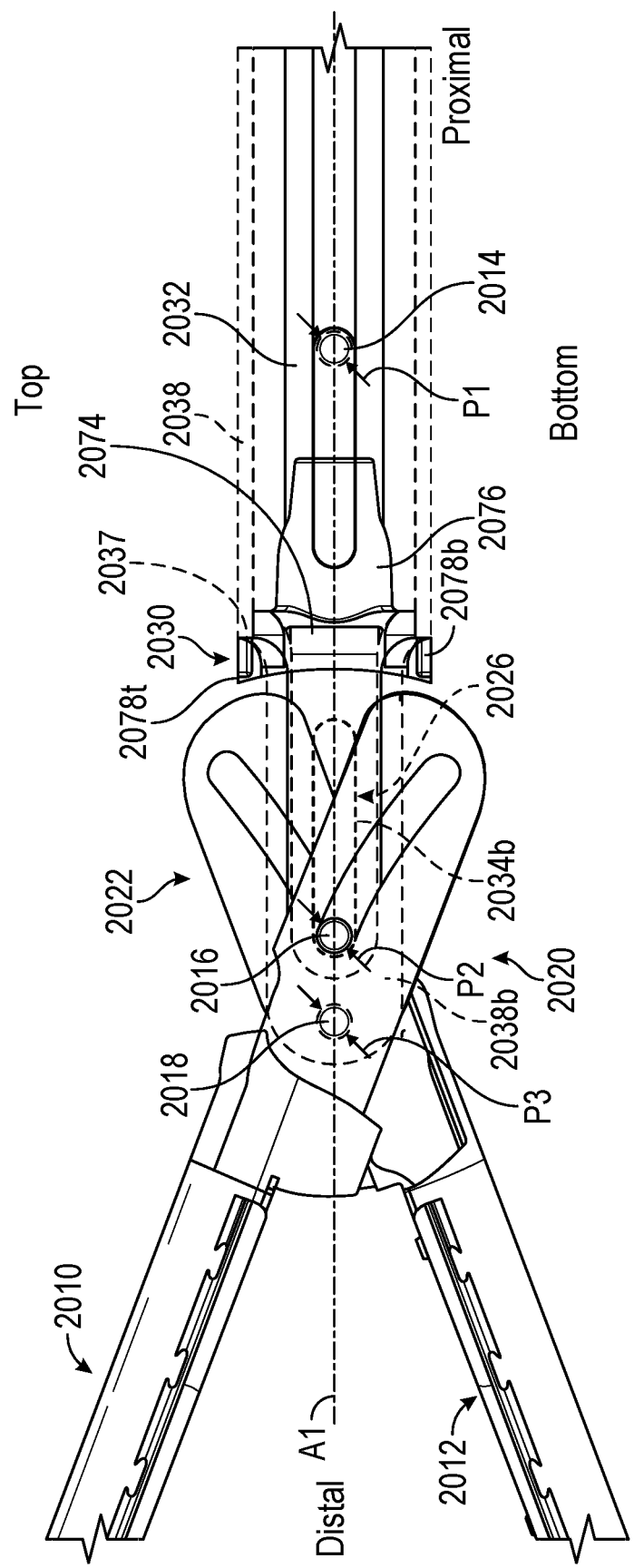
FIG. 28 illustrates an isometric view of a portion of a forceps with an inner shaft and an outer shaft shown in phantom.

FIG. 28 illustrates an isometric view of a portion of the forceps 2000 with the inner shaft 2026 and the outer shaft 2028 shown in phantom, in accordance with at least one example of this disclosure. FIG. 28 also shows orientation indicators Proximal, Distal, Top, and Bottom, and axis A1.

The forceps 2000 of FIG. 28 can be consistent with the forceps 2000 discussed above; additional details of the forceps are discussed with respect to FIG. 28. For example, FIG. 28 shows that the distal plug 2030 can be a distal plug securable to the outer tube 2028 between the pair of outer arms 2034 in a location proximal of the jaws 2010 and 2012.

More specifically, the distal guide plug 2030 can include a body 2074, a sleeve 2076, and top and bottom projections 2078T and 2078B. The body 2074 can be sized for insertion within the outer shaft 2028, such that the sleeve 2076 extends proximally into the outer shaft 2028. The projections 2078T and 2078B can extend laterally outward from the body (in some examples upwards and downwards) such that the projections 2078T and 2078B do not extend (or extend minimally) beyond an outer surface of the outer tube 2028. Further details of the distal guide plug 2030 are discussed below.

FIG. 28 also shows that the guide 2014, the drive pin 2016, and the pivot pin 2018 can have diameters P1, P2, and P3, respectively. In some examples, the diameters P1, P2, and P3 can all be the same to help simplify the bill of materials and construction of the forceps 2000. However, the diameters P1, P2, and P3 can be different in other examples.

Figure 29A:
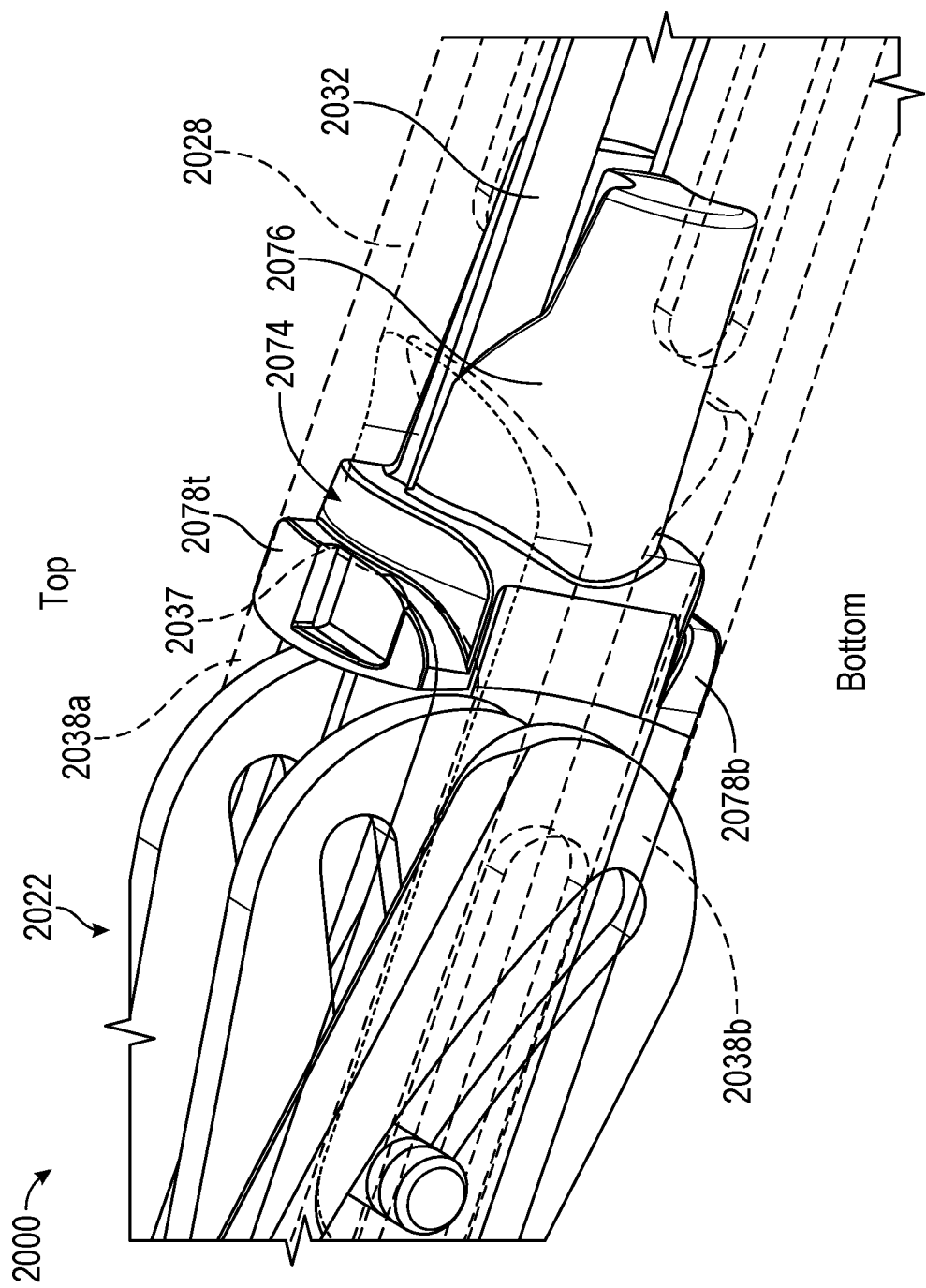
FIG. 29A illustrates an isometric view of a portion of a forceps with an inner shaft and an outer shaft shown in phantom.
Figure 29B:
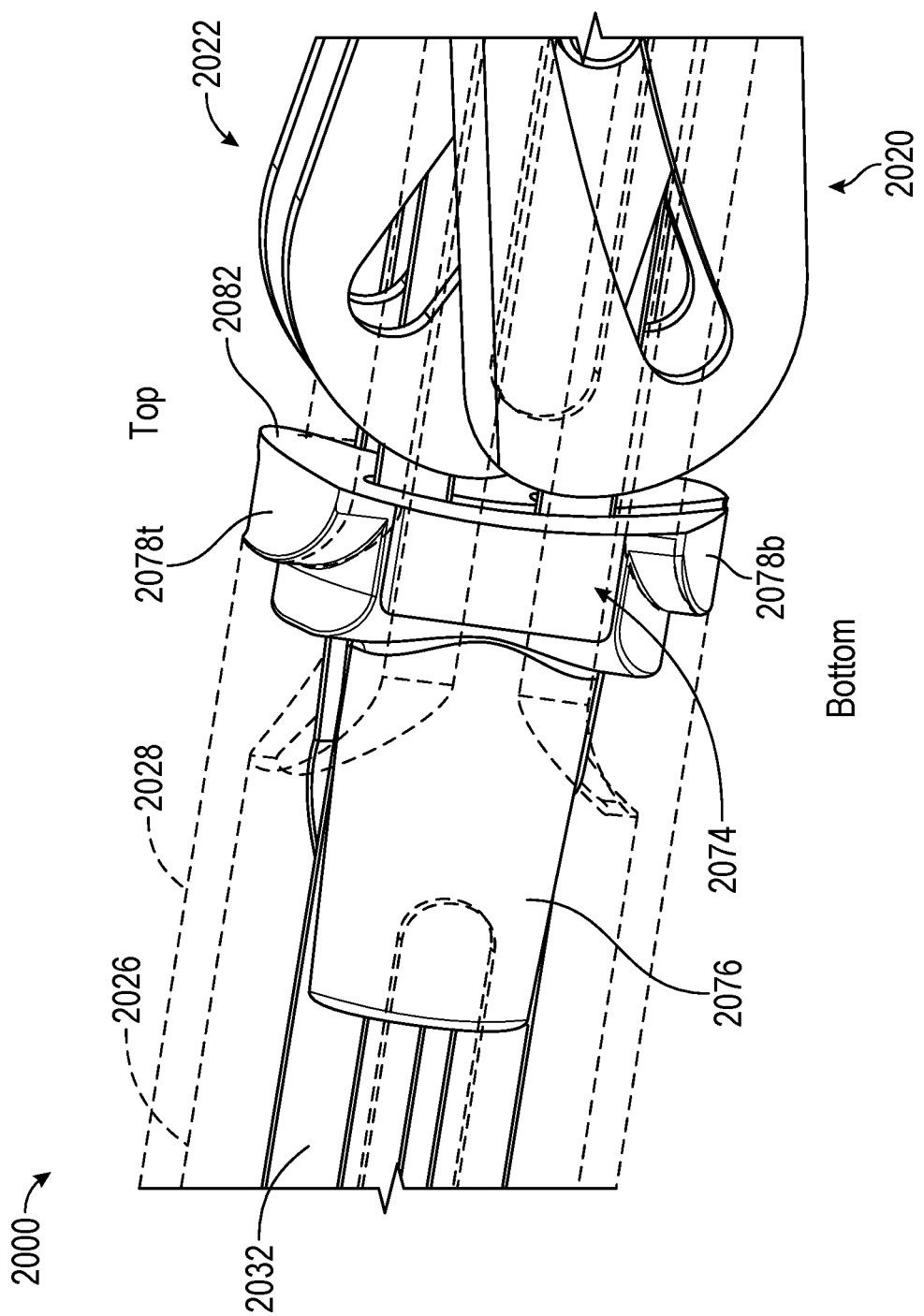
FIG. 29B illustrates an isometric view of a portion of a forceps with an inner shaft and an outer shaft shown in phantom.
Figure 29C:
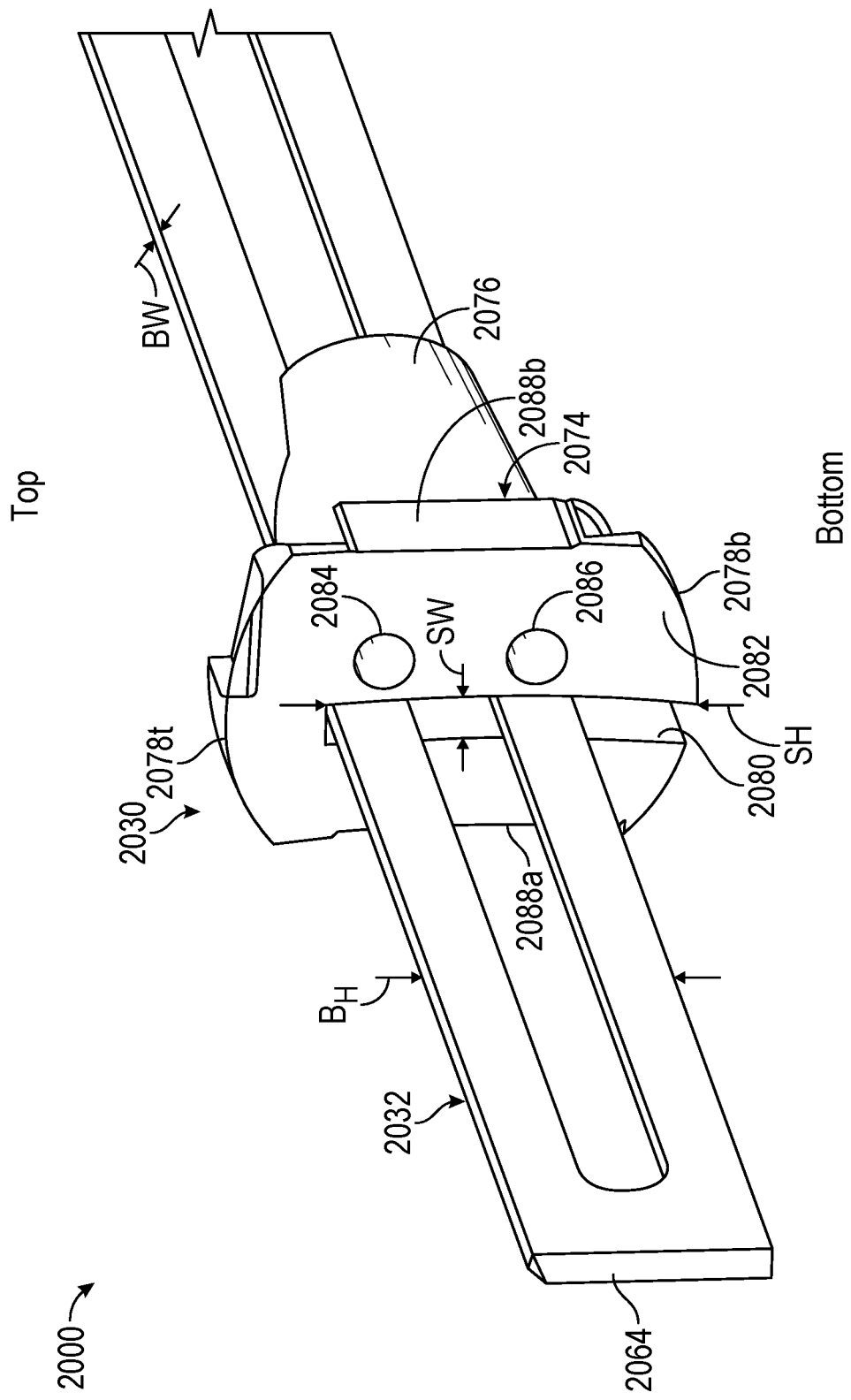
FIG. 29C illustrates an isometric view of a portion of a forceps with an inner shaft and an outer shaft shown in phantom.

FIG. 29A illustrates an isometric view of a portion of the forceps 2000 with the inner shaft 2026 and the outer shaft 2028 shown in phantom, in accordance with at least one example of this disclosure. FIG. 29B illustrates an isometric view of a portion of the forceps 2000 with the inner shaft 2026 and the outer shaft 2028 shown in phantom. FIG. 29C illustrates an isometric view of a portion of the forceps 2000 with the inner shaft 2026 and the outer shaft 2028 shown in phantom. FIGS. 29A-29C also show orientation indicators Proximal, Distal, Top, and Bottom, a blade height BH, a blade width BW, a slot height SH, and a slot width SW. FIGS. 29A-29C are discussed below concurrently.

The forceps 2000 of FIGS. 29A-29C can be consistent with the forceps 2000 discussed above; additional details of the forceps 2000 are discussed with respect to FIGS. 29A-29C. For example, FIGS. 29A-29C show that the projections 2078T and 2078B can extend upward and downward, respectively, from the body 2074 of the distal plug 2030. The projections 2078T and 2078B can be sized and shaped to nest in recesses 2037 between the arms 2034 such that the projections 2078T and 2078B can form an interference fit with the outer shaft 2028 to help limit movement of the distal guide plug 2030 with respect to the outer shaft 2028. This interference fit between the guide plug 2030 and the outer shaft 2028 can help to secure the guide plug 2030 to the outer shaft 2028. The distal plug 2030 can be additionally (or alternatively) secured to the outer shaft 2028 using fasteners, threads, and/or adhesives.

FIGS. 29A-29C also show that the guide plug 2030 can include a blade channel 2080, a distal face 2082, and wire routing bores 2084 and 2086. FIGS. 29A-29C also show that the blade channel 2080 can extend axially through the body 2074 and show that the blade channel 2080 can extend out of a lower portion of the body 2074 such as to allow for insertion of the blade 2032 into the blade channel 2080.

The slot height SH of the blade channel 2080 can be slightly larger than the blade height BH of the blade 2032 to allow movement of the blade 2032 through the blade channel 2080 while also helping to limit upward and downward movement of the blade 2032 with respect to the distal guide plug 2030 and therefore the outer tube 2028. Similarly, the slot width SW of the blade channel 2080 can be slightly wider than the blade width BW of the blade 2032 to support movement of the blade 2032 through the blade channel 2080 while also helping limit lateral movement of the blade 2032 with respect to the distal guide plug 2030 and therefore the outer tube 2028.

FIGS. 29A-29C also show that a distal face 2082 of the guide plug 2030 can be curved to allow clearance for rotation of the flanges 2020 and 2022 during opening and closing of the jaws 2010 and 2012. Further, the wire routing bores 2084 and 2086 can each extend through the distal face 2082 and through the body 2074 and the sleeve 2076 of the guide plug 2030. Each of the wire routing bores 2084 and 2086 can be sized and shaped to receive a wire (or conduit) therein and therethrough. Each of the wire routing bores 2084 and 2086 can be separated from the blade channel 2080 to help limit (or prevent or preclude) interaction between wires and the blade 2032.

FIG. 29C also shows that the body 2074 of the guide plug 2030 can include channels 2088a and 2088b on opposing laterally outer surfaces of the distal plug 2030. The channels 2088 can each be slots, tracks, channels, or flats configured to interface with the arms 2034 of the inner shaft 2026 such that the arms 2034 can translate past (or around) the distal plug 2030. The channels 2088 and other features of the guide plug 2030 are discussed in further detail below with respect to FIGS. 30A-30C.

Figure 30A:
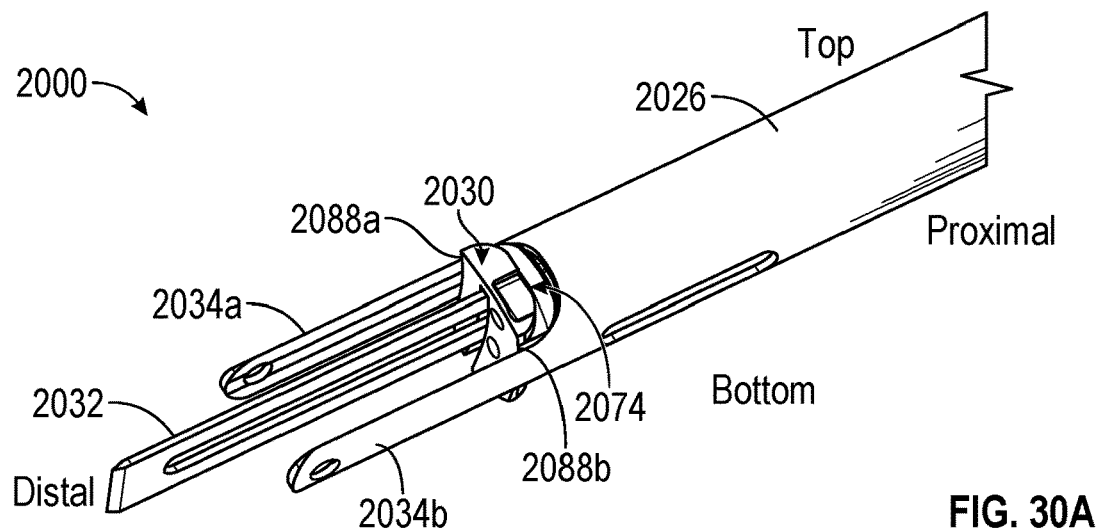
FIG. 30A illustrates an isometric view of a portion of a forceps with an inner shaft in an extended position.
Figure 30B:
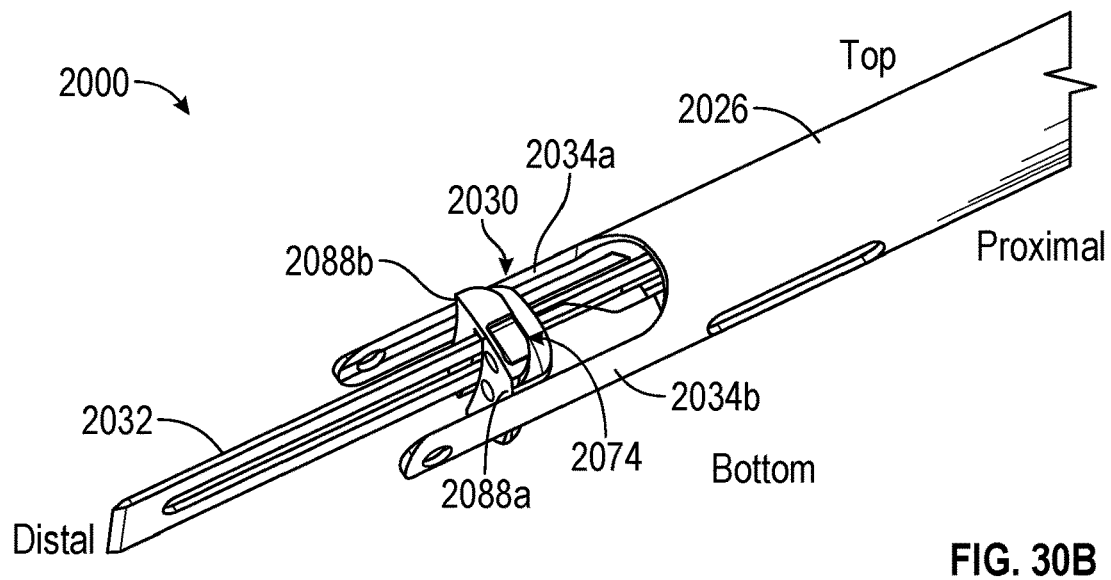
FIG. 30B illustrates an isometric view of a portion of a forceps with an inner shaft in a retracted position.
Figure 30C:
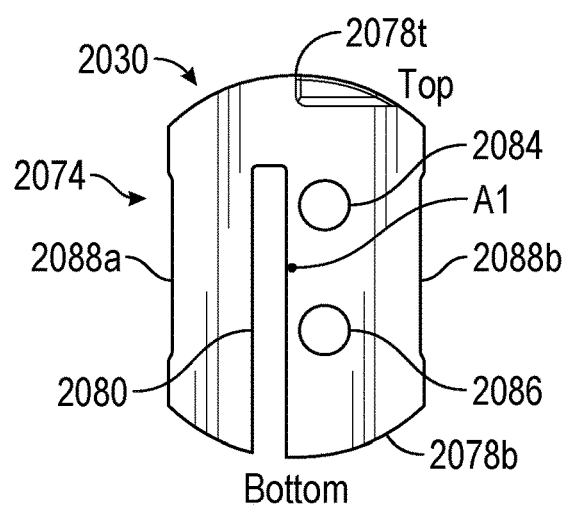
FIG. 30C illustrates an end view of a guide plug of a forceps.

FIG. 30A illustrates an isometric view of a portion of the forceps 2000 with the inner shaft 2026 in an extended position, in accordance with at least one example of this disclosure. FIG. 30B illustrates an isometric view of a portion of the forceps 2000 with the inner shaft 2026 in a retracted position. FIG. 30C illustrates an end view of the guide plug 2030 of the forceps 2000. FIGS. 30A-30B also show orientation indicators Proximal, Distal, Top, and Bottom. FIG. 30C also shows orientation indicators Top and Bottom, and axis A1. FIGS. 30A-30C are discussed below concurrently.

The forceps 2000 of FIGS. 30A-30 can be consistent with the forceps 2000 discussed above; additional details of the forceps are discussed with respect to FIGS. 29A-29C. For example, FIG. 30B shows how the arms 2034a and 2034b of the inner shaft 2026 can extend around and past the guide plug 2030 through the channels 2088a and 2088b, respectively, to allow the inner shaft 2026 to move between a distal position, as shown in FIG. 30B (closed jaws 2010 and 2012, in one example) and a proximal position, as shown in FIG. 30A, when the inner shaft 2026 translates within the outer shaft 2028 to operate the end effector (such as the jaws 2010 and 2012). That is, FIGS. 30A-30B shows how the arms 2034a and 2034b can be moved proximally around the guide plug 2030 through (or around) the channels 2088a and 2088b (such as when then arms 2034 are positioned laterally inward of the outer arms 2038), respectively 2030, to move the inner shaft 2026 to a proximal position.

FIG. 30C shows that the channels 2088 can each be a flat; however, the channels 2088 can be slots or other features allowing extension of the arms 2034 past the guide plug 2030. In some examples, the channels 2088 can be on opposing laterally outer surfaces of the guide plug 2030.

FIG. 30C also shows that the blade channel 2080 can be offset laterally from the longitudinal axis A1 of the shafts (2026 and 2028) and that the wire routing bores 2084 and 2086 can be laterally offset from the axis A1 on an opposite side from the blade channel 2080. In some examples, the distal plug 2030 can be oriented such that the blade channel 2080 is offset in other directions from the axis A1, such as above or below. FIG. 30C also shows that the wire routing bores 2084 and 2086 can be offset (above and below) the axis A1. However, in some examples, the wire routing bores 2084 and 2086 can be offset from the axis A1 in other directions, such as laterally.

FIG. 30C also clearly shows how the blade channel 2080 can extend out (or through) an end of a lower portion of the body 2074 such as to allow for insertion of the blade 2032 into the blade channel 2080 during assembly of the forceps 2000.

FIG. 31A illustrates an end view of a guide plug 2530 of a forceps, in accordance with at least one example of this disclosure. The guide plug 2530 can be similar to the guide plug 2030 discussed above, except that the blade channel 2580 of the guide plug 2530 can be merged with the wire routing bores 2584 and 2486 such that the wire routing bores 2584 and 2486 are still configured to retain wires therein. Such a design can help to simplify manufacturing of the guide plug 2530, which can be a small component with tight tolerances. Any of the forceps discussed above or below can be modified to include the guide plug 2530.

Figure 31B:
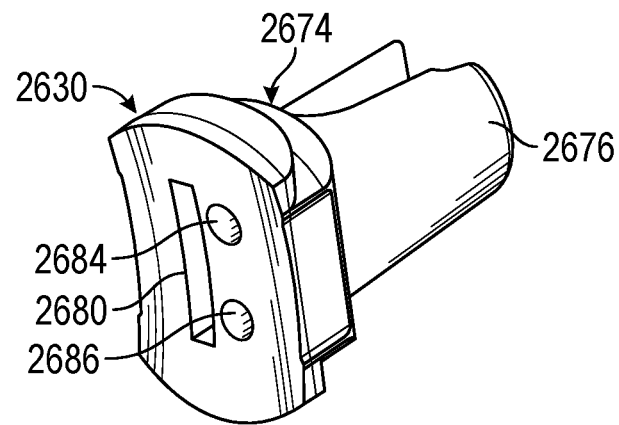
FIG. 31B illustrates an end view of a guide plug of a forceps.

FIG. 31B illustrates an end view of a guide plug 2630 of a forceps, in accordance with at least one example of this disclosure. The guide plug 2630 can be similar to the guide plug 2030 discussed above, except that the blade channel 2680 of the guide plug 2630 can terminate within the body 2674. That is, the blade channel 2680 does not extend out lateral, top, or bottom sides of the guide plug 2630. Such a blade channel can help limit downward movement of a blade within the guide plug 2030. Any of the forceps discussed above or below can be modified to include the guide plug 2630.

Figure 31C:
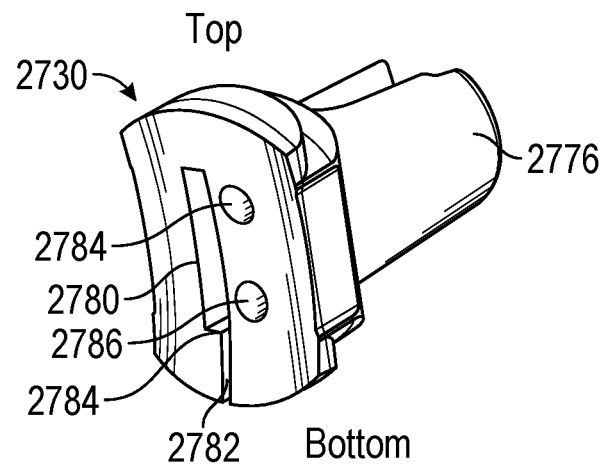
FIG. 31C illustrates an end view of a guide plug of a forceps.

FIG. 31C illustrates an end view of a guide plug 2730 of a forceps, in accordance with at least one example of this disclosure. FIG. 31C also shows orientation indicators Top and Bottom. The guide plug 2730 can be similar to the guide plug 2030 discussed above, except that the blade channel 2780 of the guide plug 2730 can include a projection 2784 extending inward across a portion (such as a lower or laterally outer portion) of the blade channel 2780 to provide a reduced size opening 2782 of the blade channel 2780 at the outward portion of the blade channel 2780. Such a blade channel can allow a blade to be inserted into the blade channel 2780 through the bottom portion of the guide plug 2730. The projection 2784 can help to limit the bottom portion of the blade channel 2780 from moving or collapsing laterally inward and pinching the blade within the slot 2780 during operation of the forceps, which can help improve use of the forceps 2000 during an operation, for example. Any of the forceps discussed above or below can be modified to include the guide plug 2730.

Figure 32A:
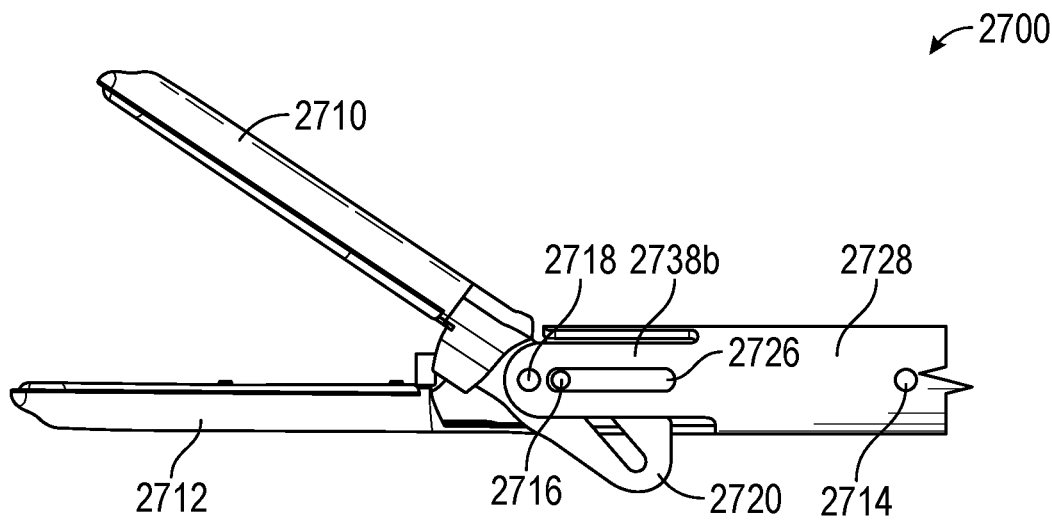
FIG. 32A illustrates a side view of a portion of a forceps.
Figure 32B:
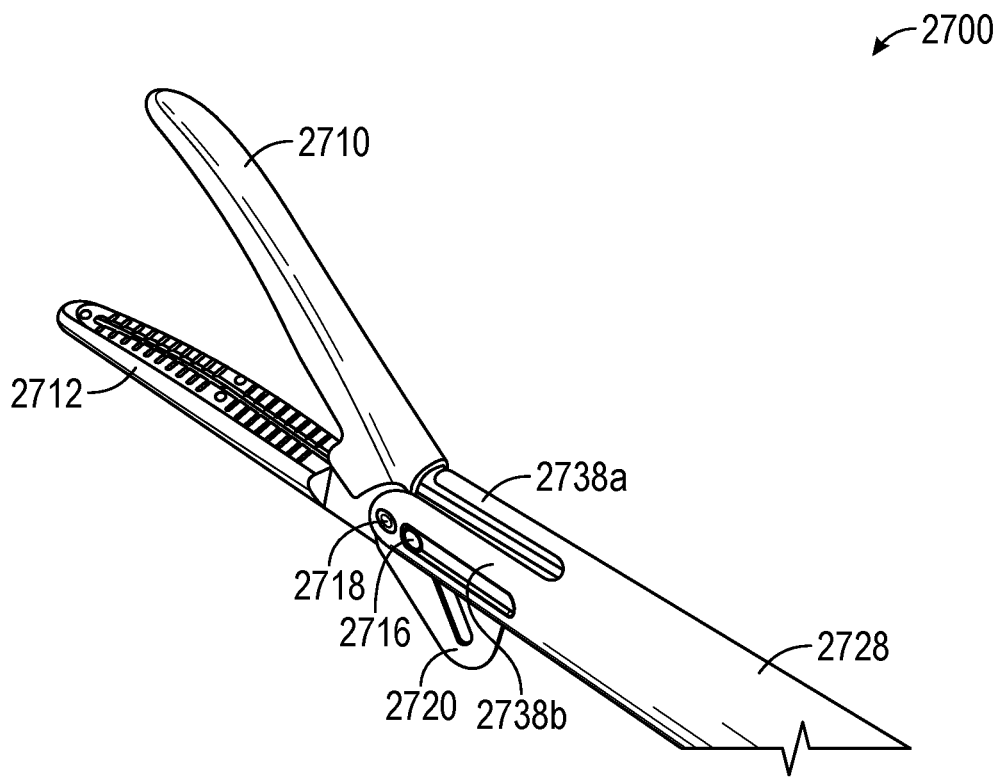
FIG. 32B illustrates a perspective view of a portion of a forceps.

FIG. 32A illustrates a side view of a portion of a forceps 2700, in accordance with at least one example of this disclosure. FIG. 32B illustrates a perspective view of a portion of the forceps 2700. FIGS. 32A-32B are discussed below concurrently.

The forceps 2700 can include a top jaw 2710 (including flanges 2720), a bottom jaw 2712, a guide 2714, a drive pin 2716, a pivot pin 2718, an inner shaft 2726, and an outer shaft 2728. The outer shaft 2728 can include outer arms 2736a and 2736b.

The forceps 2700 of FIGS. 32A and 32B can be similar to the forceps 2000 discussed above, except that only the top jaw 2710 moves relative to the bottom jaw 2712, where the bottom jaw 2712 can be fixed relative to the inner shaft 2726 and the outer shaft 2728. In some examples, the top jaw 2710 can be fixed and the bottom jaw 2712 can move.

The forceps 2700 can include any of the features discussed above with respect to any of the other forceps except that only the flanges 2720 of the upper jaw 2010 are driven by the drive pin 2716 to cause the jaw 2710 to move between open and closed positions as the jaw pivots about the pivot pin 2718. Similarly, any of the forceps discussed above or below can be modified to include the components of the forceps 2700.

Figure 33A:
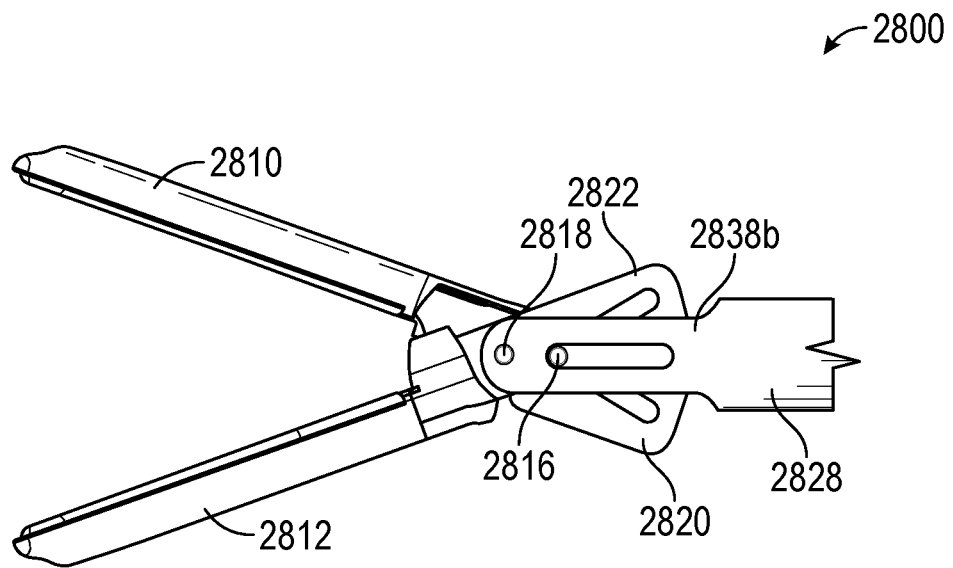
FIG. 33A illustrates a side view of a portion of a forceps
Figure 33B:
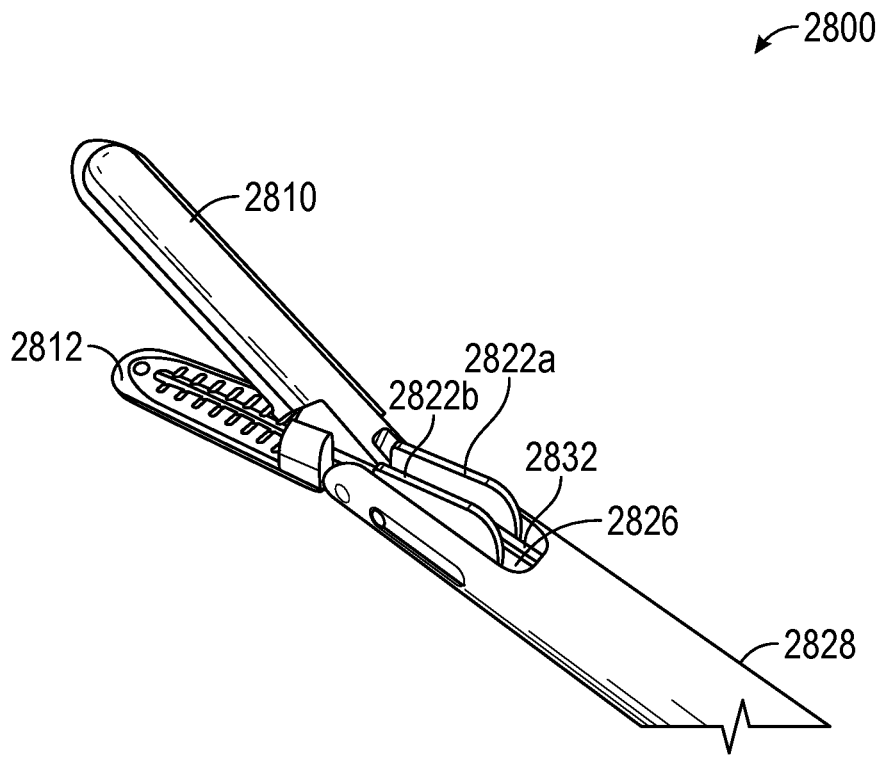
FIG. 33B illustrates a perspective view of a portion of a forceps.

FIG. 33A illustrates a side view of a portion of a forceps 2800, in accordance with at least one example of this disclosure. FIG. 33B illustrates a perspective view of a portion of the forceps 2800. FIGS. 33A-33B are discussed below concurrently.

The forceps 2800 can include a top jaw 2810 (including flanges 2820a and 2820b), a bottom jaw 2812 (including flanges 2822a and 2822b), a guide 2814, a drive pin 2816, a pivot pin 2818, an inner shaft 2826, and an outer shaft 2828. The outer shaft 2828 can include outer arms 2836a and 2836b.

The forceps 2800 of FIGS. 33A and 33B can be similar to the forceps discussed above, except that the flanges 2822 can be interlaced with the flanges 2820, which can allow for jaw assemblies (2010 and 2012) to be the same component, which can help reduce cost. In such an example, the blade 2832 can be positioned between one of the flanges 2822 and one of the flanges 2820. The forceps 2800 can include any of the features discussed above with respect to any of the other forceps. Similarly, any of the forceps discussed above or below can be modified to include the components of the forceps 2800.

Figure 34A:
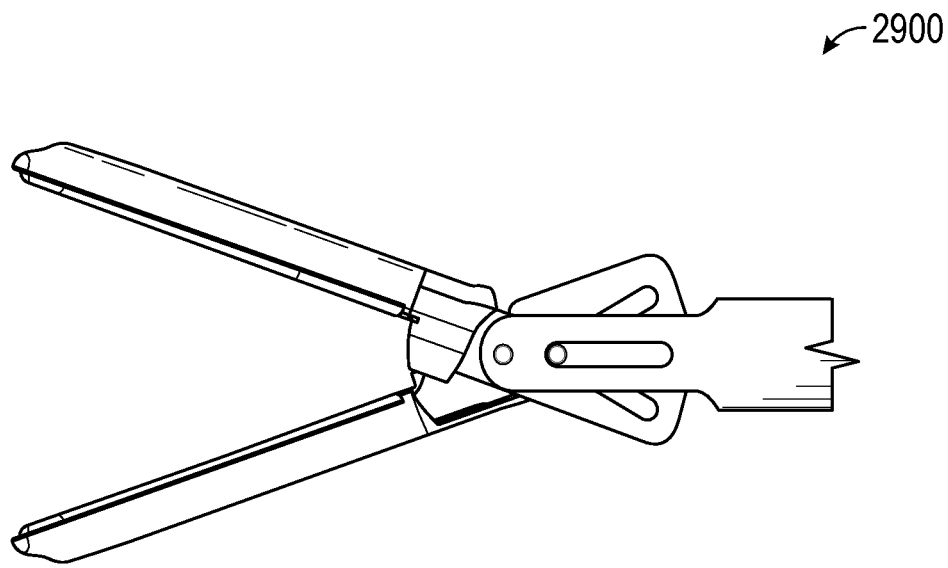
FIG. 34A illustrates a side view of a portion of a forceps.
Figure 34B:
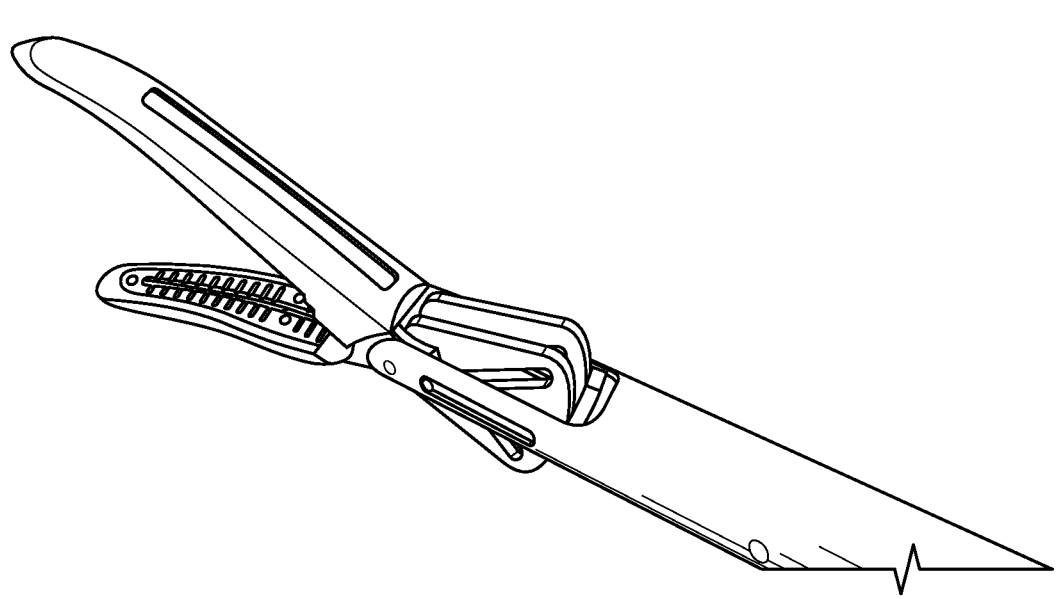
FIG. 34B illustrates a perspective view of a portion of a forceps.

FIG. 34A illustrates a side view of a portion of a forceps 2900, in accordance with at least one example of this disclosure. FIG. 34B illustrates a perspective view of a portion of the forceps 2900. The forceps 2900 can include any of the features discussed above with respect to the other forceps.

Figure 35A:
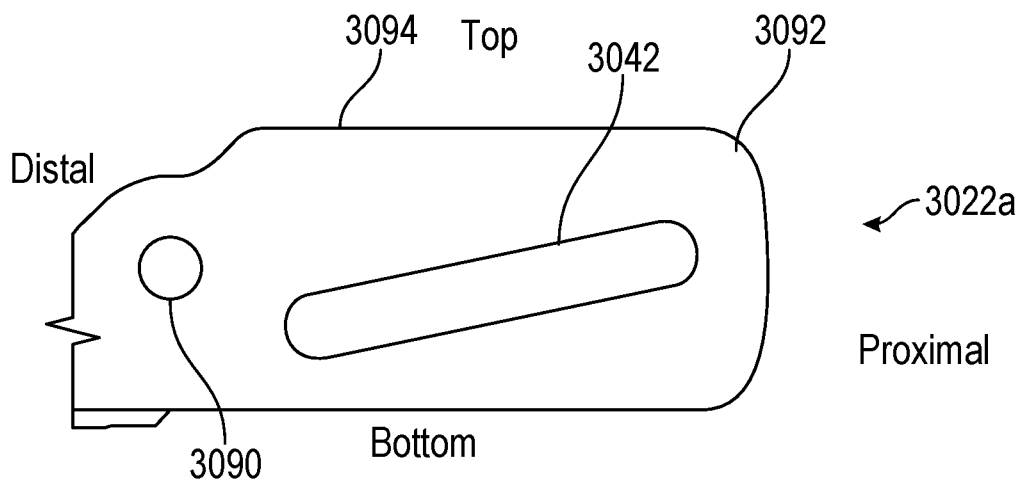
FIG. 35A illustrates a side view of a portion of a forceps.
Figure 35B:
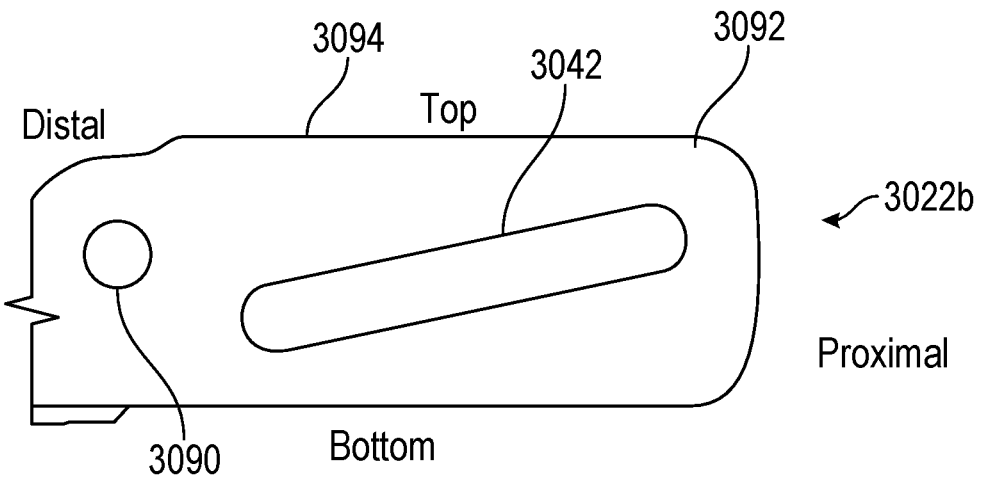
FIG. 35B illustrates a side view of a portion of a forceps.
Figure 35C:
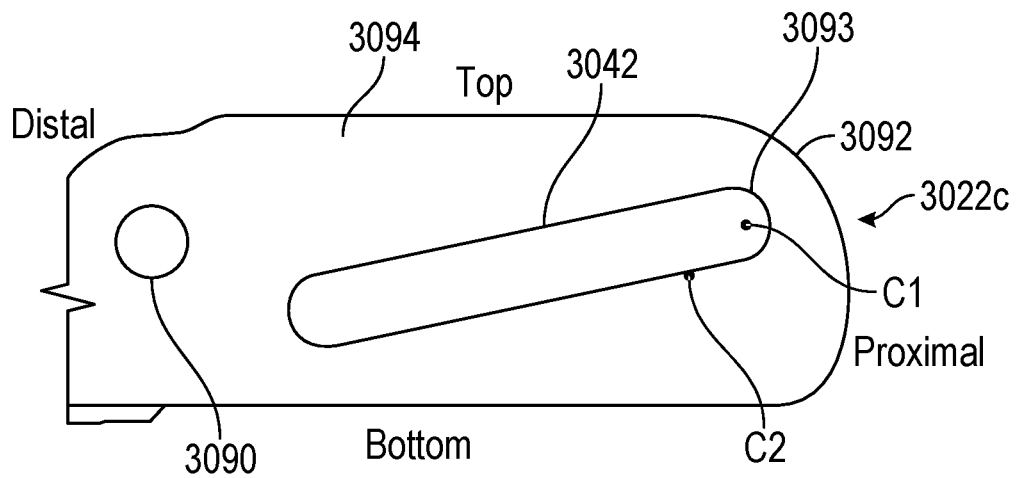
FIG. 35C illustrates a side view of a portion of a forceps.

FIG. 35A illustrates a side view of a flange 3022A of a forceps, in accordance with at least one example of this disclosure. FIG. 35B illustrates a side view of a flange 3022B of the forceps. FIG. 35C illustrates a side view of a flange 3022C of the forceps. FIGS. 35A-35C also show orientation indicators Proximal, Distal, Top, and Bottom. FIGS. 35A-35C are discussed below concurrently.

FIGS. 35A-35C show the flanges 3022A, 3022B, and 3022C, respectively, which can each include a pivot bore 3090 extending into or through the flange 3022. The pivot bore 3090 can be configured to receive a pivot pin (such as the pivot pin 2018) therethrough to secure the flanges 3022 to an outer shaft such that the flanges 3022 can pivot about the outer shaft.

FIGS. 35A-35C also show a curved proximal portion 3092 adjacent a top edge 3094 of the flanges 3022A, 3022B, and 3022C. The curved proximal portions 3092 can each be rounded or curved (or otherwise shaped or profiled) to provide a reduced lateral extension of the flange 3022 when the jaw is in the open position. The curved proximal portion 3092 of the flange 3022A can have a relatively small radius, whereas the curved proximal portion 3092 of the flange 3022C can have a relatively large radius that is not concentric with a curvature of a proximal end 3093 of a track 3042 of the flange 3022C. That is, a center of curvature C1 of the proximal end 3093 can be non-concentric with a center of curvature C2 of the curved proximal portion 3092. The relatively large radius of the curved proximal portion of the flange 3022C can further help to reduce lateral extension of the flange 3022C when the jaw is in the open position FIGS. 35A-16C also show that a top portion of the flange can be removed to further limit lateral extension of the flange 3022 when the jaw is in the open position. For example, the edge 3094 of FIGS. 35B and 16C can be moved laterally (or downward) by about 0.5 millimeters, as shown in FIG. 35A. In other examples, the edge 3094 can be moved down more or less, depending on the materials and sizes and shapes of the flange 3022, such as based on stresses applied to the flange from operation thereof. The forceps of FIGS. 35A-16C can include any of the features discussed above with respect to any of the other forceps. Similarly, any of the forceps discussed above or below can be modified to include the components of the forceps of FIGS. 35A-35C.

Figure 36A:
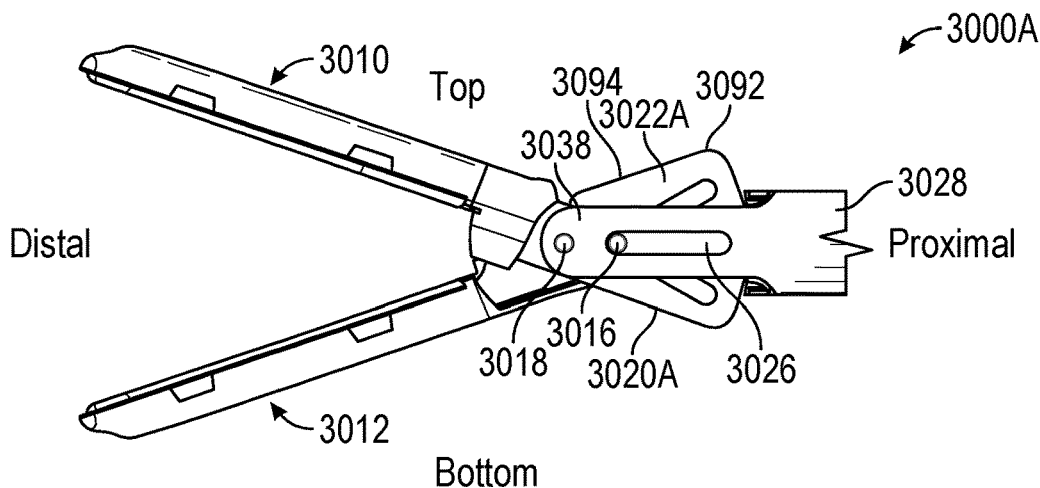
FIG. 36A illustrates a side view of a portion of a forceps.
Figure 36B:
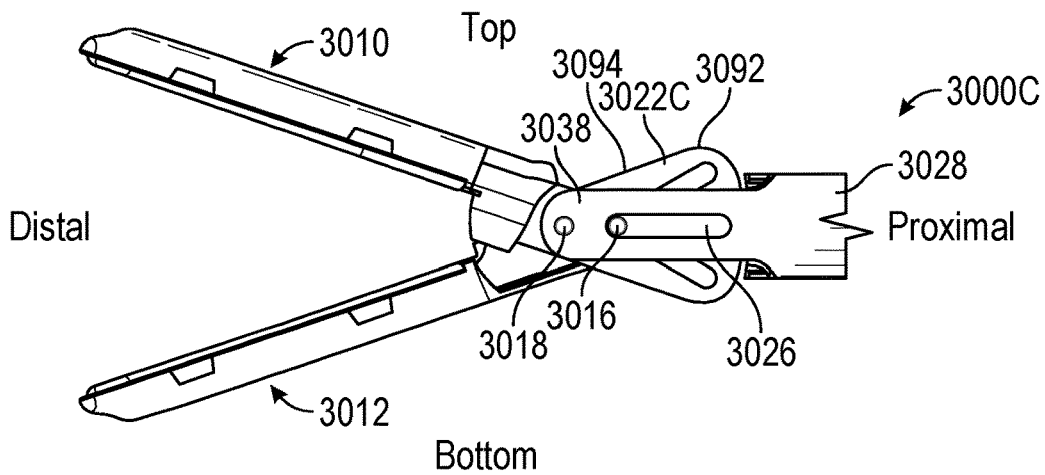
FIG. 36B illustrates a side view of a portion of a forceps.
Figure 36C:
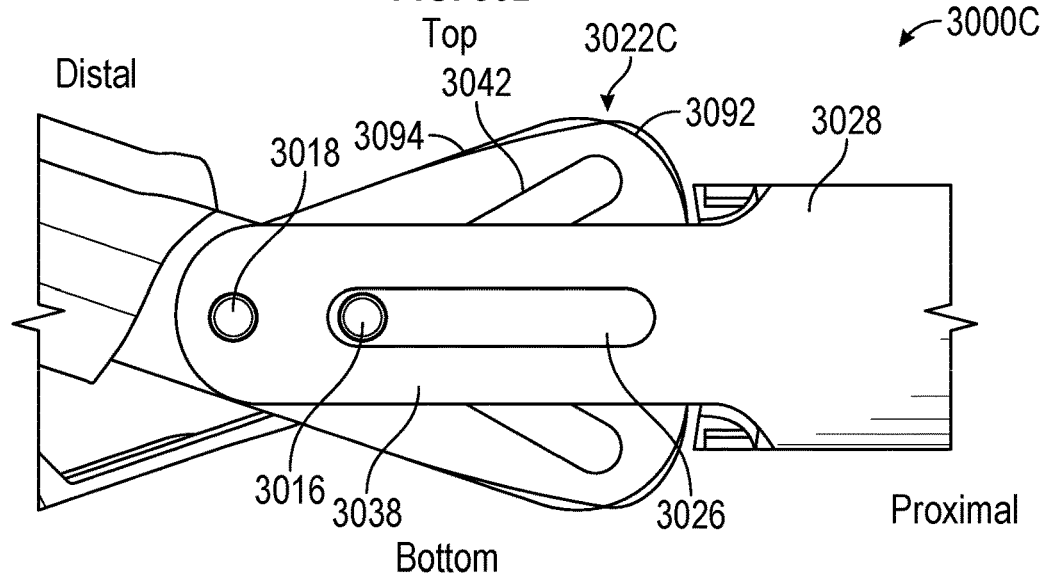
FIG. 36C illustrates a side view of a portion of a forceps.

FIG. 36A illustrates a side view of a portion of a forceps 3000A, in accordance with at least one example of this disclosure. FIG. 36B illustrates a side view of a portion of a forceps 3000C. FIG. 36C illustrates a side view of a portion of the forceps 3000C. FIGS. 36A-36C also show orientation indicators Proximal, Distal, Top, and Bottom. FIGS. 36A-36C are discussed below concurrently.

The forceps 3000A can include the flange 3022A of FIG. 16A and various components similar to forceps discussed above, such as an upper jaw 3010, a lower jaw 3012, a drive pin 3016, a pivot pin 3018, an inner shaft 3026, an outer shaft 3028, and outer arms 3036. FIG. 36A shows how the proximal rounded portion 3092A of the flange 3022A extends laterally outward (or upward) beyond the outer shaft 3028 when the jaws 3010 and 3012 are in the open position.

The forceps 3000C, as shown in FIGS. 36B and 17C show how extension of the flange 3022C laterally beyond the outer shaft 3028 can be reduced by the curved proximal portion 3092 of the flange 3022C. Such a reduction in lateral extension can help reduce contact between the flanges 3020 and 3022 and tissues within a cavity, and therefore can help reduce interference by the flanges 3020 and 3022 with tissue.

The proximal rounded portions of flanges are discussed in further detail below with regard to the forceps 2000. The forceps 3000 can include any of the features discussed above with respect to any of the other forceps. Similarly, any of the forceps discussed above or below can be modified to include the components of the forceps 3000.

Figure 37A:
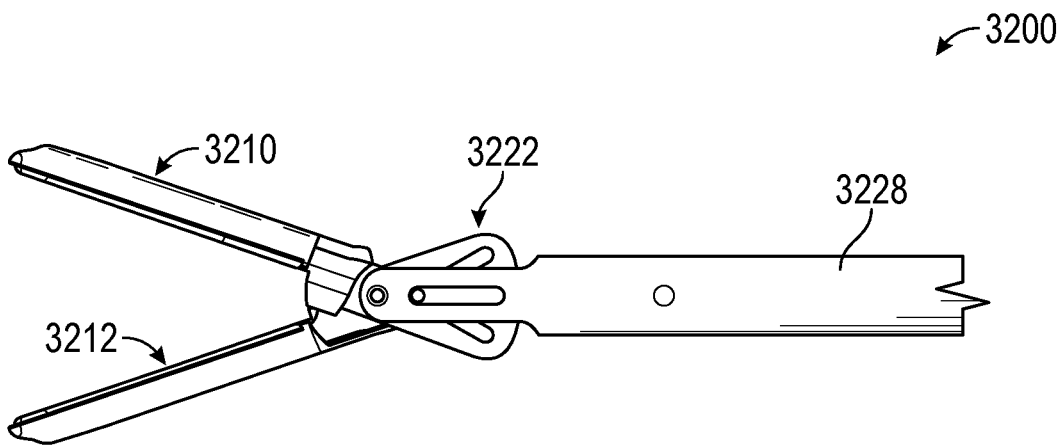
FIG. 37A illustrates a side view of a forceps.
Figure 37B:
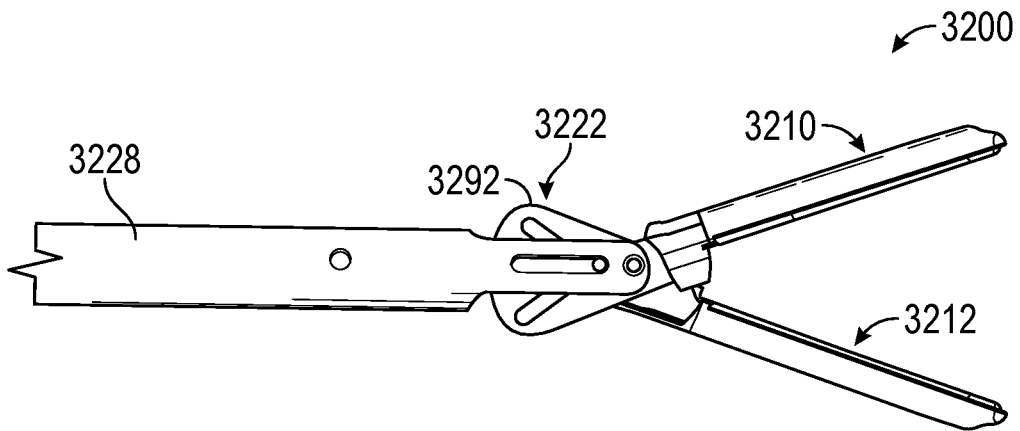
FIG. 37B illustrates a side view of a forceps.
Figure 38:
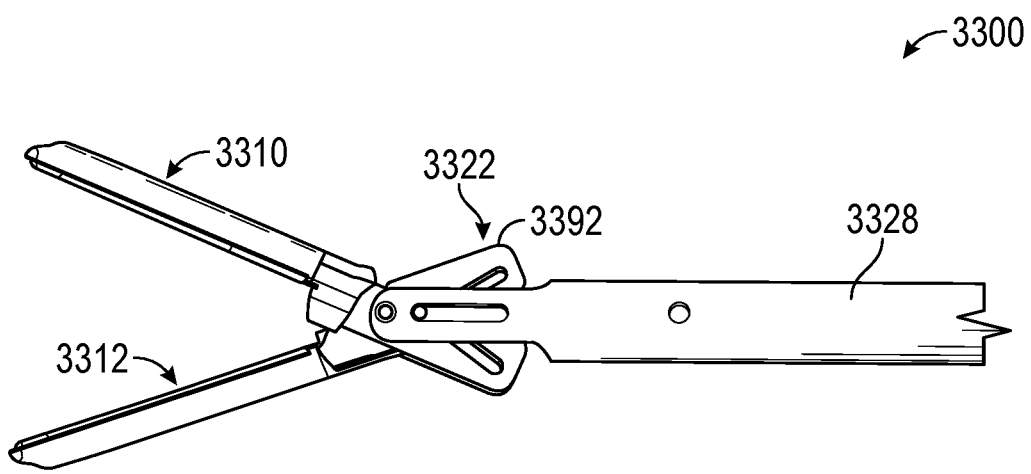
FIG. 38 illustrates a side view of a portion of a forceps.

FIG. 37A illustrates a side view of a portion of a forceps 3200, in accordance with at least one example of this disclosure. FIG. 38 illustrates a side view of a portion of a forceps 3300, in accordance with at least one example of this disclosure. FIG. 38 illustrates a side view of a portion of the forceps 3300, in accordance with at least one example of this disclosure. FIGS. 37A-38 are discussed below concurrently.

The forceps 3200 can include an upper jaw 3210, a lower jaw 3212, a and an outer shaft 3228. The lower jaw can include a flange 3222. Similarly, the forceps 3300 can include an upper jaw 3310, a lower jaw 3312, a and an outer shaft 3328. FIGS. 37A and 37B show how rounded proximal portion 3292 of the flange 3222 of the lower jaw 3212 can reduce extension of the flange laterally beyond an outer surface of the outer shaft 3228 over the less-rounded proximal portion 3392 of the flange 3322.

Figure 39A:
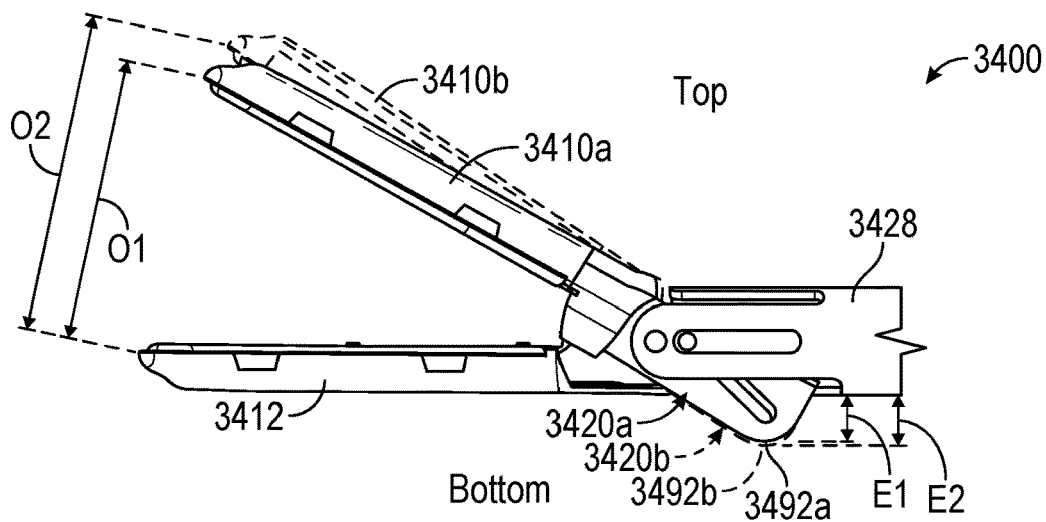
FIG. 39A illustrates a side view of a portion of a forceps.
Figure 39B:
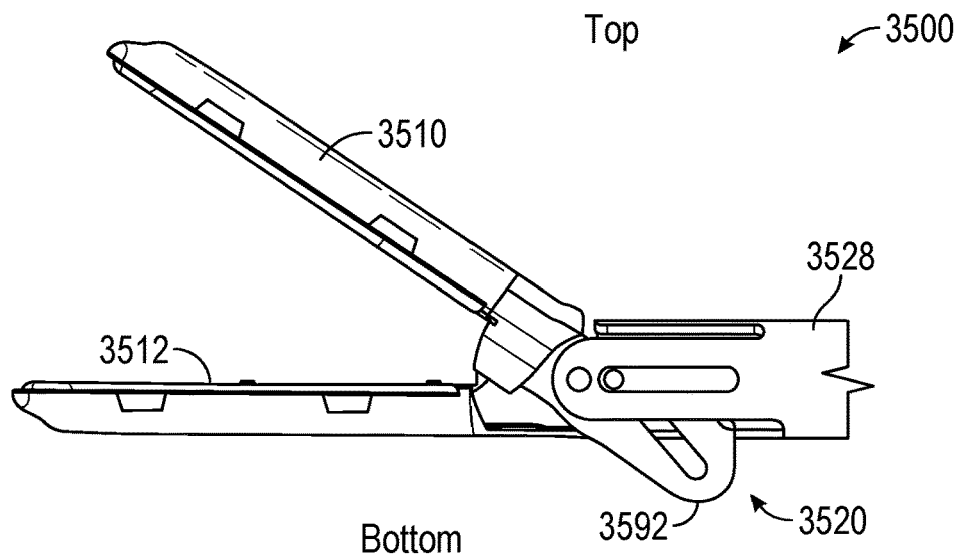
FIG. 39B illustrates a side view of a portion of a forceps.
Figure 39C:
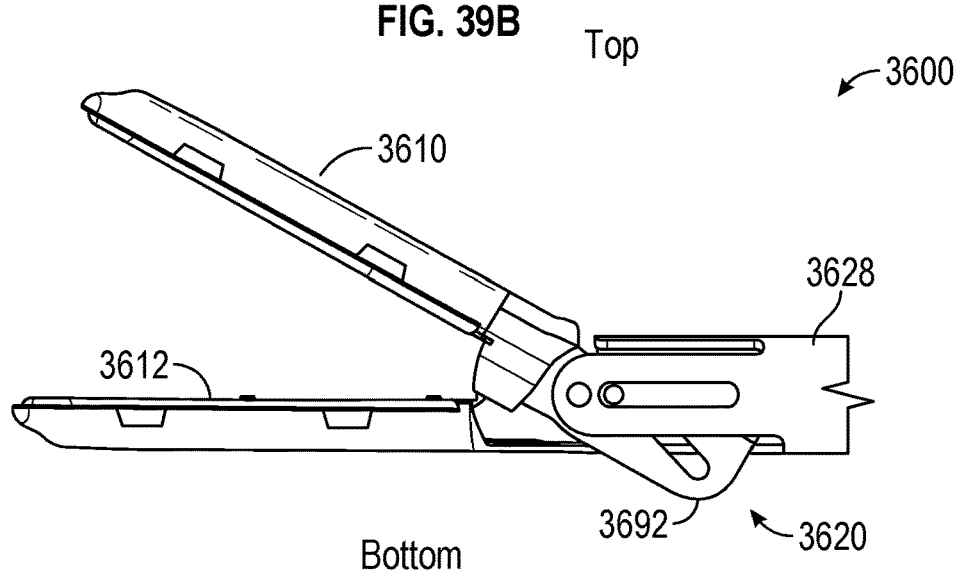
FIG. 39C illustrates a side view of a portion of a forceps.

FIG. 39A illustrates a side view of a portion of a forceps 3400, in accordance with at least one example of this disclosure. FIG. 39B illustrates a side view of a portion of a forceps 3500, in accordance with at least one example of this disclosure. FIG. 39C illustrates a side view of a portion of a forceps 3600, in accordance with at least one example of this disclosure. FIGS. 39A-39C are discussed below concurrently.

FIG. 39A shows a forceps 3400 including an upper jaw 3410 in two positions indicated by 3410a and 3410b, the jaw 3410 including a flange 3420 in two positions, indicated by 3420a and 3420b. The forceps can also include a lower jaw 31484, which can be fixed, and an outer shaft 3428. Also shown in FIG. 39A are distances E1, E2, O1, and O2.

FIG. 39A shows how when the upper jaw 3410 is in a first open position at 3410a, a distance between jaws can be O1, which can be 14.5 millimeters, in one example. In a second open position at 3410b, a distance between jaws can be O2, which can be 16.5 millimeters, in one example, a difference of about 2 millimeters. When the jaw 3410 is in the first open position at 3410a, the flange 3420 can be at a first position 3420a having a distance E1 from the outer shaft 3428 of about 2.3 millimeters, in one example. When the jaw 3410 is in the second open position at 3410b, the flange 3420 can be at a second position 3420b having a distance E2 from the outer shaft 3428 of about 3 millimeters, in one example, a difference of about 0.7 millimeters between positions.

That means a 0.7 millimeter difference in flange extension corresponds to a 2.0 millimeter difference in opening, where a larger opening between the jaws 2010 and 2012 can provide better range of operation of the forceps 3400. However, it is undesirable to have a flange that extends beyond an outer surface of the outer shaft 3428 more than necessary, because the flange 3420 can engage surrounding tissue. Therefore, as shown in FIG. 39C, the flange 3620 can have a proximal rounded portion 3692 configured to reduce an amount that the flange 3620 extends beyond an outer surface of the outer shaft 3628 as compared to the flange 3520 of the forceps 3500 of FIG. 39B, which can extend relatively further outward than the flange 3620 of the forceps 3600 of FIG. 39C.

Figure 40A:
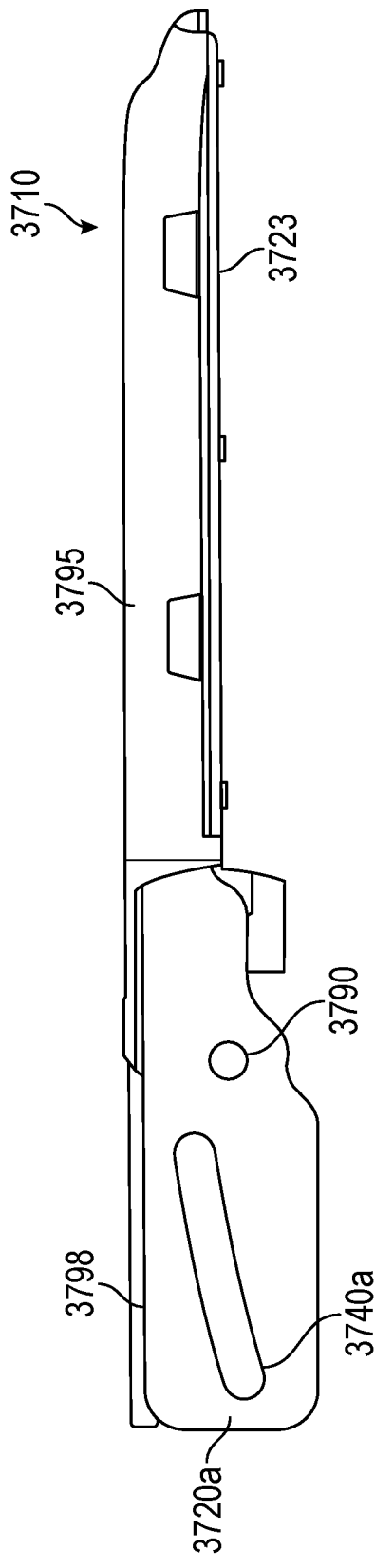
FIG. 40A illustrates a side view of a jaw.
Figure 40B:
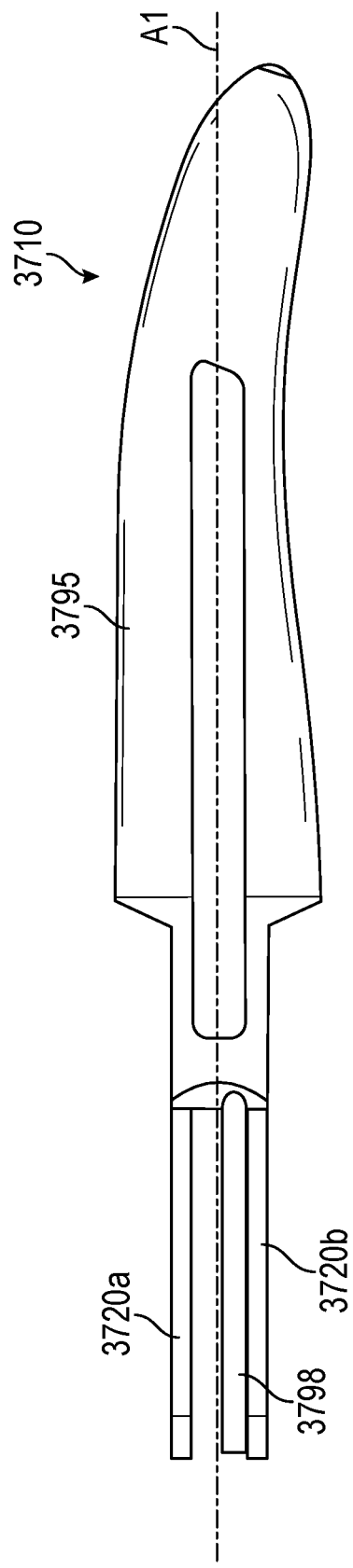
FIG. 40B illustrates a side view of a jaw.
Figure 40C:
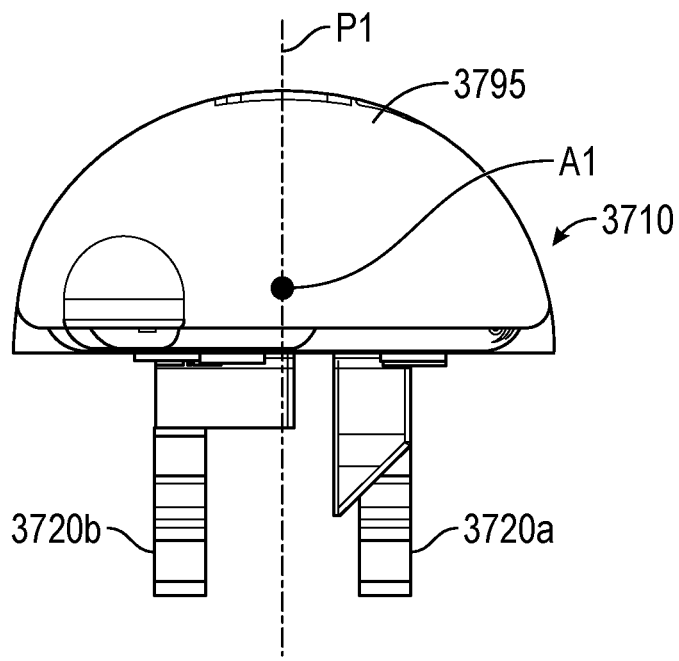
FIG. 40C illustrates an end view of a jaw.
Figure 40D:
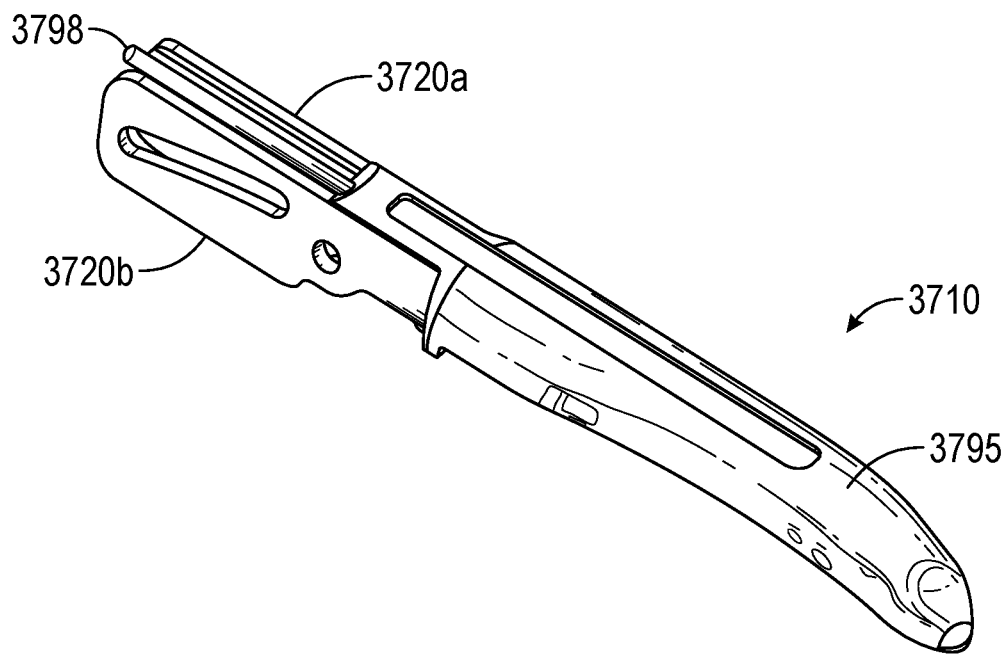
FIG. 40D illustrates an isometric view of a jaw.

FIG. 40A illustrates a side view of a jaw 3710, in accordance with at least one example of this disclosure. FIG. 40B illustrates a side view of the jaw 3710. FIG. 40C illustrates an end view of the jaw 3710. FIG. 40D illustrates an isometric view of the jaw 3710. FIGS. 40B and 40C show an axis A1 and FIG. 40C shows a vertical plane P1. FIGS. 40A-40D are discussed below concurrently.

The jaw 3710 can be similar to other jaws discussed above in that the jaw 3710 can include flanges 3720a and 3720b including tracks 3740a and 3740b and a pivot pin bore 3790. FIGS. 40A-40D also show that the jaw 3710 can have an outer shell 3795 which can be relatively round and smooth to help limit snagging or catching on tissue. FIG. 40B also shows that the jaw 3710 can be curved with respect to the axis A1. FIGS. 40B and 40D also show a top wire 3738 that can be connected to an electrode of the jaw 3710 to provide power thereto. The jaw 3710 can include any of the features discussed above with respect to any of the forceps. Similarly, any of the forceps discussed above or below can be modified to include the components of the jaw 3710.

Figure 41A:
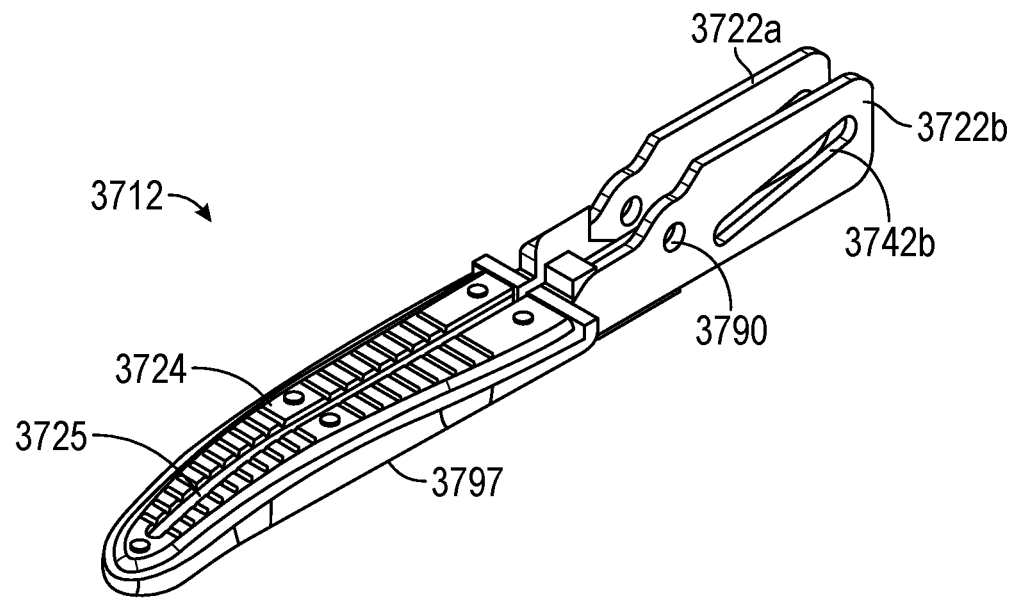
FIG. 41A illustrates an isometric view of a jaw.
Figure 41B:
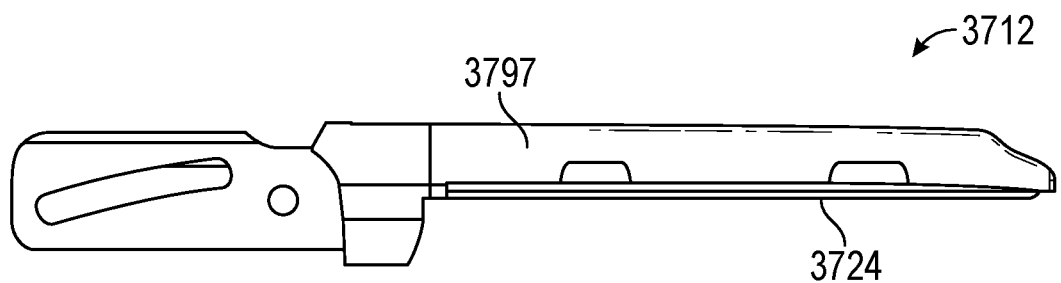
FIG. 41B illustrates a side view of a jaw.
Figure 41C:
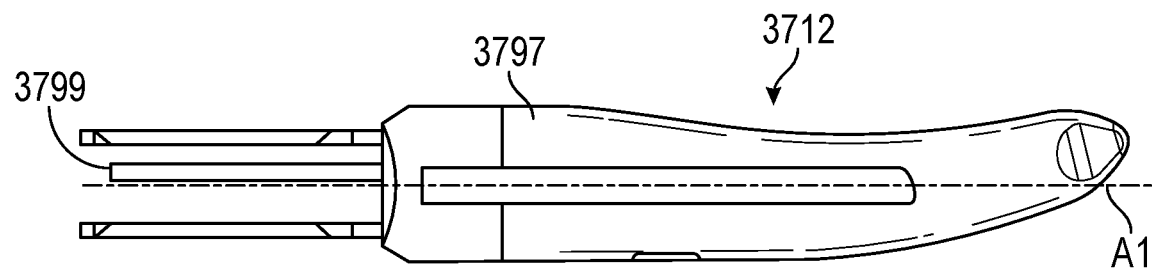
FIG. 41C illustrates a side view of a jaw.
Figure 41D:
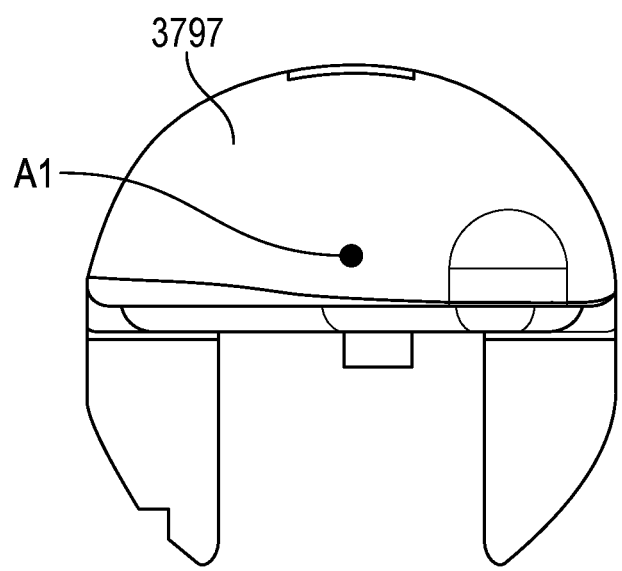
FIG. 41D illustrates an end view of a jaw.

FIG. 41A illustrates an isometric view of a jaw 3712, in accordance with at least one example of this disclosure. FIG. 41B illustrates a side view of the jaw 3712. FIG. 41C illustrates a side view of the jaw 3712. FIG. 41D illustrates an end view of the jaw 3712. FIGS. 41C and 22D show an axis A1. FIGS. 41A-22D are discussed below concurrently.

The jaw 3712 can be similar to other jaws discussed above in that the jaw 3712 can include flanges 3722a and 3722b having tracks 3742a and 3742b and a pivot pin bore 3790. FIGS. 40A-40D show that the jaw 3710 can have an outer shell 3797 which can be relatively round and smooth to help to limit (or prevent or preclude) snagging or catching of the jaw 3712 on tissue. FIG. 41C also shows that the jaw 3710 can be curved with respect to the axis A1. FIG. 41C further shows a bottom wire 3799 that can be connected to an electrode of the jaw 3712 to provide power thereto.

FIG. 41A also shows that the plate 3724 of the jaw 3712 can include a blade slot 3725, which can extend along the plate 3724 of the jaw 3712 and can be configured to receive a blade (such as the blade 2032) therein. In some examples, the blade slot 3725 can be curved with the profile of the jaw 3712. Each of the jaws discussed above and below can include such a blade slot. In some examples, the jaw 3710 can include a blade slot 3723 that can be complimentary to the blade slot 3725. That is, the blade slots 3725 and 3723 can be parallel such that each of the jaws 3710 and 3712 (when operating together) can receive a blade therein when the jaws 3710 and 3712 are in a closed position or partially closed position.

The jaw 3712 can include any of the features discussed above with respect to any of the other forceps. Similarly, any of the forceps discussed above or below can be modified to include the components of the jaw 3712.

Figure 44:
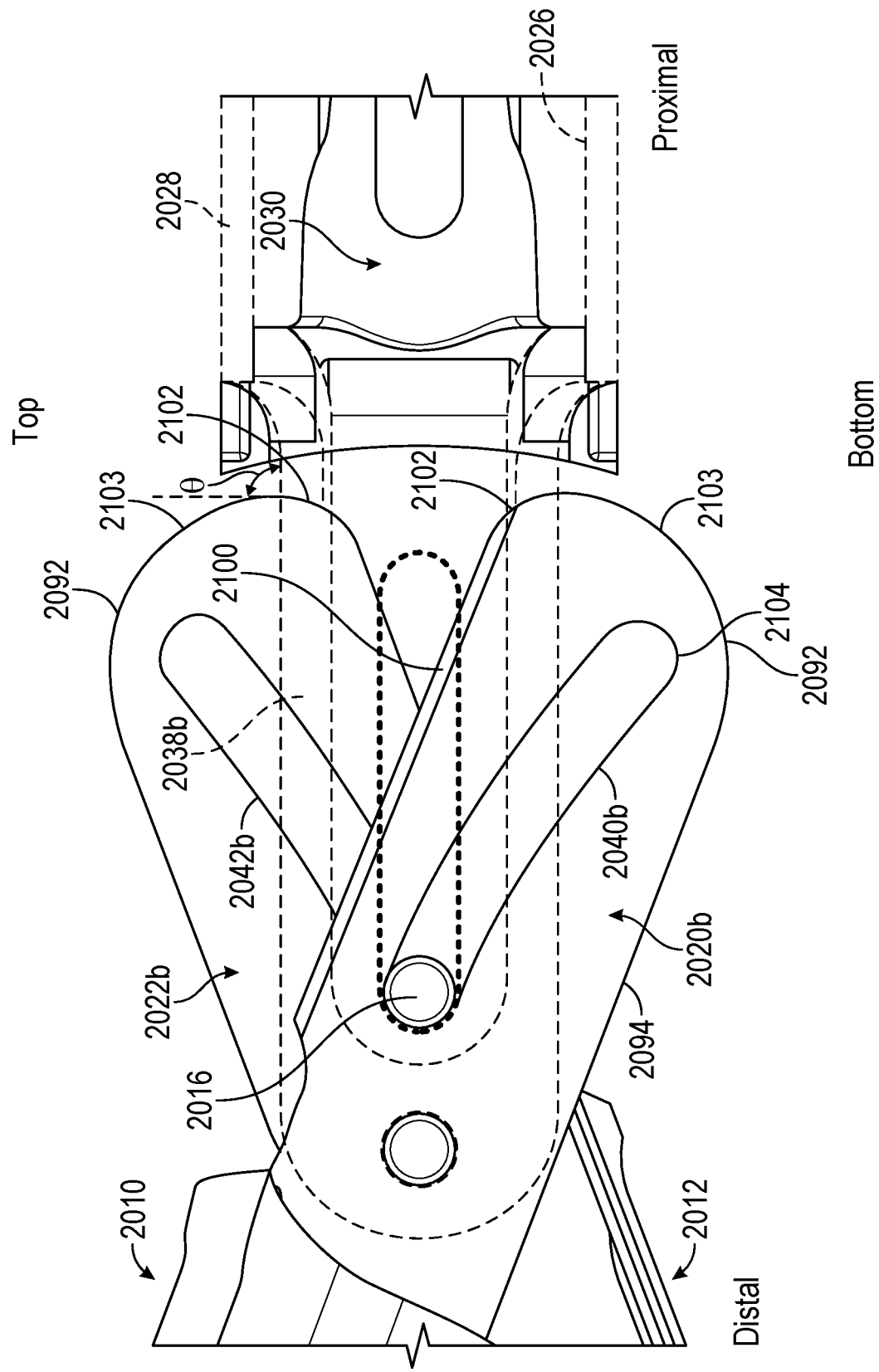
FIG. 44 illustrates a side view of a portion of a forceps with an inner shaft and an outer shaft shown in phantom.

FIG. 42 illustrates a side view of a portion of the forceps 2000 in a closed position with the inner shaft 2026 and the outer shaft 2028 shown in phantom, in accordance with at least one example of this disclosure. FIG. 43 illustrates a side view of a portion of the forceps 2000 in an open position with the inner shaft 2026 and the outer shaft 2028 shown in phantom. FIG. 44 illustrates a focused side view of a portion of the forceps 2000. FIG. 42 shows section indicators C1-C1 and C2-C2. FIGS. 42-44 show orientation indicators Proximal and Distal. FIG. 44 also shows angle θ. FIGS. 42-44 are discussed below concurrently.

The forceps 2000 of FIGS. 42-44 can be consistent with the forceps 2000 discussed above; further details are discussed below with respect to FIGS. 42-44. For example, FIGS. 43 and 44 show that the flange 2020b can include the track 2040b, a rounded proximal portion 2092, an outer (or bottom) edge 2094, a top (or inner or upper) edge 2100, and a proximal inner portion 2102. The track 2040b can include a proximal end 2104.

The rounded proximal portion 2092 can be connected to the bottom edge 2094 and the proximal inner portion 2102, such as proximal of a jaw pivot axis, which can be defined by the pivot pin 2018. The proximal inner portion 2102 can be connected to the top (or inner) edge 2100. The proximal end 2104 can be a portion of the slot 2040b that can include a termination of the slot 2040b. The proximal end 2104 can be located near the rounded proximal portion 2092.

The rounded proximal portion 2092 can be shaped, such as rounded or curved, as can the proximal inner portion 2102. The rounded proximal portion 2092 can be curved or can have a radiused edge from a lateral perspective (as shown in FIG. 44) to help limit extension of the rounded proximal portion 2092 beyond the outer shaft 2028 when the jaws 2010 and 2012 are in the open position (or between the open and closed positions). That is, one or more of the proximal portions 2092 of the flanges 2020 and 2022 can be shaped to limit extension of the proximal portions 2092 laterally beyond the arms 2038 of the outer shaft 2028, which can help limit engagement between the flanges 2020 and 2022 with surrounding tissues during a procedure. In some examples, such a rounded proximal portion 2092 can be used with only one flange 2020 and one flange 2022.

In some examples, the rounded proximal portion 2092 can be curved or can have a radiused edge from a lateral perspective that is greater than a radius of the proximal inner portion 2102 from a lateral perspective. In other words, the inner proximal portion 2102 can be rounded at a radius smaller than a radius of the rounded proximal portions 2092. In some examples, the rounded proximal portion 2092 can be located near the track 2040. The rounded proximal portion 2092 can be profiled to limit stress in the flange 2020 where the stress can be produced by interaction between the track 2040 (the flange 2020) and the inner shaft 2026, such as through the drive pin 2016.

The proximal end 2104 of the track 2040 can be a termination of the track 2040 and can have a curved or radiused shape. In some examples, the rounded proximal portion 2092 can have a curvature not concentric with a curvature of the proximal end 2104 of the track 2040. In some examples, the rounded proximal portion 2092 can have a radius as large as possible to reduce extension (such as a reduced radial extension) of the flange 2020 beyond the outer shaft 2028 without reducing a strength of the flange 2020 adjacent the track 2040 below what is required for normal operation of the flange 2020 (for example to withstand forces applied by drive pin 2016). FIG. 42 also shows that when the jaws 2010 and 2012 are in the closed position, the flanges 2020 and 2022 do not extend laterally beyond the outer shaft 2028.

In some examples, the profile of the proximal portion 2092 can be configured to maintain a minimum thickness between the track 2040 and the proximal portion 2092. In some examples, the minimum thickness can be between 0.1 millimeters and 1.5 millimeters. In other examples, the minimum thickness can be between 0.3 millimeters and 1 millimeter. In other examples, the minimum thickness can be 0.7 millimeters.

In some examples, the profile of the proximal portion 2092 of the flange 2020 can include an edge 2103 having an arc that is tangent to the outer edge 2094. In some examples, the arc of the edge 2103 can be eccentric with an arc of the proximal end 2104 of the track 2040b. In some examples, the arc of the edge 2103 can have a radius of curvature that is larger toward a laterally inner portion (toward the inner rounded portion 102) than a laterally outer portion (toward the rounded proximal portion 2092) when the flanges 2020 and/or 2022 are in the open position (or are not in the closed position). In any of the examples discussed herein, the flange 2020 can be symmetric about one or more axes.

FIG. 44 also shows the angle θ, which can be an angle formed between a top surface of the outer arms 2034 and the flange 2022b. (The flanges 2020 can form similar angles with a bottom surface of the outer arms 2034.) The rounded proximal portion 2092 of the flange 2022 can, at least in part, define the angle θ. In some examples, the rounded proximal portion 2092 can have a curvature to limit (or prevent or preclude) the angle θ from becoming an acute angle, such as when the flange 2022 (or the flange 2020) are in the open position. Minimizing the angle θ can help to limit pinching or scissoring of tissue between the flange 2022 and the outer arm 2034 during opening and closing of the jaws 2010 and 2012. Also, the proximal inner portion 2102 can be prevented (by positioning of the tracks 2042, for example) from extending laterally beyond (such as above) the top surface of the outer arm 2034, which can further help limit unwanted pinching or scissoring of tissue during opening and closing of the jaws 2010 and 2012. In some examples, a transition between the proximal inner portion 2102 and the proximal inner portion 2102 can be curved or rounded to further prevent scissoring.

Figure 45:
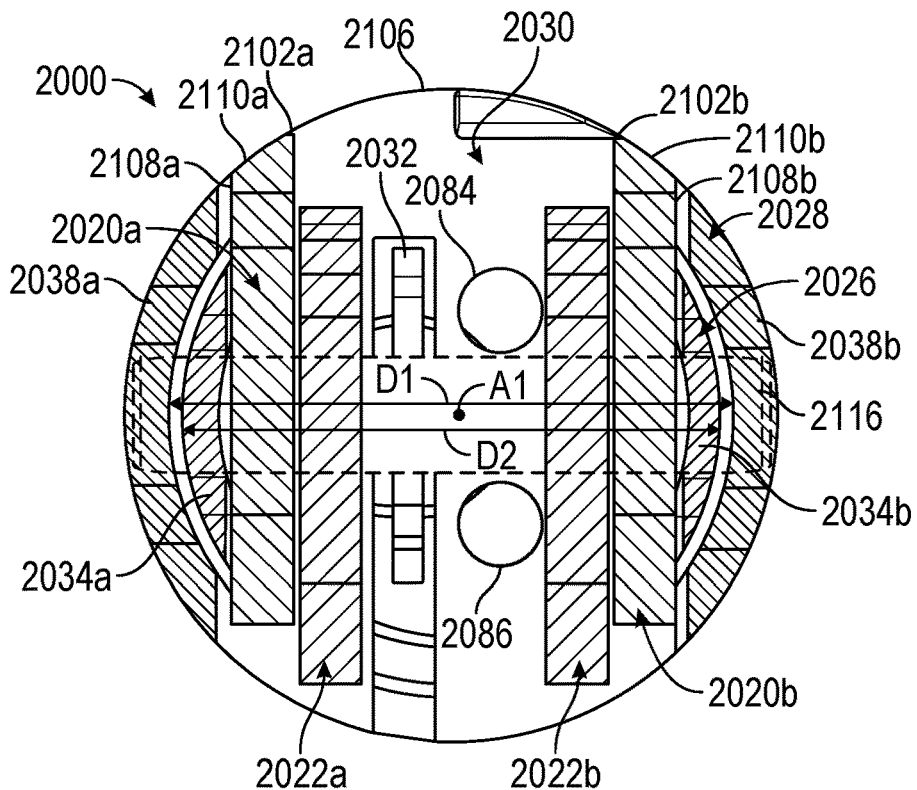
FIG. 45 illustrates a cross-section view of a portion of a forceps across section C1-C1 of FIG. 42.
Figure 46:
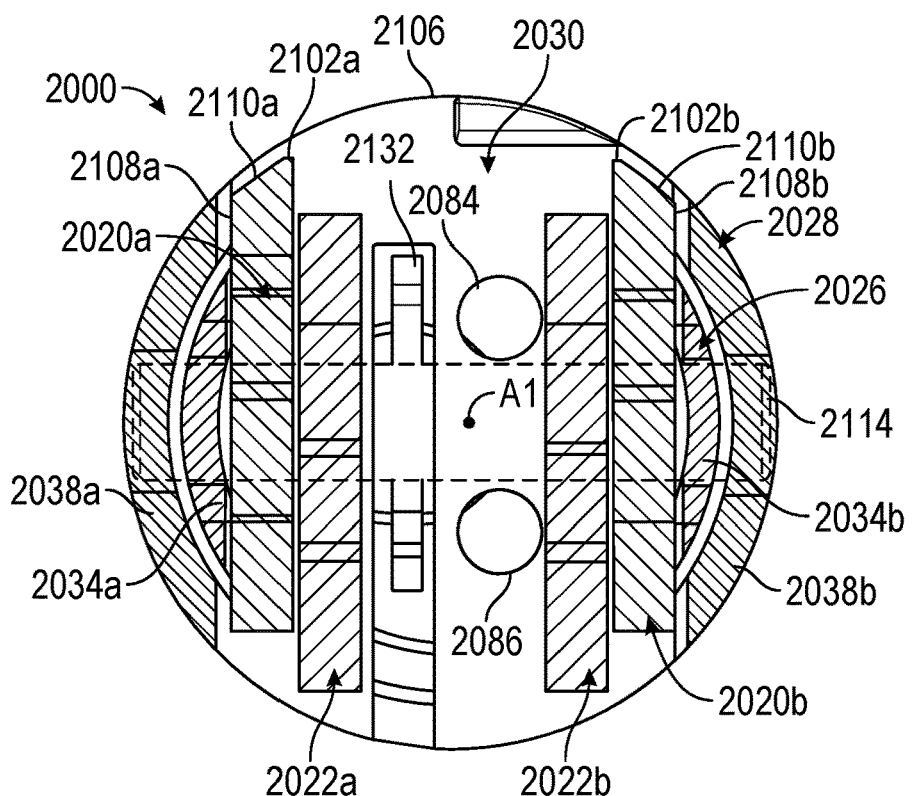
FIG. 46 illustrates a cross-section view of a portion of a forceps across section C2-C2 of FIG. 42.
Figure 47:
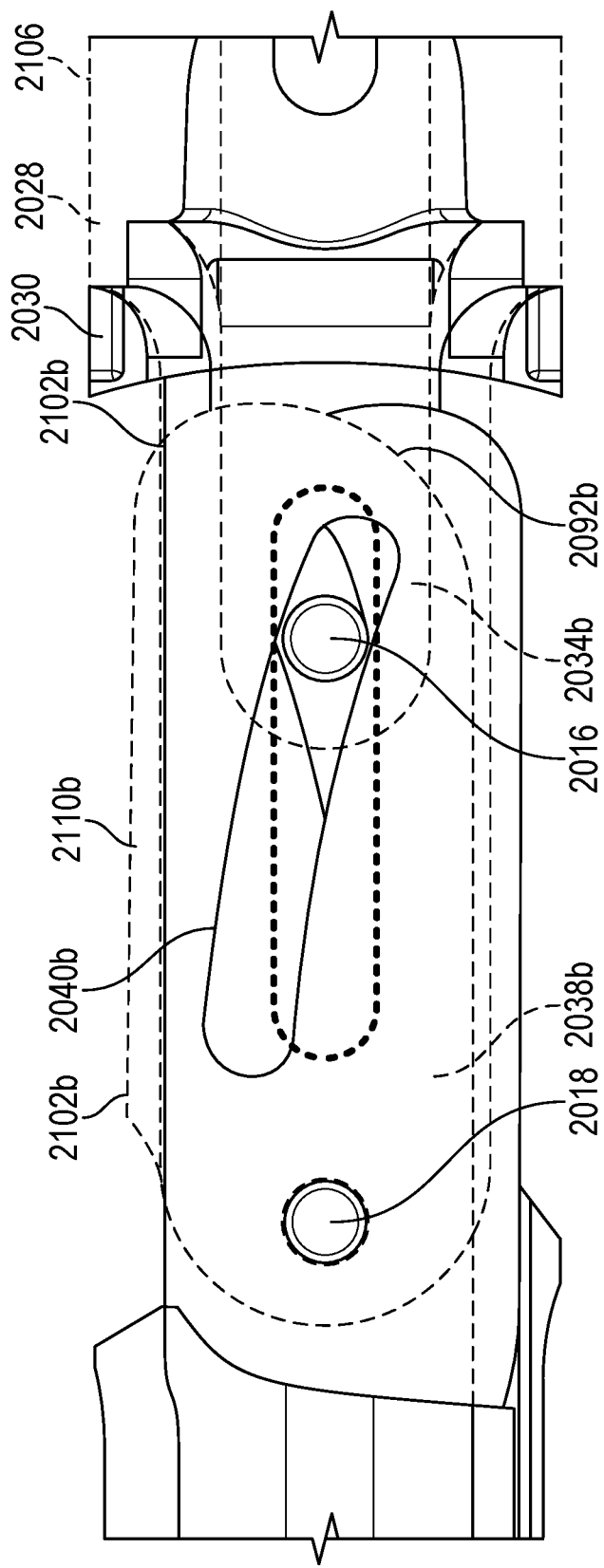
FIG. 47 illustrates a side view of a portion of a forceps with an inner shaft and an outer shaft shown in phantom.

FIG. 45 illustrates a cross-section view of a portion of the forceps 2000 across section C1-C1 of FIG. 42. FIG. 46 illustrates a cross-section view of a portion of the forceps 2000 across section C2-C2 of FIG. 42. FIG. 47 illustrates a side view of a portion of the forceps 2000 with the inner shaft 2026 and the outer shaft shown in phantom 2028. FIGS. 45-47 are discussed below concurrently.

The forceps 2000 of FIGS. 45 and 46 can be consistent with the descriptions of the forceps 2000 discussed above; FIGS. 45 and 46 show details of a chamfer of the flanges 2020 of the jaw 2010. More specifically, FIGS. 45 and 46 show the flanges 2020a and 2020b and 2022a and 2022b. Also shown is the inner shaft 2026 including the arms 2034a and 2034b and the outer shaft 2028 including the arms 2034a and 2034b and including an outer surface 2106.

Also shown are the blade 2032 in the blade channel 2080 of the guide plug 2030 offset from the axis A1 and the wire routing bores 2084 and 2086 of the guide plug 2030 offset from the axis A1 opposite the blade 2032. FIG. 45 also shows the drive pin 2016 and FIG. 46 shows the shaft pin 2014. FIGS. 45 and 46 also show further details of the flanges 2020a and 2020b, such as the upper edges 2102a and 2102b, respectively, an outer surface 2108a and 2108b, respectively, and chamfers 2110a and 2110b, respectively.

Also shown in FIG. 45 is a diameter D1, which can be an inner diameter of the outer shaft 2028, and a diameter D2, which can be an outer diameter of the inner shaft 2026. FIG. 45 shows how diameter D2 is smaller than the diameter D1 such that the inner shaft 2026 and the arms 2034 of the inner shaft 2026 fit within the outer shaft 2028, enabling relative translation of the inner shaft 2026 with respect to the outer shaft 2028.

As shown in FIGS. 45 and 46, the chamfer 2110a can extend between the outer surface 2108a and the upper edge 2102a. Similarly, the chamfer 2110b can extend between the outer surface 2108b and the upper edge 2102b. The chamfers 2110 can be sized and shaped to limit extension of the flanges 2020 of the jaw 2010 laterally beyond the outer surface of the outer shaft 2028 when the jaws 2010 and 2012 are in the closed position, helping to reduce the overall profile of the end effector 2002, which can help make insertion of the end effector 2202 into a cannula and/or opening easier.

In some examples, one or more of the chamfers 2110 can be a bevel extending between the upper edges 2102 and the outer surfaces 2108. In other examples, the chamfers 2110 can be curved or notched surfaces of the flanges 2020, configured to limit extension of the flanges 2020 beyond the outer surface 2106 of the outer shaft 2028. In some examples, one or more of the chamfers 2110 can be rounded.

As shown in FIG. 47, the chamfers 2110 can be located with respect to the tracks 2040 to extend a thickness of the flange 2020 adjacent a distal termination of the track, which can help increase a strength of the flange 2020 where the drive pin 2016 can apply a force to the track 2040. In other examples, where the track 2040 is reversed, the chamfers 2110 can be located with respect to the tracks 2040 to extend a thickness of the flange 2020 adjacent the distal end 2104 of the tracks 2040.

In some examples, one or more of the flanges 2022a and 2022b can include a chamfered outer edge configured to limit extension of the flanges 2022 beyond the outer surface 2106 of the outer shaft 2028. In an example where the flanges 2020 and 2022 are staggered, any one of the flanges 2020 and 2022 can include a chamfered edge configured to limit extension of the flanges 2022 beyond the outer surface 2106 of the outer shaft 2028.

As shown in FIG. 46 the chamfers 2110a and 2110b can be further away from the outer surface at a more proximal position of the flanges 2020a and 2020b, respectively. That is, the chamfers 2110a and 2110b can define edges extending substantially axially along the flanges 2020 when the jaws 2010 and 2012 are in the closed position. The edges (chamfers 2110) can be located laterally inward (or radially inward, in some examples) of the outer surface 2106 of the outer tube 2028.

In some examples, the chamfers 2110 (or chamfered edges) can be angled laterally inward (or radially inward) from an axially distal location to an axially proximal location. In operation of the forceps 2000, application of a larger force to compress the jaws 2010 and 2012 can cause proximal portions of the flanges 2020 and 2022 to extend radially outward beyond the outer surface of the outer shaft 2028. This effect can cause the flanges to engage a trocar during removal of the forceps from the trocar with the tissue grasped, which can complicate the procedure removal. The chamfers 2110 (or chamfered edges) being angled laterally inward (or radially inward) from an axially distal location to an axially proximal location (or the chamfered edges 2110 having a backwards rake) can help reduce lateral extension of the flanges 2020 and 2022 beyond the outer shaft 2028 caused by application of a large force on an actuator, which can help avoid engagement with a trocar (or tissue or other component) during removal of the forceps 2000 from a cavity.

Figure 48:
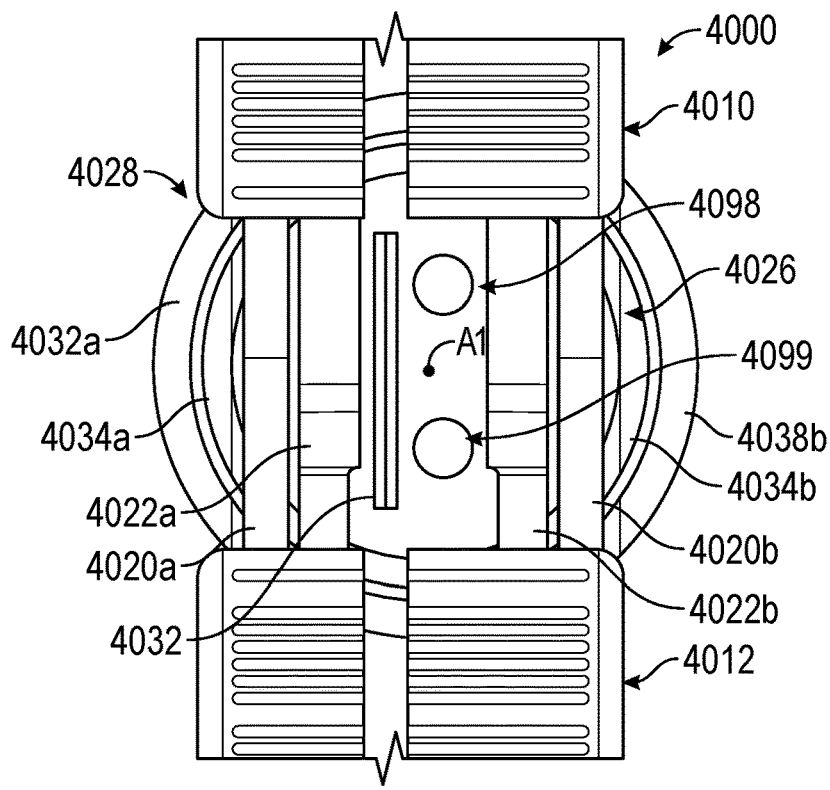
FIG. 48 illustrates a cross-section view of a portion of a forceps across section 45-45 of FIG. 42.

FIG. 48 illustrates a cross-section view of a portion of a forceps 4000 across section 45-45 of FIG. 42, in accordance with at least one example of this disclosure. The forceps 4000 can be similar to those discussed above, where the forceps can include the jaws 4010 and 4012 including flanges 4020 and 4022, respectively. The forceps 4000 can also include an inner shaft 4026 including inner arms 4034a and 4034b and the forceps 4000 can include an outer shaft 4028 including outer arms 4036a and 4036b.

FIG. 48 also shows that the flanges 4020 and 4022 can form a channel therebetween that can be configured (such as sized and shaped) to receive a blade 4032 and wires 4098 and 4099 therethrough. In some examples, the wires 4098 and 4099 can extend axially through the first set of flanges 4020 and the second set of flanges 4022 in a position laterally inward of the first set of flanges 4020 and the second set of flanges 4022.

One wire, such as the wire 4098 can be above an axis A1 of the shafts, and another wire, such as the wire 4099, can be below the axis A1. In some examples, the wire 4098 can be above a drive pin (to be routed to the upper jaw 4010) and the wire 4099 can be below the drive pin (to be routed to the lower jaw 4012). In some examples, the blade 4032 can be offset (such as laterally offset) from the axis A1 and the wires 4098 and 4099 can be offset (such as laterally offset) from the axis A1 on the opposite side from the blade 4032. In some examples, the axis A1 can be a central axis of the inner shaft 4026 where the blade 4032 can extend through the inner shaft 4026 along the axis A1.

Figure 49:
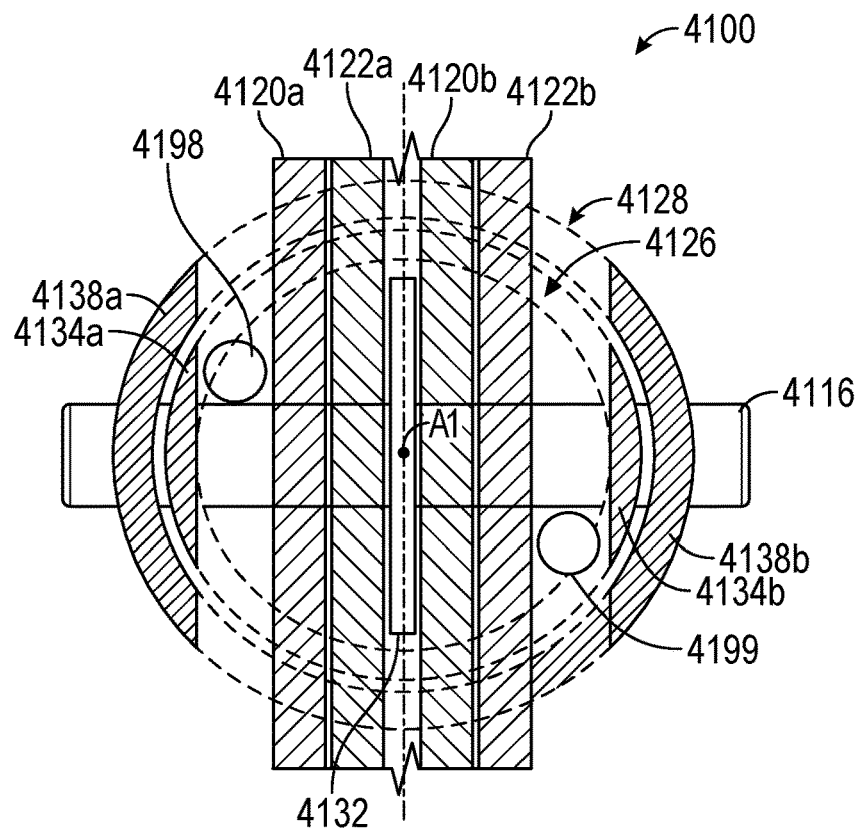
FIG. 49 illustrates a cross-section view of a portion of a forceps across section 46-46 of FIG. 42.

FIG. 49 illustrates a cross-section view of a portion of a forceps 4100 across section 46-46 of FIG. 42, in accordance with at least one example of this disclosure.

The forceps 4100 can be similar to other forceps discussed above, where the forceps can include the jaws 4110 and 4112 including flanges 4120 and 4122, respectively. The forceps 4100 can also include an inner shaft 4126 including inner arms 4134a and 4134b and the forceps 4100 can include an outer shaft 4128 including outer arms 4136a and 4136b.

FIG. 49 also shows that the flanges 4120 and 4122 can form a channel therebetween that can receive a blade 4132. The flanges 4120 and 4122 can also form laterally outer channels for the wires 4198 and 4199, respectively, such that the wires 4198 can be positioned laterally outward of the flanges 4120 and 4122 and laterally inward of the arms 4134 and 4136. One wire, such as the wire 4098 can be above an axis A1 of the shafts to be routed to the upper jaw 4110, and another wire, such as the wire 4199, can be below the axis A1 to be routed to the lower jaw 4112. In some examples, the wire 4198 can be above a drive pin 4116 and the wire 4199 can be below the drive pin 4116. In some examples of this configuration, the flanges 4120 and 4122 can be interlaced.

Figure 50:
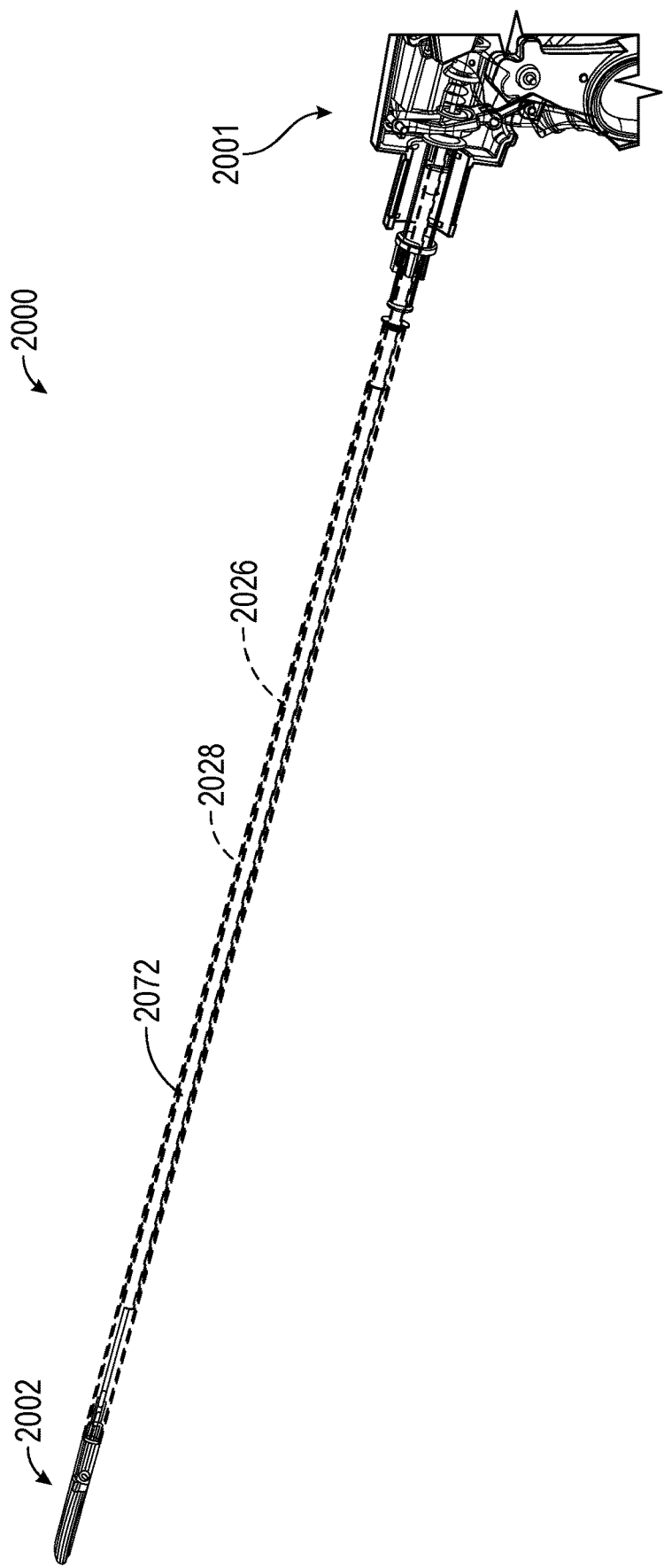
FIG. 50 illustrates a side isometric view of a portion of a forceps.

FIG. 50 illustrates a side isometric view of a portion of a forceps 2000, in accordance with at least one example of this disclosure. The forceps 2000 can be consistent with the forceps 2000 discussed above. FIG. 50 shows that a guide tube 2112 (or lumen 2112) can be positioned within the inner shaft 2026 and the outer shaft 2028 and can extend through the outer shaft 2028 and the inner shaft 2026 between the end effector 2002 and the handle 2001. More specifically, the guide tube 2112 can extend from a distal position just off a proximal edge of the blade 2032 when the blade is in the retracted position and can extend proximally to a position or location distal of a clip (such as the clip 1056) that holds a slider block (such as the drive body 1052) to the drive shaft or inner shaft 2026.

Figure 51A:
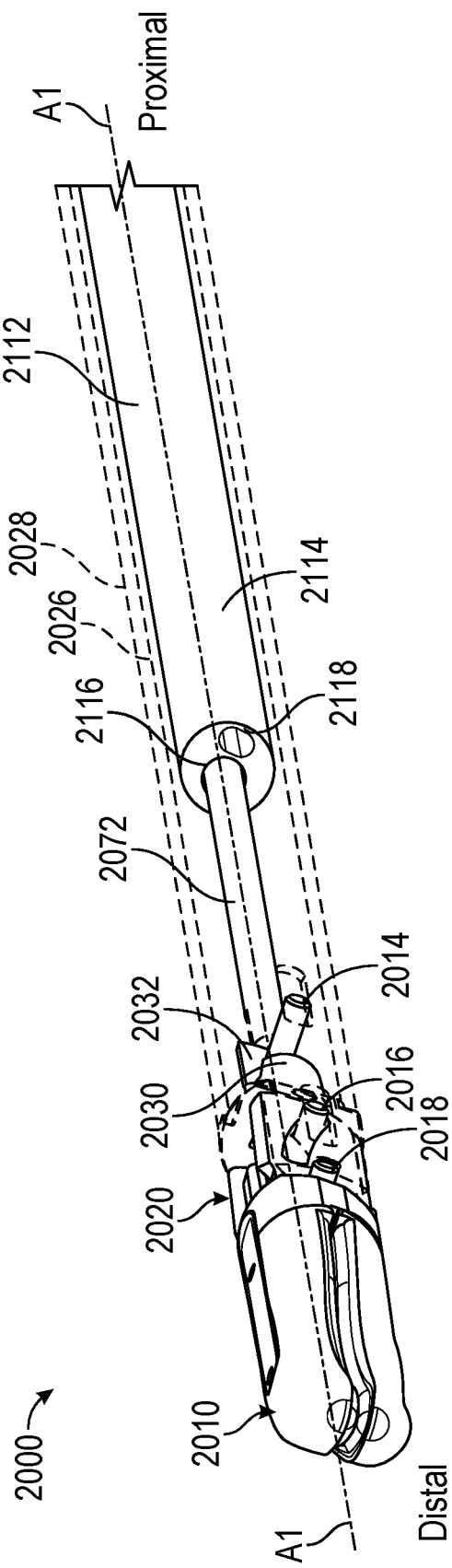
FIG. 51A illustrates an end isometric view of a portion of a forceps.
Figure 51B:
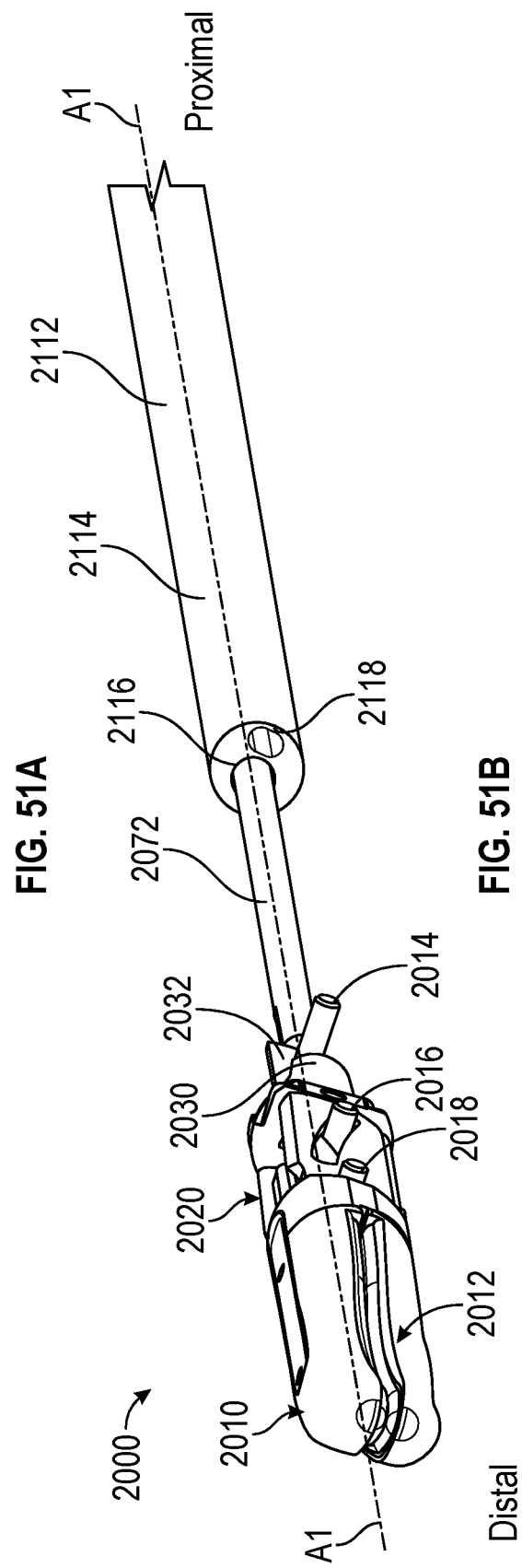
FIG. 51B illustrates an end isometric view of a portion of a forceps.

FIG. 51A illustrates an end isometric view of a portion of the forceps 2000, in accordance with at least one example of this disclosure. FIG. 51B illustrates an end isometric view of a portion of the forceps 2000. FIGS. 51A and 32B are discussed below concurrently.

The forceps 2000 can be consistent with the descriptions above; FIGS. 51A and 32B show additional details. For example, FIGS. 51A-51B show a guide tube 2112 that can include a body 2114 defining a blade bore 2116 and a wire routing bore 2118. Also shown in FIGS. 51A and 32B are orientation indicators Proximal and Distal and axis A1.

The body 2114 can extend along the axis A1 and can be substantially cylindrical in some examples, but can have other shapes in other examples, such as an oval prism, a rectangular prism, a hexagonal prism, an octagonal prism, or the like. The body 2114 can be configured, such as sized and shaped, to be complimentary to an internal bore of the inner shaft 2026 to form a pneumatic seal with the inner shaft 2026.

The blade bore 2116 and the wire routing bore 2118 can each be bores extending axially through the body 2114 along the axis A1. The blade bore 2116 can be sized and shaped to receive the shaft 2072 of the blade 2032 therethrough and can be configured to allow for translation of the shaft 2072 within the guide tube 2112 to allow the blade 2032 to be operated from the handle 2001 such that the blade 2032 can translate within the blade channels of the jaws 2010 and 2012. The blade bore 2116 can also be sized relative to the blade shaft 2072 such that a pneumatic seal, or a seal, can be formed between the blade bore 2116 and the blade shaft 2072 to help reduce pressurized air or gas from traveling through the body 2114.

The wire routing bore 2118 can be sized and shaped to receive one or more wires or conduits therethrough to allow for conduits to extend from the handle 2001 to electrodes of the jaws 2010 and 2012. In some examples, the guide tube 2112 can be formed of a non-conductive material. In some examples, the guide tube 2112 can be formed by an extrusion. The wire routing bore 2118 can also be sized relative to the conduit(s) such that a pneumatic seal, or a seal, can be formed between the wire routing bore 2118 and the conduit(s) to help reduce pressurized air or gas from traveling through the body 2114.

Figure 52A:
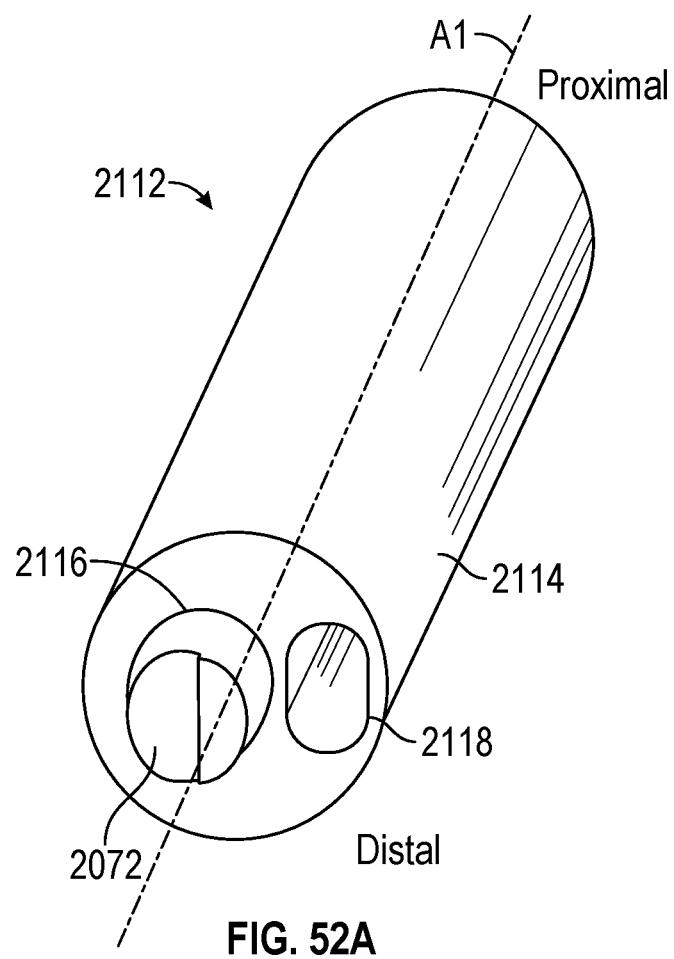
FIG. 52A illustrates an end isometric view of a guide tube and blade shaft.
Figure 52B:
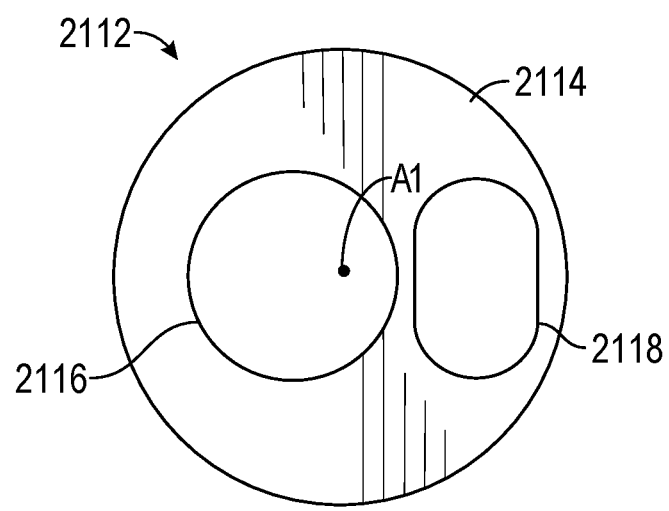
FIG. 52B illustrates an end view of a guide tube.

FIG. 52A illustrates an end isometric view of the guide tube 2112 and the blade shaft 2072, in accordance with at least one example of this disclosure. FIG. 52B illustrates an end view of the guide tube 2112e. Also shown in FIGS. 52A and 33B are orientation indicators Proximal and Distal and the axis A1. FIGS. 52A and 52B are discussed below concurrently.

The guide tube 2112 can be consistent with the descriptions above; FIGS. 52A and 33B show additional details of the guide tube 2112. For example, FIGS. 52A-52B show that the blade bore 2116 and/or the wire routing bore 2118 of the guide tube 2112 can extend axially through the body 2114 of the guide tube 2112. In some examples, one or more of the blade bore 2116 and the wire routing bore 2118 can extend through the guide tube 2112 axially parallel to the axis A1. In some examples, the blade bore 2116 can be offset of the axis A1. In some examples, the wire routing bore 2118 can be offset of the axis A1 opposite the blade channel, as shown in FIG. 52B.

In one example, the guide tube 2112 can include a second wire routing bore extending therethrough configured to receive a second conduit therethrough. The second wire routing bore can be offset of the axis A1 opposite the blade channel 2116. The second wire routing bore can be offset of the longitudinal axis and the second wire routing bore offset an opposite side of the longitudinal axis from the wire routing bore.

Figure 53:
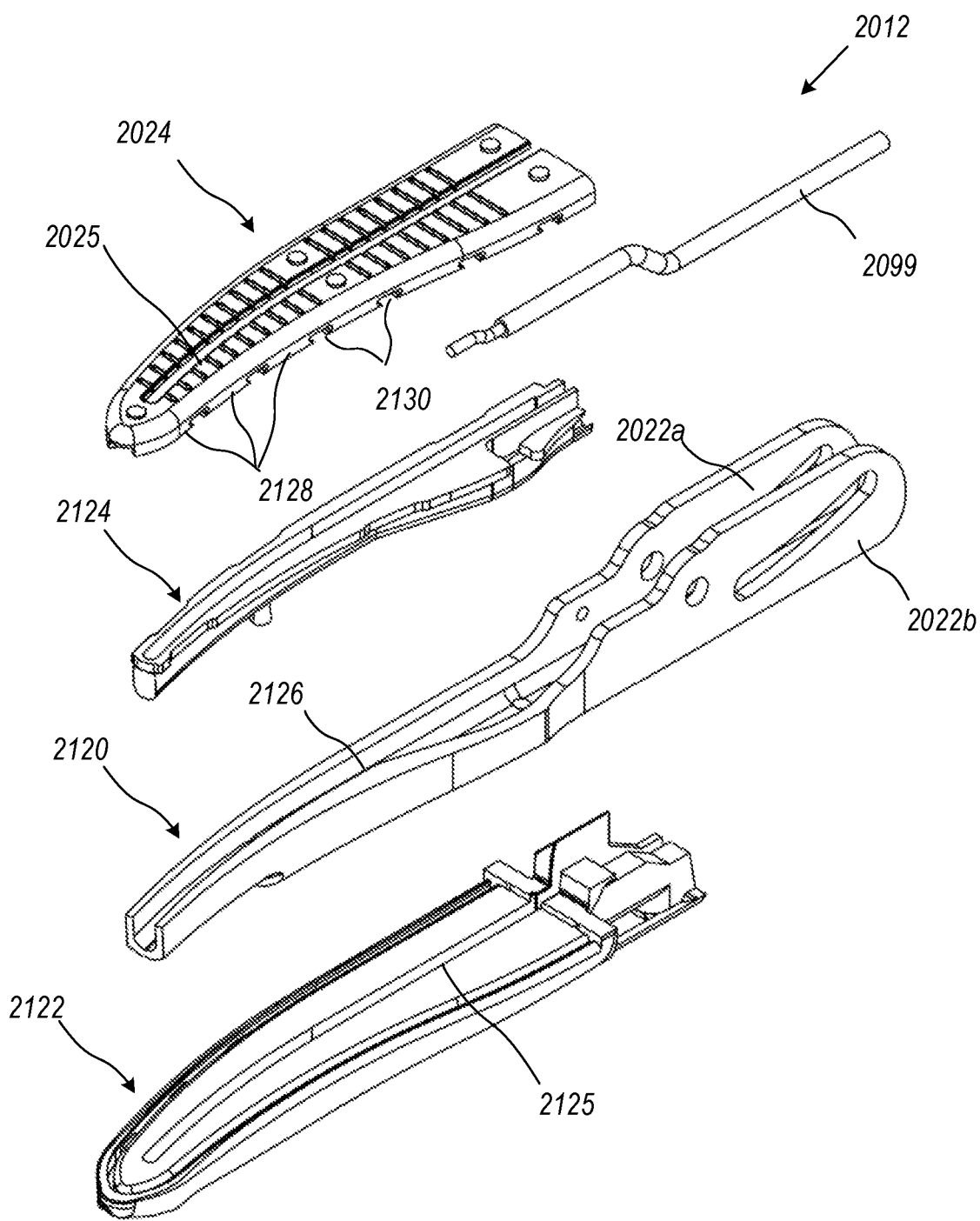
FIG. 53 illustrates an exploded view of a jaw.

FIG. 53. illustrates an exploded view of the jaw 2012. The jaw 2012 can include the grip plate 2024 (including a blade slot 2025), a wire 2099, a frame 2120 (including flanges 2022a and 2022b), an overmold 2122 (including a blade slot 2125), and a support 2124.

The jaw 2012 can be consistent with the description above; FIG. 53 shows additional details of the jaw 2012. For example, FIG. 53 shows that the overmold 2122 can include a blade slot 2125, which can be aligned with the blade slot 2025 of the grip plate 2024 when the overmold 2122 is secured to the grip plate 2024 (such as when the overmold 2122 is overmolded to the frame 2120 and the grip plate 2024. FIG. 53 also shows that the frame 2120 can include a slot 2126 that can receive the support 2124 therein. The support 2124 can help to support the grip plate 2024 on the frame 2120.

FIG. 53 also shows that the grip plate 2024 can include teeth 2128 that can define recesses 2130. The recesses 2130 can be located on a side edge of the grip plate 2024. The recesses 2130 can be configured to let material of the overmold 2122 infiltrate (or fill in) the recesses (or spaces or gaps) 2130 so that the grip plate 2024 is secured to the overmold 2122. The grip plate 2024 can also be an electrode (or can include an electrode) which can be electrically connected to the wire (or conduit) 2099.

While illustrative examples of a medical device are shown and described in this disclosure with respect to a forceps, the features can be used in other medical devices besides forceps for controlling end effectors used in diagnosis, treatment or surgery. Any representation of a forceps or description thereto is shown primarily for illustrative purposes to disclose features of various examples.

The forceps illustrated in the examples can be an electrosurgical device, however, the forceps may be any type of medical device that facilitates mechanical and/or electrical actuation of one or more end effectors or other elements arranged distal from the handpiece having one or more actuation systems. The actuation systems described, which can extend, retract or rotate one or more shafts to produce this result, can be used to effect actions in other medical devices (e.g., medical instruments).

The directional descriptors described herein are used with their normal and customary use in the art. For example, proximal, distal, lateral, up, down, top and bottom may be used to describe the apparatus with the longitudinal axis arranged parallel to a ground with the device in an upright position. The proximal direction refers to a direction towards the user end of the apparatus, and the distal direction represents a direction towards the patient end of the apparatus.

Relative terms described herein, such as, "about" or "substantially" may be used to indicate a possible variation of ±10% in a stated numeric value, or a manufacturing variation.

As described throughout this disclosure, components and assemblies can be operably connected to each other and interact with one another in a manner that provides improved actuation, a more compact and simpler design, lower cost, and better user satisfaction than traditional medical devices.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

In the event of inconsistent usages between this document and any documents so incorporated by reference, the usage in this document controls. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. An actuation system for a medical device, the system comprising:
   a housing;
   a body that is longitudinally slidable relative to the housing, the body having a peripheral flange extending outward towards the housing; and
   a trigger having an actuation surface configured to receive a force input from a user to pivot the trigger about a pivot point, and at least one arm on an opposite side of the pivot point from the actuation surface and extending away from the actuation surface to a free end, the trigger being configured to transfer the force input to the body,
   wherein the housing includes a first control surface configured to inhibit lateral splaying of the free end of the at least one arm when the trigger is actuated.

2. The system of claim 1, wherein the peripheral flange is a tapered flange.

3. The system of claim 1, wherein a gap is located between the at least one arm and the first control surface along at least a portion of the first control surface.

4. The system of claim 3, wherein the gap is less than a thickness of the at least one arm.

5. The system of claim 3, wherein the gap is in a range between 10-90% of the arm thickness.

6. The system of claim 3, wherein the at least one arm and the first control surface are in contact with one another along at least a portion of a full range of travel of the at least one arm.

7. The system of claim 1, wherein the at least one arm includes a yoke having a first arm and a second arm, and wherein the second arm is laterally spaced apart from the first arm.

8. The system of claim 7, wherein the housing further includes a second control surface that extends towards the second arm, and wherein lateral splay of the second arm is controlled by the second control surface.

9. The system of claim 8, wherein the housing comprises:
   a first housing portion; and
   a second housing portion,
   wherein the first control surface is formed in the first housing portion,
   wherein the second control surface is formed in the second housing portion, and
   wherein the first housing portion is joined to the second housing portion along a coupling joint, and the yoke is disposed around the body in between the first control surface and the second control surface.

10. The system of claim 8, wherein the first control surface and the second control surface are configured to inhibit splaying of the yoke.

11. The system of claim 1, wherein the body includes a spool.

12. The system of claim 1, wherein the body includes a spool that extends from a proximal end portion to a distal end portion, and wherein the proximal end portion and distal end portion provide dual-acting tapered flanges.

13. The system of claim 1, further comprising a blade coupled to the body, wherein movement of the body distally causes the blade to be extended distally, and wherein movement of the body proximally causes the blade to be retracted proximally.

14. An actuation system for a medical device, the system comprising:
- a housing;
- a body that is longitudinally slidable relative to the housing, the body having a tapered peripheral flange extending outward towards the housing; and
- a trigger having an actuation surface configured to receive a force input from a user, and at least one arm extending away from the actuation surface, passed a lateral side of the body, and upward to a free end, the trigger being configured to transfer the force input to the body,
- wherein the housing includes a first control surface configured to inhibit lateral splaying of the free end of the at least one arm when the trigger is actuated.

15. The system of claim 14, wherein a gap is located between the at least one arm and the first control surface along at least a portion of the first control surface.

16. The system of claim 14, wherein the at least one arm and the first control surface are in contact with one another along at least a portion of a full range of travel of the at least one arm.

17. The system of claim 14, wherein the body includes a spool that extends from a proximal end portion to a distal end portion, and wherein the proximal end portion and distal end portion provide dual-acting tapered flanges.

18. The system of claim 14, further comprising a blade coupled to the body, wherein movement of the body distally causes the blade to be extended distally, and wherein movement of the body proximally causes the blade to be retracted proximally.

19. An actuation system for a medical device, the system comprising:
- a housing;
- a body that is longitudinally slidable relative to the housing, the body including a spool and having a peripheral flange extending outward towards the housing; and
- a trigger having an actuation surface configured to receive a force input from a user, and at least one arm extending away from the actuation surface, passed a lateral side of the body, and upward to a free end, the trigger being configured to transfer the force input to the body,
- wherein the housing includes a first control surface configured to inhibit lateral splaying of the free end of the at least one arm when the trigger is actuated.

20. The system of claim 19, wherein the peripheral flange is a tapered flange.

21. The system of claim 19, wherein the spool extends from a proximal end portion to a distal end portion, and wherein the proximal end portion and distal end portion provide dual-acting tapered flanges.

22. The system of claim 19, further comprising a blade coupled to the body, wherein movement of the body distally causes the blade to be extended distally, and wherein movement of the body proximally causes the blade to be retracted proximally.

23. The system of claim 19, wherein a gap is located between the at least one arm and the first control surface along at least a portion of the first control surface.

24. The system of claim 19, wherein the at least one arm and the first control surface are in contact with one another along at least a portion of a full range of travel of the at least one arm.

* * * * *